United States Patent
Mizojiri et al.

(10) Patent No.: US 10,301,292 B2
(45) Date of Patent: May 28, 2019

(54) BICYCLIC COMPOUND

(71) Applicant: Takeda Pharmaceutical Company Limited, Chuo-ku, Osaka-shi, Osaka (JP)

(72) Inventors: Ryo Mizojiri, Kanagawa (JP); Hiroshi Banno, Kanagawa (JP); Moriteru Asano, Naruto (JP); Daisuke Tomita, New York, NY (US); Noriyuki Nii, Wakayama (JP); Hironobu Maezaki, Kanagawa (JP); Michiko Tawada, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 15/529,816

(22) PCT Filed: Nov. 25, 2015

(86) PCT No.: PCT/JP2015/082974
§ 371 (c)(1),
(2) Date: May 25, 2017

(87) PCT Pub. No.: WO2016/084816
PCT Pub. Date: Jun. 2, 2016

(65) Prior Publication Data
US 2018/0002322 A1    Jan. 4, 2018

(30) Foreign Application Priority Data

Nov. 26, 2014  (JP) ................................. 2014-239376

(51) Int. Cl.
| | | |
|---|---|---|
| C07D 413/04 | (2006.01) |
| C07D 413/14 | (2006.01) |
| A61K 31/343 | (2006.01) |
| A61K 31/381 | (2006.01) |
| A61K 31/416 | (2006.01) |
| A61K 31/423 | (2006.01) |
| A61K 31/428 | (2006.01) |
| A61K 31/437 | (2006.01) |
| A61K 31/443 | (2006.01) |
| A61K 31/4439 | (2006.01) |
| A61K 31/497 | (2006.01) |
| A61K 31/501 | (2006.01) |
| A61K 31/517 | (2006.01) |
| A61K 31/5377 | (2006.01) |
| C07D 231/56 | (2006.01) |
| C07D 333/56 | (2006.01) |
| C07D 401/04 | (2006.01) |
| C07D 403/04 | (2006.01) |

(Continued)

(52) U.S. Cl.
CPC ........ C07D 413/04 (2013.01); A61K 31/343 (2013.01); A61K 31/381 (2013.01); A61K 31/416 (2013.01); A61K 31/423 (2013.01); A61K 31/428 (2013.01); A61K 31/437 (2013.01); A61K 31/443 (2013.01); A61K 31/4439 (2013.01); A61K 31/497 (2013.01); A61K 31/501 (2013.01); A61K 31/517 (2013.01); A61K 31/5377 (2013.01); C07D 231/56 (2013.01); C07D 263/54 (2013.01); C07D 263/57 (2013.01); C07D 307/81 (2013.01); C07D 333/56 (2013.01); C07D 401/04 (2013.01); C07D 403/04 (2013.01); C07D 405/04 (2013.01); C07D 413/12 (2013.01); C07D 413/14 (2013.01); C07D 417/04 (2013.01); C07D 471/04 (2013.01); C07D 498/04 (2013.01); C12N 15/09 (2013.01)

(58) Field of Classification Search
CPC ................................................. C07D 413/04
See application file for complete search history.

(56) References Cited

U.S. PATENT DOCUMENTS

| 9,278,925 B2 | 3/2016 | Liu et al. |
| 2007/0219251 A1 | 9/2007 | Gu et al. |

(Continued)

FOREIGN PATENT DOCUMENTS

| WO | WO 2007/095601 A2 | 8/2007 |
| WO | WO 2007/095602 A2 | 8/2007 |

(Continued)

OTHER PUBLICATIONS

Pinedo et al. (2000).*

(Continued)

*Primary Examiner* — Paul V Ward
(74) *Attorney, Agent, or Firm* — Foley & Lardner LLP

(57) ABSTRACT

Provided is a bicyclic compound having an acetyl-CoA carboxylase inhibitory action. A compound represented by the formula:

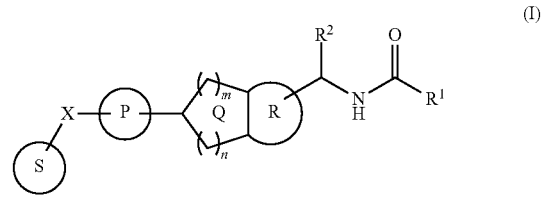

(I)

wherein each symbol is as described in the DESCRIPTION, or a salt thereof has an acetyl-CoA carboxylase inhibitory action, is useful for the prophylaxis or treatment of cancer, inflammatory diseases and the like, and has superior efficacy.

9 Claims, 1 Drawing Sheet
Specification includes a Sequence Listing.

(51) Int. Cl.
  *C07D 405/04* (2006.01)
  *C07D 413/12* (2006.01)
  *C07D 417/04* (2006.01)
  *C07D 471/04* (2006.01)
  *C07D 263/54* (2006.01)
  *C07D 498/04* (2006.01)
  *C07D 307/81* (2006.01)
  *C07D 263/57* (2006.01)
  *C12N 15/09* (2006.01)

(56) References Cited

U.S. PATENT DOCUMENTS

| 2007/0219258 | A1 | 9/2007 | Keyes et al. |
| 2007/0225332 | A1 | 9/2007 | Gu et al. |
| 2009/0048298 | A1 | 2/2009 | Keyes et al. |
| 2012/0010247 | A1 | 1/2012 | Kamata et al. |
| 2014/0243310 | A1 | 8/2014 | Yamashita et al. |
| 2014/0275199 | A1 | 9/2014 | Liu et al. |
| 2017/0145028 | A1 | 5/2017 | Ghosh et al. |

FOREIGN PATENT DOCUMENTS

| WO | WO 2007/095603 A2 | 8/2007 |
| WO | WO 2010/050445 A1 | 5/2010 |
| WO | WO 2010/082044 A1 | 7/2010 |
| WO | WO 2010/127212 A1 | 11/2010 |
| WO | WO 2012/069917 A1 | 5/2012 |
| WO | WO 2012/090219 A2 | 7/2012 |
| WO | WO 2012/146666 A1 | 11/2012 |
| WO | WO 2013/017600 A1 | 2/2013 |
| WO | WO 2013/061962 A1 | 5/2013 |
| WO | WO 2013/098373 A1 | 7/2013 |
| WO | WO 2014/061693 A1 | 4/2014 |
| WO | WO 2014/182945 A1 | 11/2014 |
| WO | WO 2017/075056 A1 | 5/2017 |

OTHER PUBLICATIONS

McMahon et al. (2000).*

Haque et al., "Potent biphenyl- and 3-phenyl pyridine-based inhibitors of acetyl-CoA carboxylase," Bioorganic & Medicinal Chemistry Letters, 2009, 19:5872-5876.

* cited by examiner

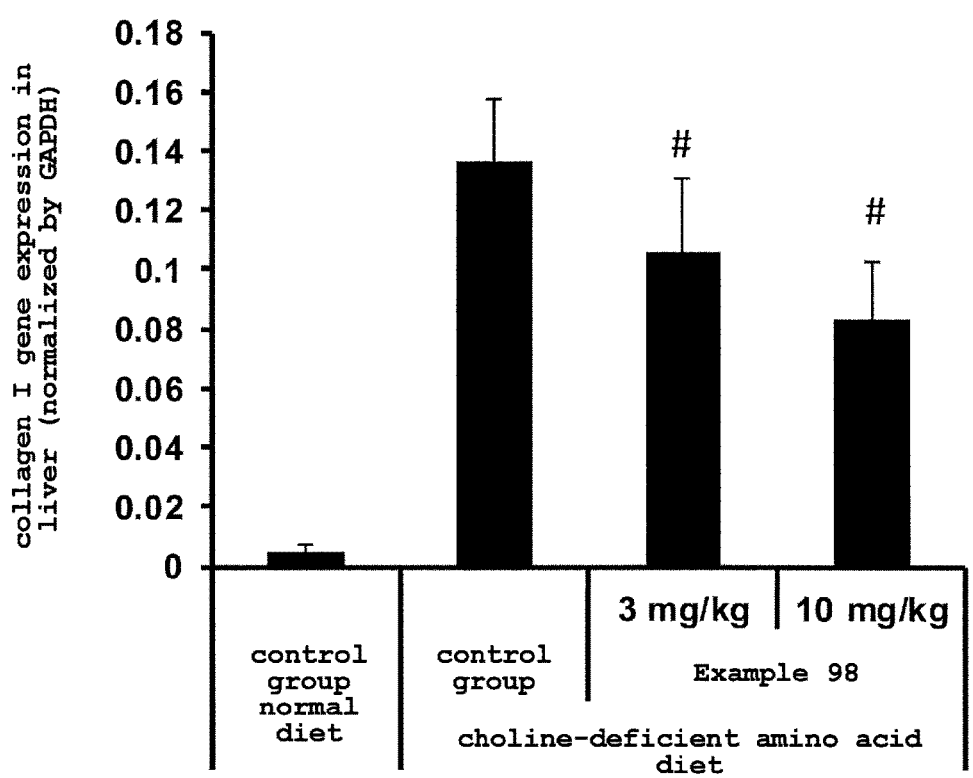

SEQUENCE LISTING

<160> NUMBER OF SEQ ID NOS: 2

<210> SEQ ID NO 1
<211> LENGTH: 40
<212> TYPE: DNA
<213> ORGANISM: Artificial
<220> FEATURE:
<223> OTHER INFORMATION: PCR primer

```
<400> SEQUENCE: 1
aaaagtcgac ccaccatgga tgaaccttct cccttggccc                    40

<210> SEQ ID NO 2
<211> LENGTH: 37
<212> TYPE: DNA
<213> ORGANISM: Artificial
<220> FEATURE:
<223> OTHER INFORMATION: PCR primer

<400> SEQUENCE: 2
aaaagcggcc gcctacgtag aagggagtc catagtg                        37
```

BICYCLIC COMPOUND

TECHNICAL FIELD

The present invention relates to a bicyclic compound having an acetyl-CoA carboxylase (in the present specification, sometimes to be abbreviated as ACC) inhibitory action, which is useful for the prophylaxis or treatment of cancer, inflammatory diseases and the like.

BACKGROUND OF THE INVENTION

ACC is involved in ATP-dependent carboxylation of acetyl-CoA to malonyl-CoA, which is a rate-limiting step in fatty acid synthesis. This reaction proceeds in two half reactions, that is, a biotin carboxylase reaction and a carboxyltransferase reaction. Malonyl-CoA is a carbon donor in the synthesis and elongation reaction of long chain fatty acids and is also a regulator of the palmitoyl CoA carnitine shuttle system involved in mitochondrial oxidation of long chain fatty acids.

ACC exists as two isozymes, that is, ACC1 present in adipogenic tissues such as liver and fat, and ACC2 present in oxidized tissues such as liver, heart and skeletal muscle. ACC1 and ACC2 are encoded by different genes.

ACC1 is abundantly present in the cytoplasm and controls de novo synthesis of fatty acids. Malonyl-CoA, which is a product thereof, acts as a substrate for fatty acid synthase (FASN) and is used for the biosynthesis of long chain fatty acids, phospholipids, triglycerides (TG) and the like. On the other hand, ACC2 is abundantly present in the mitochondrial outer membrane, and controls fatty acid oxidation. Malonyl-CoA, which is a product thereof, inhibits uptake of fatty acid into mitochondria and inhibits fatty acid oxidation in mitochondria, based on the feedback inhibition of carnitine palmitoyl transferase-1 (CPT-1).

In many cancer cells, de novo fatty acid synthesis is flourishing regardless of the number of exogenous fatty acids compared to normal cells. It is already known that several lipid metabolic enzymes, such as FASN, promote the development and malignancy of cancer, and these are expected to become new target molecules for cancer treatment. It is also known that ACC1 is highly expressed in a wide variety of cancer cells. Therefore, inhibition of the biosynthesis of fatty acid in cancer cells by inhibition of ACC1 is extremely useful for the prophylaxis and treatment of cancer. In fact, as a compound having ACC1 inhibitory activity and cancer cell proliferation inhibitory activity, the compound described in patent document 1 is known.

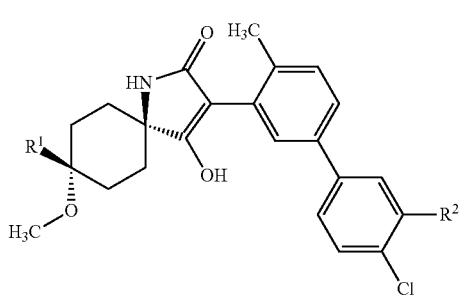

wherein each symbol is as defined in the document.

On the other hand, ACC1 is present in lipogenic tissues such as liver and fat, and controls fatty acid synthesis. Therefore, inhibition of ACC1 reduces fatty acid synthesis and is extremely useful for the prophylaxis or treatment of metabolic syndrome, obesity, hypertension, diabetes, fatty liver disease, non-alcoholic steatohepatitis (sometimes to be abbreviated as NASH in the present specification), nonalcardiovascular diseases associated with atherosclerosis and the like.

Patent document 2 discloses the following compound having a GPR119 regulating action and useful for the prophylaxis or treatment of diabetes and the like.

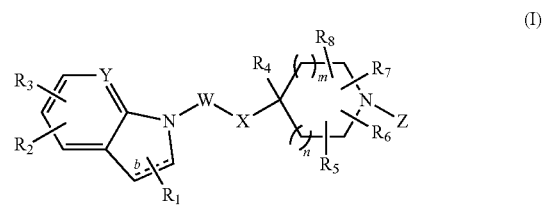

wherein each symbol is as defined in the document.

Patent document 3 discloses the following compound having an SMO antagonistic action and useful for the prophylaxis or treatment of cancer and the like.

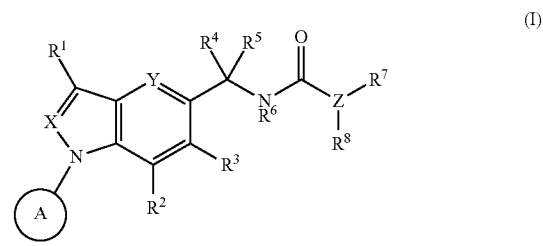

wherein each symbol is as defined in the document.

Patent document 4 discloses the following compound having an ACC2 inhibitory action and useful for the prophylaxis or treatment of obesity, hepatitis (including NASH), cancer and the like.

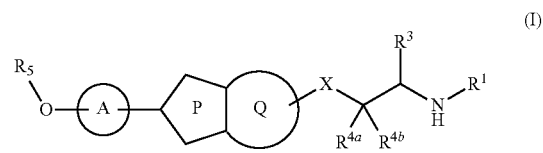

wherein each symbol is as defined in the document.

Patent document 5 discloses the following compound having a PI3K inhibitory action and useful for the prophylaxis or treatment of respiratory diseases, cancer and the like.

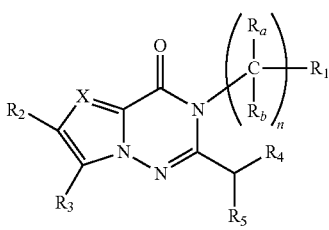

wherein each symbol is as defined in the document.

Patent document 6 discloses the following compound having an ACC inhibitory action and useful for the prophylaxis or treatment of cancer, NASH and the like.

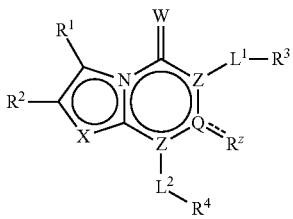

wherein each symbol is as defined in the document.

DOCUMENT LIST

Patent Documents patent document 1: WO 2013/017600
patent document 2: WO 2012/069917
patent document 3: WO 2010/082044
patent document 4: WO 2013/061962
patent document 5: WO 2012/146666
patent document 6: WO 2014/182945

SUMMARY OF THE INVENTION

Problems to be Solved by the Invention

There is a demand for the development of a compound having an ACC inhibitory action, which is useful for the prophylaxis or treatment of cancer, inflammatory diseases and the like, and has superior efficacy.

Means of Solving the Problems

The present inventors have found for the first time that a compound represented by the following formula (I) or a salt thereof [hereinafter sometimes to be referred to as compound (I)] has a superior ACC inhibitory action, is useful for the prophylaxis or treatment of cancer, inflammatory diseases and the like, and has superior efficacy. Based on this finding, the present inventors have conducted intensive studies and completed the present invention.

Accordingly, the present invention relates to
[1] a compound represented by the formula:

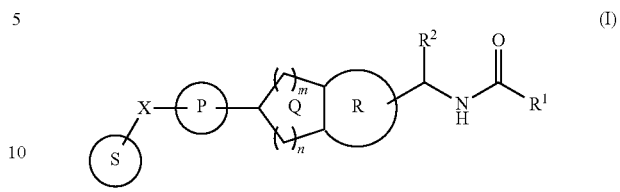

wherein
ring P is an optionally further substituted, optionally crosslinked 4- to 8-membered ring;
ring Q is an optionally further substituted 5- or 6-membered ring;
ring R is an optionally further substituted 5- or 6-membered ring;
ring S is an optionally further substituted 4- to 7-membered ring;
X is —O—, —C($R^3$)($R^4$)— or —N($R^5$)—;
$R^1$ is an amino group optionally mono- or di-substituted by an optionally substituted $C_{1-6}$ alkyl group, a $C_{1-6}$ alkyl group optionally substituted by a halogen atom, an optionally substituted $C_{3-6}$ cycloalkyl group or an optionally substituted $C_{1-6}$ alkoxy group;
$R^2$ is a $C_{1-6}$ alkyl group optionally substituted by a halogen atom or an optionally substituted $C_{3-6}$ cycloalkyl group;
$R^3$, $R^4$ and $R^5$ are the same or different and each is a hydrogen atom or a substituent;
m and n are the same or different and each is 1 or 2, and m+n is 2 or 3,
or a salt thereof;
[2] The compound of [1], wherein ring P is
(1) a cyclobutane ring,
(2) a cyclohexane ring,
(3) a benzene ring optionally further substituted by 1-4 substituents selected from a halogen atom, a cyano group and a $C_{1-6}$ alkyl group,
(4) an azetidine ring optionally further substituted by 1-4 substituents selected from a $C_{1-6}$ alkyl group,
(5) a pyrrolidine ring,
(6) a piperidine ring,
(7) a hexahydrocyclopenta[c]pyrrole ring,
(8) a pyrazole ring optionally further substituted by 1-4 substituents selected from a $C_{1-6}$ alkyl group,
(9) a pyridine ring optionally further substituted by 1-4 substituents selected from a $C_{1-6}$ alkyl group,
(10) a pyridazine ring, or
(11) a pyrazine ring,
ring Q is
(1) a benzene ring,
(2) a dihydrofuran ring,
(3) a furan ring,
(4) a thiophene ring,
(5) a pyrazole ring,
(6) an imidazole ring optionally further substituted by 1-4 substituents selected from a $C_{1-6}$ alkyl group,
(7) an oxazole ring,
(8) a thiazole ring, or
(9) a pyrimidine ring;

ring R is
(1) a cyclohexene ring,
(2) a benzene ring optionally further substituted by 1-4 substituents selected from a halogen atom and a $C_{1-6}$ alkyl group,
(3) a furan ring, or
(4) a pyridine ring;
ring S is
(1) a benzene ring optionally further substituted by 1-4 substituents selected from
(i) a $C_{1-6}$ alkyl group optionally further substituted by 1-4 substituents selected from a $C_{1-6}$ alkoxy group and a halogen atom,
(ii) a $C_{1-6}$ alkoxy group optionally substituted by 1-5 substituents selected from
(a) a halogen atom,
(b) a $C_{3-6}$ cycloalkyl group optionally substituted by 1-4 substituents selected from a halogen atom and a $C_{1-6}$ alkyl group,
(c) a $C_{1-6}$ alkoxy group,
(d) a 4- to 7-membered nonaromatic heterocyclic group optionally substituted by a $C_{1-6}$ alkyl group, and
(e) a $C_{6-14}$ aryl group,
(iii) a $C_{3-6}$ cycloalkyloxy group, and
(iv) a di-$C_{1-6}$ alkylamino group, or
(2) a pyridine ring optionally further substituted by 1-4 substituents selected from
(i) a $C_{1-6}$ alkoxy group optionally substituted by a $C_{3-6}$ cycloalkyl group,
(ii) an oxo group, and
(iii) a $C_{1-6}$ alkyl group;
X is —$CH_2$—, —NH—, —N($CH_3$)— or —O—;
$R^1$ is
(1) a $C_{1-6}$ alkyl group optionally substituted by 1 to 3 halogen atoms,
(2) a $C_{1-6}$ alkoxy group, or
(3) an amino group optionally mono- or di-substituted by a $C_{1-6}$ alkyl group;
$R^2$ is a $C_{1-6}$ alkyl group;
m and n are the same or different and each is 1 or 2, and m+n is 2 or 3;
or a salt thereof;
[3] the compound of the above-mentioned [1] or [2], wherein the fused ring constituted of ring Q and ring R, that is, a partial structure:

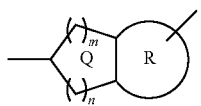

is

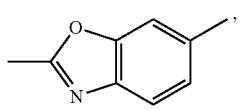, or a salt thereof;
[4] N-(1-(2-(6-(3-(cyclopropylmethoxy)phenoxy)pyridin-3-yl)-1,3-benzoxazol-6-yl)ethyl)acetamide, or a salt thereof;
[5] 1-(1-(2-(6-(3-(cyclopropylmethoxy)phenoxy)pyridin-3-yl)-1,3-benzoxazol-6-yl)ethyl)urea, or a salt thereof;
[6] N-(1-(2-(6-((6-oxo-1-propyl-1,6-dihydropyridin-3-yl)oxy)pyridin-3-yl)-1,3-benzoxazol-6-yl)ethyl)acetamide, or a salt thereof;
[7] a medicament containing the compound of any of the above-mentioned [1] to [6] or a salt thereof;
[8] the medicament of the above-mentioned [7], which is an ACC1 inhibitor;
[9] the medicament of the above-mentioned [7] or [8], which is a prophylactic or therapeutic agent for cancer;
[10] the medicament of the above-mentioned [7] or [8], which is a prophylactic or therapeutic agent for non-alcoholic steatohepatitis;
[11] a method of inhibiting ACC1 in a mammal, comprising administering an effective amount of the compound of any of the above-mentioned [1] to [6] or a salt thereof to the mammal;
[12] a method for the prophylaxis or treatment of cancer in a mammal, comprising administering an effective amount of the compound of any of the above-mentioned [1] to [6] or a salt thereof to the mammal;
[13] a method for the prophylaxis or treatment of non-alcoholic steatohepatitis in a mammal, comprising administering an effective amount of the compound of any of the above-mentioned [1] to [6] or a salt thereof to the mammal;
[14] the compound of any of the above-mentioned [1] to [6] or a salt thereof for use in the prophylaxis or treatment of cancer;
[15] the compound of any of the above-mentioned [1] to [6] or a salt thereof for use in the prophylaxis or treatment of non-alcoholic steatohepatitis;
[16] Use of the compound of any of the above-mentioned [1] to [6] or a salt thereof for the production of an agent for the prophylaxis or treatment of cancer;
[17] Use of the compound of any of the above-mentioned [1] to [6] or a salt thereof for the production of an agent for the prophylaxis or treatment of non-alcoholic steatohepatitis; and the like.

Effect of the Invention

Compound (I) has an ACC inhibitory action, is useful for the prophylaxis or treatment of cancer, inflammatory diseases and the like, and has superior efficacy.

BRIEF DESCRIPTION OF THE DRAWINGS

FIG. 1 shows the effect of the present compound for liver fibrosis caused by non-alcoholic steatohepatitis (liver collagen I gene expression level of non-alcoholic steatohepatitis model).

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1}$-6 alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered nonaromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclyl-sulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkyl-sulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-3-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "$C_{3-6}$ cycloalkyl group" include the above-mentioned "$C_{3-10}$ cycloalkyl group" having 3-6 carbon atoms.

In the present specification, Examples of the "4- to 8-membered ring" of the "optionally further substituted, optionally crosslinked 4- to 8-membered ring" include 4- to 8-membered ones from the above-mentioned "hydrocarbon ring" and "heterocycle", and the substituent thereof is, for example, the above-mentioned "substituent".

In the present specification, the "4- to 8-membered ring" of the "optionally further substituted, optionally crosslinked 4- to 8-membered ring" may be crosslinked to form a crosslinked cyclic ring. Examples of such crosslinked cyclic ring include azabicyclo[3.1.1]heptane, azabicyclo[3.2.1]octane and the like.

In the present specification, examples of the "non-aromatic heterocycle" include hexahydrocyclopenta[c]pyrrole ring and the like.

In the present specification, examples of the "5- or 6-membered ring" of the "optionally further substituted 5- or 6-membered ring" include 5- or 6-membered ones from the above-mentioned "hydrocarbon ring" and "heterocycle", and the substituent thereof is, for example, the above-mentioned "substituent".

In the present specification, examples of the "4- to 7-membered ring" of the "optionally further substituted 4- to 7-membered ring" include 4- to 7-membered ones from the above-mentioned "hydrocarbon ring" and "heterocycle", and the substituent thereof is, for example, the above-mentioned "substituent".

The definition of each symbol in the formula (I) is explained in detail below.

Ring P is an optionally further substituted, optionally crosslinked 4- to 8-membered ring.

Examples of the "4- to 8-membered ring" of the "optionally further substituted, optionally crosslinked 4- to 8-membered ring" for ring P include 4- to 8-membered nonaromatic hydrocarbon ring (e.g., cyclobutane ring, cyclohexane ring), 4- to 8-membered aromatic hydrocarbon ring (e.g., benzene ring), 4- to 8-membered non-aromatic heterocycle (e.g., azetidine ring, pyrrolidine ring, piperidine ring, hexahydrocyclopenta[c]pyrrole ring), 4- to 8-membered aromatic heterocycle (e.g., a pyrazole ring, a pyridine ring, a pyridazine ring, a pyrazine ring) and the like.

The "4- to 8-membered ring" of the "optionally further substituted, optionally crosslinked 4- to 8-membered ring" for ring P is optionally further substituted at substitutable position(s) by 1-4 (preferably 1-3, more preferably 1 or 2) substituents other than ring S—X— group and $R^1$—C(=O)—NH—CH($R^2$)— ring R ring Q— group. Examples of such substituent include the above-mentioned "substituent", and a halogen atom (e.g., fluorine, chlorine, bromine), a cyano group, $C_{1-6}$ alkyl group (e.g., methyl, ethyl) and the like are preferable.

The "4- to 8-membered ring" of the "optionally further substituted, optionally crosslinked 4- to 8-membered ring" for ring P may be crosslinked to form a crosslinked cyclic ring. Examples of such crosslinked cyclic ring include azabicyclo[3.1.1]heptane and azabicyclo[3.2.1]octane and the like.

Ring P is preferably a cyclobutane ring, a cyclohexane ring, a benzene ring, an azetidine ring, a pyrrolidine ring, a piperidine ring, a hexahydrocyclopenta[c]pyrrole ring, a pyrazole ring, a pyridine ring, a pyridazine ring or a pyrazine ring, each of which is optionally further substituted.

Ring P is more preferably
(1) a cyclobutane ring,
(2) a cyclohexane ring,
(3) a benzene ring optionally further substituted by 1-4 (preferably 1-3, more preferably 1 or 2) substituents selected from a halogen atom (e.g., fluorine, chlorine, bromine), a cyano group and a $C_{1-6}$ alkyl group (e.g., methyl, ethyl) and
(4) an azetidine ring optionally further substituted by 1-4 (preferably 1-3, more preferably 1 or 2) substituents selected from a $C_{1-6}$ alkyl group (e.g., methyl),
(5) a pyrrolidine ring,
(6) a piperidine ring,
(7) a hexahydrocyclopenta[c]pyrrole ring,
(8) a pyrazole ring optionally further substituted by 1-4 (preferably 1-3, more preferably 1 or 2) substituents selected from a $C_{1-6}$ alkyl group (e.g., methyl),
(9) a pyridine ring optionally further substituted by 1-4 (preferably 1-3, more preferably 1 or 2) substituents selected from a $C_{1-6}$ alkyl group (e.g., methyl),
(10) a pyridazine ring, or
(11) a pyrazine ring.

Ring P is further preferably
(1) a benzene ring,
(2) an azetidine ring,
(3) a pyridine ring optionally further substituted by 1-4 (preferably 1-3, more preferably 1 or 2) substituents selected from a $C_{1-6}$ alkyl group (e.g., methyl),
(4) a pyridazine ring, or
(5) a pyrazine ring.

Ring P is still more preferably a pyridine ring.

Ring Q is an optionally further substituted 5- or 6-membered ring.

Examples of the "5- or 6-membered ring" of the "optionally further substituted 5- or 6-membered ring" for ring Q include a 5- or 6-membered nonaromatic hydrocarbon ring (e.g., cyclohexene ring), a 5- or 6-membered aromatic hydrocarbon ring (e.g., benzene ring), a 5- or 6-membered non-aromatic heterocycle (e.g., dihydrofuran ring), a 5- or 6-membered aromatic heterocycle (e.g., furan ring, pyridine ring, thiophene ring, pyrazole ring, imidazole ring, oxazole ring, thiazole ring, pyrimidine ring) and the like. The above-mentioned "5- or 6-membered ring" is preferably a 5- or 6-membered aromatic hydrocarbon ring (e.g., benzene ring), a 5- or 6-membered non-aromatic heterocycle (e.g., dihydrofuran ring), or a 5- or 6-membered aromatic heterocycle (e.g., furan ring, thiophene ring, pyrazole ring, imidazole ring, oxazole ring, thiazole ring, pyrimidine ring).

The "5- or 6-membered ring" of the "optionally further substituted 5- or 6-membered ring" for ring Q is optionally further substituted at substitutable position(s) by 1-4 (preferably 1-3, more preferably 1 or 2) substituents other than ring S—X-ring P— group. Examples of such substituent include the above-mentioned "substituent", and a $C_{1-6}$ alkyl group (e.g., methyl, ethyl) and the like are preferable.

Ring Q is preferably a benzene ring, a dihydrofuran ring, a furan ring, a thiophene ring, a pyrazole ring, an imidazole ring, an oxazole ring, a thiazole ring or a pyrimidine ring, each of which is optionally further substituted.

Ring Q is more preferably
(1) a benzene ring,
(2) a dihydrofuran ring,
(3) a furan ring,
(4) a thiophene ring,
(5) a pyrazole ring,
(6) an imidazole ring optionally further substituted by 1-4 (preferably 1-3, more preferably 1 or 2) substituents selected from a $C_{1-6}$ alkyl group (e.g., methyl, ethyl),
(7) an oxazole ring,
(8) a thiazole ring, or
(9) a pyrimidine ring.

Ring Q is further preferably
(1) a benzene ring,
(2) a dihydrofuran ring,
(3) a furan ring,
(4) a thiophene ring,
(5) a pyrazole ring,
(6) an oxazole ring, or
(7) a thiazole ring.

Ring Q is still more preferably an oxazole ring.

Ring R is an optionally further substituted 5- or 6-membered ring.

Examples of the "5- or 6-membered ring" of the "optionally further substituted 5- or 6-membered ring" for ring R include a 5- or 6-membered nonaromatic hydrocarbon ring (e.g., cyclohexene ring), a 5- or 6-membered aromatic hydrocarbon ring (e.g., benzene ring), a 5- or 6-membered non-aromatic heterocycle (e.g., dihydrofuran ring), a 5- or 6-membered aromatic heterocycle (e.g., furan ring, pyridine ring, thiophene ring, pyrazole ring, imidazole ring, oxazole ring, thiazole ring, pyrimidine ring) and the like. The above-mentioned "5- or 6-membered ring" is preferably a 5- or 6-membered nonaromatic hydrocarbon ring (e.g., cyclohexene ring), a 5- or 6-membered aromatic hydrocarbon ring (e.g., benzene ring), or a 5- or 6-membered aromatic heterocycle (e.g., furan ring, a pyridine ring).

The "5- or 6-membered ring" of the "optionally further substituted 5- or 6-membered ring" for ring R is optionally further substituted at substitutable position(s) by 1-4 (preferably 1-3, more preferably 1 or 2) substituents other than $R—C(=O)—NH—CH(R^2)—$ group. Examples of such substituent include the above-mentioned "substituent", and a halogen atom (e.g., fluorine), a $C_{1-6}$ alkyl group (e.g., methyl) and the like are preferable.

Ring R is preferably a cyclohexene ring, a benzene ring, a furan ring or a pyridine ring, each of which is optionally further substituted.

Ring R is more preferably
(1) a cyclohexene ring,
(2) a benzene ring optionally further substituted by 1-4 (preferably 1-3, more preferably 1 or 2) substituents selected from a halogen atom (e.g., fluorine) and a $C_{1-6}$ alkyl group (e.g., methyl),
(3) a furan ring, or
(4) a pyridine ring.

Ring R is further preferably a benzene ring optionally further substituted by 1-4 (preferably 1-3, more preferably 1 or 2) substituents selected from a halogen atom (e.g., fluorine), particularly preferably a benzene ring.

As the fused ring constituted of ring Q and ring R in another embodiment of the present invention, that is, a partial structure:

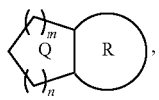

a tetrahydrobenzoxazole ring (e.g., 4,5,6,7-tetrahydro-1,3-benzoxazole ring), a benzoxazole ring (e.g., 1,3-benzoxazole ring), a dihydrobenzofuran ring (e.g., 2,3-dihydro-1-benzofuran ring), a benzofuran ring (e.g., 1-benzofuran ring), a benzothiophene ring (e.g., 1-benzothiophene ring), a benzoimidazole ring (e.g., 1H-benzoimidazole ring), a benzothiazole ring (e.g., 1,3-benzothiazole ring), an indazole ring (e.g., 2H-indazole ring), an imidazopyridine ring (e.g., imidazo[1,2-a]pyridine ring), a pyrazolopyridine ring (e.g., pyrazolo[1,5-a]pyridine ring), an oxazolopyridine ring (e.g., [1,3]oxazolo[5,4-b]pyridine ring) or a quinazoline ring is preferable, a tetrahydrobenzoxazole ring (e.g., 4,5,6,7-tetrahydro-1,3-benzoxazole ring), a benzoxazole ring (e.g., 1,3-benzoxazole ring), a dihydrobenzofuran ring (e.g., 2,3-dihydro-1-benzofuran ring), a benzofuran ring (e.g., 1-benzofuran ring), a benzothiophene ring (e.g., 1-benzothiophene ring), a benzothiazole ring (e.g., 1,3-benzothiazole ring), an indazole ring (e.g., 2H-indazole ring), an oxazolopyridine ring (e.g., [1,3]oxazolo[5,4-b]pyridine ring) or a pyrazolopyridine ring (e.g., pyrazolo[1,5-a]pyridine ring) is more preferable, and a benzoxazole ring (e.g., 1,3-benzoxazole ring) is particularly preferable.

The fused ring constituted of ring Q and ring R in a particularly preferable embodiment of the present invention, that is, a partial structure:

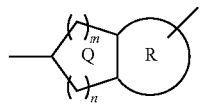

is

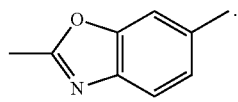

Ring S is an optionally further substituted 4- to 7-membered ring.

Examples of the "4- to 7-membered ring" of the "optionally further substituted 4- to 7-membered ring" for ring S include a 4- to 7-membered aromatic hydrocarbon ring (e.g., benzene ring), a 4- to 7-membered aromatic heterocycle (e.g., a pyridine ring) and the like.

As the "4- to 7-membered ring" of the "optionally further substituted 4- to 7-membered ring" for ring S, a 5- or 6-membered ring is preferable.

The "4- to 7-membered ring" of the "optionally further substituted 4- to 7-membered ring" for ring S is optionally further substituted at substitutable position(s) by 1-4 (preferably 1-3, more preferably 1 or 2) substituents other than $R^1—C(=O)—NH—CH(R^2)$-ring R ring Q-ring P—X— group. Examples of such substituent include the above-mentioned "substituent", and an oxo group, an optionally substituted $C_{1-6}$ alkyl group (e.g., methyl, propyl, butyl, pentyl), an optionally substituted $C_{1-6}$ alkoxy group (e.g., methoxy, ethoxy, propoxy, butoxy, isobutoxy, pentoxy, neopentoxy), a $C_{3-6}$ cycloalkyloxy group (e.g., cyclobutyloxy), a di-$C_{1-6}$ alkylamino group (e.g., dimethylamino) and the like are preferable.

Ring S is preferably a benzene ring or a pyridine ring, each of which is optionally further substituted.

Ring S is more preferably
(1) a benzene ring optionally further substituted by 1-4 (preferably 1-3, more preferably 1 or 2) substituents selected from
(i) a $C_{1-6}$ alkyl group (e.g., methyl, propyl, pentyl) optionally further substituted by 1-4 (preferably 1-3, more preferably 1 or 2) substituents selected from a $C_{1-6}$ alkoxy group (e.g., methoxy) and a halogen atom (e.g., fluorine),
(ii) a $C_{1-6}$ alkoxy group (e.g., methoxy, ethoxy, propoxy, butoxy, isobutoxy, neopentoxy) optionally substituted by 1-5 (preferably 1-4, more preferably 1-3, further preferably or 2) substituents selected from
(a) a halogen atom (e.g., fluorine),
(b) a $C_{3-6}$ cycloalkyl group (e.g., cyclopropyl, cyclobutyl) optionally substituted by 1-4 (preferably 1-3, more preferably 1 or 2) substituents selected from a halogen atom (e.g., fluorine) and a $C_{1-6}$ alkyl group (e.g., methyl),
(c) a $C_{1-6}$ alkoxy group (e.g., methoxy, ethoxy), (d) a 4- to 7-membered nonaromatic heterocyclic group (e.g., oxetanyl, tetrahydrofuranyl, morpholinyl) optionally substituted by a $C_{1-6}$ alkyl group (e.g., methyl), and (e) a $C_{6-14}$ aryl group (e.g., phenyl), (iii) a $C_{3-6}$ cycloalkyloxy group (e.g., cyclobutyloxy), and (iv) a di-$C_{1-6}$ alkylamino group (e.g., dimethylamino), or (2) a pyridine ring optionally further substituted by 1-4 (preferably 1-3, more preferably 1 or 2) substituents selected from (i) a $C_{1-6}$ alkoxy group (e.g., methoxy) optionally substituted by a $C_{3-6}$ cycloalkyl group (e.g., cyclopropyl), (ii) an oxo group, and (iii) a $C_{1-6}$ alkyl group (e.g., propyl, butyl).

Ring S is further preferably (1) a benzene ring optionally further substituted by 1-4 (preferably 1-3, more preferably 1 or 2) substituents selected from (i) a $C_{1-6}$ alkoxy group (e.g., methoxy, propoxy, butoxy) optionally substituted by 1-5 (preferably 1-4, more preferably 1-3, further preferably 1 or 2) substituents selected from a halogen atom (e.g., fluorine) and a $C_{3-6}$ cycloalkyl group (e.g., cyclopropyl) optionally substituted by 1-4 (preferably 1-3, more preferably 1 or 2) halogen atoms (e.g., fluorine), and (ii) a $C_{1-6}$ alkyl group (e.g., pentyl), or (2) a pyridine ring optionally further substituted by 1-4 (preferably 1-3, more preferably 1 or 2) substituents selected from a $C_{1-6}$ alkoxy group (e.g., methoxy) optionally substituted by a $C_{3-6}$ cycloalkyl group (e.g., cyclopropyl), an oxo group, and a $C_{1-6}$ alkyl group (e.g., propyl, butyl).

Ring S is further more preferably (1) a benzene ring further substituted by 1 or 2 substituents selected from a $C_{1-6}$ alkoxy group (e.g., methoxy) substituted by 1 or 2 substituents selected from a $C_{3-6}$ cycloalkyl group (e.g., cyclopropyl), or (2) a pyridine ring further substituted by 1-4 (preferably 1-3, more preferably 1 or 2) substituents selected from an oxo group and a $C_{1-6}$ alkyl group (e.g., propyl)

X is —C($R^3$)($R^4$)—, —N($R^5$)— or —O—, wherein $R^3$, $R^4$ and $R^5$ are the same or different and each is a hydrogen atom or a substituent.

As the "substituent" for $R^3$, $R^4$ or $R^5$, the above-mentioned "substituent" can be mentioned, and a $C_{1-6}$ alkyl group (e.g., methyl) is preferable.

X is preferably —C($R^3$)($R^4$)— ($R^3$ and $R^4$ are each a hydrogen atom), —N($R^5$)— ($R^5$ is a hydrogen atom or a $C_{1-6}$ alkyl group (e.g., methyl)) or —O—, more preferably —CH$_2$—, —NH—, —N(CH$_3$)— or —O—, further preferably —O—.

$R^1$ is a $C_{1-6}$ alkyl group optionally substituted by a halogen atom, an optionally substituted $C_{3-6}$ cycloalkyl group, an optionally substituted $C_{1-6}$ alkoxy group, or an amino group optionally mono- or di-substituted by an optionally substituted $C_{1-6}$ alkyl group.

The "$C_{1-6}$ alkyl group" of the "$C_{1-6}$ alkyl group optionally substituted by a halogen atom" for $R^1$ is preferably methyl or ethyl.

The "$C_{3-6}$ cycloalkyl group" of the "optionally substituted $C_{3-6}$ cycloalkyl group" for $R^1$ is preferably cyclopropyl. As the "substituent" of the "optionally substituted $C_{3-6}$ cycloalkyl group" for $R^1$, the above-mentioned "substituent" can be mentioned.

The "$C_{1-6}$ alkoxy group" of the "optionally substituted $C_{1-6}$ alkoxy group" for $R^1$ is preferably methoxy. As the "substituent" of the "optionally substituted $C_{1-6}$ alkoxy group" for $R^1$, the above-mentioned "substituent" can be mentioned.

The "$C_{1-6}$ alkyl group" of the "amino group optionally mono- or di-substituted by an optionally substituted $C_{1-6}$ alkyl group" for $R^1$ is preferably methyl. As the "substituent" of the "optionally substituted $C_{1-6}$ alkyl group", the above-mentioned "substituent" can be mentioned.

$R^1$ is preferably (1) a $C_{1-6}$ alkyl group (e.g., methyl, ethyl) optionally substituted by 1 to 3 halogen atoms (e.g., fluorine), (2) a $C_{1-6}$ alkoxy group (e.g., methoxy), or (3) an amino group optionally mono- or di-substituted by a $C_{1-6}$ alkyl group (e.g., methyl), more preferably, a $C_{1-6}$ alkyl group (e.g., methyl), or an amino group optionally mono- or di-substituted by a $C_{1-6}$ alkyl group (e.g., methyl), particularly preferably a $C_{1-6}$ alkyl group (e.g., methyl) or an amino group.

$R^1$ is particularly preferably an amino group.

$R^2$ is a $C_{1-6}$ alkyl group optionally substituted by a halogen atom or an optionally substituted $C_{3-6}$ cycloalkyl group.

The "$C_{1-6}$ alkyl group" of the "$C_{1-6}$ alkyl group optionally substituted by a halogen atom" for $R^2$ is preferably methyl or ethyl.

The "$C_{3-6}$ cycloalkyl group" of the "optionally substituted $C_{3-6}$ cycloalkyl group" for $R^2$ is preferably cyclopropyl. As the "substituent" of the "optionally substituted $C_{3-6}$ cycloalkyl group" for $R^2$, the above-mentioned "substituent" can be mentioned.

$R^2$ is preferably a $C_{1-6}$ alkyl group (e.g., methyl, ethyl) optionally substituted by a halogen atom, more preferably a $C_{1-6}$ alkyl group (e.g., methyl), and particularly preferably methyl.

m and n are the same or different and each is 1 or 2, and m+n is 2 or 3. The combination of m, n (m, n) is preferably (1, 1), (2, 1) and (1, 2), more preferably (1, 1).

Preferable examples of compound (I) include the following compounds.

[Compound A]

Compound (I) wherein ring P is a cyclobutane ring, a cyclohexane ring, a benzene ring, azetidine ring, a pyrrolidine ring, a piperidine ring, a hexahydrocyclopenta[c]pyrrole ring, a pyrazole ring, a pyridine ring, a pyridazine ring or a pyrazine ring, each of which is optionally further substituted;

ring Q is a benzene ring, a dihydrofuran ring, a furan ring, a thiophene ring, a pyrazole ring, an imidazole ring, an oxazole ring, a thiazole ring or a pyrimidine ring, each of which is optionally further substituted;

ring R is a cyclohexene ring, a benzene ring, a furan ring or a pyridine ring, each of which is optionally further substituted;

ring S is a benzene ring or a pyridine ring, each of which is optionally further substituted;

X is —C($R^3$)($R^4$)— ($R^3$ and $R^4$ are each a hydrogen atom), —N($R^5$)— ($R^5$ is a hydrogen atom or a $C_{1-6}$ alkyl group (e.g., methyl)) or —O—;

$R^1$ is (1) a $C_{1-6}$ alkyl group (e.g., methyl, ethyl) optionally substituted by 1 to 3 halogen atoms (e.g., fluorine), (2) a $C_{1-6}$ alkoxy group (e.g., methoxy), or (3) an amino group optionally mono- or di-substituted by a $C_{1-6}$ alkyl group (e.g., methyl);

$R^2$ is a $C_{1-6}$ alkyl group (e.g., methyl, ethyl) optionally substituted by a halogen atom;

m and n are the same or different and each is 1 or 2, and m+n is 2 or 3.

[Compound B]
Compound (I) wherein
ring P is
(1) a cyclobutane ring,
(2) a cyclohexane ring,
(3) a benzene ring optionally further substituted by 1-4 (preferably 1-3, more preferably 1 or 2) substituents selected from a halogen atom (e.g., fluorine, chlorine, bromine), a cyano group and a $C_{1-6}$ alkyl group (e.g., methyl, ethyl),
(4) an azetidine ring optionally further substituted by 1-4 (preferably 1-3, more preferably 1 or 2) substituents selected from a $C_{1-6}$ alkyl group (e.g., methyl),
(5) a pyrrolidine ring,
(6) a piperidine ring,
(7) a hexahydrocyclopenta[c]pyrrole ring,
(8) a pyrazole ring optionally further substituted by 1-4 (preferably 1-3, more preferably 1 or 2) substituents selected from a $C_{1-6}$ alkyl group (e.g., methyl),
(9) a pyridine ring optionally further substituted by 1-4 (preferably 1-3, more preferably 1 or 2) substituents selected from a $C_{1-6}$ alkyl group (e.g., methyl),
(10) a pyridazine ring, or
(11) a pyrazine ring,
ring Q is
(1) a benzene ring,
(2) a dihydrofuran ring,
(3) a furan ring,
(4) a thiophene ring,
(5) a pyrazole ring,
(6) an imidazole ring optionally further substituted by 1-4 (preferably 1-3, more preferably 1 or 2) substituents selected from a $C_{1-6}$ alkyl group (e.g., methyl, ethyl),
(7) an oxazole ring,
(8) a thiazole ring, or
(9) a pyrimidine ring;
ring R is
(1) a cyclohexene ring,
(2) a benzene ring optionally further substituted by 1-4 (preferably 1-3, more preferably 1 or 2) substituents selected from a halogen atom (e.g., fluorine) and a $C_{1-6}$ alkyl group (e.g., methyl),
(3) a furan ring, or
(4) a pyridine ring;
ring S is
(1) a benzene ring optionally further substituted by 1-4 (preferably 1-3, more preferably 1 or 2) substituents selected from
(i) a $C_{1-6}$ alkyl group (e.g., methyl, propyl, pentyl) optionally further substituted by 1-4 (preferably 1-3, more preferably 1 or 2) substituents selected from a $C_{1-6}$ alkoxy group (e.g., methoxy) and a halogen atom (e.g., fluorine),
(ii) a $C_{1-6}$ alkoxy group (e.g., methoxy, ethoxy, propoxy, butoxy, isobutoxy, neopentoxy) optionally substituted by 1-5 (preferably 1-4, more preferably 1-3, further preferably 1 or 2) substituents selected from
(a) a halogen atom (e.g., fluorine),
(b) a $C_{3-6}$ cycloalkyl group (e.g., cyclopropyl, cyclobutyl) optionally substituted by 1-4 (preferably 1-3, more preferably 1 or 2) substituents selected from a halogen atom (e.g., fluorine) and a $C_{1-6}$ alkyl group (e.g., methyl), (c) a $C_{1-6}$ alkoxy group (e.g., methoxy, ethoxy),
(d) a 4- to 7-membered nonaromatic heterocyclic group (e.g., oxetanyl, tetrahydrofuranyl, morpholinyl) optionally substituted by a $C_{1-6}$ alkyl group (e.g., methyl), and
(e) a $C_{6-14}$ aryl group (e.g., phenyl),
(iii) a $C_{3-6}$ cycloalkyloxy group (e.g., cyclobutyloxy), and
(iv) a di-$C_{1-6}$ alkylamino group (e.g., dimethylamino), or
(2) a pyridine ring optionally further substituted by 1-4 (preferably 1-3, more preferably 1 or 2) substituents selected from
(i) a $C_{1-6}$ alkoxy group (e.g., methoxy) optionally substituted by a $C_{3-6}$ cycloalkyl group (e.g., cyclopropyl),
(ii) an oxo group, and
(iii) a $C_{1-6}$ alkyl group (e.g., propyl, butyl);
X is —CH$_2$—, —NH—, —N(CH$_3$)— or —O—;
$R^1$ is
(1) a $C_{1-6}$ alkyl group (e.g., methyl, ethyl) optionally substituted by 1 to 3 halogen atoms (e.g., fluorine),
(2) a $C_{1-6}$ alkoxy group (e.g., methoxy), or
(3) an amino group optionally mono- or di-substituted by a $C_{1-6}$ alkyl group (e.g., methyl);
$R^2$ is a $C_{1-6}$ alkyl group (e.g., methyl, ethyl);
m and n are the same or different and each is 1 or 2, and m+n is 2 or 3.
[Compound C]
Compound (I) wherein
ring P is
(1) a benzene ring,
(2) an azetidine ring,
(3) a pyridine ring optionally further substituted by 1-4 (preferably 1-3, more preferably 1 or 2) substituents selected from a $C_{1-6}$ alkyl group (e.g., methyl),
(4) a pyridazine ring, or
(5) a pyrazine ring,
ring Q is
(1) a benzene ring,
(2) a dihydrofuran ring,
(3) a furan ring,
(4) a thiophene ring,
(5) a pyrazole ring,
(6) an oxazole ring, or
(7) a thiazole ring;
ring R is
(1) a cyclohexene ring,
(2) a benzene ring optionally further substituted by 1-4 (preferably 1-3, more preferably 1 or 2) substituents selected from a halogen atom (e.g., fluorine) and a $C_{1-6}$ alkyl group (e.g., methyl),
(3) a furan ring, or
(4) a pyridine ring;
ring S is
(1) a benzene ring optionally further substituted by 1-4 (preferably 1-3, more preferably 1 or 2) substituents selected from
(i) a $C_{1-6}$ alkoxy group (e.g., methoxy, propoxy, butoxy) optionally substituted by 1-5 (preferably 1-4, more preferably 1-3, further preferably 1 or 2) substituents selected from a halogen atom (e.g., fluorine) and a $C_{3-6}$ cycloalkyl group (e.g., cyclopropyl) optionally substituted by 1-4 (preferably 1-3, more preferably 1 or 2) halogen atoms (e.g., fluorine), and
(ii) a $C_{1-6}$ alkyl group (e.g., pentyl), or
(2) a pyridine ring optionally further substituted by 1-4 (preferably 1-3, more preferably 1 or 2) substituents selected from
(i) a $C_{1-6}$ alkoxy group (e.g., methoxy) optionally substituted by a $C_{3-6}$ cycloalkyl group (e.g., cyclopropyl),
(ii) an oxo group, and
(iii) a $C_{1-6}$ alkyl group (e.g., propyl, butyl);
X is —O—;
$R^1$ is a $C_{1-6}$ alkyl group (e.g., methyl) or an amino group optionally mono- or di-substituted by a $C_{1-6}$ alkyl group (e.g., methyl);

R² is a C_{1-6} alkyl group (e.g., methyl);
m and n are the same or different and each is 1 or 2, and m+n is 2 or 3.
[Compound D]
Compound (I) wherein
ring P is a pyridine ring;
ring Q is an oxazole ring;
ring R is a benzene ring;
ring S is
(1) a benzene ring further substituted by 1 or 2 substituents selected from a C_{1-6} alkoxy group (e.g., methoxy) substituted by 1 or 2 substituents selected from a C_{3-6} cycloalkyl group (e.g., cyclopropyl), or
(2) a pyridine ring further substituted by 1-4 (preferably 1-3, more preferably 1 or 2) substituents selected from an oxo group and a C_{1-6} alkyl group (e.g., propyl);
X is —O—;
R¹ is a C_{1-6} alkyl group (e.g., methyl) or an amino group;
R² is a C_{1-6} alkyl group (e.g., methyl); and
m and n are each 1.
[Compound D(1)]
Compound D wherein
ring S is
(1) a benzene ring further substituted by 1 or 2 substituents selected from a C_{1-6} alkoxy group (e.g., methoxy) substituted by 1 or 2 substituents selected from a C_{3-6} cycloalkyl group (e.g., cyclopropyl).
[Compound D(2)]
Compound D wherein
ring S is
(2) a pyridine ring further substituted by 1-4 (preferably 1-3, more preferably 1 or 2) substituents selected from an oxo group and a C_{1-6} alkyl group (e.g., propyl).

Specific examples of compound (I) include the compounds of the below-mentioned Examples 1-110, preferably
N-(1-(2-(6-(3-(cyclopropylmethoxy)phenoxy)pyridin-3-yl)-1,3-benzoxazol-6-yl)ethyl)acetamide (Example 37);
1-(1-(2-(6-(3-(cyclopropylmethoxy)phenoxy)pyridin-3-yl)-1,3-benzoxazol-6-yl)ethyl)urea (Example 98); and
N-(1-(2-(6-((6-oxo-1-propyl-1,6-dihydropyridin-3-yl)oxy)pyridin-3-yl)-1,3-benzoxazol-6-yl)ethyl)acetamide (Example 102).

The present invention also relates to a compound represented by the formula:

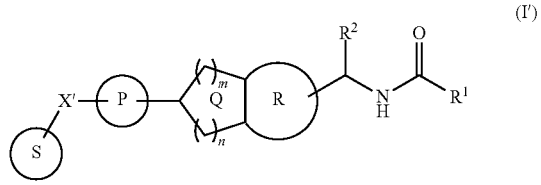

(I')

wherein
X' is —S—; and other symbols are as defined above, or a salt thereof.

A salt of the compound represented by the formula (I) is preferably a pharmacologically acceptable salt. Examples of such salt include salts with inorganic base, salts with organic base, salts with inorganic acid, salts with organic acid, salts with basic or acidic amino acid.

Preferable examples of the salt with inorganic base include alkali metal salts such as sodium salt, potassium salt and the like; alkaline earth metal salts such as calcium salt, magnesium salt and the like; aluminum salt; ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine.

Preferable examples of the salt with inorganic acid include salts with hydrogen chloride, hydrogen bromide, nitric acid, sulfuric acid, phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid.

Preferable examples of the salt with basic amino acid include salts with arginine, lysine, ornithine.

Preferable examples of the salt with acidic amino acid include salts with aspartic acid, glutamic acid.

Compound (I) may be used in the form of a prodrug.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. due to an enzyme; a compound which is converted to compound (I) by hydrolysis etc. due to gastric acid, etc.

Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);
a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);
a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.)
and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

Compound (I) may be labeled with an isotope (e.g., ³H, ¹³C, ¹⁴C, ¹⁸F, ³⁵S, ¹²⁵I) and the like.

Compound (I) labeled with or substituted by an isotope can be used, for example, as a tracer (PET tracer) in Positron Emission Tomography (PET), and useful in the field of medical diagnosis and the like.

Compound (I) may be a hydrate or a non-hydrate, and a non-solvate or a solvate.

Compound (I) also encompasses a deuterium conversion form wherein $^1$H is converted to $^2$H(D).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability). The cocrystal and cocrystal salt can be produced by cocrystallization method known per se.

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition (hereinafter sometimes to be abbreviated as the medicament of the present invention) by admixing with a pharmacologically acceptable carrier and the like.

Examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfites, ascorbates.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

Examples of the medicament of the present invention include tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop, and they are orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be controlled-release preparations such as immediate-release preparations, sustained-release preparations and the like (e.g., sustained-release microcapsule).

The medicament of the present invention can be produced by a method conventionally used in the technical field of pharmaceutical preparation, for example, the method described in the Japanese Pharmacopoeia.

While the content of the compound of the present invention in the medicament of the present invention varies depending on the dosage form, dose of the compound of the present invention, and the like, it is, for example, about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax may be used in combination.

Examples of the water-soluble film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)].

The above-mentioned coating bases may be used after mixing with two or more kinds thereof at appropriate ratios. For coating, for example, a light shielding agent such as titanium oxide, ferric oxide can be used.

The compound of the present invention shows low toxicity (e.g., acute toxicity, chronic toxicity, genetic toxicity, reproductive toxicity, pneumotoxicity, carcinogenicity and the like) and a few side effects. Therefore, it can be used as an agent for the prophylaxis or treatment or a diagnostic of various diseases in a mammal.

The compound of the present invention has an ACC (particularly, ACC1) inhibitory activity, and can be used as a prophylactic or therapeutic agent for cancer, a cancer growth inhibitor, a cancer metastasis inhibitor and the like. In addition, the compound of the present invention can be used as a prophylactic or therapeutic agent for ACC (particularly, ACC1) dependent diseases.

The compound of the present invention (particularly, the aforementioned compound B, compound C, compound D, compound D(1) and compound D(2)) is useful as a selective inhibitor of ACC1.

The compound of the present invention is used as a medicament such as a prophylactic or therapeutic agent for ACC (particularly, ACC1)-associated diseases (e.g., proliferative disease, inflammatory diseases, specifically cancer [for example, colorectal cancer (e.g., familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer), gastric cancer (e.g., papillary adenocarcinoma, mucinous adenocarcinoma, adenosquamous carcinoma), breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), prostate cancer (e.g., hormone-dependent prostate cancer, non-hormone dependent prostate cancer), liver cancer (e.g., primary liver cancer, extrahepatic bile duct cancer), thyroid cancer (e.g., medullary thyroid carcinoma), renal cancer (e.g., renal cell carcinoma, transitional cell carcinoma in kidney and urinary duct), uterine cancer, brain tumor (e.g., pineal astrocytoma, pilocytic astrocytoma, diffuse astrocytoma, anaplastic astrocytoma), melanoma (melanoma), sarcoma, urinary bladder cancer, colorectal cancer, hematologic cancer including multiple myeloma], angiogenesis, diabetic retinopathy, rheumatoid arthritis, psoriasis, atherosclerosis, restenosis, cardiac failure, Kaposi's sarcoma, COPD (chronic obstructive pulmonary diseases), cystic fibrosis, pain, asthma, endometriosis, cystic kidney, inflammation such as nephritis, hepatitis, dermatitis, osteoarthritis and the like, hypertension and the like; a growth inhibitor of cancer; a metastasis inhibitor of cancer; an apoptosis promoter; and the like.

Among these, the compound of the present invention is effective for colorectal cancer, lung cancer, pancreatic cancer, gastric cancer, breast cancer, ovarian cancer, prostate cancer, liver cancer, thyroid cancer, renal cancer, brain tumor, melanoma, urinary bladder cancer, and hematologic cancer. Particularly, the compound of the present invention is effective for melanoma, thyroid cancer, lung cancer, colorectal cancer, ovarian cancer, prostate cancer, renal cancer, and colorectal cancer.

In addition, the compound of the present invention can be used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, hypoHDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia and the like.

Also, the compound of the present invention can also be used as a body weight increase inhibitor or an agent for the prophylaxis or treatment of metabolic syndrome of mammals.

Furthermore, the compound of the present invention can also be used, for example, as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, acute or chronic diarrhea, inflammatory disease (e.g., chronic rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, enteritis, inflammatory bowel disease (including inflammatory colitis), ulcerative colitis, stomach mucosal injury (including stomach mucosal injury caused by aspirin)), small intestine mucosal injury, malabsorption, testis dysfunction, visceral obesity syndrome, sarcopenia, fatty liver diseases (e.g., non-alcoholic fatty liver diseases, simple steatosis), and cirrhosis or liver cancer due to the progression of non-alcoholic steatohepatitis. Particularly, the compound of the present invention is effective for non-alcoholic steatohepatitis.

While the dose of the compound of the present invention varies depending on the subject of administration, administration route, target disease, symptom and the like, for example, for oral administration of the compound of the present invention to an adult cancer patient, it is generally about 0.01 to 100 mg/kg body weight, preferably 0.1 to 30 mg/kg body weight, further preferably 0.5 to 10 mg/kg body weight for one dose, which is desirably administered once to 3 times a day.

With the aim of enhancing the action of the compound of the present invention or decreasing the dose of the compound and the like, the compound can be used in combination with other drug. Specifically, the compound of the present invention can be used in combination with drugs such as hormonal therapeutic agent, chemotherapeutic agent, immunotherapeutic agent or medicament inhibiting actions of cell growth factor and receptor thereof and the like. In the following, a drug that can be used in combination with the compound of the present invention is to be abbreviated as a "concomitant drug".

As the "hormonal therapeutic agent", for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testrolactone, aminoglutethimide, LH-RH agonist (e.g., goserelin acetate, buserelin, leuprorelin acetate), droloxifene, epitiostanol, ethinylestradiol sulfonate, aromatase inhibitor (e.g., fadrozole hydrochloride, anastrozole, retrozole, exemestane, vorozole, formestane), anti-androgen (e.g., flutamide, bicartamide, nilutamide), 5α-reductase inhibitor (e.g., finasteride, episteride), adrenocortical hormone drug (e.g., dexamethasone, predonisolone, betamethasone, triamcinolone), androgen synthesis inhibitor (e.g., abiraterone), retinoid and drugs that retard retinoid metabolism (e.g., liarozole) are used.

As the "chemotherapeutic agent", for example, alkylating agents, metabolic antagonists, antitumor antibiotics, and plant-derived antitumor drugs are used.

As the "alkylating agent", for example, nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof are used.

As the "metabolic antagonist", for example, mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurin, ambamustine, bendamustine, and DDS preparations thereof are used.

As the "antitumor antibiotic", for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS preparations thereof are used.

As the "plant-derived antitumor agent", for example, etoposide, etoposide phosphate, vinblastine sulfate, vincristine sulfate, vindesine sulfate, teniposide, paclitaxel, docetaxel, vinorelbine, and DDS preparations thereof are used.

As the "immunotherapeutic agent", biological response modifiers (e.g., picibanil, krestin, schizophyllan, lentinan, ubenimex, interferon, interleukin, macrophage colony stimulating factor, granulocyte colony stimulating factor, erythropoietin, lymphotoxin, BCG vaccine, *corynebacterium parvum*, levamisole, polysaccharide K, procodazole and anti-CTLA4 antibody) are used.

The "cell growth factors" in the "medicament inhibiting actions of cell growth factor and receptor thereof" may be any substance that promotes cell proliferation, which is normally peptide having not more than 20,000 molecular weight, and capable of exhibiting the activity at low concentrations by binding to a receptor, and specifically
(1) EGF (epidermal growth factor) or substances possessing substantially the same activity as EGF (e.g., TGFα);
(2) insulin or substances possessing substantially the same activity as insulin (e.g., insulin, IGF (insulin-like growth factor)-1, IGF-2),
(3) FGF (fibroblast growth factor) or substances possessing substantially the same activity as FGF (e.g., acidic FGF, basic FGF, KGF (keratinocyte growth factor), FGF-10), and
(4) other cell growth factors (e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin); and the like are used.

The "cell growth factor receptor" may be any receptor capable of binding to the aforementioned cell growth factors, and specifically, EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor, and the like are used.

As the "medicament inhibiting actions of cell growth factor and receptor thereof", for example, EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, and ERK inhibitor are used. As such medicament, more specifically, anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, Imatinib, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1 (R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), 2-[N-[3-[4-[5-[N-(3-fluorophenyl)carbamoylmethyl]-1H-pyrazol-3-ylamino] quinazolin-7-yloxy]propyl]-N-ethylamino]ethyl phosphate (AZD-1152), 4-[9-chloro-7-(2,6-difluorophenyl)-5H-primido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R),3-dihydroxypropoxy]-3,4-difluoro-2-(2-fluoro-4-iodophenylamino)benzamide (PD-0325901) and the like are used.

Besides the above-mentioned medicaments, L-asparaginase, aceglatone, procarbazine hydrochloride, protoporphyrin-cobalt complex salt, mercuric hematoporphyrin-sodium, topoisomerase I inhibitor (e.g., irinotecan, topotecan), topoisomerase II inhibitor (e.g., sobuzoxane), differentiation-inducing factor (e.g., retinoid, vitamin D), other angiogenesis inhibitor (e.g., fumagillin, shark extract, COX-2 inhibitor), α-blocker (e.g., tamsulosin hydrochloride), bisphosphonic acid (e.g., pamidronate, zoledronate), thalidomide, 5-azacytidine, decitabine, bortezomib, antitumor antibody (e.g., anti-CD20 antibody), toxin labeled antibody and the like can also be used.

In addition, the compound of the present invention can also be used in combination with medicaments such as therapeutic or prophylactic agents for NAFLD, therapeutic agents for diabetes, therapeutic agents for diabetic complications, therapeutic agents for hyperlipidemia, antihypertensive agents, antiobesity agents, diuretics, antithrombotic agents, therapeutic agents for liver diseases and the like.

As the therapeutic or prophylactic agents for NAFLD, obeticholic acid, Oltipraz, GFT-505, Cenicriviroc, Aramchol, Tipelukast, GR-MD-02, Px-102, Simtuzumab, GS-4997, ZYH-1, Liraglutide, Remogliflozin, MB12066, Emricasan, Cysteamine, ND-L02-s0201, GWP-42003, RO-5093151, TM-38837, F-652, NDI-010976, Testosterone undecanoate and the like are used.

As the "therapeutic agents for diabetes", insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, the compound described in WO 2007/013694, WO 2007/018314, WO 2008/093639 or WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [e.g., sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin or a salt thereof (preferably, benzoate), trelagliptin or a salt thereof (preferably, succinate), Vildagliptin, Sitagliptin, Saxagliptin, BI356, GRC8200, MP-513, PF-00734200, PHX1149, SK-0403, ALS2-0426, TA-6666, TS-021, KRP-104, 33 agonists (e.g., N-5984), GPR40 agonists (e.g., fasiglifam, the compound described in WO 2004/041266, WO 2004/106276, WO 2005/063729, WO 2005/063725, WO 2005/087710, WO 2005/095338, WO 2007/013689 or WO 2008/001931), GLP-1 receptor agonists (e.g., GLP-1, GLP-1MR preparation, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance improving drugs, somatostatin receptor agonists, glucokinase activators (e.g., Piragliatin, AZD1656, AZD6370, TTP-355, the compound described in WO 2006/112549, WO 2007/028135, WO 2008/047821, WO 2008/050821, WO 2008/136428 or WO2008/156757), GIP (Glucose-dependent insulinotropic peptide), GPR119 agonist (e.g., PSN821, MBX-2982, APD597), FGF21, FGF analogue and the like are used.

As the "therapeutic agents for diabetic complications", aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF, neutrophin production-secretion promoters thereof (e.g., 4-(4-chlorophenyl)-2-(2-methyl-1-imidazolyl)-5-[3-(2-methylphenoxy)propyl]oxazole) described in WO 01/14372, a compound described in WO 2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, Pregabalin), serotonin-noradrenaline re-uptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1(ASK-1) inhibitors and the like are used.

As the "therapeutic agent for hyperlipidemia", HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., a compound described in WO 97/10224, for example, N-[[(3R,5S)-1-(3-acetoxy-2,2-dimethylpropyl)-7-chloro-5-(2,3-dimethoxyphenyl)-2-oxo-1,2, 3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., cohlestyramine), probucol, nicotinic acid drugs (e.g., nicomol, niceritrol, niaspan), ethyl icosapentate, phytosterols (e.g., soysterol, γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like are used.

Examples of the "antihypertensive agent" include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol), clonidine and the like.

Examples of the "antiobesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor modulators, GABA modulators (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylating enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), 33 agonists (e.g., N-5984), diacylglycerol acyltransferase 1 (DGAT1) inhibitors, acetylCoA carboxylase (ACC) inhibitors, stearoyl-CoA desaturase inhibitors, microsomal triglyceride transfer protein inhibitors (e.g., R-256918), Na-glucose cotransporter inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine and pig; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine and pig; human FGF21 preparations genetically synthesized using *Escherichia coli* or yeast; fragments or derivatives of FGF21)), anorexigenic agents (e.g., P-57) and the like.

Examples of the "diuretics" include xanthine derivatives (e.g., theobromine sodium salicylate, theobromine calcium salicylate etc.), thiazide preparations (e.g., ethiazide, cyclopenthiazide, trichloromethiazide, hydrochlorothiazide, hydroflumethiazide, benzylhydrochlorothiazide, penflutizide, poly5thiazide, methyclothiazide etc.), antialdosterone preparations (e.g., spironolactone, triamterene etc.), carbonic anhydrase inhibitors (e.g., acetazolamide etc.), chlorobenzenesulfonamide agents (e.g., chlortalidone, mefruside, indapamide etc.), azosemide, isosorbide, ethacrynic acid, piretanide, bumetanide, furosemide and the like.

Examples of the "antithrombotic agent" include heparins (e.g., heparin sodium, heparin calcium, enoxaparin sodium, dalteparin sodium), warfarins (e.g., warfarin potassium), anti-thrombin drugs (e.g., argatroban, dabigatran), FXa inhibitors (e.g., rivaroxaban, apixaban, edoxaban, YM150, compound described in WO 02/06234, WO 2004/048363, WO 2005/030740, WO 2005/058823 or WO 2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the "therapeutic agents for liver diseases" include viral hepatitis drug (e.g., interferon preparation (e.g., interferon alpha-2a, PEGylated interferon alpha-2a, interferon alfacon-1, natural interferon, interferon beta-1a, omega interferon), Ribavirin, telaprevir, sofosbuvir, ledipasvir, entecavir and the like), antioxidant (vitamin E preparation and the like), liver protecting agent (ursodeoxycholic acid, glycyrrhizin, glucuronic acid and the like), therapeutic drugs for liver cancer (sorafenib and the like), immunosuppressant (steroids such as predonisolone and the like, azathioprine and the like), therapeutic drug for decompensated liver cirrhosis (spironolactone, furosemide, amino acid preparation, vitamin K preparation and the like) and the like.

The administration time of the aforementioned concomitant drug is not limited, and the compound of the present invention and the concomitant drug may be administered to an administration subject simultaneously, or may be administered at different times. The dosage of the concomitant drug may be determined according to the dosage clinically used, and can be appropriately selected depending on the administration subject, administration route, diseases, combination thereof and the like.

The administration mode of the concomitant drug is not particularly limited, and the compound of the present invention and the concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route(s), diseases and the like.

In addition, the compound of the present invention can also be used in combination with a non-medication therapy. Specific examples of the non-medication therapy include (1) operation; (2) hypertensive chemical therapy using angiotensin II and the like; (3) gene therapy; (4) hyperthermic therapy; (5) cryotherapy; (6) laser ablation method; and (7) radiation therapy.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be jo used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature-300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like; metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, t-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as t-butylcarbonate and the like, and the like.

Examples of the protecting group of the carbonyl group of aldehyde include acetal protecting groups such as dimethyl acetal and the like; cyclic acetal protecting groups such as cyclic 1,3-dioxane and the like, and the like.

Examples of the protecting group of the carbonyl group of ketone include ketal protecting groups such as dimethyl ketal and the like; cyclic ketal protecting groups such as cyclic 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic hetero ring such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid, triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include a combination of phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride and a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., basic salts, organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include arylmagnesium halides such as phenylmagnesium bromide and the like; and alkylmagnesium halides such as methylmagnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium borohydride, sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases, basic salts and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a halogenated alkyl form from alcohol by reacting with triphenylphosphine and carbon tetrachloride or carbon tetrabromide, and the like may be used. Alternatively, a method of synthesizing a halogenated alkyl form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of t-butyl ester is performed, formic acid, triethylsilane and the like are sometimes added to reductively trap the by-produced t-butyl cation.

When a dehydrating reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Specific examples of the solvent to be used for the reaction of each step also include the following.

"aromatic amines": pyridine, imidazole, 2,6-lutidine and the like;

"tertiary amines": triethylamine, diisopropylethylamine, N-methylmorpholine, 1,8-diazabicyclo[5.4.0]undec-7-ene (DBU), 1,5-diazabicyclo[4.3.0]non-5-ene (DBN), 1,1,3,3-tetramethylguanidine and the like;

"ethers": 1,4-dioxane and the like;

"amides": N,N-dimethylacetamide and the like.

The aforementioned "organic bases" also includes 1,1,3,3-tetramethylguanidine.

As a reducing agent to be used when a reduction reaction is performed in each step, triphenylphosphine can be mentioned. Boranes recited as an example of the reducing agent also includes a borane pyridine complex.

As a reagent to be used when a Mitsunobu reaction is performed in each step, hexachloroethane can also be mentioned.

When a coupling reaction is performed in each step, an organic base may be added to the reaction.

As the aforementioned sulfonating agent, trifluoromethanesulfonic anhydride and N-phenylbis(trifluoromethanesulfonimide) can also be mentioned.

The production method of compound (I) is explained below.

Each symbol in the following reaction scheme means the same as above, unless otherwise specified. When a specific production method of a starting compound is not described, it is easily commercially available or can be produced by a method known per se or a method analogous thereto.

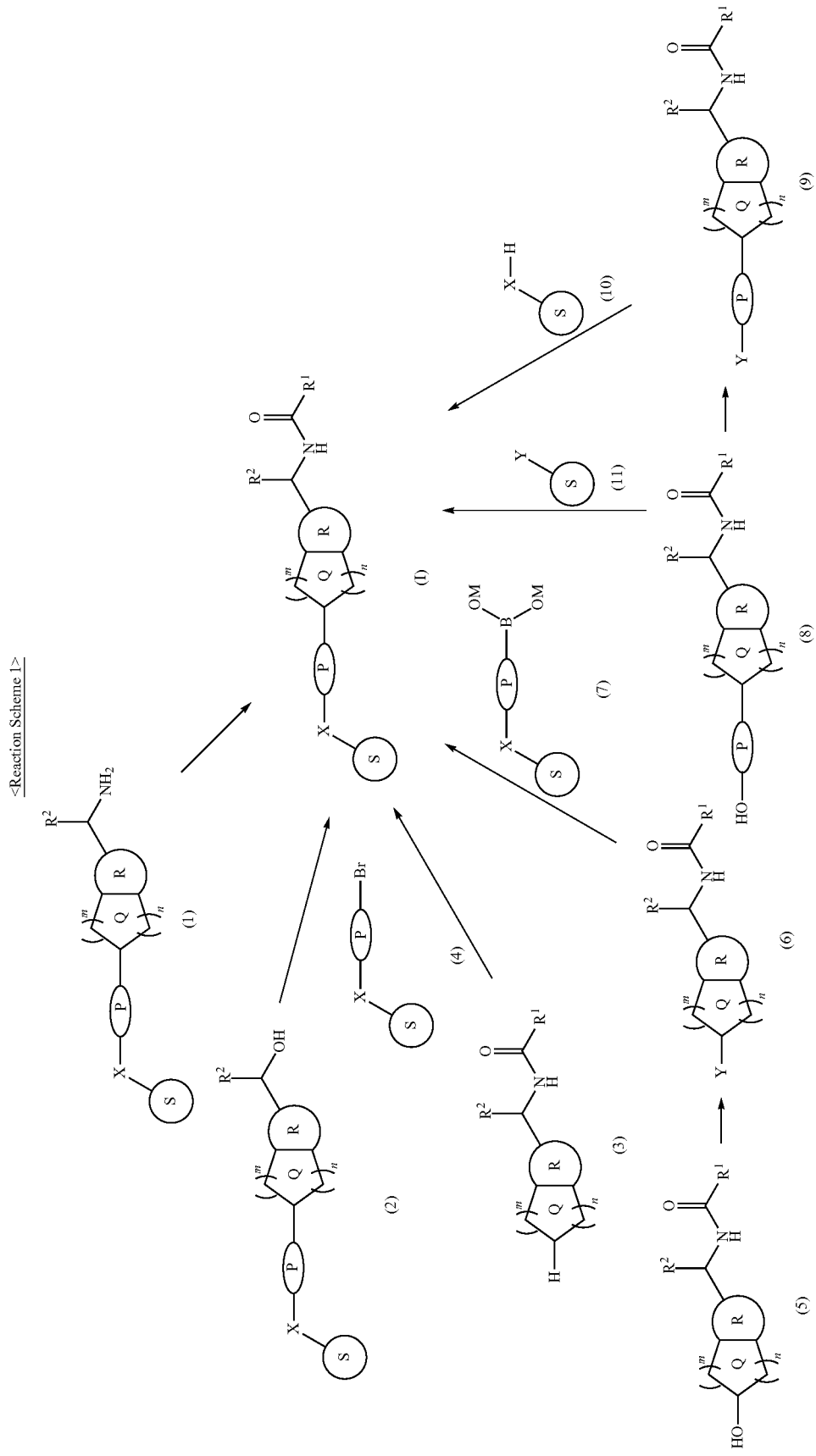

wherein each symbol is as defined above, Y is a halogen atom or a sulfonate group, M is a hydrogen atom or an optionally substituted $C_{1-6}$ alkyl group, which may be bonded to each other to form a ring.

Compound (1) can be produced, for example, according to the method described in the below-mentioned Reaction Scheme 4 or a method known per se or a method analogous thereto.

Compound (I) can be produced by an acylation reaction of compound (1).

The above-mentioned "acylation reaction" includes, for example, a reaction to produce (A) amide derivative, a reaction to produce (B) carbamate derivative or a reaction to produce (C) urea derivative, which is described in detail below.

The above-mentioned "reaction to produce (A) amide derivative" is performed by, for example, "a method using a dehydrating condensing agent" or "a method using a reactive derivative of carboxylic acid" shown below.

i) Method Using Dehydrating Condensing Agent

In this method, compound (1) and carboxylic acid are reacted in the presence of a dehydrating condensing agent in an inert solvent. This method can be performed, for example, in the presence of a catalytic amount to 5 equivalents of 1-hydroxybenzotriazole (HOBt) or a catalytic amount to 5 equivalents of a base.

The amount of the above-mentioned "carboxylic acid" to be used is generally 0.5 to 10 equivalents, preferably 0.8 to 5 equivalents, relative to compound (1).

Examples of the above-mentioned "dehydrating condensing agent" include dicyclohexylcarbodiimide (DCC), 1-ethyl-3-(3-dimethylaminopropyl)carbodiimide hydrochloride (WSCD), and O-(7-azabenzotriazol-1-yl)-N,N,N', N'-tetramethyluronium hexafluorophosphate (HATU). Of these, WSCD or HATU is preferable. The amount of the "dehydrating condensing agent" to be used is generally 0.5 to 10 equivalents, preferably 0.8 to 5 equivalents, relative to compound (1).

Examples of the above-mentioned "inert solvent" include "nitriles", "amides", "halogenated hydrocarbons" and "ethers", and two or more kinds of these may be used in a mixture at an appropriate ratio. As the above-mentioned "inert solvent", "amides" are preferable.

Examples of the above-mentioned "base" include "aromatic amines" and "tertiary amines".

The reaction temperature is generally −70° C. to 150° C., preferably −20° C. to 100° C.

The reaction time is generally 0.1 hr to 100 hr, preferably 1 hr to 48 hr.

ii) Method Using Reactive Derivative of Carboxylic Acid

In this method, compound (1) and 0.5 to 10 equivalents, preferably 0.8 to 5 equivalents, of the reactive derivative of carboxylic acid are reacted in an inert solvent. This method can also be performed in the presence of 0.5 to 10 equivalents, preferably 0.8 to 5 equivalents, of a base.

Examples of the above-mentioned "reactive derivative of carboxylic acid" include acid anhydride, acid halide (e.g., acid chloride, acid bromide), mixed acid anhydride (e.g., acid anhydride with $C_{1-6}$ alkyl-carboxylic acid, $C_{6-10}$ aryl-carboxylic acid, $C_{1-6}$ alkylcarbonic acid), active ester (e.g., ester with phenol optionally having substituent(s), HOBt, N-hydroxysuccinimide), and active amide (e.g., amide at imidazole or triazole).

Examples of the above-mentioned "phenol optionally having substituent(s)" include phenol, pentachlorophenol, pentafluorophenol, and p-nitrophenol.

The above-mentioned "reactive derivative of carboxylic acid" is preferably acid anhydride.

Examples of the above-mentioned "inert solvent" include "ethers", "halogenated hydrocarbons", "aromatic hydrocarbons", "saturated saturated hydrocarbons", "nitriles", "amides", and "sulfoxides". Two or more kinds of these inert solvents may be used in a mixture at an appropriate ratio. As the above-mentioned "inert solvent", pyridine, acetonitrile, THF, dichloromethane or chloroform is preferable.

Examples of the above-mentioned "base" include "aromatic amines" and "tertiary amines".

The reaction temperature is generally −20° C. to 200° C., preferably −20° C. to 100° C.

The reaction time is generally 5 min to 40 hr, preferably 30 min to 18 hr.

The aforementioned "method of producing (B) carbamate derivative" is performed by reacting compound (1) and 0.5 to 10 equivalents, preferably 0.8 to 5 equivalents, of dicarbonate or chloroformic acid ester in an inert solvent. This reaction can be performed in the presence of a catalytic amount to 5 equivalents of a base.

Examples of the above-mentioned "inert solvent" include "ethers", "halogenated hydrocarbons", "aromatic hydrocarbons", "saturated hydrocarbons", "nitriles", and "amides". Two or more kinds of these "inert solvents" may be used in a mixture at an appropriate ratio. As the above-mentioned "inert solvent", pyridine, acetonitrile, THF, DMF, dichloromethane, chloroform is preferable.

Examples of the above-mentioned "base" include "aromatic amines" and "tertiary amines".

The reaction temperature is generally −20° C. to 200° C., preferably −20° C. to 100° C.

The reaction time is generally 5 min to 40 hr, preferably min to 18 hr.

The aforementioned "method of producing (C) urea derivative" is performed by reacting compound (1) and 0.5 to 10 equivalents, preferably 0.8 to 5 equivalents, of isocyanic acid ester or a carbamoyl chloride derivative in an inert solvent. This reaction can be performed in the presence of a catalytic amount to 5 equivalents of a base. This method is also performed by reacting the carbamate derivative produced by the above-mentioned "method of producing (B) carbamate derivative" with an amine derivative in an inert solvent.

Examples of the above-mentioned "inert solvent" include "ethers", "halogenated hydrocarbons", "aromatic hydrocarbons", "saturated hydrocarbons", "nitriles", and "amides". Two or more kinds of these "inert solvents" may be used in a mixture at an appropriate ratio. As the above-mentioned "inert solvent", pyridine, acetonitrile, THF, DMF, dichloromethane or chloroform is preferable.

Examples of the above-mentioned "base" include "aromatic amines" and "tertiary amines".

The reaction temperature is generally −20° C. to 200° C., preferably −20° C. to 100° C.

The reaction time is generally 5 min to 40 hr, preferably 30 min to 18 hr.

As shown in Reaction Scheme 1, compound (I) can also be produced by Ritter reaction of compound (2).

Compound (2) can be produced, for example, according to the method described in the below-mentioned Reaction Scheme 4 or a method known per se or a method analogous thereto.

This reaction is performed, for example, by reacting compound (2) and an acid and a nitrile compound in an inert solvent. Where necessary, the nitrile compound may be used as a solvent.

Examples of the above-mentioned "acid" include "inorganic acids" and "Lewis acid". The amount of the "acid" to be used is generally 0.01 to 20 equivalents, preferably 0.1 to 10 equivalents, relative to compound (2).

Examples of the above-mentioned "nitrile compound" include acetonitrile and propionitrile. The amount of the "nitrile compound" to be used is generally 0.1 equivalent to a solvent amount, preferably 1 equivalent to a solvent amount, relative to compound (2).

Examples of the above-mentioned "inert solvent" include "nitriles", "aromatic hydrocarbons", "saturated hydrocarbons", "ethers", "amides", "halogenated hydrocarbons", "sulfoxides", and "esters". Two or more kinds of these "inert solvents" may be used in a mixture at an appropriate ratio.

The reaction temperature is generally −78° C. to 150° C., preferably −20° C. to 100° C.

The reaction time is generally 0.1 hr to 100 hr, preferably 0.5 hr to 48 hr.

As shown in Reaction Scheme 1, compound (I) can also be produced by a coupling reaction of compound (3) and compound (4).

Compound (3) can be produced, for example, according to the method described in the below-mentioned Reaction Scheme 14 or a method known per se or a method analogous thereto.

The above-mentioned "coupling reaction" is performed by reacting compound (3) and compound (4) in the presence of a metal catalyst, in an inert solvent. This reaction is preferably performed under an inert gas atmosphere. This reaction may be performed in the presence of a ligand and a base, or may be performed under microwave irradiation.

Examples of the above-mentioned "metal catalyst" include bis(triphenylphosphine)dichloropalladium(II), bis(di-tert-butyl(4-dimethylaminophenyl)phosphine)dichloropalladium(II), palladium(II) acetate, tetrakis(triphenylphosphine)palladium(0), tris(dibenzylideneacetone)dipalladium(0), and [1,1-bis(diphenylphosphino)ferrocene]dichloropalladium(II) dichloromethane adduct. The amount of the "metal catalyst" to be used is generally 0.001 to 10 equivalents, preferably 0.01 to 2 equivalents, relative to compound (3).

Examples of the above-mentioned "ligand" include tri(tert-butylphosphonium)tetrafluoroborate, dicyclohexyl(2',6'-dimethoxybiphenyl-2-yl)phosphine, tricyclohexylphosphine, and triphenylphosphine. The amount of the "ligand" to be used is generally 0.001 to 50 equivalents, preferably 0.01 to 10 equivalents, relative to compound (3).

Examples of the above-mentioned "base" include "basic salts". As the above-mentioned "base", potassium tert-butoxide or lithium tert-butoxide is preferable. The amount of the "base" to be used is generally 1 to 50 equivalents, preferably 1 to 20 equivalents, relative to compound (3).

Examples of the above-mentioned "inert solvent" include "nitriles", "amides", "halogenated hydrocarbons", "ethers", "aromatic hydrocarbons", "sulfoxides" and "esters". Two or more kinds of these "inert solvents" may be used in a mixture at an appropriate ratio. As the above-mentioned "inert solvent", DMF, DMSO, N,N-dimethylacetamide, 1,2-dimethoxyethane and toluene are preferable.

Examples of the above-mentioned "inert gas" include argon gas and nitrogen gas.

The reaction temperature is generally −78° C. to 200° C., preferably 0° C. to 150° C.

The reaction time is generally 0.1 hr to 100 hr, preferably 0.5 hr to 48 hr.

As shown in Reaction Scheme 1, compound (I) can also be produced by a coupling reaction of compound (6) and compound (7).

The above-mentioned "coupling reaction" can be performed by reacting compound (6) and compound (7) in an inert solvent in the presence of a metal catalyst. This reaction is preferably performed under an inert gas atmosphere. This reaction may be performed in the presence of a ligand, a base and an additive, and may be further performed under microwave irradiation. The amount of compound (7) to be used is generally 0.5 to 10 equivalents, preferably 0.8 to 5 equivalents, relative to compound (6).

Examples of the above-mentioned "metal catalyst" include bis(triphenylphosphine)dichloropalladium(II), bis(di-tert-butyl(4-dimethylaminophenyl)phosphine)dichloropalladium(II), palladium(II) acetate, tetrakis(triphenylphosphine)palladium(0), tris(dibenzylideneacetone)dipalladium(0), and [1,1-bis(diphenylphosphino)ferrocene]dichloropalladium(II) dichloromethane adduct. The amount of the "metal catalyst" to be used is 0.001 to 10 equivalents, preferably 0.01 to 2 equivalents, relative to compound (6).

Examples of the above-mentioned "ligand" include tri(tert-butylphosphonium)tetrafluoroborate, dicyclohexyl(2',6'-dimethoxybiphenyl-2-yl)phosphine, tricyclohexylphosphine, and triphenylphosphine. The amount of the "ligand" to be used is generally 0.001 to 20 equivalents, preferably 0.01 to 10 equivalents, relative to compound (6).

Examples of the above-mentioned "base" include "basic salts", of which potassium tert-butoxide, lithium tert-butoxide, cesium carbonate, potassium carbonate, and sodium carbonate are preferable. The amount of the "base" to be used is generally 0.5 to 20 equivalents, preferably 0.8 to 10 equivalents, relative to compound (6).

Examples of the above-mentioned "inert solvent" include water, "nitriles", "amides", "halogenated hydrocarbons", "ethers", "aromatic hydrocarbons", "sulfoxides" and "esters". Two or more kinds of these "inert solvents" may be used in a mixture at an appropriate ratio. As the above-mentioned "inert solvent", water, DMF, DMSO, N,N-dimethylacetamide, 1,2-dimethoxyethane and toluene are preferable.

Examples of the above-mentioned "inert gas" include argon gas and nitrogen gas.

The reaction temperature is generally −78° C. to 200° C., preferably 0° C. to 150° C.

The reaction time is generally 0.1 hr to 100 hr, preferably 0.5 hr to 48 hr.

Compound (6) wherein Y is a sulfonate group can be produced by subjecting the compound (5) to, for example, a trifluoromethanesulfonylation reaction.

This reaction can be performed by reacting compound (5) and a trifluoromethanesulfonylating agent in an inert solvent in the presence of a base.

Examples of the above-mentioned "trifluoromethanesulfonylating agent" include trifluoromethanesulfonic anhydride, and N-phenylbis(trifluoromethanesulfonimide). The amount of the "trifluoromethanesulfonylating agent" to be used is generally 0.5 to 20 equivalents, preferably 0.8 to 10 equivalents, relative to compound (5).

Examples of the above-mentioned "base" include "basic salts", "tertiary amines", and "aromatic amines", of which tripotassium phosphate, cesium carbonate, cesium fluoride, sodium carbonate, triethylamine, N,N-diisopropylethylamine, and pyridine are preferable. The amount of the "base" to be used is generally 0.5 to 20 equivalents, preferably 0.8 to 10 equivalents, relative to compound (5).

Examples of the above-mentioned "inert solvent" include "nitriles", "aromatic hydrocarbons", "saturated hydrocarbons", "ethers", "esters", and "amides". Two or more kinds of these "inert solvents" may be used in a mixture at an appropriate ratio. As the above-mentioned "inert solvent", DMF, THF, toluene, and pyridine are preferable.

The reaction temperature is generally −70° C. to 150° C., preferably −20° C. to 100° C.

The reaction time is generally 0.1 hr to 100 hr, preferably 0.1 hr to 48 hr.

As shown in Reaction Scheme 1, compound (I) can also be produced by a "coupling reaction using a metal catalyst" or "substitution reaction" of compound (9) and compound (10).

The above-mentioned "coupling reaction using a metal catalyst" can be performed by reacting compound (9) and compound (10) in an inert solvent in the presence of a metal catalyst. This reaction is preferably performed under an inert gas atmosphere. This reaction may be performed in the presence of a ligand, a base and an additive, or may be performed under microwave irradiation. The amount of compound (10) to be used is generally 0.8 to 10 equivalents, preferably 1 to 5 equivalents, relative to compound (9).

Examples of the above-mentioned "metal catalyst" include bis(triphenylphosphine)dichloropalladium(II), bis(di-tert-butyl(4-dimethylaminophenyl)phosphine)dichloropalladium(II), palladium(II) acetate, tetrakis(triphenylphosphine)palladium(0), tris(dibenzylideneacetone)dipalladium(0), and [1,1-bis(diphenylphosphino)ferrocene]dichloropalladium(II) dichloromethane adduct. The amount of the "metal catalyst" to be used is generally 0.001 to 20 equivalents, preferably 0.01 to 10 equivalents, relative to compound (9).

Examples of the above-mentioned "ligand" include tri(tert-butylphosphonium)tetrafluoroborate, dicyclohexyl(2′,6′-dimethoxybiphenyl-2-yl)phosphine, tricyclohexylphosphine, and triphenylphosphine. The amount of the "ligand" to be used is generally 0.001 to 50 equivalents, preferably 0.01 to 20 equivalents, relative to compound (9).

Examples of the above-mentioned "base" include "basic salts", of which potassium tert-butoxide, lithium tert-butoxide, cesium carbonate, potassium carbonate, and sodium carbonate are preferable. The amount of the "base" to be used is generally 0.5 to 50 equivalents, preferably 0.8 to 20 equivalents, relative to compound (9).

Examples of the above-mentioned "inert solvent" include water, "nitriles", "amides", "halogenated hydrocarbons", "ethers", "aromatic hydrocarbons", "sulfoxides" and "esters". Two or more kinds of these "inert solvents" may be used in a mixture at an appropriate ratio. As the above-mentioned "inert solvent", water, DMF, DMSO, N,N-dimethylacetamide, 1,2-dimethoxyethane and toluene are preferable.

Examples of the above-mentioned "inert gas" include argon gas and nitrogen gas.

The reaction temperature is generally −78° C. to 200° C., preferably 0° C. to 150° C.

The reaction time is generally 0.1 hr to 100 hr, preferably 0.5 hr to 48 hr.

The above-mentioned "substitution reaction" can be performed by reacting compound (9) and compound (10) in an inert solvent in the presence of a base. This reaction can also be performed under microwave irradiation as necessary.

Examples of the above-mentioned "base" include "basic salts" and "tertiary amines". As the above-mentioned "base", cesium carbonate, potassium carbonate, potassium tert-butoxide, triethylamine, and N,N-diisopropylethylamine are preferable. The amount of the "base" to be used is generally 0.5 to 50 equivalents, preferably 0.8 to 20 equivalents, relative to compound (9).

Examples of the above-mentioned "inert solvent" include "nitriles", "amides", "halogenated hydrocarbons", "ethers", "aromatic hydrocarbons", "sulfoxides" and "esters". Two or more kinds of these "inert solvents" may be used in a mixture at an appropriate ratio. As the above-mentioned "inert solvent", DMF, DMSO, N,N-dimethylacetamide, 1,2-dimethoxyethane and toluene are preferable.

The reaction temperature is generally −78° C. to 300° C., preferably 0° C. to 200° C.

The reaction time is generally 0.1 hr to 100 hr, preferably 0.5 hr to 48 hr.

Compound (9) in Reaction Scheme 1 can be produced, for example, according to the methods described in the below-mentioned Reaction Scheme 26 or a method known per se or a method analogous thereto.

Compound (9) can also be produced by a sulfonylation reaction of compound (8).

Compound (8) can be produced, for example, according to the methods described in the below-mentioned Reaction Scheme 20 and Reaction Scheme 22 or a method known per se or a method analogous thereto.

The above-mentioned sulfonylation reaction is performed, for example, by reacting compound (8) and a sulfonylating agent in the presence of a base in an inert solvent.

Examples of the above-mentioned "sulfonylating agent" include methanesulfonyl chloride, p-toluenesulfonyl chloride, trifluoromethanesulfonic anhydride, and N-phenylbis(trifluoromethanesulfonimide). The amount of the "sulfonylating agent" to be used is generally 0.5 to 10 equivalents, preferably 0.8 to 5 equivalents, relative to compound (8).

Examples of the above-mentioned "base" include "basic salts", "aromatic amines", and "tertiary amines". As the above-mentioned "base", tripotassium phosphate, cesium carbonate, cesium fluoride, sodium carbonate, pyridine, triethylamine, and N,N-diisopropylethylamine are preferable. The amount of the "base" to be used is generally 0.5 to 20 equivalents, preferably 0.8 to 10 equivalents, relative to compound (8).

Examples of the above-mentioned "inert solvent" include "aromatic hydrocarbons", "saturated hydrocarbons", "ethers", "esters" and "amides". Two or more kinds of these "inert solvents" may be used in a mixture at an appropriate ratio. As the above-mentioned "inert solvent", DMF, THF, toluene and pyridine are preferable.

The reaction temperature is generally −70° C. to 150° C., preferably −20° C. to 100° C.

The reaction time is generally 0.1 hr to 100 hr, preferably 0.1 hr to 48 hr.

As shown in Reaction Scheme 1, compound (I) can also be produced by, for example, a substitution reaction of compound (8) and compound (11).

This reaction is performed in the same manner as in the method of producing compound (I) from compound (9) and compound (10) of the formula 1.

<Reaction Scheme 2>

The production method of compound (I-1) encompassed in compound (I) is explained below.
wherein each symbol is as defined above.

Compound (12) can be produced, for example, according to the method described in Reaction Scheme 23 or a method known per se or a method analogous thereto.

Compound (14) can be produced, for example, by an amidation reaction of compound (12) and compound (13).

The above-mentioned "amidation reaction" includes the following "method using dehydrating condensing agent" and "method using reactive derivative of carboxylic acid".

i) Method Using Dehydrating Condensing Agent

The above-mentioned "amidation reaction" is performed, for example, by reacting compound (12) and compound (13) in the presence of a dehydrating condensing agent in an inert solvent. The above-mentioned "amidation reaction" can be performed in the presence of, where necessary, a catalytic amount to 5 equivalents of 1-hydroxybenzotriazole (HOBt), a catalytic amount to 5 equivalents of a base and the like. The amount of the above-mentioned compound (13) to be used is generally 0.5 to 10 equivalents, preferably 0.8 to 5 equivalents, relative to compound (12).

Examples of the above-mentioned "dehydrating condensing agent" include dicyclohexylcarbodiimide (DCC), 1-ethyl-3-(3-dimethylaminopropyl)carbodiimide hydrochloride (WSCD), and O-(7-azabenzotriazol-1-yl)-N,N,N',N'-tetramethyluronium hexafluorophosphate (HATU). As the above-mentioned "dehydrating condensing agent", WSCD or HATU is preferable. The amount of the "dehydrating condensing agent" to be used is generally 0.5 to 20 equivalents, preferably 0.8 to 10 equivalents, relative to compound (12).

Examples of the above-mentioned "inert solvent" include "nitriles", "amides", "halogenated hydrocarbons" and "ethers". Two or more kinds of these "inert solvents" may be used in a mixture at an appropriate ratio. As the above-mentioned "inert solvent", DMF, THF or acetonitrile is preferable.

Examples of the above-mentioned "base" include "aromatic amines" and "tertiary amines". The amount of the "base" to be used is generally 0.5 to 20 equivalents, preferably 0.8 to 10 equivalents, relative to compound (12).

The reaction temperature is generally −70° C. to 150° C., preferably −20° C. to 100° C.

The reaction time is generally 0.1 hr to 100 hr, preferably 1 hr to 48 hr.

ii) Method Using Reactive Derivative of Carboxylic Acid

The above-mentioned "amidation reaction" can be performed, for example, by reacting a reactive derivative of compound (13) and compound (12) in an inert solvent. The above-mentioned "amidation reaction" can also be performed in the presence of 1 equivalent to a solvent amount, preferably 1 to 3 equivalents, of a base.

Examples of the above-mentioned "reactive derivative of compound (13)" include acid halide (e.g., acid chloride, acid bromide), mixed acid anhydride (e.g., acid anhydrides with $C_{1-6}$ alkyl-carboxylic acid, $C_{6-10}$ aryl-carboxylic acid, $C_{1-6}$ alkylcarbonic acid and the like), and active ester (e.g., esters with phenol optionally having substituent(s), HOBt, N-hydroxysuccinimide and the like).

Examples of the above-mentioned "phenol optionally having substituent(s)" include phenol, pentachlorophenol, pentafluorophenol, and p-nitrophenol.

The "reactive derivative of compound (13)" is preferably acid halide.

The amount of the "reactive derivative of compound (13)" to be used is generally 0.5 to 20 equivalents, preferably 0.8 to 10 equivalents, relative to compound (12).

Examples of the above-mentioned "inert solvent" include "ethers", "halogenated hydrocarbons", "aromatic hydrocarbons", "nitriles", "amides", "ketone solvents", "sulfoxides", and water. Two or more kinds of these "inert solvents" may be used in a mixture at an appropriate ratio. As the above-mentioned "inert solvent", acetonitrile, THF, toluene, dichloromethane, and chloroform are preferable.

Examples of the above-mentioned "base" include "aromatic amines" and "tertiary amines". The amount of the "base" to be used is generally 0.5 to 20 equivalents, preferably 0.8 to 10 equivalents, relative to compound (12).

The reaction temperature is generally −20 to 150° C., preferably −20° C. to 100° C.

The reaction time is generally 0.1 hr to 40 hr, preferably 0.5 hr to 24 hr.

Compound (I-1) can be produced, for example, by a ring closure reaction of compound (14).

Examples of the above-mentioned "ring closure reaction" include a method by "Mitsunobu reaction" and "a method using an acid".

The above-mentioned method by "Mitsunobu reaction" is performed by reacting compound (14) in the presence of an activator in an inert solvent. This reaction can also be performed in the presence of a base or an additive.

Examples of the above-mentioned "activator" include p-toluenesulfonic acid, diisopropyl azodicarboxylate and triphenylphosphine, hexachloroethane and triphenylphosphine. The amount of the "activator" to be used is generally 0.01 to 10 equivalents, preferably 0.1 to 8 equivalents, relative to compound (14).

Examples of the above-mentioned "inert solvent" include "aromatic hydrocarbons", "saturated hydrocarbons", "ethers", "esters", "amides", "nitriles", and "halogenated hydrocarbons". Two or more kinds of these "inert solvents" may be used in a mixture at an appropriate ratio.

Examples of the above-mentioned "base" include "aromatic amines" and "tertiary amines". The amount of the "base" to be used is generally 0.5 to 20 equivalents, preferably 0.8 to 10 equivalents, relative to compound (14).

"ethers", "halogenated hydrocarbons", and "organic acids". Two or more kinds of these "inert solvents" may be used in a mixture at an appropriate ratio. As the above-mentioned "inert solvent", acetic acid is preferable.

The reaction temperature is generally −70° C. to 300° C., preferably −20° C. to 200° C.

The reaction time is generally 0.1 hr to 100 hr, preferably 0.1 hr to 40 hr.

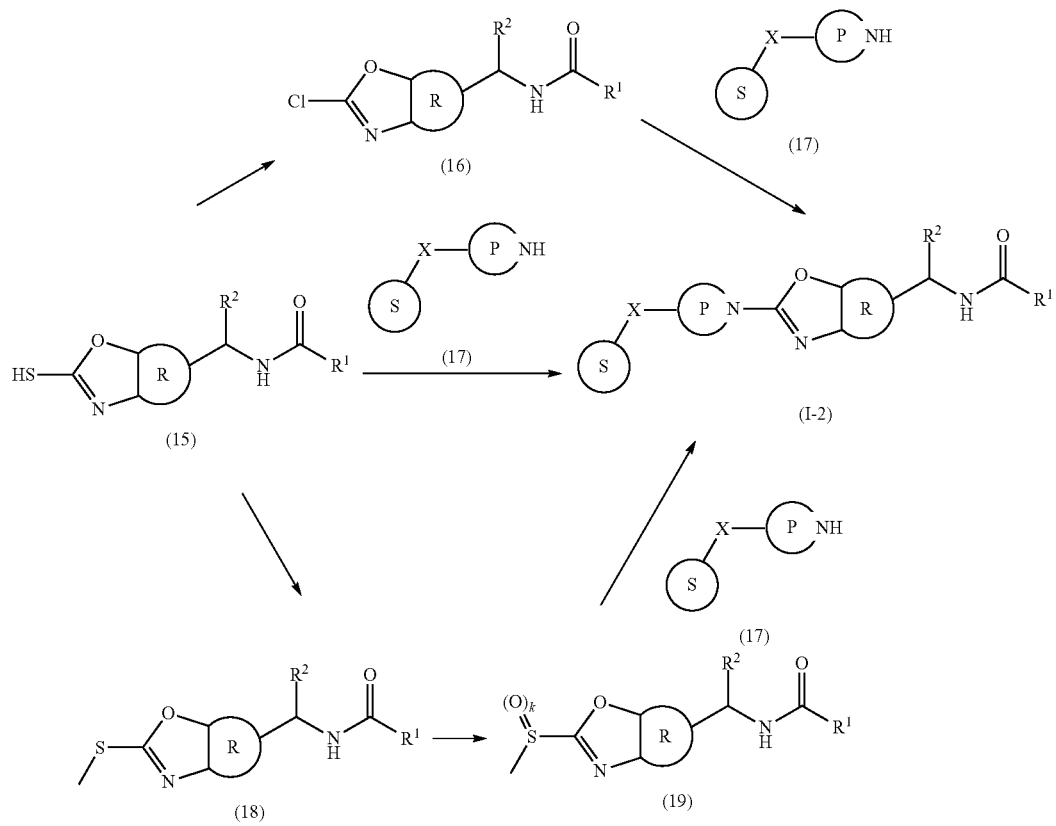

<Reaction Scheme 3>

Examples of the above-mentioned "additive" include phosphorus pentaoxide. The amount of the "additive" to be used is generally 0.5 to 10 equivalents, preferably 0.8 to 5 equivalents, relative to compound (14).

The reaction temperature is generally −70° C. to 200° C., preferably −20° C. to 150° C.

The reaction time is generally 0.1 hr to 100 hr, preferably 0.1 hr to 40 hr.

The aforementioned "method using acid" is performed by reacting compound (14) in the presence of an acid in an inert solvent. This method can also be performed under microwave irradiation.

Examples of the above-mentioned "acid" include "inorganic acid" and "organic acid". Of these, trifluoroacetic acid is preferable. The amount of the "acid" to be used is generally 0.5 equivalents to a solvent amount, preferably 0.8 equivalents to a solvent amount, relative to compound (14).

Examples of the above-mentioned "inert solvent" include "aromatic hydrocarbons", "saturated hydrocarbons", The production method of compound (I-2) encompassed in compound (I) is explained below.
wherein k is 1 or 2, and other symbols are each as defined above.

The above-mentioned compound (15) can be produced, for example, according to the method described in Reaction Scheme 23 or a method known per se or a method analogous thereto.

Compound (16) can be produced, for example, by a chlorination reaction of compound (15).

This reaction is performed, for example, by reacting compound (15) in the presence of a chlorinating agent in an inert solvent.

Examples of the above-mentioned "chlorinating agent" include thionyl chloride, oxalyl chloride, phosphorus oxychloride, and phosphorus pentachloride. The amount of the "chlorinating agent" to be used is generally 0.1 equivalent to a solvent amount, preferably 0.8 equivalent to a solvent amount, relative to compound (15).

Examples of the above-mentioned "inert solvent" include "aromatic hydrocarbons", "saturated hydrocarbons", "ethers", "esters", "amides", "nitriles", and "halogenated hydrocarbons". Two or more kinds of these "inert solvents" may be used in a mixture at an appropriate ratio.

The reaction temperature is generally −70° C. to 200° C., preferably −20° C. to 150° C.

The reaction time is generally 0.1 hr to 100 hr, preferably 0.1 hr to 40 hr.

Compound (1-2) can be produced, for example, by subjecting compound (16) and compound (17) to a substitution reaction.

This reaction is performed, for example, by reacting compound (16) and compound (17) in the presence of a base in an inert solvent. This reaction can also be performed under microwave irradiation. The amount of compound (17) to be used is generally 0.5 to 10 equivalents, preferably 0.8 to 5 equivalents, relative to compound (16).

Examples of the above-mentioned "base" include "inorganic bases", "basic salts", "aromatic amines", and "tertiary amines". The amount of the "base" to be used is generally 0.5 to 20 equivalents, preferably 0.8 to 10 equivalents, relative to compound (16).

Examples of the above-mentioned "inert solvent" include "alcohols", "nitriles", "amides", "halogenated hydrocarbons", "ethers", and "aromatic hydrocarbons". Two or more kinds of these "inert solvents" may be used in a mixture at an appropriate ratio. As the above-mentioned "inert solvent", methanol, ethanol, n-butanol, THF, DMF, or toluene is preferable.

The reaction temperature is generally −100° C. to 300° C., preferably 0° C. to 250° C.

The reaction time is generally 0.1 hr to 60 hr, preferably 0.5 hr to 24 hr.

As shown in Reaction Scheme 3, compound (1-2) can also be produced, for example, by a coupling reaction of compound (15) and compound (17).

This reaction is performed, for example, by reacting compound (15) and compound (17) in the presence of an activator and a base in an inert solvent. This reaction can also be performed under microwave irradiation.

Examples of the above-mentioned "activator" include (chloromethylene)dimethyliminium chloride, DMF and phosphorus oxychloride, DMF and thionyl chloride. The amount of the "activator" to be used is generally 0.5 to 20 equivalents, preferably 0.8 to 10 equivalents, relative to compound (15).

Examples of the above-mentioned "base" include "inorganic bases", "basic salts", "aromatic amines", and "tertiary amines". The amount of the "base" to be used is generally 0.5 to 20 equivalents, preferably 0.8 to 10 equivalents, relative to compound (15).

Examples of the above-mentioned "inert solvent" include "aromatic hydrocarbons", "saturated hydrocarbons", "ethers", "esters", "amides", "nitriles", and "halogenated hydrocarbons". Two or more kinds of these "inert solvents" may be used in a mixture at an appropriate ratio.

The reaction temperature is generally −70° C. to 300° C., preferably −20° C. to 200° C.

The reaction time is generally 0.1 hr to 100 hr, preferably 0.1 hr to 40 hr.

Compound (18) can be produced, for example, by a methylation reaction of compound (15).

This reaction is performed, for example, by reacting compound (15) in the presence of a methylating agent and a base in an inert solvent.

Examples of the above-mentioned "methylating agent" include iodomethane, dimethylsulfuric acid, and dimethyl carbonate. The amount of the "methylating agent" to be used is generally 0.5 to 20 equivalents, preferably 0.8 to 10 equivalents, relative to compound (15).

Examples of the above-mentioned "base" include "inorganic bases", "basic salts", "aromatic amines", and "tertiary amines". The amount of the "base" to be used is generally 0.5 to 20 equivalents, preferably 0.8 to 10 equivalents, relative to compound (15).

Examples of the above-mentioned "inert solvent" include "aromatic hydrocarbons", "saturated hydrocarbons", "ethers", "esters", "amides", "nitriles", and "halogenated hydrocarbons". Two or more kinds of these "inert solvents" may be used in a mixture at an appropriate ratio. As the above-mentioned "inert solvent", DMF, N,N-dimethylacetamide, or acetonitrile is preferable.

The reaction temperature is generally −70° C. to 200° C., preferably −20° C. to 100° C.

The reaction time is generally 0.1 hr to 100 hr, preferably 0.1 hr to 40 hr.

Compound (19) can be produced, for example, by an oxidation reaction of compound (18).

This reaction of compound (18) is performed, for example, in the presence of an oxidant in an inert solvent. This reaction can also be performed in the presence of a base.

Examples of the above-mentioned "oxidant" include oxygen, hydrogen peroxide, organic peroxide (e.g., m-chloroperbenzoic acid), and inorganic peroxide (e.g., sodium perborate). The amount of the "oxidant" to be used is generally 0.5 to 20 equivalents, preferably 0.8 to 10 equivalents, relative to compound (18).

Examples of the above-mentioned "base" include "inorganic bases". The amount of the "base" to be used is generally 0.5 to 20 equivalents, preferably 0.8 to 10 equivalents, relative to compound (18).

Examples of the above-mentioned "inert solvent" include water, "aromatic hydrocarbons", "saturated hydrocarbons", "ethers", "ketone solvents", "halogenated hydrocarbons" and the like. Two or more kinds of these "inert solvents" may be used in a mixture at an appropriate ratio.

The reaction temperature is generally −70° C. to 200° C., preferably −20° C. to 100° C.

The reaction time is generally 0.1 hr to 100 hr, preferably 0.1 hr to 40 hr.

As shown in Reaction Scheme 3, compound (1-2) can also be produced by a coupling reaction of compound (19) and compound (17).

This reaction is performed, for example, by reacting compound (19) and compound (17) in the presence of a base in an inert solvent. This reaction can also be performed under microwave irradiation.

Examples of the above-mentioned "base" include "inorganic bases", "basic salts", "aromatic amines", and "tertiary amines". The amount of the "base" to be used is generally 0.5 to 20 equivalents, preferably 0.8 to 10 equivalents, relative to compound (19).

Examples of the above-mentioned "inert solvent" include "aromatic hydrocarbons", "saturated hydrocarbons", "ethers", "esters", "amides", "nitriles", and "halogenated hydrocarbons". Two or more kinds of these "inert solvents" may be used in a mixture at an appropriate ratio. As the above-mentioned "inert solvent", DMF, N,N-dimethylacetamide, or acetonitrile is preferable.

The reaction temperature is generally −70° C. to 200° C., preferably −20° C. to 150° C.

The reaction time is generally 0.1 hr to 100 hr, preferably 0.1 hr to 40 hr.

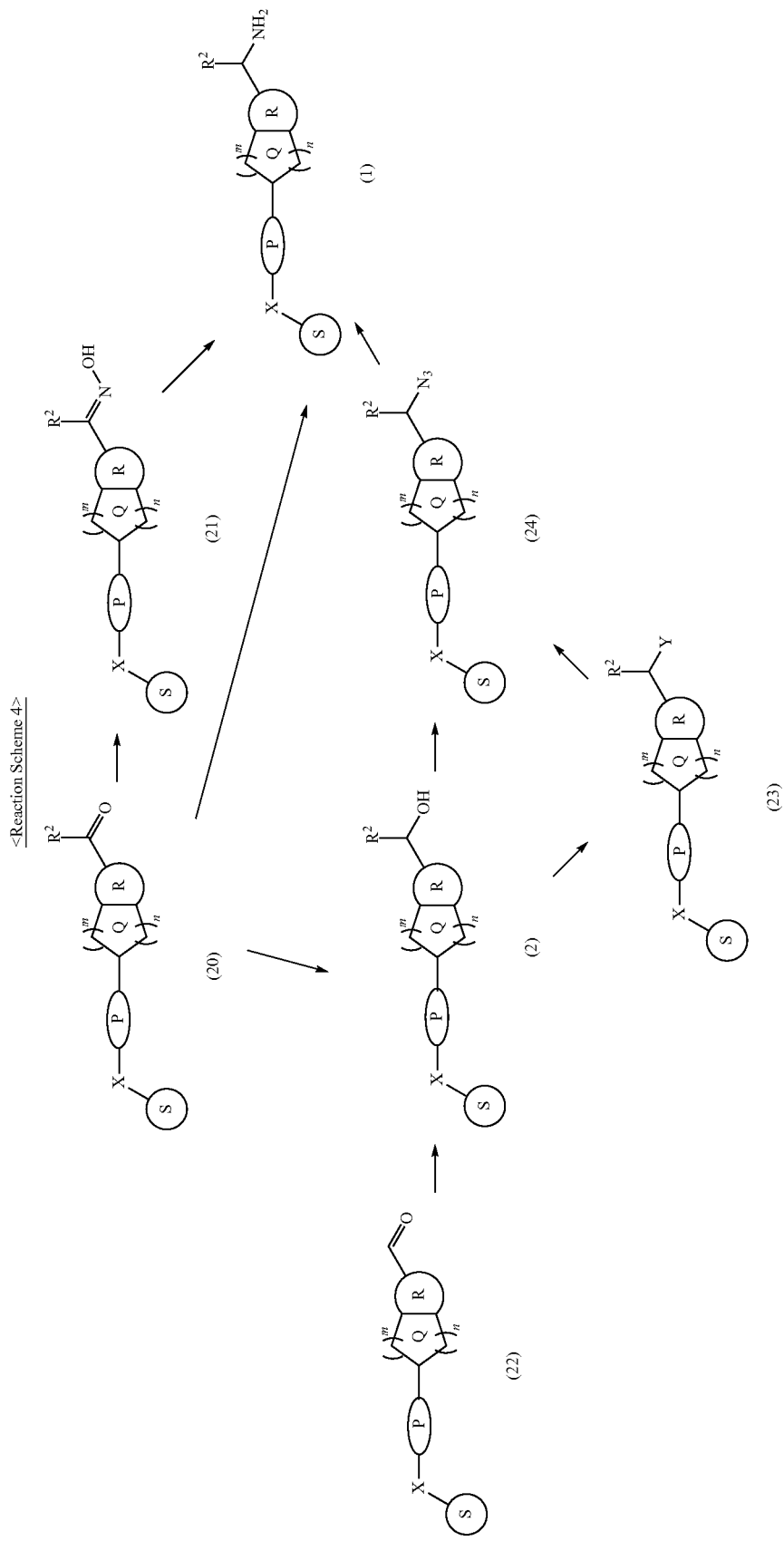

The production method of compound (1) is explained below.
wherein each symbol is as defined above.

The above-mentioned compound (20) can be produced, for example, according to the methods described in the below-mentioned Reaction Scheme 5, Reaction Scheme 7, Reaction Scheme and Reaction Scheme 16 or a method known per se or a method analogous thereto.

Compound (1) can be produced, for example, by a reductive amination reaction of compound (20).

The above-mentioned "reductive amination reaction" is performed, for example, by reacting compound (20) in the presence of an ammonia source and a reducing agent in an inert solvent. The above-mentioned "reductive amination reaction" can also be performed in the presence of a catalytic amount to a solvent amount of organic acid or 1 equivalent to 50 equivalents of hydrogen chloride.

Examples of the above-mentioned "ammonia source" include ammonium acetate, ammonium chloride, ammonium carbonate, and aqueous ammonia. The amount of the "ammonia source" to be used is generally 0.1 to 100 equivalents, preferably 0.8 to 50 equivalents, relative to compound (20).

Examples of the above-mentioned "reducing agent" include sodium borohydride, sodium cyanoborohydride, sodium triacetoxyborohydride, and lithium borohydride.

Examples of the above-mentioned "organic acid" include acetic acid.

Examples of the above-mentioned "inert solvent" include "alcohols", "nitriles", "aromatic hydrocarbons", "saturated hydrocarbons", "ethers", "amides" and "halogenated hydrocarbons". These "inert solvent" may also be used in a mixture with water at an appropriate ratio. Two or more kinds of these "inert solvents" may be used in a mixture at an appropriate ratio. As the above-mentioned "inert solvent", methanol and ethanol are preferable.

The reaction temperature is generally −70° C. to 200° C., preferably −20° C. to 150° C.

The reaction time is generally 0.1 hr to 100 hr, preferably 0.5 hr to 40 hr.

Compound (21) can be produced, for example, by an oximation reaction of compound (20).

This reaction is performed, for example, by reacting compound (20) and hydroxylamine hydrochloride in the presence of a base in an inert solvent.

The amount of the above-mentioned "hydroxylamine hydrochloride" to be used is generally 0.5 to 20 equivalents, preferably 0.8 to 10 equivalents, relative to compound (20).

Examples of the above-mentioned "base" include "basic salts", "aromatic amines", and "tertiary amines". The amount of the above-mentioned "base" to be used is generally 0.5 to 20 equivalents, preferably 0.8 to 10 equivalents, relative to compound (20).

Examples of the above-mentioned "inert solvent" include "alcohols", "nitriles", "aromatic hydrocarbons", "ethers", "amides", "halogenated hydrocarbons" and "esters". Two or more kinds of these "inert solvents" may be used in a mixture at an appropriate ratio. As the above-mentioned "inert solvent", methanol, ethanol, DMF, THF or toluene is preferable. The reaction temperature is generally −78° C. to 150° C., preferably −20° C. to 100° C.

The reaction time is generally 0.1 hr to 100 hr, preferably 0.5 hr to 48 hr.

As another method, compound (1) can also be produced, for example, by a reduction reaction of compound (21).

The above-mentioned "reduction reaction" is performed, for example, by reacting compound (21) in the presence of a metal catalyst and a hydrogen source, in an inert solvent. The above-mentioned "reduction reaction" can also be performed in the presence of a catalytic amount to a solvent amount of an organic acid or 1 equivalent to 50 equivalents of hydrogen chloride.

Examples of the above-mentioned "metal catalyst" include palladium-carbon, palladium black, palladium chloride, palladium hydroxide, rhodium-carbon, platinum oxide, platinum black, platinum-palladium, Raney nickel, and Raney cobalt. The amount of the "metal catalyst" to be used is generally 0.001 to 100 equivalents, preferably 0.01 to 50 equivalents, relative to compound (21).

Examples of the above-mentioned "hydrogen source" include hydrogen gas, and formic acid.

Examples of the above-mentioned "organic acid" include acetic acid.

Examples of the above-mentioned "inert solvent" include "alcohols", "nitriles", "aromatic hydrocarbons", "saturated hydrocarbons", "ethers", "amides" and "halogenated hydrocarbons". These "inert solvents" are preferably used as a mixture with water at an appropriate ratio. Two or more kinds of these "inert solvents" may be used in a mixture at an appropriate ratio. As the above-mentioned "inert solvent", THF, methanol and ethanol are preferable.

The reaction temperature is generally −70° C. to 150° C., preferably −20° C. to 100° C.

The reaction time is generally 0.1 hr to 100 hr, preferably 0.5 hr to 40 hr.

The above-mentioned "reduction reaction" is also performed, for example, by reacting compound (21) and a reducing agent in an inert solvent.

Examples of the above-mentioned "reducing agent" include borane tetrahydrofuran complex, diisobutylaluminum hydride, sodium triacetoxyborohydride, sodium borohydride, sodium cyanoborohydride, lithium aluminum hydride, sodium aluminum hydride, and sodium bis(2-methoxyethoxy) aluminum hydride. The amount of the "reducing agent" to be used is generally 0.5 to 20 equivalents, preferably 0.8 to 10 equivalents, relative to compound (21).

Examples of the above-mentioned "inert solvent" include "aromatic hydrocarbons", "saturated hydrocarbons", "ethers", and "halogenated hydrocarbons". Two or more kinds of these "inert solvents" may be used in a mixture at an appropriate ratio. As the above-mentioned "inert solvent", THF or toluene is preferable.

The reaction temperature is generally −78° C. to 150° C., preferably −20° C. to 100° C.

The reaction time is generally 0.1 hr to 48 hr, preferably 0.5 hr to 24 hr.

Compound (2) can also be produced, for example, by nucleophilic addition reaction of compound (22).

The above-mentioned compound (22) can be produced, for example, according to the method described in Reaction Scheme 5 or a method known per se or a method analogous thereto. This reaction is performed by reacting compound (22) and an organic metal reagent in an inert solvent.

Examples of the above-mentioned "organic metal reagent" include organic Grignard reagent (e.g., methylmagnesium bromide, methylmagnesium chloride), and organic lithium reagent (e.g., methyllithium). The amount of the "organic metal reagent" to be used is generally 0.5 to 20 equivalents, preferably 0.8 to 10 equivalents, relative to compound (22).

Examples of the above-mentioned "inert solvent" include "aromatic hydrocarbons", "saturated hydrocarbons", "ethers", "amides", and "halogenated hydrocarbons". Two or more kinds of these "inert solvents" may be used in a mixture at an appropriate ratio. As the above-mentioned "inert solvent", THF is preferable.

The reaction temperature is generally −78° C. to 150° C., preferably −20° C. to 100° C.

The reaction time is generally 5 min to 48 hr, preferably 30 min to 24 hr.

As another method, compound (2) can also be produced, for example, a reduction reaction of compound (20).

This reaction is performed by reacting compound (20) and a reducing agent in an inert solvent.

Examples of the above-mentioned "reducing agent" include metal hydrogen compound (e.g., diisobutylaluminum hydride), metal hydride complex compound (e.g., sodium borohydride, sodium cyanoborohydride, lithium aluminum hydride, sodium aluminum hydride, and sodium bis(2-methoxyethoxy)aluminum hydride). The amount of the "reducing agent" to be used is generally 0.5 to 20 equivalents, preferably 0.8 to 10 equivalents, relative to compound (20).

Examples of the above-mentioned "inert solvent" include "alcohols", "aromatic hydrocarbons", "saturated hydrocarbons", "ethers", and "halogenated hydrocarbons". Two or more kinds of these "inert solvents" may be used in a mixture at an appropriate ratio. As the above-mentioned "inert solvent", THF, ethanol, methanol is preferable.

The reaction temperature is generally −78° C. to 150° C., preferably −20° C. to 100° C.

The reaction time is generally 5 min to 48 hr, preferably 30 min to 24 hr.

Compound (23) can be produced, for example, by a sulfonylation reaction of compound (2).

This reaction is performed by reacting compound (2) and a sulfonylating agent in the presence of a base in an inert solvent.

Examples of the above-mentioned "sulfonylating agent" include methanesulfonyl chloride, and p-toluenesulfonyl chloride. The amount of the "sulfonylating agent" to be used is generally 0.5 to 20 equivalents, preferably 0.8 to 10 equivalents, relative to compound (2).

Examples of the above-mentioned "base" include "basic salts", "aromatic amines", and "tertiary amines". The amount of the "base" to be used is generally 0.5 to 20 equivalents, preferably 0.8 to 10 equivalents, relative to compound (2).

Examples of the above-mentioned "inert solvent" include "aromatic hydrocarbons", "saturated hydrocarbons", "ethers", "esters" and "amides". Two or more kinds of these "inert solvents" may be used in a mixture at an appropriate ratio. The reaction temperature is generally −70° C. to 150° C., preferably −20° C. to 100° C.

The reaction time is generally 0.1 hr to 100 hr, preferably 0.1 hr to 48 hr.

Compound (23) can also be produced, for example, by halogenation reaction of compound (2).

This reaction is performed by reacting compound (2) and a halogenating agent in an inert solvent. This reaction can also be performed in the presence of a base.

Examples of the above-mentioned "halogenating agent" include thionyl chloride, phosphorus oxychloride, phosphorus trichloride, and phosphorus tribromide. The amount of the "halogenating agent" to be used is generally 0.5 to 20 equivalents, preferably 0.8 to 10 equivalents, relative to compound (2).

Examples of the above-mentioned "base" include "aromatic amines" and "tertiary amines". The amount of the "base" to be used is generally 0.5 to 20 equivalents, preferably 0.8 to 10 equivalents, relative to compound (2).

Examples of the above-mentioned "inert solvent" include "aromatic hydrocarbons", "saturated hydrocarbons", "ethers", "esters" and "amides". Two or more kinds of these "inert solvents" may be used in a mixture at an appropriate ratio.

The reaction temperature is generally −70° C. to 150° C., preferably −20° C. to 100° C.

The reaction time is generally 0.1 hr to 100 hr, preferably 0.1 hr to 48 hr.

Compound (24) can be produced, for example, by a azidation reaction of compound (23).

This reaction is performed by reacting compound (23) and an azidating agent in an inert solvent.

Examples of the above-mentioned "azidating agent" include sodium azide, lithium azide, and trimethylsilyl azide. The amount of the "azidating agent" to be used is generally 0.5 to 20 equivalents, preferably 0.8 to 10 equivalents, relative to compound (23).

Examples of the above-mentioned "inert solvent" include "ethers", "amides", and "sulfoxides". As the above-mentioned "inert solvent", DMF is preferable.

The reaction temperature is generally −70° C. to 200° C., preferably 0° C. to 150° C.

The reaction time is generally 0.1 hr to 100 hr, preferably 0.1 hr to 48 hr.

Compound (24) can also be produced, for example, by an azidation reaction of compound (2).

This reaction is performed by reacting compound (2) and an azidating agent in the presence of a base in an inert solvent.

Examples of the above-mentioned "azidating agent" include diphenylphosphoryl azide. The amount of the "azidating agent" to be used is generally 0.5 to 20 equivalents, preferably 0.8 to 10 equivalents, relative to compound (2).

Examples of the above-mentioned "base" include "aromatic amines" and "tertiary amines". As the above-mentioned "base", DBU is preferable. The amount of the "base" to be used is generally 0.5 to 20 equivalents, preferably 0.8 to 10 equivalents, relative to compound (2).

Examples of the above-mentioned "inert solvent" include "aromatic hydrocarbons", "ethers", "amides", and "sulfoxides". Two or more kinds of these "inert solvents" may be used in a mixture at an appropriate ratio. As the above-mentioned "inert solvent", THF or toluene is preferable.

The reaction temperature is generally −70° C. to 200° C., preferably 0° C. to 150° C.

The reaction time is generally 0.1 hr to 100 hr, preferably 0.1 hr to 48 hr.

As shown in Reaction Scheme 4, compound (1) can also be produced, for example, by a reduction reaction of compound (24)

This reaction is performed by reacting compound (24) in the presence of a metal catalyst and a hydrogen source in an inert solvent.

Examples of the above-mentioned "metal catalyst" include palladium-carbon, palladium black, palladium chloride, palladium hydroxide, platinum oxide, platinum black, Raney nickel, and Raney cobalt. The amount of the "metal catalyst" to be used is generally 0.001 to 10 equivalents, preferably 0.01 to 5 equivalents, relative to compound (24).

Examples of the above-mentioned "hydrogen source" include hydrogen gas, formic acid, formic acid amine salt, phosphinic acid salt, and hydrazine.

Examples of the above-mentioned "inert solvent" include "alcohols", "esters", "ethers", "amides", and "halogenated hydrocarbons". These "inert solvents" may be used in a mixture with water at an appropriate ratio. As the above-mentioned "inert solvent", "alcohols" and "ethers" are preferable.

The reaction temperature is generally −70 to 150° C., preferably −20 to 100° C.

The reaction time is generally 0.1 to 100 hr, preferably 0.1 to 48 hr.

This reaction can be performed by reacting compound (24), triphenylphosphine and water in an inert solvent.

The amount of the above-mentioned "triphenylphosphine" to be used is generally 0.5 to 20 equivalents, preferably 0.8 to 10 equivalents, relative to compound (24).

Examples of the above-mentioned "inert solvent" include "aromatic hydrocarbons", "saturated hydrocarbons", "ethers", "amides", "sulfoxides", and "halogenated hydrocarbons". As the above-mentioned "inert solvent", "ethers" are preferable.

The reaction temperature is generally −70 to 150° C., preferably −20 to 100° C.

The reaction time is generally 0.1 to 100 hr, preferably 0.1 to 40 hr.

Reaction Scheme 19 and Reaction Scheme 24 or a method known per se or a method analogous thereto.

Compound (26) can be produced, for example, by hydrolysis reaction of compound (25).

This reaction is performed, for example, by reacting compound (25) and a base in an inert solvent.

Examples of the above-mentioned "base" include "inorganic bases". The amount of the "base" to be used is generally 0.5 to 100 equivalents, preferably 0.8 to 50 equivalents, relative to compound (25).

Examples of the above-mentioned "inert solvent" include "alcohols", "aromatic hydrocarbons", "ethers", and "halogenated hydrocarbons". These "inert solvents" are preferably used by mixing with water at an appropriate ratio, and water-containing "alcohols" are particularly preferable.

The reaction temperature is generally −78° C. to 150° C., preferably −20° C. to 100° C.

The reaction time is generally 0.1 hr to 100 hr, preferably 0.5 hr to 60 hr.

Compound (27) can be produced, for example, by an amidation reaction of compound (26) and N,O-dimethylhydroxylamine.

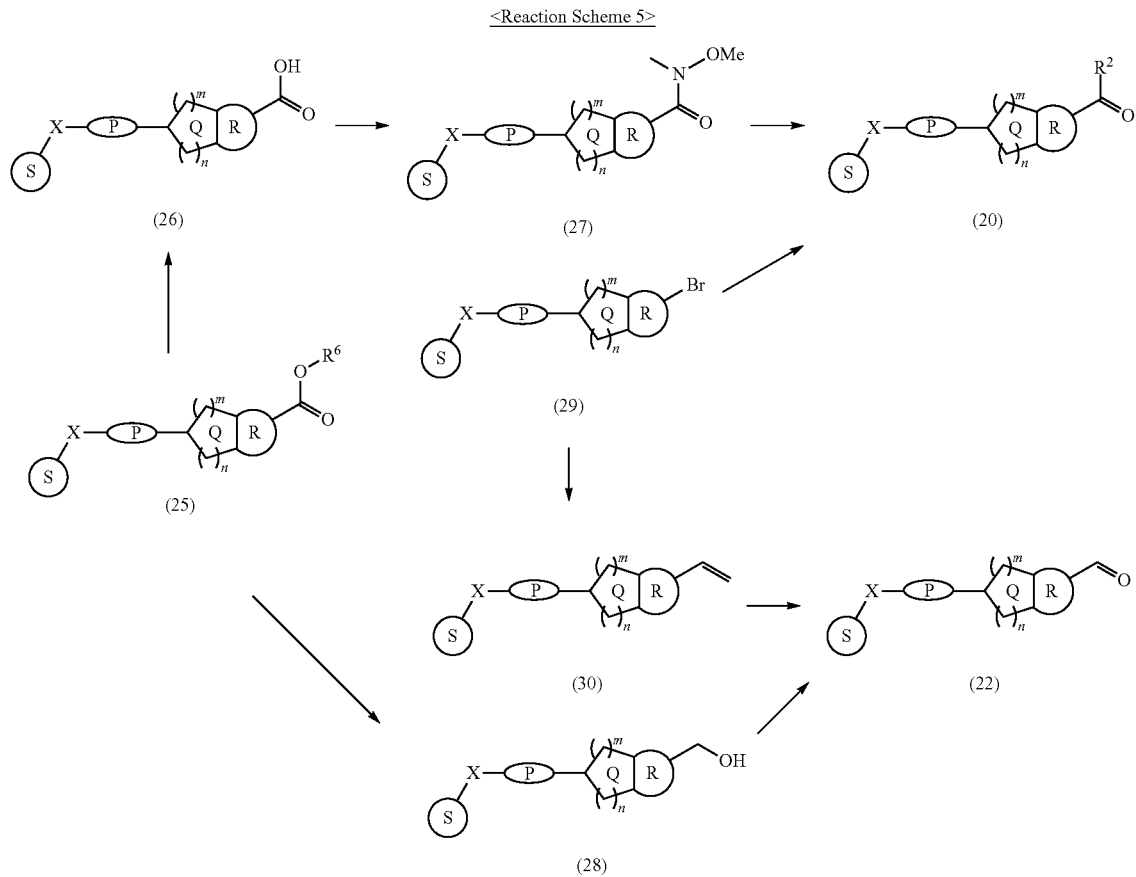

<Reaction Scheme 5>

The production methods of compound (20) and compound (22) are explained below.
wherein each symbol is as defined above, and $R^6$ is a substituent.

Compound (25) can be produced, for example, according to the methods described in the below-mentioned Reaction Scheme 8, Reaction Scheme 9, Reaction Scheme 10, Reaction Scheme 11, Reaction Scheme 12, Reaction Scheme 13, This reaction is performed, for example, by reacting compound (26) and N,O-dimethylhydroxylamine hydrochloride in the presence of a dehydrating condensing agent in an inert solvent. This reaction can also be performed in the presence of a catalytic amount to 5 equivalents of 1-hydroxybenzotriazole (HOBt), and a catalytic amount to 5 equivalents of a base.

The amount of the above-mentioned "N,O-dimethylhydroxylamine hydrochloride" to be used is generally 0.5 to 20 equivalents, preferably 0.8 to 10 equivalents, relative to compound (26).

Examples of the above-mentioned "dehydrating condensing agent" include dicyclohexylcarbodiimide (DCC), 1-ethyl-3-(3-dimethylaminopropyl)carbodiimide hydrochloride (WSCD), and 0-(7-azabenzotriazol-1-yl)-N,N,N',N'-tetramethyluronium hexafluorophosphate (HATU). Of these, WSCD or HATU is preferable. The amount of the "dehydrating condensing agent" to be used is generally 0.5 to 20 equivalents, preferably 0.8 to 10 equivalents, relative to compound (26).

Examples of the above-mentioned "inert solvent" include "nitriles", "amides", "halogenated hydrocarbons", and "ethers". Two or more kinds of these "inert solvents" may be used in a mixture at an appropriate ratio. As the above-mentioned "inert solvent", "amides" is preferable.

Examples of the above-mentioned "base" include "aromatic amines" and "tertiary amines".

The reaction temperature is generally −70° C. to 150° C., preferably −20° C. to 100° C.

The reaction time is generally 0.1 hr to 100 hr, preferably 1 hr to 48 hr.

Compound (20) can be produced, for example, by a substitution reaction of compound (27).

This reaction is performed in the same manner as in the method for producing compound (2) from compound (22) in Reaction Scheme 4.

Compound (20) can also be produced, for example, by a vinyl etherification reaction of compound (29) and subsequent hydrolysis reaction.

Compound (29) can be produced, for example, according to the methods described in the below-mentioned Reaction Scheme 6, Reaction Scheme 17 and Reaction Scheme 18 or a method known per se or a method analogous thereto.

The above-mentioned "vinyl etherification reaction" is performed by reacting compound (29) and a vinyl etherifying agent in the presence of a metal catalyst in an inert solvent. This reaction is preferably performed under an inert gas atmosphere. This reaction can also be performed in the presence of a ligand and a base or can also be performed under microwave irradiation.

Examples of the above-mentioned "vinyl etherifying agent" include (1-ethoxyvinyl)tributyltin, ethoxyvinyl ether, and butyl vinyl ether. The amount of the "vinyl etherifying agent" is to be used is generally 0.5 to 20 equivalents, preferably 0.8 to 10 equivalents, relative to compound (29).

Examples of the above-mentioned "metal catalyst" include bis(triphenylphosphine)dichloropalladium(II), bis(di-tert-butyl(4-dimethylaminophenyl)phosphine)dichloropalladium(II), palladium(II) acetate, tetrakis(triphenylphosphine)palladium(0), tris(dibenzylideneacetone)dipalladium(0), and [1,1-bis(diphenylphosphino)ferrocene] dichloropalladium(II) dichloromethane adduct. The amount of the "metal catalyst" to be used is generally 0.001 to 10 equivalents, preferably 0.01 to 5 equivalents, relative to compound (29).

Examples of the above-mentioned "ligand" include tri(tert-butylphosphonium)tetrafluoroborate, dicyclohexyl(2',6'-dimethoxybiphenyl-2-yl)phosphine, tricyclohexylphosphine, and triphenylphosphine. The amount of the "ligand" to be used is generally 0.01 to 20 equivalents, preferably 0.1 to 10 equivalents, relative to compound (29).

Examples of the above-mentioned "base" include "basic salts". Of these, tripotassium phosphate, cesium carbonate, cesium fluoride, or sodium carbonate is preferable. The amount of the "base" to be used is generally 0.5 to 20 equivalents, preferably 0.8 to 10 equivalents, relative to compound (29).

Examples of the above-mentioned "inert solvent" include "nitriles", "amides", "halogenated hydrocarbons", "ethers", "aromatic hydrocarbons", "sulfoxides", and "esters". Two or more kinds of these "inert solvents" may be used in a mixture at an appropriate ratio. As the above-mentioned "inert solvent", DMF, DMSO, THF, 1,2-dimethoxyethane or toluene is preferable.

Examples of the above-mentioned "inert gas" include argon gas and nitrogen gas.

The reaction temperature is generally −78° C. to 200° C., preferably 0° C. to 150° C.

The reaction time is generally 0.1 hr to 100 hr, preferably 0.5 hr to 48 hr.

The above-mentioned "hydrolysis reaction" is performed by reacting a product resultant from the aforementioned "vinyl etherification reaction and an acid in an inert solvent.

Examples of the above-mentioned "acid" include "inorganic acids". The amount of the "acid" to be used is generally 0.5 to excess amount, preferably 0.8 to 100 equivalents, relative to compound (29).

Examples of the above-mentioned "inert solvent" include "alcohols", "nitriles", "aromatic hydrocarbons", "saturated hydrocarbons", "ethers", "amides", and "halogenated hydrocarbons". These "inert solvents" are preferably used by mixing with water at an appropriate ratio. As the above-mentioned "inert solvent", water-containing "alcohols" are preferable.

The reaction temperature is generally −78° C. to 150° C., preferably −20° C. to 100° C.

The reaction time is generally 0.1 hr to 100 hr, preferably 0.5 hr to 60 hr.

Compound (28) can be produced, for example, by a reduction reaction of compound (25).

This reaction is performed in the same manner as in the method for producing compound (2) from compound (20) in Reaction Scheme 4.

Compound (22) can be produced, for example, by an oxidation reaction of compound (28).

This reaction is performed, for example, by reacting compound (28) and an oxidant in an inert solvent. Where necessary, the reaction may be performed in the presence of a reoxidant.

Examples of the above-mentioned "oxidant" include sulfur trioxide pyridine complex, manganese dioxide, tetrapropylammonium perruthenate, chromium trioxide, and Dess-Martin periodinane. The amount of the "oxidant" to be used is generally 0.01 to 20 equivalents, preferably 0.05 to 10 equivalents, relative to compound (28).

Examples of the above-mentioned "reoxidant" include N-methylmorpholine-N-oxide, and sodium periodate. The amount of the "reoxidant" to be used is generally 0.5 to 20 equivalents, preferably 0.8 to 20 equivalents, relative to compound (28).

Examples of the above-mentioned "inert solvent" include "nitriles", "aromatic hydrocarbons", "saturated hydrocarbons", "ethers", "amides", "halogenated hydrocarbons", "sulfoxides", and "esters". Two or more kinds of these "inert solvents" may be used in a mixture at an appropriate ratio. As the above-mentioned "inert solvent", DMSO, THF, toluene, acetonitrile, ethyl acetate, or dichloromethane is preferable.

The reaction temperature is generally −78° C. to 150° C., preferably −20° C. to 100° C.

The reaction time is generally 0.1 hr to 100 hr, preferably 0.5 hr to 48 hr.

Compound (30) can be produced, for example, by a vinylation reaction of compound (29).

This reaction is performed by reacting compound (29) and a vinylating agent in the presence of a metal catalyst in an inert solvent. This reaction is preferably performed under an inert gas atmosphere. This reaction can also be performed in the presence of a ligand and a base, and can also be performed under microwave irradiation.

Examples of the above-mentioned "vinylating agent" include vinyltributyltin, vinylmagnesium bromide, and vinylboric acid. The amount of the "vinylating agent" to be used is generally 0.5 to 20 equivalents, preferably 0.8 to 10 equivalents, relative to compound (29).

Examples of the above-mentioned "metal catalyst" include bis(triphenylphosphine)dichloropalladium(II), bis(di-tert-butyl(4-dimethylaminophenyl)phosphine)dichloropalladium(II), palladium(II) acetate, tetrakis(triphenylphosphine)palladium(0), tris(dibenzylideneacetone)dipalladium (0), and [1,1-bis(diphenylphosphino)ferrocene]dichloropalladium(II) dichloromethane adduct. The amount of the "metal catalyst" to be used is generally 0.001 to 10 equivalents, preferably 0.01 to 5 equivalents, relative to compound (29).

Examples of the above-mentioned "ligand" include tri(tert-butylphosphonium)tetrafluoroborate, dicyclohexyl(2',6'-dimethoxybiphenyl-2-yl)phosphine, tricyclohexylphosphine, and triphenylphosphine. The amount of the "ligand" to be used is generally 0.001 to 20 equivalents, preferably 0.01 to 10 equivalents, relative to compound (29).

Examples of the above-mentioned "base" include "basic salts". As the above-mentioned "base", tripotassium phosphate, cesium carbonate, cesium fluoride, or sodium carbonate is preferable. The amount of the "base" to be used is generally 0.5 to 20 equivalents, preferably 0.8 to 10 equivalents, relative to compound (29).

Examples of the above-mentioned "inert solvent" include "nitriles", "amides", "halogenated hydrocarbons", "ethers", "aromatic hydrocarbons", "sulfoxides", and "esters". Two or more kinds of these "inert solvents" may be used in a mixture at an appropriate ratio. As the above-mentioned "inert solvent", DMF, DMSO, THF, 1,2-dimethoxyethane or toluene is preferable.

Examples of the above-mentioned "inert gas" include argon gas and nitrogen gas.

The reaction temperature is generally −78° C. to 200° C., preferably 0° C. to 150° C.

The reaction time is generally 0.1 hr to 100 hr, preferably 0.5 hr to 48 hr.

As shown in Reaction Scheme 5, compound (22) can also be produced, for example, by an oxidation reaction of compound (30).

This reaction is performed, for example, by reacting compound (30) and an oxidant in an inert solvent. This reaction can also be performed in the presence of a reoxidant.

Examples of the above-mentioned "oxidant" include osmic acid (IV), and potassium osmate (IV) dihydrate. The amount of the "oxidant" to be used is generally 0.01 to 20 equivalents, preferably 0.05 to 10 equivalents, relative to compound (30).

Examples of the above-mentioned "reoxidant" include sodium periodate. The amount of the "reoxidant" to be used is generally 0.5 to 20 equivalents, preferably 0.8 to 10 equivalents, relative to compound (30).

Examples of the above-mentioned "inert solvent" include water, "nitriles", "aromatic hydrocarbons", "saturated hydrocarbons", "ethers", "amides", "halogenated hydrocarbons", "sulfoxides", and "esters". Two or more kinds of these "inert solvents" may be used in a mixture at an appropriate ratio. As the above-mentioned "inert solvent", water, DMSO, THF, toluene, acetonitrile, ethyl acetate, or dichloromethane is preferable.

The reaction temperature is generally −78° C. to 150° C., preferably −20° C. to 100° C.

The reaction time is generally 0.1 hr to 100 hr, preferably 0.5 hr to 48 hr.

<Reaction Scheme 6>

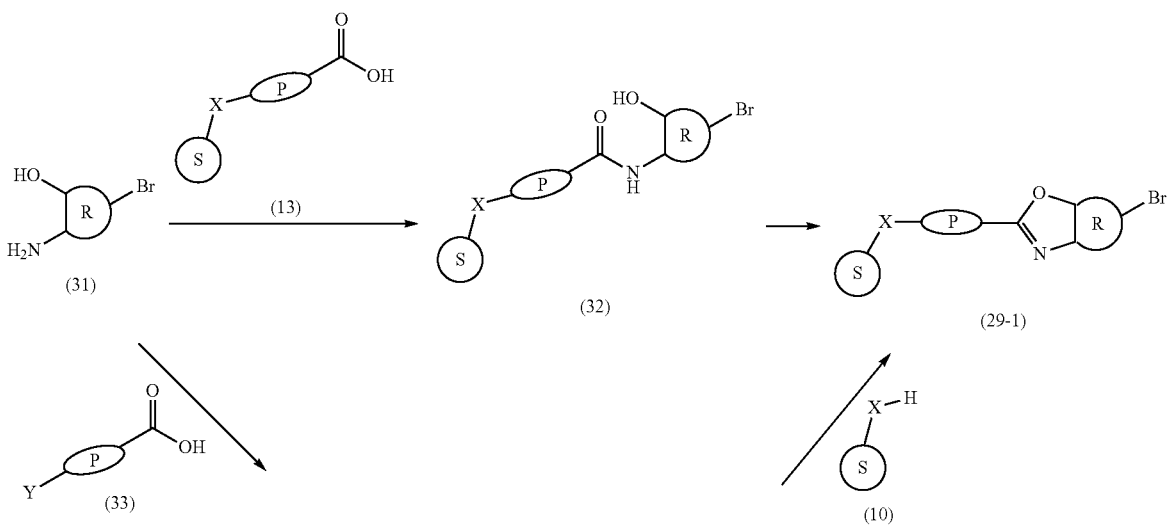

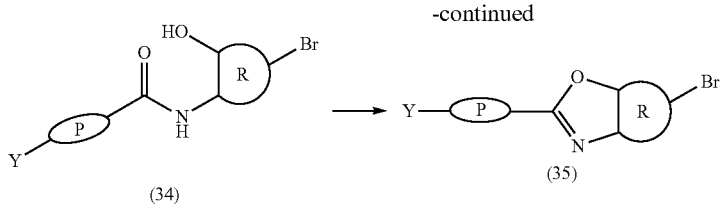

The production method of compound (29-1) encompassed in compound (29) is explained below.
wherein each symbol is as defined above.

Compound (32) can be produced, for example, by an amidation reaction of compound (31) and compound (13).

As another method, compound (29-1) can also be produced, for example, by a substitution reaction of compound (35) and compound (10).

This reaction is performed in the same manner as in the method for producing compound (I) from compound (9) in Reaction Scheme 1.

<Reaction Scheme 7>

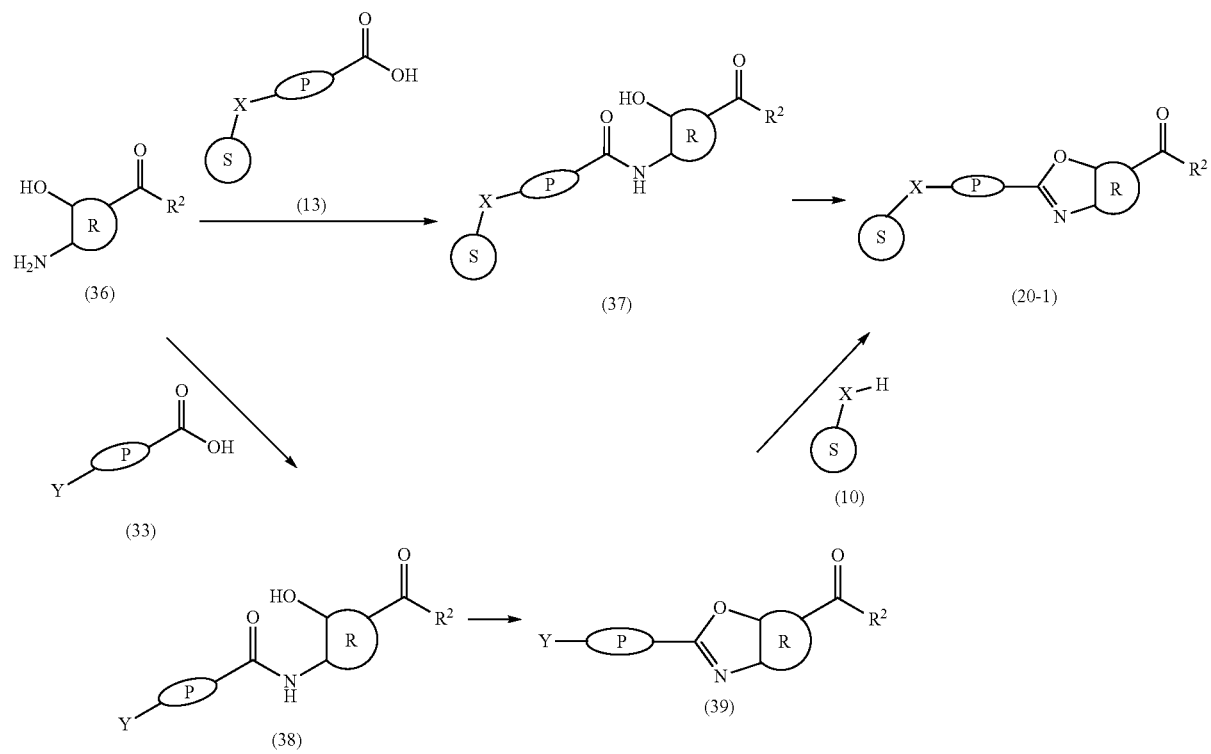

This reaction is performed in the same manner as in the method for producing compound (14) in Reaction Scheme 2.

Compound (29-1) can be produced, for example, by a ring closure reaction of compound (32).

This reaction is performed in the same manner as in the method for producing compound (I-1) in Reaction Scheme 2.

Compound (34) can be produced, for example, by an amidation reaction of compound (31) and compound (33) This reaction is performed in the same manner as in the method for producing compound (14) in Reaction Scheme 2.

Compound (35) can be produced, for example, by a ring closure reaction of compound (34)

This reaction is performed in the same manner as in the method for producing compound (I-1) in Reaction Scheme 2.

The production method of compound (20-1) encompassed in compound (20) is explained below.
wherein each symbol is as defined above.

Compound (37) can be produced, for example, by an amidation reaction of compound (36) and compound (13).

This reaction is performed in the same manner as in the method for producing compound (14) in Reaction Scheme 2.

Compound (20-1) can be produced, for example, by a ring closure reaction of compound (37)

This reaction is performed in the same manner as in the method for producing compound (I-1) in Reaction Scheme 2.

Compound (38) can be produced, for example, by an amidation reaction of compound (36) and compound (33).

This reaction is performed in the same manner as in the method for producing compound (14) in Reaction Scheme 2.

Compound (39) can be produced, for example, by a ring closure reaction of compound (38).

This reaction is performed in the same manner as in the method for producing compound (I-1) in Reaction Scheme 2.

As shown in Reaction Scheme 7, compound (20-1) can also be produced, for example, by a substitution reaction of compound (39) and compound (10).

This reaction is performed in the same manner as in the method for producing compound (I) from compound (9) in Reaction Scheme 1.

The production method of compound (25-1) encompassed in compound (25) is explained below.

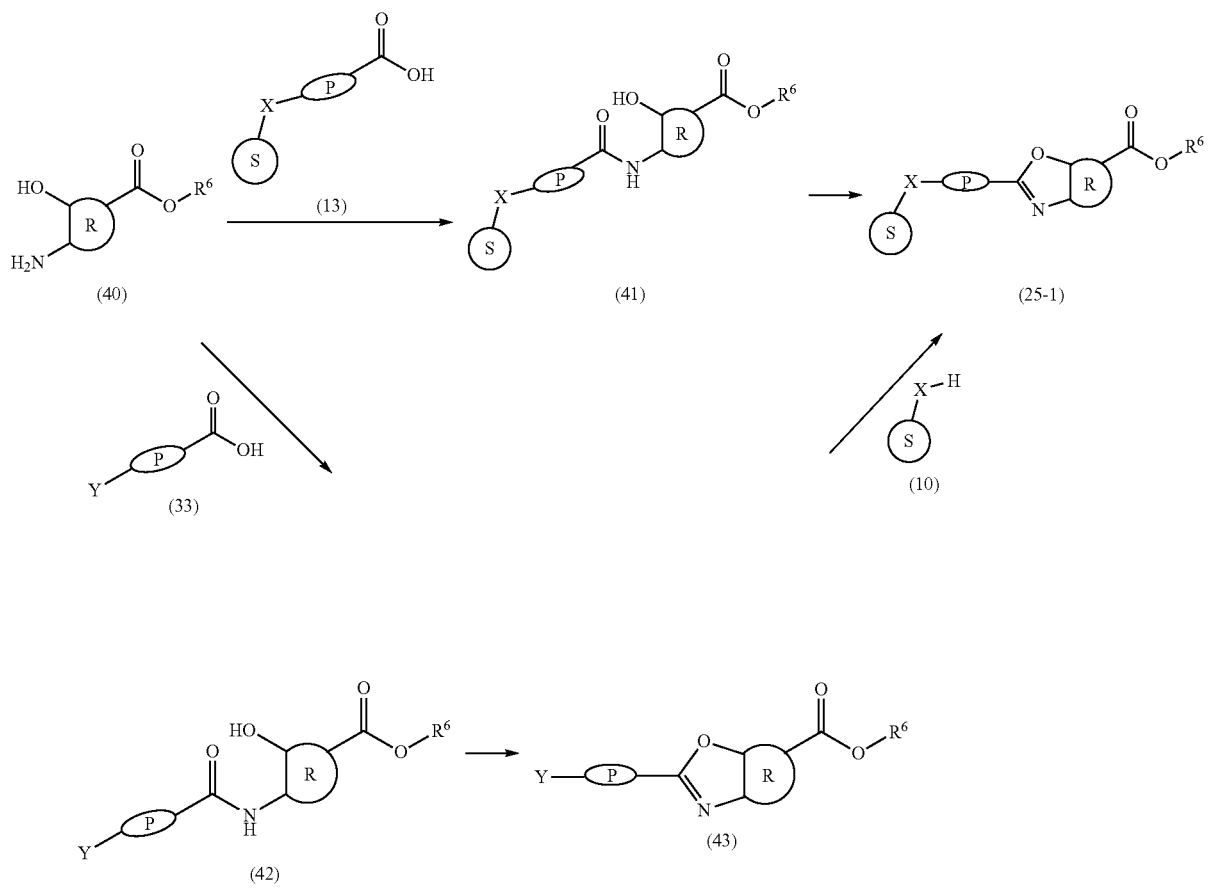

<Reaction Scheme 8> wherein each symbol is as defined above.

Compound (41) can be produced, for example, by an amidation reaction of compound (40) and compound (13).

This reaction is performed in the same manner as in the method for producing compound (14) in Reaction Scheme 2.

Compound (25-1) can be produced, for example, by a ring closure reaction of compound (41).

This reaction is performed in the same manner as in the method for producing compound (I-1) in Reaction Scheme 2.

Compound (42) can be produced, for example, by an amidation reaction of compound (40) and compound (33).

This reaction is performed in the same manner as in the method for producing compound (14) in Reaction Scheme 2.

Compound (43) can be produced, for example, by a ring closure reaction of compound (42).

This reaction is performed in the same manner as in the method for producing compound (I-1) in Reaction Scheme 2.

As shown in Reaction Scheme 8, compound (25-1) can also be produced, for example, by a substitution reaction of compound (43) and compound (10).

This reaction is performed in the same manner as in the method for producing compound (I) from compound (9) in Reaction Scheme 1.

<Reaction Scheme 9>

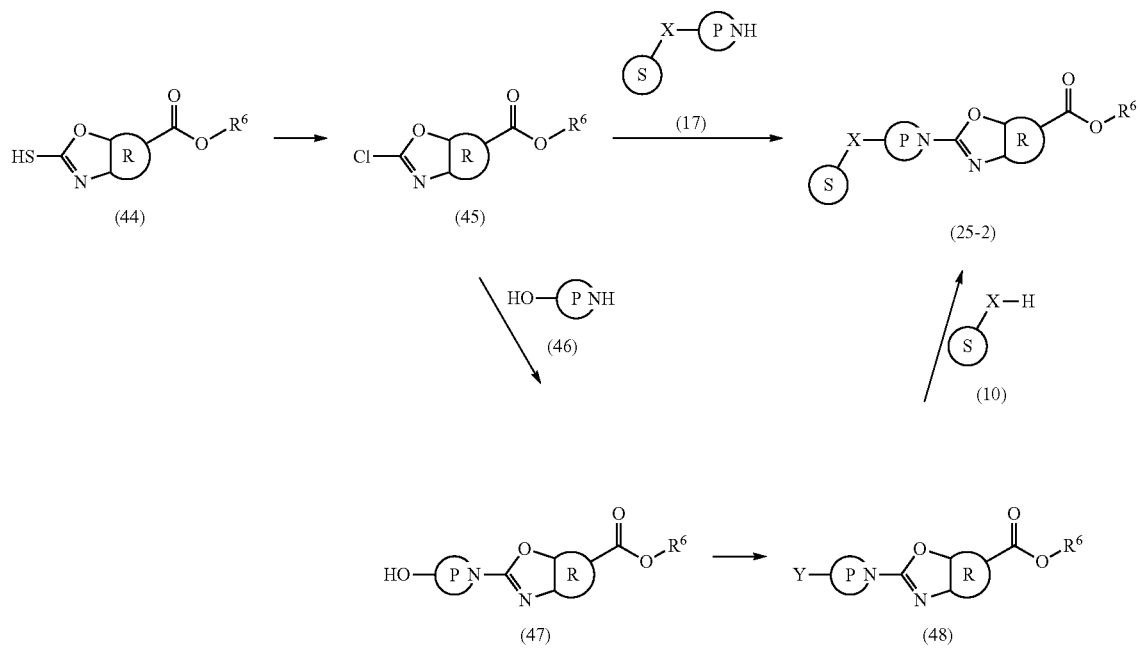

The production method of compound (25-2) encompassed in compound (25) is explained below.

wherein each symbol is as defined above.

Compound (45) can be produced, for example, by a chlorination reaction of compound (44)

This reaction is performed in the same manner as in the method for producing compound (16) in Reaction Scheme 3.

Compound (25-2) can be produced, for example, by a substitution reaction of compound (45) and compound (17).

This reaction is performed in the same manner as in the method for producing compound (I-2) from compound (16) in Reaction Scheme 3.

Compound (47) can be produced, for example, by a substitution reaction of compound (45) and compound (46).

This reaction is performed in the same manner as in the method for producing compound (I-2) from compound (16) in Reaction Scheme 3.

Compound (48) can be produced, for example, by a sulfonylation reaction of compound (47).

This reaction is performed in the same manner as in the method for producing compound (9) from compound (8) in Reaction Scheme 1.

As shown in Reaction Scheme 9, compound (25-2) can also be produced, for example, by a substitution reaction of compound (48) and compound (10).

This reaction is performed in the same manner as in the method for producing compound (I) from compound (9) in Reaction Scheme 1.

<Reaction Scheme 10>

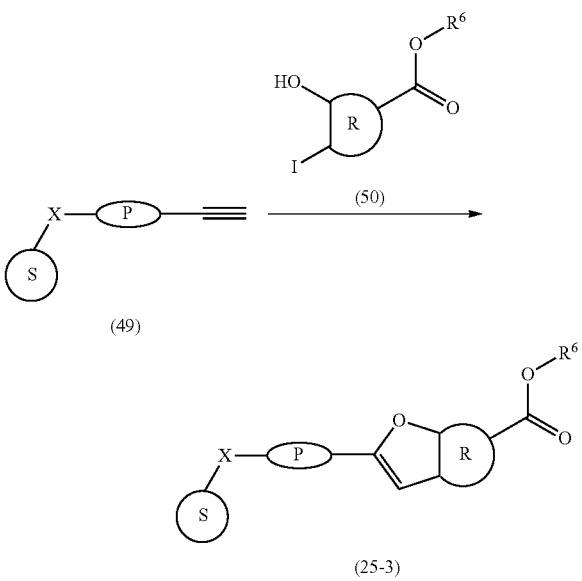

The production method of compound (25-3) encompassed in compound (25) is explained below.

wherein each symbol is as defined above.

Compound (25-3) can be produced, for example, by a Sonogashira coupling reaction of compound (49) and compound (50).

The above-mentioned "Sonogashira coupling reaction" is performed by reacting compound (49) and compound (50) in the presence of a metal catalyst and a base in an inert solvent. This reaction is preferably performed under an inert gas atmosphere. The amount of compound (50) to be used is generally 0.5 to 10 equivalents, preferably 0.8 to 5 equivalents, relative to compound (49).

Examples of the above-mentioned "metal catalyst" include a combination of bis(triphenylphosphine)palladium (II) dichloride and copper(I) iodide. The amount of the "metal catalyst" to be used is generally 0.001 to 10 equivalents, preferably 0.01 to 5 equivalents, relative to compound (49).

Examples of the above-mentioned "base" include "aromatic amines" and "tertiary amines". As the above-mentioned "base", 1,1,3,3-tetramethylguanidine is preferable. The amount of the "base" to be used is generally 0.5 to 20 equivalents, preferably 0.8 to 10 equivalents, relative to compound (49).

Examples of the above-mentioned "inert solvent" include "amides", "aromatic hydrocarbons", and "halogenated hydrocarbons".

Examples of the above-mentioned "inert gas" include argon gas and nitrogen gas.

The reaction temperature is generally −20° C. to 200° C., preferably 0° C. to 150° C.

The reaction time is generally 0.1 hr to 100 hr, preferably 0.5 hr to 48 hr.

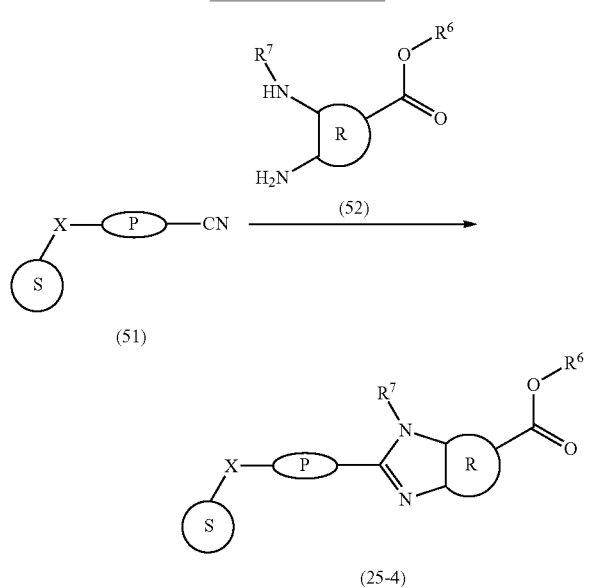

<Reaction Scheme 11>

(25-4)

The production method of compound (25-4) encompassed in compound (25) is explained below.
wherein each symbol is as defined above, and $R^7$ is a substituent.

Compound (25-4) can be produced, for example, by a ring closure reaction of compound (51) and compound (52).

This reaction is performed, for example, by reacting compound (51) and compound (52) in the presence of metal alkoxide and acid in an inert solvent. The amount of compound (52) to be used is generally 0.5 to 5 equivalents, preferably 0.8 to 2 equivalents, relative to compound (51).

Examples of the above-mentioned "metal alkoxides" include sodium methoxide and sodium ethoxide. The amount of the "metal alkoxides" to be used is generally 0.01 to 10 equivalents, preferably 0.1 to 5 equivalents, relative to compound (51).

Examples of the above-mentioned "acid" include "inorganic acids". The amount of the "acid" to be used is generally 0.5 to 20 equivalents, preferably 0.8 to 10 equivalents, relative to compound (51).

Examples of the above-mentioned "inert solvent" include "alcohols", "ethers", "amides", and "aromatic hydrocarbons". Of these, "alcohols" are preferable.

The reaction temperature is generally −20° C. to 200° C., preferably 0° C. to 150° C.

The reaction time is generally 0.1 hr to 100 hr, preferably 0.5 hr to 48 hr.

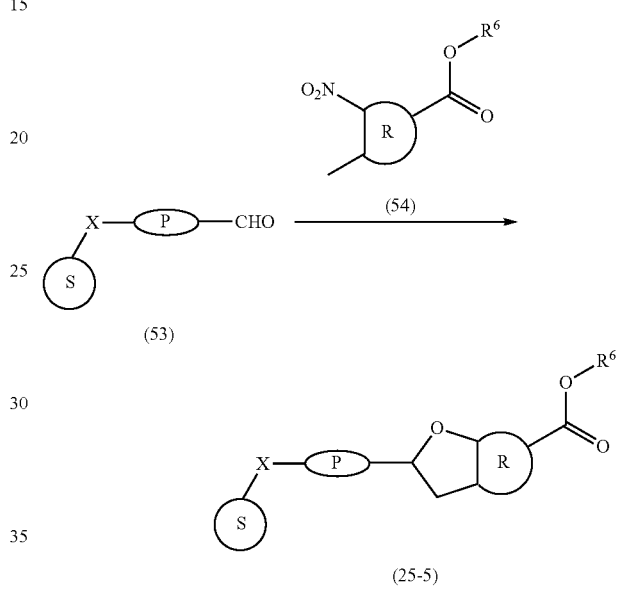

<Reaction Scheme 12>

(25-5)

The production method of compound (25-5) encompassed in compound (25) is explained below.
wherein each symbol is as defined above.

Compound (25-5) can be produced, for example, by a ring closure reaction of compound (53) and compound (54).

This reaction is performed, for example, by reacting compound (53) and compound (54) in the presence of a fluorine-containing quaternary ammonium salt and a base in an inert solvent. The amount of compound (54) to be used is generally 0.5 to 10 equivalents, preferably 0.8 to 5 equivalents, relative to compound (53).

Examples of the above-mentioned "fluorine-containing quaternary ammonium salt" include tetrabutylammonium fluoride. The amount of the "fluorine-containing quaternary ammonium salt" to be used is generally 0.5 to 20 equivalents, preferably 0.8 to 10 equivalents, relative to compound (53).

Examples of the above-mentioned "base" include "tertiary amines". The amount of the "base" to be used is generally 0.5 to 20 equivalents, preferably 0.8 to 10 equivalents, relative to compound (53).

Examples of the above-mentioned "inert solvent" include "alcohols", "ethers", "amides" and "aromatic hydrocarbons".

The reaction temperature is generally −20° C. to 200° C., preferably 0° C. to 150° C.

The reaction time is generally 0.1 hr to 100 hr, preferably 0.5 hr to 48 hr.

<Reaction Scheme 13>

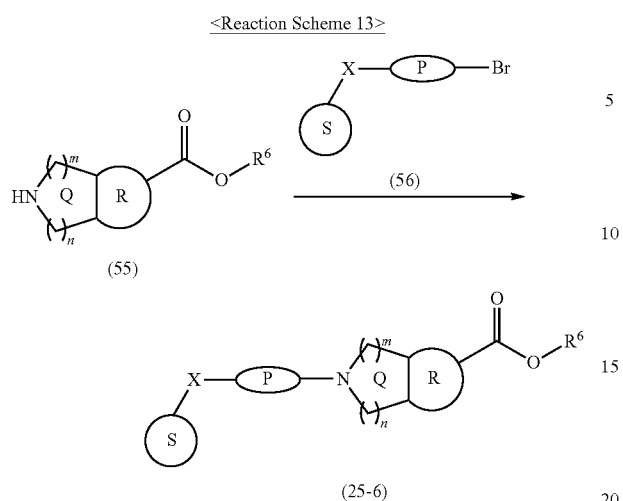

(55)

(25-6)

The production method of compound (25-6) encompassed in compound (25) is explained below.

wherein each symbol is as defined above.

Compound (25-6) can be produced, for example, by a coupling reaction of compound (55) and compound (56).

This reaction is performed, for example, by reacting compound (55) and compound (56) in the presence of a metal catalyst and a base in an inert solvent. This reaction can be performed in the presence of a ligand, and further, can also be performed under microwave irradiation. This reaction is preferably performed under an inert gas atmosphere. The amount of compound (56) to be used is generally 0.5 to 10 equivalents, preferably 0.8 to 5 equivalents, relative to compound (55).

Examples of the above-mentioned "metal catalyst" include copper(I) iodide, copper(I) bromide, and copper(II) oxide. The amount of the "metal catalyst" to be used is generally 0.001 to 20 equivalents, preferably 0.01 to 10 equivalents, relative to compound (55).

Examples of the above-mentioned "base" include "basic bases", "aromatic bases", and "tertiary amines". The amount of the "base" to be used is generally 0.5 to 50 equivalents, preferably 0.8 to 20 equivalents, relative to compound (55).

Examples of the above-mentioned "ligand" include N,N-dimethylcyclohexane-1,2-diamine, and N,N-dimethylglycine. The amount of the "ligand" to be used is generally 0.001 to 20 equivalents, preferably 0.01 to 10 equivalents, relative to compound (55).

Examples of the above-mentioned "inert solvent" include "nitriles", "ethers", "amides", "aromatic hydrocarbons", and "halogenated hydrocarbons".

Examples of the above-mentioned "inert gas" include nitrogen gas, and argon gas.

The reaction temperature is generally −20° C. to 300° C., preferably 0° C. to 200° C.

The reaction time is generally 0.1 hr to 100 hr, preferably 0.5 hr to 48 hr.

<Reaction Scheme 14>

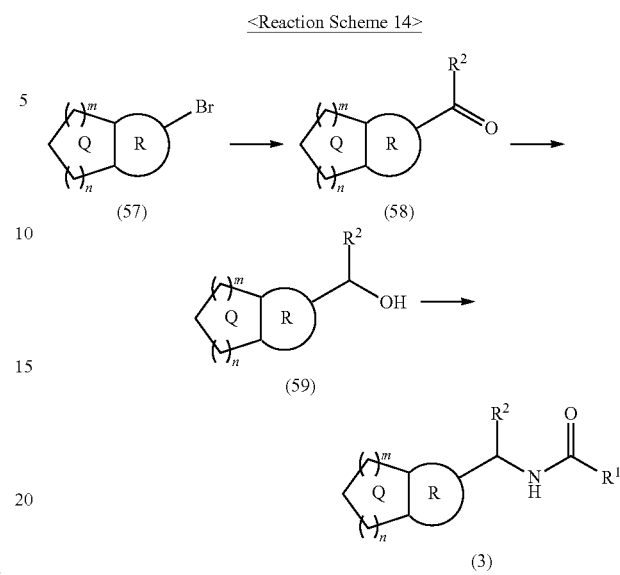

The production method of compound (3) is explained below.

wherein each symbol is as defined above.

Compound (58) can be produced, for example, by a vinyl etherification reaction of compound (57) and subsequent hydrolysis reaction.

This reaction is performed in the same manner as in the method for producing compound (20) from compound (29) in Reaction Scheme 5.

Compound (59) can be produced, for example, by a reduction reaction of compound (58).

This reaction is performed in the same manner as in the method for producing compound (2) from compound (20) in Reaction Scheme 4.

Compound (3) can be produced, for example, by a Ritter reaction of compound (59).

This reaction is performed in the same manner as in the method for producing compound (I) from compound (2) in Reaction Scheme 1.

<Reaction Scheme 15>

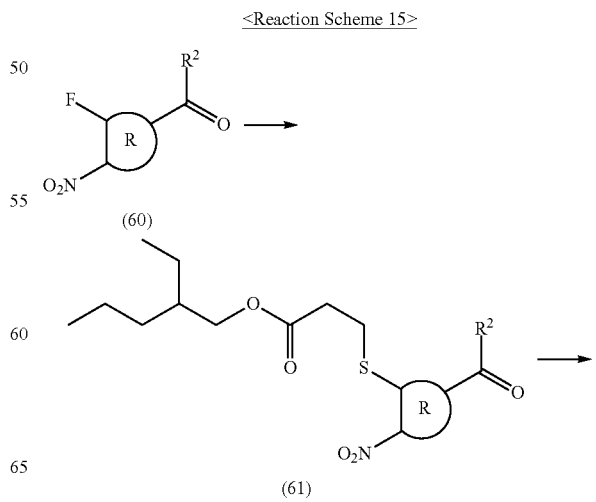

-continued

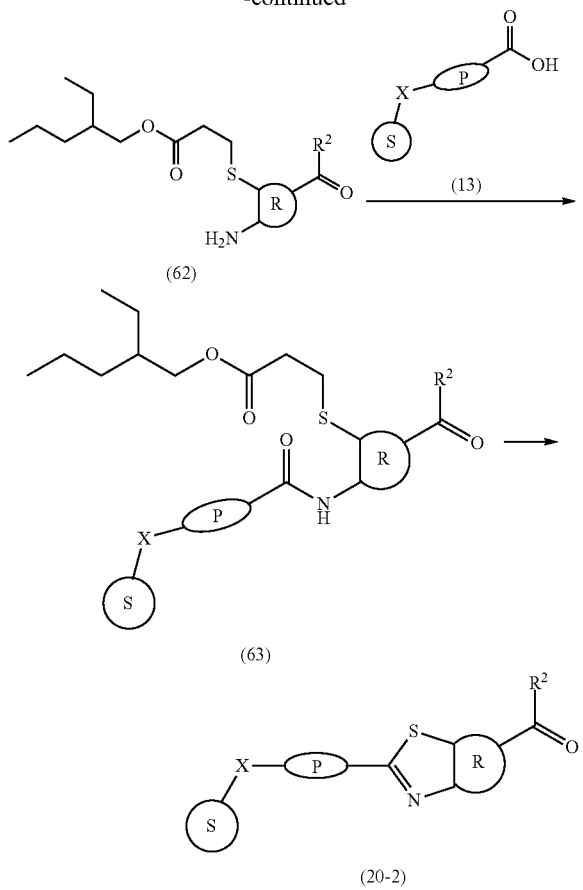

The production method of compound (20-2) encompassed in compound (20) is explained below.
wherein each symbol is as defined above.

Compound (61) can be produced, for example, by a coupling reaction of compound (60) and 2-ethylhexyl 3-sulfanylpropanoate.

This reaction is performed by reacting compound (60) and 2-ethylhexyl 3-sulfanylpropanoate in the presence of a base in an inert solvent. The amount of 2-ethylhexyl 3-sulfanylpropanoate to be used is generally 0.5 to 20 equivalents, preferably 0.8 to 10 equivalents, relative to compound (60).

Examples of the above-mentioned "base" include "basic salts", "aromatic amines", and "tertiary amines". The amount of the base to be used is generally 0.5 to 20 equivalents, preferably 0.8 to 10 equivalents, relative to compound (60).

Examples of the above-mentioned "inert solvent" include "amides", "ethers", "alcohols", and "halogenated hydrocarbons".

The reaction temperature is generally −20° C. to 200° C., preferably 0° C. to 150° C.

The reaction time is generally 0.1 hr to 40 hr, preferably 0.5 hr to 24 hr.

Compound (62) can be produced, for example, by a reduction reaction of compound (61).

This reaction is performed by reacting compound (61) in the presence of a metal in an inert solvent. This reaction can also be performed in the presence of an acid or an inorganic salt.

Examples of the above-mentioned "metal" include reduced iron, and iron sulfate. The amount of the metal to be used is generally 0.5 to 20 equivalents, preferably 0.8 to 10 equivalents, relative to compound (61).

Examples of the above-mentioned "acid or inorganic salt" include hydrochloric acid, and ammonium chloride. The amount of the "acid or inorganic salt" to be used is generally 0.5 to 20 equivalents, preferably 0.8 to 10 equivalents, relative to compound (61).

Examples of the above-mentioned "inert solvent" include water, "amides", "ethers", and "alcohols". Two or more kinds of these "inert solvents" may be used in a mixture at an appropriate ratio. As the above-mentioned "inert solvent", water-containing "alcohols" are preferable.

The reaction temperature is generally −20° C. to 200° C., preferably 0° C. to 150° C.

The reaction time is generally 0.1 hr to 100 hr, preferably 0.5 hr to 50 hr.

Compound (63) can be produced, for example, by an amidation reaction of compound (62) and compound (13).

This reaction is performed in the same manner as in the method for producing compound (14) in Reaction Scheme 2.

Compound (20-2) can be produced, for example, by a ring closure reaction of compound (63).

This reaction is performed by reacting compound (63) with metal alkoxide and acid in an inert solvent.

Examples of the above-mentioned "metal alkoxides" include sodium methoxide, and sodium ethoxide. The amount of the "metal alkoxides" to be used is generally 0.5 to 20 equivalents, preferably 0.8 to 10 equivalents, relative to compound (63).

Examples of the above-mentioned "acid" include trifluoroacetic acid, and trifluoromethanesulfonic acid. The amount of the "acid" to be used is generally 0.5 to 20 equivalents, preferably 0.8 to 10 equivalents, relative to compound (63).

Examples of the above-mentioned "inert solvent" include "alcohols", "ethers", "aromatic hydrocarbons", and "halogenated hydrocarbons". Two or more kinds of these "inert solvents" may be used in a mixture at an appropriate ratio.

The reaction temperature is generally −20° C. to 200° C., preferably 0° C. to 150° C.

The reaction time is generally 0.1 hr to 100 hr, preferably 0.5 hr to 50 hr.

The production method of compound (20-3) encompassed in compound (20) is explained below.

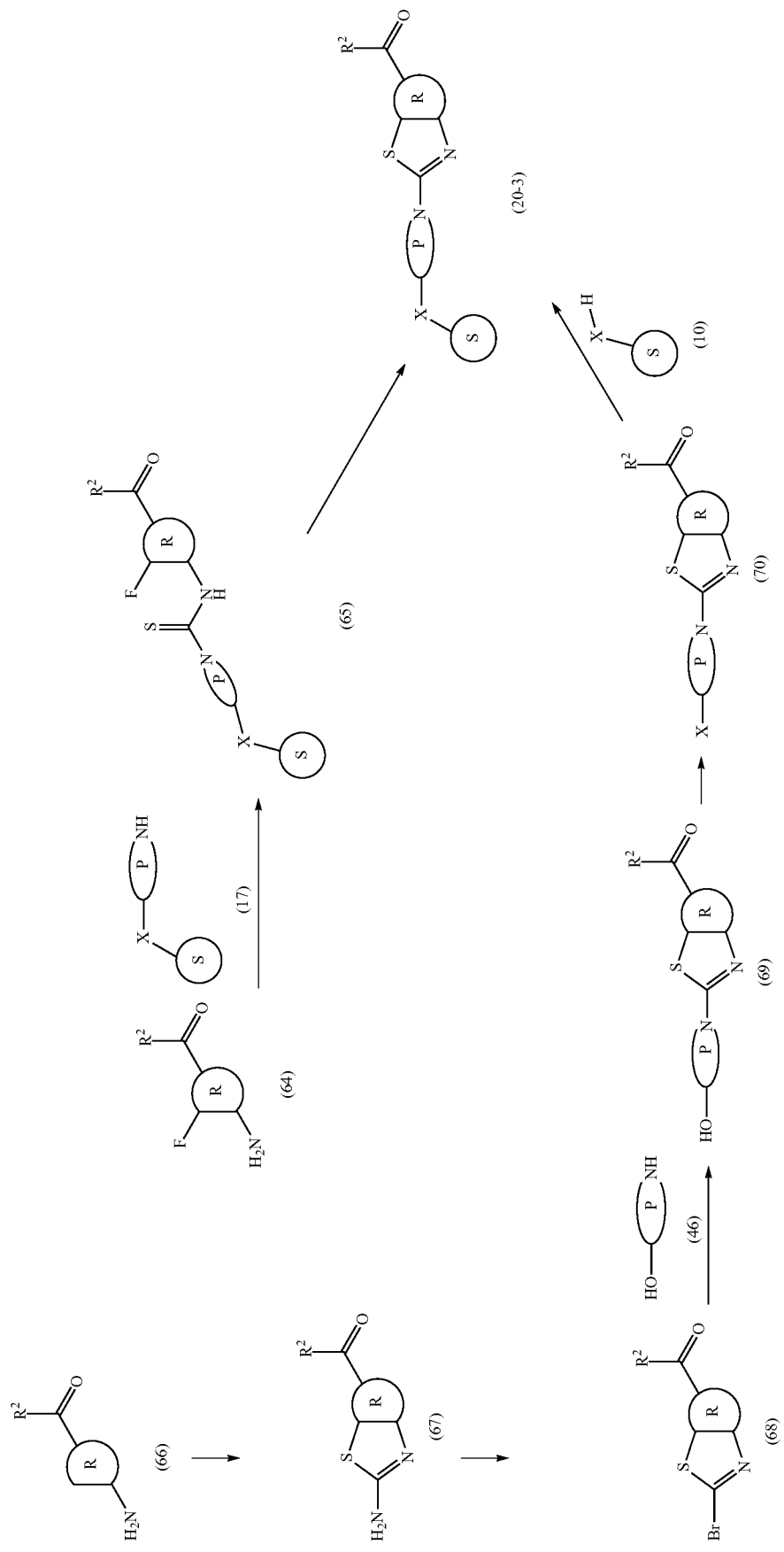
<Reaction Scheme 16> wherein each symbol is as defined above.

Compound (65) can be produced, for example, by a thioureation reaction of compound (64) and compound (17).

This reaction is performed by reacting compound (64) and compound (17) in the presence of a thioureating agent in an inert solvent. The amount of compound (17) to be used is generally 0.5 to 20 equivalents, preferably 0.8 to 10 equivalents, relative to compound (64).

Examples of the above-mentioned "thioureating agent" include di-1H-imidazol-1-ylmethanethion, and thiophosgene. The amount of the "thioureating agent" to be used is generally 0.5 to 20 equivalents, preferably 0.8 to 10 equivalents, relative to compound (64).

Examples of the above-mentioned "inert solvent" include "nitriles", "amides", "aromatic hydrocarbons", "ethers", and "halogenated hydrocarbons". Two or more kinds of these "inert solvents" may be used in a mixture at an appropriate ratio.

The reaction temperature is generally −20° C. to 150° C., preferably 0° C. to 100° C.

The reaction time is generally 0.1 hr to 100 hr, preferably 0.5 hr to 50 hr.

Compound (20-3) can be produced, for example, by a ring closure reaction of compound (65).

This reaction is performed by reacting compound (65) in the presence of a base in an inert solvent.

Examples of the above-mentioned "base" include "basic salts". Of these, cesium carbonate, or potassium carbonate is preferable. The amount of the "base" to be used is generally 0.5 to 20 equivalents, preferably 0.8 to 10 equivalents, relative to compound (65).

Examples of the above-mentioned "inert solvent" include "nitriles", "amides", "ethers", "aromatic hydrocarbons", and "halogenated hydrocarbons". Two or more kinds of these "inert solvents" may be used in a mixture at an appropriate ratio. As the above-mentioned "inert solvent", acetonitrile or DMF is preferable.

The reaction temperature is generally −20° C. to 150° C., preferably 0° C. to 100° C.

The reaction time is generally 0.1 hr to 100 hr, preferably 0.5 hr to 50 hr.

Compound (67) can be produced, for example, by a ring closure reaction of compound (66).

This reaction is performed by reacting compound (66) in the presence of bromine and potassium thiocyanate in an inert solvent.

The amount of the above-mentioned "bromine" to be used is generally 0.5 to 20 equivalents, preferably 0.8 to 10 equivalents, relative to compound (66).

The amount of the above-mentioned "potassium thiocyanate" to be used is generally 0.5 to 20 equivalents, preferably 0.8 to 10 equivalents, relative to compound (66).

Examples of the above-mentioned "inert solvent" include "organic acids". As the above-mentioned "inert solvent", acetic acid is preferable.

The reaction temperature is generally −20° C. to 150° C., preferably 0° C. to 100° C.

The reaction time is generally 0.1 hr to 100 hr, preferably 0.5 hr to 50 hr.

Compound (68) can be produced, for example, by a bromination reaction of compound (67).

This reaction is performed by reacting compound (67) in the presence of nitrous acid ester and a brominating agent in an inert solvent.

Examples of the above-mentioned "nitrous acid ester" include 1-pentyl nitrite. The amount of the "nitrous acid ester" to be used is generally 0.5 to 20 equivalents, preferably 0.8 to 10 equivalents, relative to compound (67).

Examples of the above-mentioned "brominating agent" include copper(II) bromide, and bromine. The amount of the "brominating agent" to be used is generally 0.5 to 20 equivalents, preferably 0.8 to 10 equivalents, relative to compound (67).

Examples of the above-mentioned "inert solvent" include "nitriles", "amides", "ethers", "aromatic hydrocarbons", and "halogenated hydrocarbons". Two or more kinds of these "inert solvents" may be used in a mixture at an appropriate ratio. As the above-mentioned "inert solvent", acetonitrile is preferable.

The reaction temperature is generally −20° C. to 150° C., preferably 0° C. to 100° C.

The reaction time is generally 0.1 hr to 100 hr, preferably 0.5 hr to 50 hr.

Compound (69) can be produced, for example, by a substitution reaction of compound (68) and compound (46).

This reaction is performed in the same manner as in the method for producing compound (I-2) from compound (16) in Reaction Scheme 3.

Compound (70) can be produced, for example, by a sulfonylation reaction of compound (69).

This reaction is performed in the same manner as in the method for producing compound (9) from compound (8) in Reaction Scheme 1.

As shown in Reaction Scheme 16, compound (20-3) can also be produced, for example, by a substitution reaction of compound (70) and compound (10).

This reaction is performed in the same manner as in the method for producing compound (I) from compound (9) in Reaction Scheme 1.

The production method of compound (29-2) encompassed in compound (29) is explained below.

<Reaction Scheme 17>

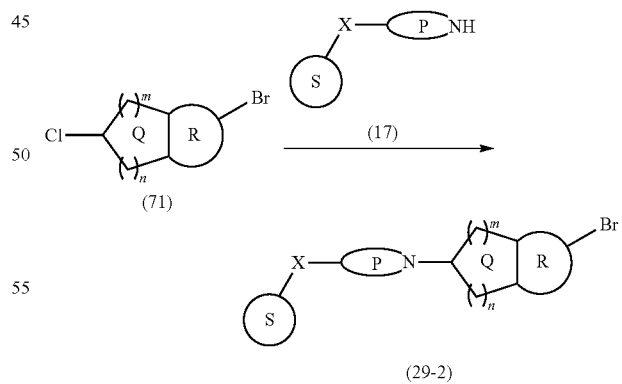

wherein each symbol is as defined above.

Compound (29-2) can be produced, for example, by a substitution reaction of compound (71) and compound (17).

This reaction is performed in the same manner as in the method for producing compound (I-2) from compound (16) in Reaction Scheme 3.

<Reaction Scheme 18>

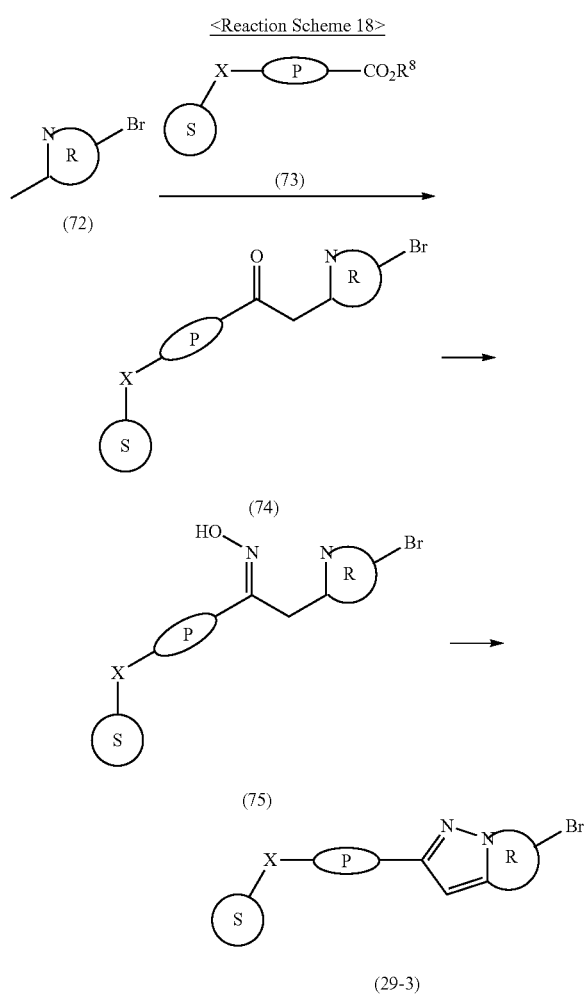

The production method of compound (29-3) encompassed in compound (29) is explained below.
wherein $R^8$ is a substituent, and other symbols are each as defined above.

Compound (74) can be produced, for example, by a substitution reaction of compound (72) and compound (73). This reaction is performed, for example, by reacting compound (72) and compound (73) in the presence of an organic metal reagent in an inert solvent. The amount of compound (73) to be used is generally 0.5 to 10 equivalents, preferably 0.8 to 5 equivalents, relative to compound (72).

Examples of the above-mentioned "organic metal reagent" include "organic magnesiums" (e.g., methylmagnesium bromide, methylmagnesium chloride), "organic lithiums" (e.g., methyllithium), "metal amides" (e.g., lithium bis(trimethylsilyl)amide, and sodium bis(trimethylsilyl)amide. The amount of the "organic metal reagent" to be used is generally 0.5 to 20 equivalents, preferably 0.8 to 10 equivalents, relative to compound (72).

Examples of the above-mentioned "inert solvent" include "aromatic hydrocarbons", "saturated hydrocarbons", "ethers", and "halogenated hydrocarbons". Two or more kinds of these "inert solvents" may be used in a mixture at an appropriate ratio. As the above-mentioned "inert solvent", THF is preferable.

The reaction temperature is generally −78° C. to 150° C., preferably −20° C. to 100° C.

The reaction time is generally 0.1 hr to 48 hr, preferably 0.5 hr to 24 hr.

Compound (75) can be produced, for example, by an oximation reaction of compound (74).

This reaction is performed in the same manner as in the method for producing compound (21) in Reaction Scheme 4.

Compound (29-3) can be produced, for example, by a ring closure reaction of compound (75).

This reaction is performed, for example, by reacting compound (75) in the presence of acid anhydride and a base in an inert solvent. This reaction can also be performed in the presence of a metal.

Examples of the above-mentioned "acid anhydride" include trifluoroacetic anhydride, and trifluoromethanesulfonic anhydride. The amount of the "acid anhydride" to be used is generally 0.5 to 20 equivalents, preferably 0.8 to 10 equivalents, relative to compound (75).

Examples of the above-mentioned "base" include "tertiary amines". The amount of the "base" to be used is generally 0.5 to 20 equivalents, preferably 0.8 to 10 equivalents, relative to compound (75).

Examples of the above-mentioned "metal" include iron (II) chloride, and iron(II) bromide. The amount of the "metal" to be used is generally 0.001 to 10 equivalents, preferably 0.01 to 5 equivalents, relative to compound (75).

Examples of the above-mentioned "inert solvent" include "aromatic hydrocarbons", "saturated hydrocarbons", "ethers", and "halogenated hydrocarbons". Two or more kinds of these "inert solvents" may be used in a mixture at an appropriate ratio.

The reaction temperature is generally −78° C. to 150° C., preferably −20° C. to 100° C.

The reaction time is generally 0.1 hr to 48 hr, preferably 0.5 hr to 24 hr.

<Reaction Scheme 19>

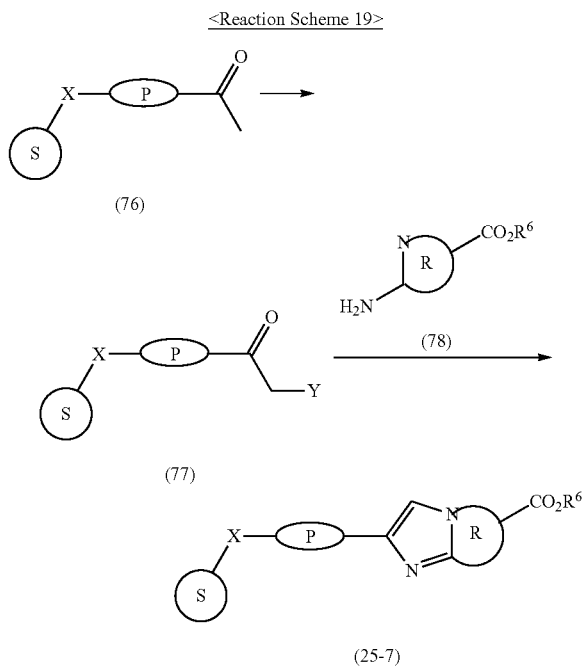

The production method of compound (25-7) encompassed in compound (25) is explained below.
wherein each symbol is as defined above.

Compound (77) can be produced, for example, by halogenation reaction of compound (76).

This reaction is performed, for example, by reacting compound (76) in the presence of a halogenating agent in an inert solvent.

Examples of the above-mentioned "halogenating agent" include N-chlorosuccinimide, N-bromosuccinimide, bromine, and tetrabutylammonium tribromide. The amount of the "halogenating agent" to be used is generally 0.5 to 20 equivalents, preferably 0.8 to 10 equivalents, relative to compound (76).

Examples of the above-mentioned "inert solvent" include "aromatic hydrocarbons", "saturated hydrocarbons", "nitriles", and "halogenated hydrocarbons". Two or more kinds of these "inert solvents" may be used in a mixture at an appropriate ratio.

The reaction temperature is generally −78° C. to 150° C., preferably −20° C. to 100° C.

The reaction time is generally 0.1 hr to 48 hr, preferably 0.5 hr to 24 hr.

Compound (25-7) can be produced, for example, by a cyclization reaction of compound (77) and compound (78).

This reaction is performed, for example, by reacting compound (77) and compound (78) in the presence of a base in an inert solvent. The amount of compound (78) to be used is generally 0.5 to 10 equivalents, preferably 0.8 to 5 equivalents, relative to compound (77).

Examples of the above-mentioned "base" include "tertiary amines". The amount of the "base" to be used is generally 0.5 to 20 equivalents, preferably 0.8 to 10 equivalents, relative to compound (77).

Examples of the above-mentioned "inert solvent" include "aromatic hydrocarbons", "saturated hydrocarbons", "nitriles", and "halogenated hydrocarbons". Two or more kinds of these "inert solvents" may be used in a mixture at an appropriate ratio.

The reaction temperature is generally −78° C. to 150° C., preferably −20° C. to 100° C.

The reaction time is generally 0.1 hr to 48 hr, preferably 0.5 hr to 24 hr.

The production method of compound (8-1) encompassed in compound (8) is explained below.

<Reaction Scheme 20>

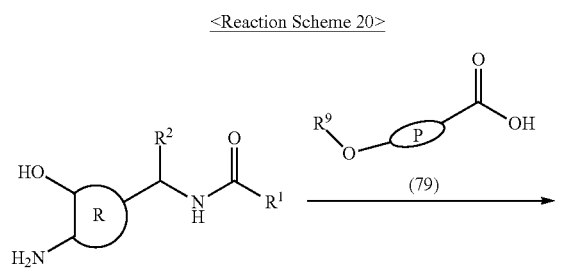

(12)

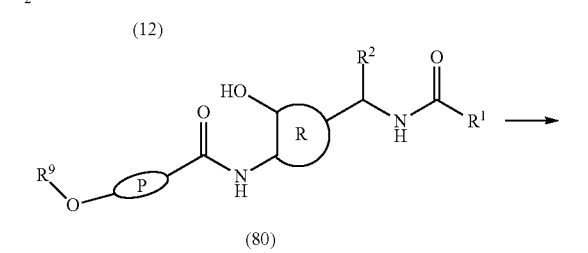

(80)

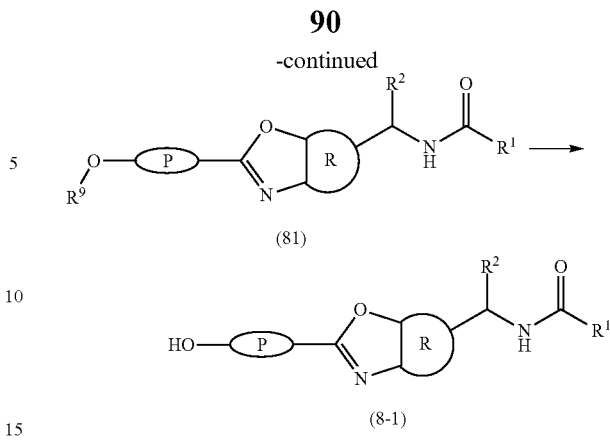

(81)

(8-1)

wherein each symbol is as defined above, and $R^9$ is a hydroxyl-protecting group.

Compound (80) can be produced, for example, by an amidation reaction of compound (12) and compound (79).

This reaction is performed in the same manner as in the method for producing compound (14) in Reaction Scheme 2.

Compound (81) can be produced, for example, by a ring closure reaction of compound (80).

This reaction is performed in the same manner as in the method for producing compound (I-1) in Reaction Scheme 2.

Compound (8-1) can be produced, for example, by deprotection reaction of compound (81).

This reaction can be performed according to a method known per se, for example, the method described in Protective Groups in Organic Synthesis, John Wiley and Sons (1980) and the like.

<Reaction Scheme 21>

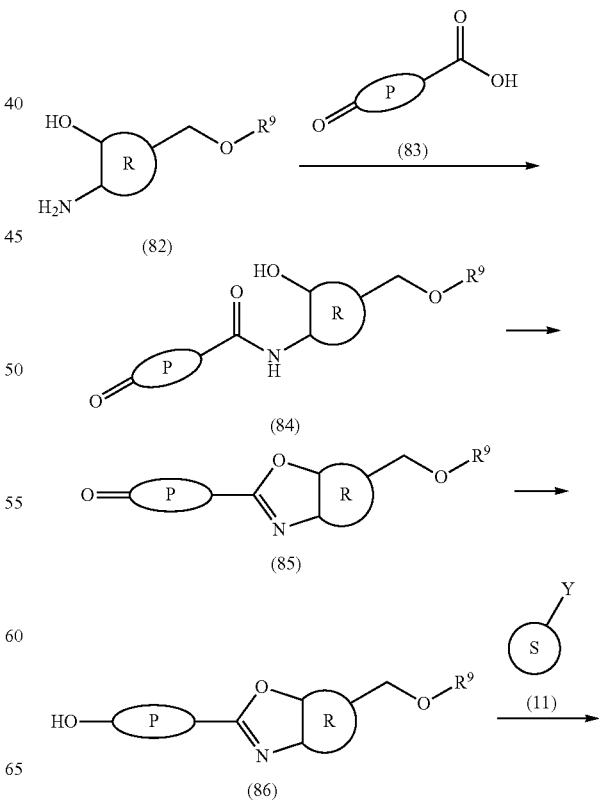

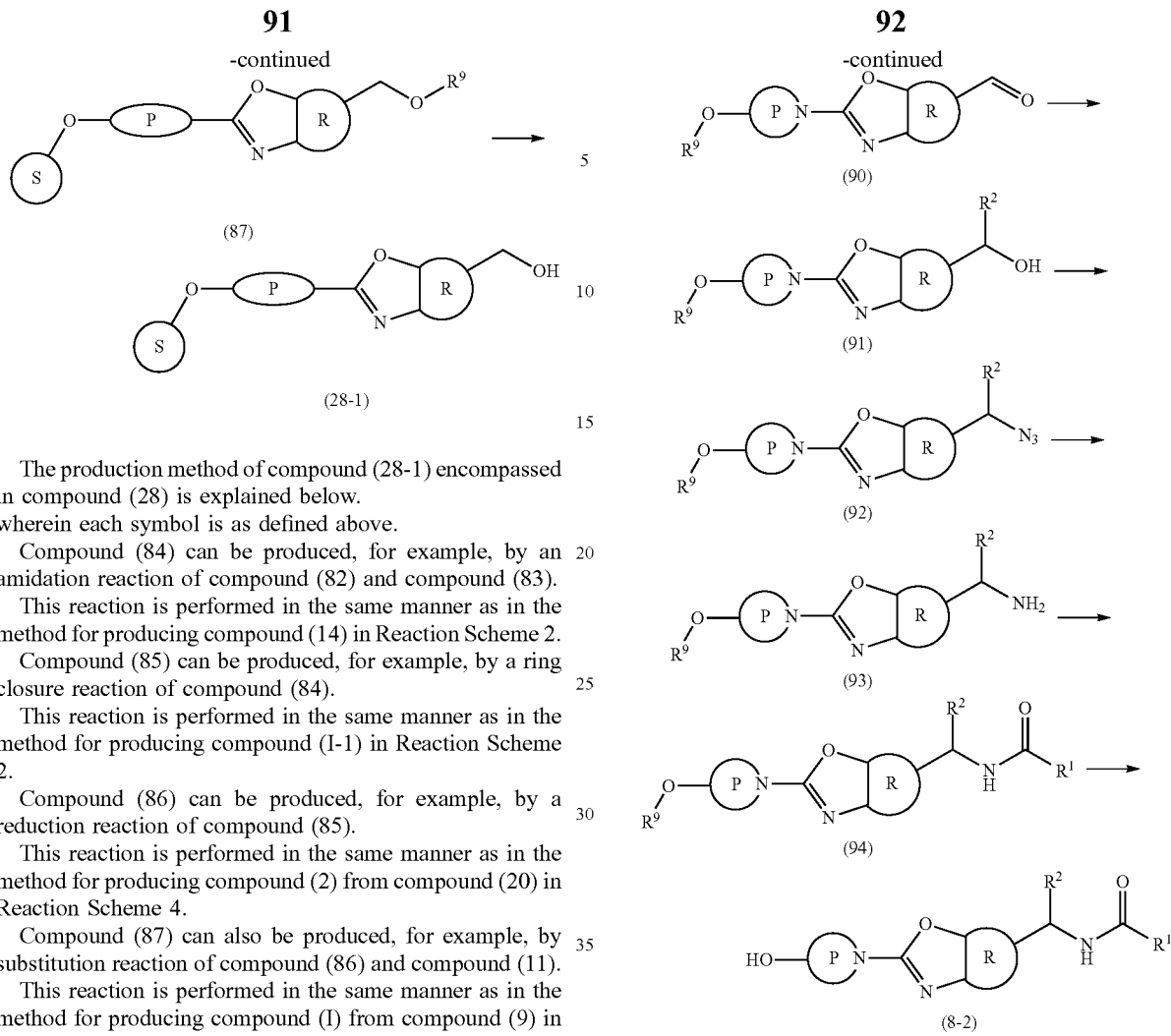

The production method of compound (28-1) encompassed in compound (28) is explained below.
wherein each symbol is as defined above.

Compound (84) can be produced, for example, by an amidation reaction of compound (82) and compound (83).

This reaction is performed in the same manner as in the method for producing compound (14) in Reaction Scheme 2.

Compound (85) can be produced, for example, by a ring closure reaction of compound (84).

This reaction is performed in the same manner as in the method for producing compound (I-1) in Reaction Scheme 2.

Compound (86) can be produced, for example, by a reduction reaction of compound (85).

This reaction is performed in the same manner as in the method for producing compound (2) from compound (20) in Reaction Scheme 4.

Compound (87) can also be produced, for example, by substitution reaction of compound (86) and compound (11).

This reaction is performed in the same manner as in the method for producing compound (I) from compound (9) in Reaction Scheme 1.

Compound (28-1) can be produced, for example, by deprotection reaction of compound (87).

This reaction can be performed according to a method known per se, for example, the method described in Protective Groups in Organic Synthesis, John Wiley and Sons (1980) and the like.

<Reaction Scheme 22>

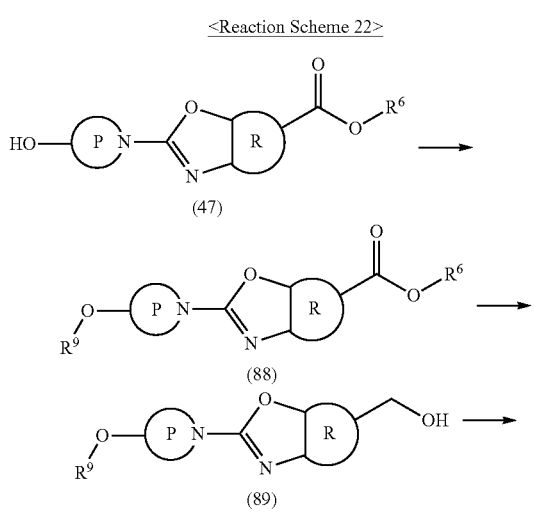

The production method of compound (8-2) encompassed in compound (8) is explained below.
wherein each symbol is as defined above.

Compound (88) can also be produced, for example, by protection reaction of compound (47).

This reaction can be performed according to a method known per se, for example, the method described in Protective Groups in Organic Synthesis, John Wiley and Sons (1980) and the like.

Compound (89) can be produced, for example, by a reduction reaction of compound (88).

This reaction is performed in the same manner as in the method for producing compound (28) in Reaction Scheme 5.

Compound (90) can be produced, for example, by an oxidation reaction of compound (89).

This reaction is performed in the same manner as in the method for producing compound (22) from compound (28) in Reaction Scheme 5.

Compound (91) can be produced, for example, by a substitution reaction of compound (90).

This reaction is performed in the same manner as in the method for producing compound (2) from compound (22) in Reaction Scheme 4.

Compound (92) can be produced, for example, by a azidation reaction of compound (91).

This reaction is performed in the same manner as in the method for producing compound (24) from compound (2) in Reaction Scheme 4.

Compound (93) can be produced, for example, by a reduction reaction of compound (92).

This reaction is performed in the same manner as in the method for producing compound (1) from compound (24) in Reaction Scheme 4.

Compound (94) can be produced, for example, by an amidation reaction of compound (93).

This reaction is performed in the same manner as in the method for producing compound (I) from compound (1) in Reaction Scheme 1.

Compound (8-2) can also be produced, for example, by deprotection reaction of compound (94).

This reaction can be performed according to a method known per se, for example, the method described in Protective Groups in Organic Synthesis, John Wiley and Sons (1980) and the like.

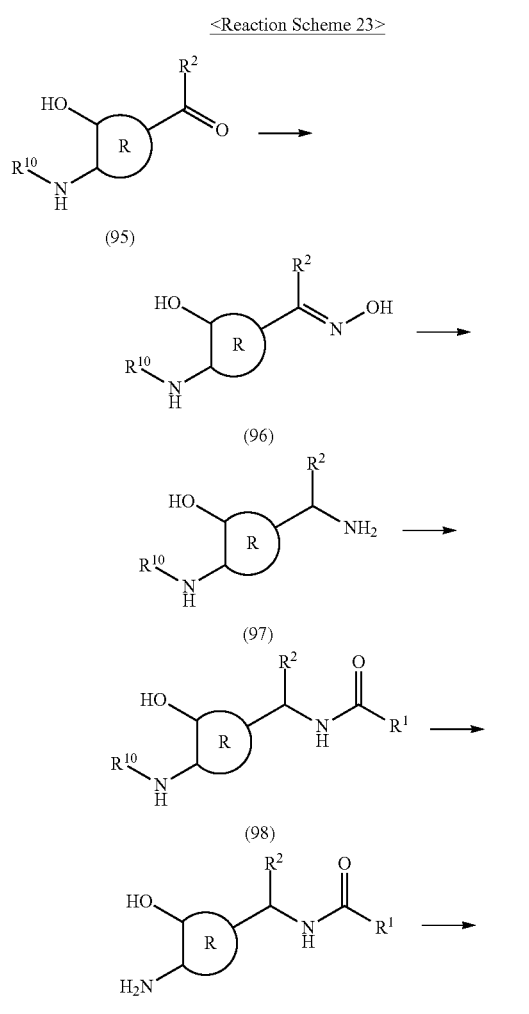

wherein $R^{10}$ is an amine-protecting group, and other symbols are each as defined above.

Compound (96) can be produced, for example, by an oximation reaction of compound (95).

This reaction is performed in the same manner as in the method for producing compound (21) in Reaction Scheme 4.

Compound (97) can be produced, for example, by a reduction reaction of compound (96).

This reaction is performed in the same manner as in the method for producing compound (1) from compound (21) in Reaction Scheme 4.

Compound (98) can be produced, for example, by an amidation reaction of compound (97).

This reaction is performed in the same manner as in the method for producing compound (I) from compound (1) in Reaction Scheme 1.

Compound (12) can also be produced, for example, by deprotection reaction of compound (98).

This reaction can be performed according to a method known per se, for example, the method described in Protective Groups in Organic Synthesis, John Wiley and Sons (1980) and the like.

Compound (15) can be produced, for example, by a ring closure reaction of compound (12).

This reaction is performed, for example, by reacting compound (12) in the presence of potassium O-ethyl carbonodithioate and a base in an inert solvent. The amount of The above-mentioned "potassium O-ethyl carbonodithioate" to be used is generally 0.5 to 20 equivalents, preferably 0.8 to 10 equivalents, relative to compound (12).

Examples of the above-mentioned "base" include "aromatic amines" and "tertiary amines". As the above-mentioned "base", pyridine is preferable. The amount of the "base" to be used is generally 0.5 equivalent to a solvent amount, preferably 0.8 equivalent to a solvent amount, relative to compound (12).

Examples of the above-mentioned "inert solvent" include "aromatic hydrocarbons", "saturated hydrocarbons", "nitriles", "amides" and "halogenated hydrocarbons". Two or more kinds of these "inert solvents" may be used in a mixture at an appropriate ratio. As the above-mentioned "inert solvent", pyridine is preferable.

The reaction temperature is generally −78° C. to 200° C., preferably −20° C. to 150° C.

The reaction time is generally 0.1 hr to 48 hr, preferably 0.5 hr to 24 hr.

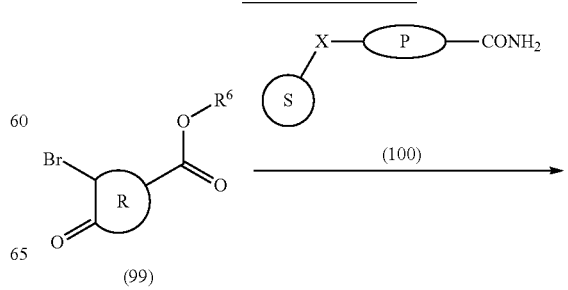

The production method of compound (15) is explained below.

-continued

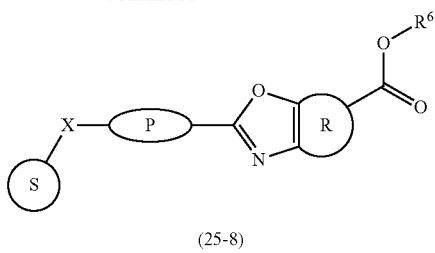

(25-8)

The production method of compound (25-8) encompassed in compound (25) is explained below.

wherein each symbol is as defined above.

Compound (25-8) can be produced, for example, by a cyclization reaction of compound (99) and compound (100).

This reaction is performed, for example, by reacting compound (99) and compound (100) in an inert solvent. This reaction can be performed in the presence of a base, and can also be performed under microwave irradiation. The amount of compound (100) to be used is generally 0.5 to 10 equivalents, preferably 0.8 to 5 equivalents, relative to compound (99).

Examples of the above-mentioned "inert solvent" include "nitriles", "amides", "aromatic hydrocarbons" and "halogenated hydrocarbons".

Examples of the above-mentioned "base" include "basic salts", "aromatic amines", and "tertiary amines". The above-mentioned The amount of the "base" to be used is generally 0.5 to 20 equivalents, preferably 0.8 to 10 equivalents, relative to compound (99).

The reaction temperature is generally −78° C. to 300° C., preferably −20° C. to 200° C.

The reaction time is generally 0.1 hr to 48 hr, preferably 0.5 hr to 24 hr.

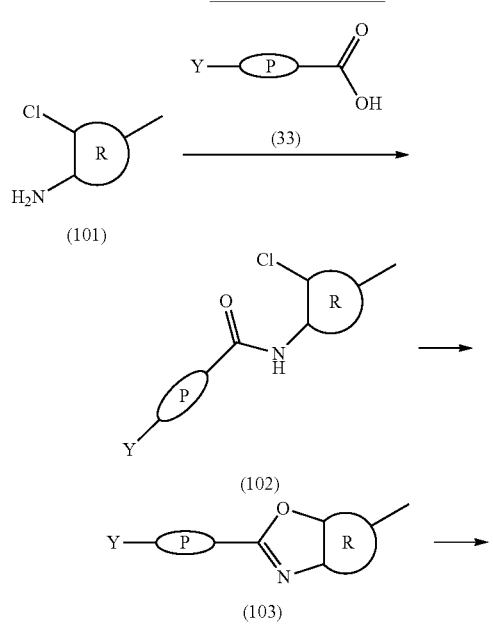

-continued

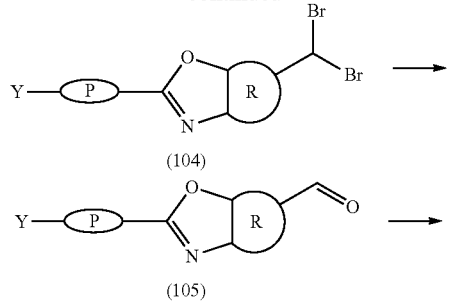

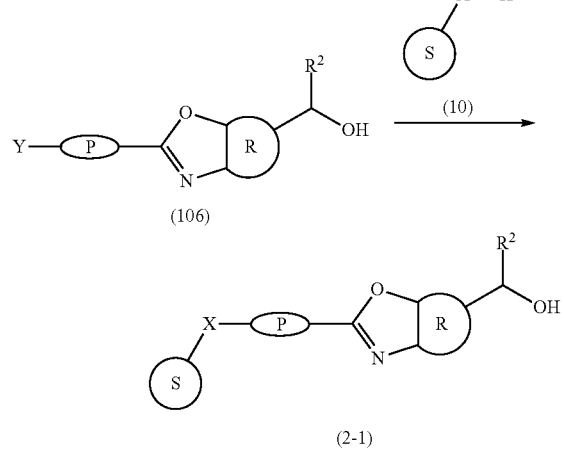

The production method of compound (2-1) encompassed in compound (2) is explained below.

wherein each symbol is as defined above.

Compound (102) can be produced, for example, by an amidation reaction of compound (101) and compound (33).

This reaction is performed in the same manner as in the method for producing compound (14) in Reaction Scheme 2.

Compound (103) can be produced, for example, by a ring closure reaction of compound (102).

This reaction is performed, for example, by reacting compound (102) in the presence of a dehydrating agent in an inert solvent. This reaction can also be performed in the presence of an additive.

Examples of the above-mentioned "dehydrating agent" include phosphorus oxychloride, phosphorus pentaoxide, phosphoric acid, polyphosphoric acid, and concentrated sulfuric acid. The amount of the "dehydrating agent" to be used is generally 0.01 to 10 equivalents, preferably 0.1 to 8 equivalents, relative to compound (102).

Examples of the above-mentioned "inert solvent" include "aromatic hydrocarbons", "saturated hydrocarbons", "ethers", "esters", "amides", "nitriles", and "halogenated hydrocarbons". Two or more kinds of these "inert solvents" may be used in a mixture at an appropriate ratio.

Examples of the above-mentioned "additive" include trimethylsilanol, hexamethylsilyl ether, copper(II) acetate and copper(II) oxide. The amount of the "additive" to be used is generally 0.5 to 10 equivalents, preferably 0.8 to 5 equivalents, relative to compound (102).

The reaction temperature is generally −70° C. to 300° C., preferably −20° C. to 200° C.

The reaction time is generally 0.1 hr to 100 hr, preferably 0.1 hr to 40 hr.

Compound (104) can be produced, for example, by halogenation reaction of compound (103).

This reaction is performed, for example, by reacting compound (103) in the presence of a halogenating agent in an inert solvent.

Examples of the above-mentioned "halogenating agent" include N-chlorosuccinimide, N-bromosuccinimide, bromine, and tetrabutylammonium tribromide. The amount of the "halogenating agent" to be used is generally 0.5 to 20 equivalents, preferably 0.8 to 10 equivalents, relative to compound (103).

Examples of the above-mentioned "inert solvent" include "aromatic hydrocarbons", "saturated hydrocarbons", "nitriles", and "halogenated hydrocarbons". Two or more kinds of these "inert solvents" may be used in a mixture at an appropriate ratio.

The reaction temperature is generally −78° C. to 150° C., preferably −20° C. to 100° C.

The reaction time is generally 0.1 hr to 48 hr, preferably 0.5 hr to 24 hr.

Compound (105) can be produced, for example, by hydrolysis reaction of compound (104).

This reaction is performed, for example, by reacting compound (104) in the presence of a base in an inert solvent.

Examples of the above-mentioned "base" include "basic salts", "aromatic amines", and "tertiary amines". The amount of the "base" to be used is generally 0.5 to 20 equivalents, preferably 0.8 to 10 equivalents, relative to compound (104).

Examples of the above-mentioned "inert solvent" include water, "aromatic hydrocarbons", "saturated hydrocarbons", "ethers", "esters", "amides", "nitriles", and "halogenated hydrocarbons". Two or more kinds of these "inert solvents" may be used in a mixture at an appropriate ratio.

The reaction temperature is generally −70° C. to 200° C., preferably −20° C. to 150° C.

The reaction time is generally 0.1 hr to 100 hr, preferably 0.1 hr to 40 hr.

Compound (106) can also be produced, for example, by a substitution reaction of compound (105).

This reaction is performed in the same manner as in the method for producing compound (2) in Reaction Scheme 4.

Compound (2-1) can also be produced, for example, a substitution reaction of compound (106) and compound (10).

This reaction is performed in the same manner as in the method for producing compound (I) from compound (9) in Reaction Scheme 1.

<Reaction Scheme 26>

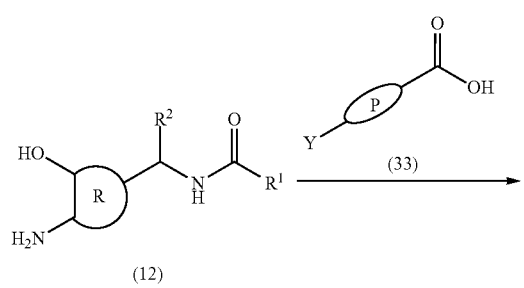

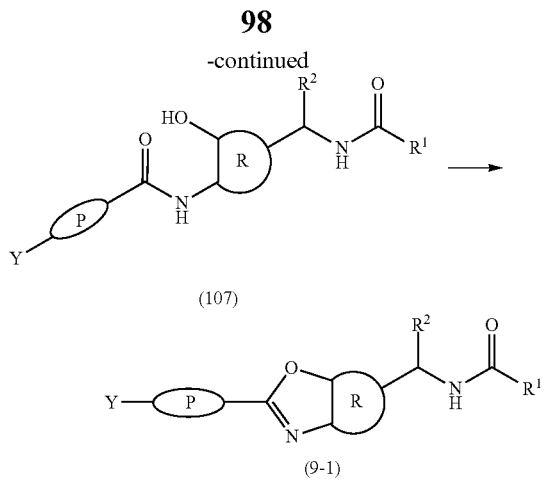

The production method of compound (9-1) encompassed in compound (9) is explained below.
wherein each symbol is as defined above.

Compound (107) can be produced, for example, by an amidation reaction of compound (12) and compound (33).

This reaction is performed in the same manner as in the method for producing compound (14) in Reaction Scheme 2.

Compound (9-1) can be produced, for example, by a ring closure reaction of compound (107).

This reaction is performed in the same manner as in the method for producing compound (I-1) in Reaction Scheme 2.

In addition, a compound represented by the formula (I') can be produced in the same manner as in the production method of compound (I) explained above.

In compound (I) thus obtained, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production methods can be isolated and purified according to a known means, for example, solvent extraction, pH control of solution, phase transfer, crystallization, recrystallization, chromatography.

When compound (I) contains an optical isomer, a stereoisomer, a regioisomer or a rotamer, these are also encompassed in compound (I), and can be obtained as a single product according to synthesis methods and separation methods known per se. For example, when compound (I) contains an optical isomer, an optical isomer resolved from this compound is also encompassed in compound (I).

The optical isomer can be produced according to a method known per se.

Compound (I) may be a crystal.

Crystals of compound (I) (hereinafter sometimes to be abbreviated as the crystals of the present invention) can be produced by crystallization according to crystallization methods known per se.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bonded silica gel. The ratios of elution solvents are volume mixing ratios, unless otherwise specified.

In Examples, the following abbreviations are used.
THF: tetrahydrofuran
DMF: N,N-dimethylformamide
WSCD: 1-ethyl-3-(3-dimethylaminopropyl)carbodiimide hydrochloride
HATU: O-(7-azabenzotriazol-1-yl)-N,N,N',N'-tetramethyluronium hexafluorophosphate $^1$H NMR (proton nuclear magnetic resonance spectrum) was measured by Fourier-transform type NMR. For the analysis, ACD/SpecManager (trade name) and the like were used. Very mild peaks for protons such as hydroxyl group, amino group and the like are not described.

Other abbreviations used in the specification mean the following.
s: singlet
d: doublet
t: triplet
q: quartet
m: multiplet
br: broad
J: coupling constant
Hz: Hertz
CDCl$_3$: deuterated chloroform
DMSO-d$_6$: d$_6$-dimethyl sulfoxide
$^1$H NMR: proton nuclear magnetic resonance
TFA: trifluoroacetic acid MS (mass spectrum) was measured by LC/MS (liquid chromatography mass spectrometer). As the ionization method, ESI (ElectroSpray Ionization) method, or APCI (Atmospheric Pressure Chemical Ionization) method was used. As the ionization mode, either or both the positive mode (ESI+) and the negative mode (ESI−) was/were used, and the data of either of them is indicated. The data indicate those found. Generally, a molecular ion peak is observed. In the case of a compound having a tert-butoxycarbonyl group (—Boc), a peak after elimination of the tert-butoxycarbonyl group or tert-butyl group may be observed as a fragment ion. A peak after addition of sodium ion (+Na) may be observed as a fragment ion, depending on the kind of the compound. In the case of a compound having a hydroxyl group (—OH), a peak after elimination of H$_2$O may be observed as a fragment ion. In the case of a salt, a molecular ion peak or fragment ion peak of free form is generally observed.

Example 1

N-(1-(2-(3-(3-(cyclopropylmethoxy)phenoxy)azetidin-1-yl)-1,3-benzoxazol-6-yl)ethyl)acetamide A) ethyl 2-sulfanyl-1,3-benzoxazole-6-carboxylate A mixture of potassium O-ethyl carbonodithioate (6.64 g), ethyl 4-amino-3-hydroxybenzoate (5.0 g) and pyridine (50 ml) was stirred at 100° C. for 2 hr. The reaction mixture was cooled to room temperature, and acidified with 3N hydrochloric acid. The mixture was stirred at room temperature for 1 hr, the obtained solid was collected by filtration, and washed with ethanol/water to give the title compound (5.62 g).

$^1$H NMR (300 MHz, DMSO-d$_6$) δ 1.33 (3H, t, J=7.2 Hz), 4.33 (2H, q, J=6.9 Hz), 7.34 (1H, d, J=8.3 Hz), 7.80-8.05 (2H, m), 13.87-14.50 (1H, m).

B) ethyl 2-chloro-1,3-benzoxazole-6-carboxylate

A mixture of ethyl 2-sulfanyl-1,3-benzoxazole-6-carboxylate (5.62 g), DMF (1.17 ml) and thionyl chloride (18.37 ml) was stirred at 80° C. for 30 min. The reaction mixture was cooled to room temperature, and concentrated under reduced pressure. Ethyl acetate was added to the obtained residue, and the mixture was concentrated under reduced pressure. To the obtained residue was added under ice-cooling saturated aqueous sodium hydrogen carbonate solution, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (5.24 g).

$^1$H NMR (300 MHz, DMSO-d$_6$) δ 1.35 (4H, t, J=7.2 Hz), 4.36 (2H, q, J=7.2 Hz), 7.82-7.92 (1H, m), 7.98-8.11 (1H, m), 8.29 (1H, d, J=1.5 Hz).

C) 3-(cyclopropylmethoxy)phenol

A mixture of resorcinol (60 g), (bromomethyl)cyclopropane (35.9 ml), potassium carbonate (154 g) and DMF (500 ml) was stirred at room temperature overnight. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (42.4 g).

$^1$H NMR (300 MHz, DMSO-d$_6$) δ 0.22-0.34 (2H, m), 0.50-0.60 (2H, m), 1.16-1.24 (1H, m), 3.72 (2H, d, J=6.9 Hz), 6.24-6.38 (3H, m), 7.02 (1H, t, J=8.1 Hz), 9.32 (1H, s).

D) 3-(3-(cyclopropylmethoxy)phenoxy)-1-(diphenylmethyl)azetidine

A mixture of 3-(cyclopropylmethoxy)phenol (40.9 g), 1-(diphenylmethyl)azetidin-3-yl methanesulfonate (52.7 g), cesium carbonate (108 g) and DMF (400 ml) was stirred at 100° C. for 4 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (64.0 g).

$^1$H NMR (300 MHz, DMSO-d$_6$) δ 0.23-0.33 (2H, m), 0.48-0.58 (2H, m), 1.12-1.17 (1H, m), 2.91-3.00 (2H, m), 3.55-3.66 (2H, m), 3.75 (2H, d, J=7.0 Hz), 4.51 (1H, s), 4.76-4.87 (1H, m), 6.30-6.41 (2H, m), 6.44-6.51 (1H, m), 7.15-7.24 (3H, m), 7.24-7.32 (4H, m), 7.38-7.48 (4H, m).

E) ethyl 2-(3-(3-(cyclopropylmethoxy)phenoxy) azetidin-1-yl)-1,3-benzoxazole-6-carboxylate A mixture of 3-(3-(cyclopropylmethoxy)phenoxy)-1-(diphenylmethyl)azetidine (10.5 g), 20% palladium hydroxide (containing water (50%), 1.9 g), concentrated hydrochloric acid (2.7 ml), THF (100 ml) and methanol (100 ml) was stirred under a hydrogen atmosphere at room temperature for 5 hr. The reaction mixture was filtered through celite and concentrated under reduced pressure. To the obtained residue were added DMF (70 ml), ethyl 2-chloro-1,3-benzoxazole-6-carboxylate (6.15 g) and N,N-diisopropylethylamine (14.3 ml). The reaction mixture was stirred at room temperature for 4 hr, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (11.0 g).
$^1$H NMR (300 MHz, DMSO-$d_6$) δ 0.24-0.37 (2H, m), 0.49-0.63 (2H, m), 1.10-1.24 (1H, m), 1.32 (3H, t, J=7.1 Hz), 3.74-3.86 (2H, m), 4.18-4.25 (2H, m), 4.30 (2H, q, J=7.2 Hz), 4.66-4.77 (2H, m), 5.10-5.28 (1H, m), 6.38-6.49 (2H, m), 6.52-6.62 (1H, m), 7.12-7.25 (1H, m), 7.32-7.43 (1H, m), 7.82-7.89 (1H, m), 7.91-7.94 (1H, m).

F) 1-(2-(3-(3-(cyclopropylmethoxy)phenoxy)azetidin-1-yl)-1,3-benzoxazol-6-yl)ethanol To a mixture of lithium aluminum hydride (1.0 g) and THF (70 ml) was added dropwise a mixture of ethyl 2-(3-(3-(cyclopropylmethoxy)phenoxy) azetidin-1-yl)-1,3-benzoxazole-6-carboxylate (11.0 g) and THF (70 ml) under ice-cooling. The reaction mixture was stirred under ice-cooling for 30 min, and water (1.0 ml), 1N aqueous sodium hydroxide solution (1.0 ml) and water (3.0 ml) were successively added. The obtained mixture was stirred at room temperature for 30 min, filtered through celite, and the filtrate was concentrated under reduced pressure. To a mixture of the obtained residue and acetonitrile (100 ml) were added tetrapropylammonium perruthenate (0.47 g), 4-methylmorpholine 4-oxide (4.7 g) and molecular sieves 4A (15 g). The reaction mixture was stirred at room temperature for 2 hr, filtered, and the filtrate was concentrated under reduced pressure. The obtained residue was passed through a silica gel short column (hexane/ethyl acetate), and concentrated under reduced pressure. To a mixture of the obtained residue and THF (100 ml) was added dropwise methylmagnesium bromide (1.0 M THF solution, 53.9 ml) under ice-cooling. The reaction mixture was stirred under ice-cooling for 30 min, saturated aqueous ammonium chloride solution was added, and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (4.57 g).
$^1$H NMR (300 MHz, DMSO-$d_6$) δ 0.27-0.35 (2H, m), 0.52-0.61 (2H, m), 1.12-1.26 (1H, m), 1.33 (3H, d, J=6.3 Hz), 3.80 (2H, d, J=7.1 Hz), 4.15 (2H, dd, J=9.5, 4.0 Hz), 4.66 (2H, dd, J=9.1, 6.7 Hz), 4.71-4.82 (1H, m), 5.15 (1H, d, J=4.1 Hz), 5.17-5.25 (1H, m), 6.37-6.47 (2H, m), 6.52-6.61 (1H, m), 7.11-7.28 (3H, m), 7.38 (1H, s).

G) 6-(1-azidoethyl)-2-(3-(3-(cyclopropylmethoxy) phenoxy)azetidin-1-yl)-1,3-benzoxazole A mixture of 1-(2-(3-(3-(cyclopropylmethoxy)phenoxy) azetidin-1-yl)-1,3-benzoxazol-6-yl)ethanol (4.57 g), diphenylphosphoryl azide (6.6 g), DBU (5.43 ml) and toluene (50 ml) was stirred at room temperature for 2 hr. To the reaction mixture was added water, and the mixture was extracted with toluene. The obtained organic layer was washed with saturated brine, dried over anhydrous magnesium sulfate, and concentrated under reduced pressure. The obtained residue was purified by silica gel column chromatography (hexane/ethyl acetate) to give the title compound (4.0 g).
$^1$H NMR (300 MHz, DMSO-$d_6$) δ 0.27-0.35 (2H, m), 0.52-0.62 (2H, m), 1.20-1.27 (1H, m), 1.47 (3H, d, J=6.8 Hz), 3.80 (2H, d, J=7.0 Hz), 4.17 (2H, dd, J=9.5, 4.0 Hz), 4.68 (2H, dd, J=9.3, 6.5 Hz), 4.88 (1H, q, J=6.8 Hz), 5.15-5.26 (1H, m), 6.39-6.47 (2H, m), 6.57 (1H, dd, J=9.0, 1.7 Hz), 7.14-7.25 (2H, m), 7.30-7.36 (1H, m), 7.51 (1H, d, J=1.5 Hz).

H) N-(1-(2-(3-(3-(cyclopropylmethoxy)phenoxy) azetidin-1-yl)-1,3-benzoxazol-6-yl)ethyl)acetamide A mixture of 6-(1-azidoethyl)-2-(3-(3-(cyclopropylmethoxy)phenoxy)azetidin-1-yl)-1,3-benzoxazole (4.0 g), 10% palladium carbon (containing water (50%), 0.5 g) and THF (100 ml) was stirred under a hydrogen atmosphere at room temperature for 2 hr. The reaction mixture was filtered through celite and concentrated under reduced pressure. To the obtained residue were added pyridine (20 ml) and acetic anhydride (5.0 ml), and the mixture was stirred at room temperature for 30 min. The reaction mixture was concentrated under reduced pressure. The obtained residue was purified by silica gel column chromatography (NH, hexane/ethyl acetate), and crystallized from hexane/ethyl acetate to give the title compound (2.6 g).
$^1$H NMR (300 MHz, DMSO-$d_6$) δ 0.25-0.35 (2H, m), 0.50-0.62 (2H, m), 1.14-1.28 (1H, m), 1.34 (3H, d, J=7.0 Hz), 1.83 (3H, s), 3.79 (2H, d, J=7.1 Hz), 4.09-4.19 (2H, m), 4.61-4.71 (2H, m), 4.87-5.01 (1H, m), 5.15-5.27 (1H, m), 6.38-6.47 (2H, m), 6.53-6.60 (1H, m), 7.09-7.14 (1H, m), 7.16-7.28 (2H, m), 7.33-7.38 (1H, m), 8.26 (1H, d, J=8.1 Hz).

Example 1a

N-(1-(2-(3-(3-(cyclopropylmethoxy)phenoxy)azetidin-1-yl)-1,3-benzoxazol-6-yl)ethyl)acetamide (optical isomer)

A racemate (198 mg) of N-(1-(2-(3-(3-(cyclopropylmethoxy)phenoxy)azetidin-1-yl)-1,3-benzoxazol-6-yl) ethyl)acetamide was fractionated by HPLC (column: CHIRALPAK AD (trade name), 50 mmID×500 mL, Daicel Corporation, mobile phase: hexane/ethanol=500/500(v/v)) to give a compound having a shorter retention time as the title compound (95.6 mg).
$^1$H NMR (300 MHz, DMSO-$d_6$) δ 0.26-0.35 (2H, m), 0.51-0.61 (2H, m), 1.14-1.27 (1H, m), 1.34 (3H, d, J=7.0 Hz), 1.82 (3H, s), 3.79 (2H, d, J=7.0 Hz), 4.07-4.20 (2H, m), 4.60-4.70 (2H, m), 4.87-5.01 (1H, m), 5.15-5.26 (1H, m), 6.38-6.47 (2H, m), 6.53-6.61 (1H, m), 7.07-7.29 (3H, m), 7.35 (1H, d, J=1.5 Hz), 8.25 (1H, d, J=8.0 Hz).
retention time (AD) 12.934 min Example 1b N-(1-(2-(3-(3-(cyclopropylmethoxy)phenoxy)azetidin-1-yl)-1,3-benzoxazol-6-yl)ethyl)acetamide (optical isomer)

A racemate (198 mg) of N-(1-(2-(3-(3-(cyclopropylmethoxy)phenoxy)azetidin-1-yl)-1,3-benzoxazol-6-yl)

ethyl)acetamide was fractionated by HPLC (column: CHI-RALPAK AD (trade name), 50 mmIDx500 mL, Daicel Corporation, mobile phase:hexane/ethanol=500/500(v/v)) to give a compound having a longer retention time as the title compound (92.3 mg).

$^1$H NMR (300 MHz, DMSO-$d_6$) δ 0.26-0.37 (2H, m), 0.50-0.64 (2H, m), 1.13-1.26 (1H, m), 1.34 (3H, d, J=7.0 Hz), 1.83 (3H, s), 3.79 (2H, d, J=7.1 Hz), 4.08-4.21 (2H, m), 4.56-4.73 (2H, m), 4.84-5.03 (1H, m), 5.14-5.26 (1H, m), 6.38-6.47 (2H, m), 6.51-6.61 (1H, m), 7.06-7.29 (3H, m), 7.32-7.41 (1H, m), 8.25 (1H, d, J=8.1 Hz).

retention time (AD) 15.684 min

Example 2

N-(1-(2-(4-(3-(cyclopropylmethoxy)phenoxy) piperidin-1-yl)-1,3-benzoxazol-6-yl)ethyl) acetamide

A) tert-butyl 4-(3-(benzyloxy)phenoxy)piperidine-1-carboxylate

A mixture of 3-(benzyloxy)phenol (2.0 g), tert-butyl 4-hydroxypiperidine-1-carboxylate (2.2 g), diisopropyl azodicarboxylate (5.8 ml), triphenylphosphine (3.14 g) and THF (30 ml) was stirred at room temperature overnight. The reaction mixture was concentrated under reduced pressure. The obtained residue was purified by silica gel column chromatography (hexane/ethyl acetate) to give the title compound (2.98 g).

$^1$H NMR (300 MHz, DMSO-$d_6$) δ 1.40 (9H, s), 1.44-1.55 (2H, m), 1.76-1.94 (2H, m), 3.01-3.26 (2H, m), 3.57-3.75 (2H, m), 4.43-4.62 (1H, m), 5.07 (2H, s), 6.49-6.65 (3H, m), 7.10-7.23 (1H, m), 7.25-7.49 (5H, m).

B) tert-butyl 4-(3-hydroxyphenoxy)piperidine-1-carboxylate

A mixture of tert-butyl 4-(3-(benzyloxy)phenoxy)piperidine-1-carboxylate (2.98 g), 10% palladium carbon (containing water (50%), 0.83 g) and methanol (100 ml) was stirred under a hydrogen atmosphere at room temperature for 2 hr. The reaction mixture was filtered through celite and concentrated under reduced pressure. The obtained residue was purified by silica gel column chromatography (hexane/ethyl acetate) to give the title compound (1.02 g).

$^1$H NMR (300 MHz, DMSO-$d_6$) δ 1.40 (9H, s), 1.44-1.58 (2H, m), 1.79-1.93 (2H, m), 3.07-3.24 (2H, m), 3.54-3.74 (2H, m), 4.36-4.56 (1H, m), 6.26-6.50 (3H, m), 6.94-7.12 (1H, m), 9.34 (1H, s).

C) tert-butyl 4-(3-(cyclopropylmethoxy)phenoxy) piperidine-1-carboxylate

A mixture of tert-butyl 4-(3-hydroxyphenoxy)piperidine-1-carboxylate (1.0 g), (bromomethyl)cyclopropane (0.5 ml), potassium carbonate (0.94 g) and DMF (10 ml) was stirred at 60° C. overnight. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (1.08 g).

$^1$H NMR (300 MHz, DMSO-$d_6$) δ 0.22-0.36 (2H, m), 0.50-0.60 (2H, m), 1.18-1.25 (1H, m), 1.40 (9H, s), 1.43-1.59 (2H, m), 1.79-1.94 (2H, m), 3.07-3.26 (2H, m), 3.56-3.71 (2H, m), 3.77 (2H, d, J=7.2 Hz), 4.40-4.63 (1H, m), 6.39-6.59 (3H, m), 7.04-7.22 (1H, m).

D) 4-(3-(cyclopropylmethoxy)phenoxy)piperidine hydrochloride

A mixture of tert-butyl 4-(3-(cyclopropylmethoxy)phenoxy)piperidine-1-carboxylate (1.08 g), 4 M hydrogen chloride-ethyl acetate solution (7.77 ml) and ethyl acetate (8 ml) was stirred at room temperature for 4 hr. The reaction mixture was concentrated under reduced pressure. The obtained residue was crystallized from ethyl acetate to give the title compound (0.66 g).

$^1$H NMR (300 MHz, DMSO-$d_6$) δ 0.18-0.37 (2H, m), 0.49-0.64 (2H, m), 1.07-1.30 (1H, m), 1.69-1.90 (2H, m), 1.97-2.17 (2H, m), 2.95-3.13 (2H, m), 3.13-3.26 (2H, m), 3.78 (2H, d, J=7.2 Hz), 4.46-4.69 (1H, m), 6.40-6.64 (3H, m), 7.16 (1H, t, J=8.5 Hz), 8.75 (2H, brs).

E) ethyl 2-(4-(3-(cyclopropylmethoxy)phenoxy) piperidin-1-yl)-1, 3-benzoxazole-6-carboxylate A mixture of 4-(3-(cyclopropylmethoxy)phenoxy)piperidine hydrochloride (755 mg), 2-chloro-1,3-benzoxazole-6-carboxylate (400 mg), N,N-diisopropylethylamine (0.93 ml) and DMF (4 ml) was stirred at room temperature overnight. To the reaction mixture was added water and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (277 mg).

$^1$H NMR (300 MHz, DMSO-$d_6$) δ 0.26-0.35 (2H, m), 0.51-0.62 (2H, m), 1.20-1.26 (1H, m), 1.32 (3H, t, J=7.2 Hz), 1.62-1.82 (2H, m), 2.00-2.13 (2H, m), 3.54-3.70 (2H, m), 3.78 (2H, d, J=7.2 Hz), 3.87-3.99 (2H, m), 4.30 (2H, q, J=7.2 Hz), 4.61-4.76 (1H, m), 6.47-6.62 (3H, m), 7.17 (1H, t, J=8.1 Hz), 7.33 (1H, d, J=8.3 Hz), 7.83 (1H, dd, J=8.3, 1.5 Hz), 7.89 (1H, d, J=1.5 Hz).

F) 2-(4-(3-(cyclopropylmethoxy)phenoxy)piperidin-1-yl)-1,3-benzoxazole-6-carbaldehyde To a mixture of lithium aluminum hydride (24 mg) and THF (3 ml) was added dropwise a mixture of ethyl 2-(4-(3-(cyclopropylmethoxy)phenoxy)piperidin-1-yl)-1,3-benzoxazole-6-carboxylate (277 mg) and THF (3 ml) under ice-cooling. The reaction mixture was stirred for 30 min under ice-cooling, and water (0.025 ml), 1N aqueous sodium hydroxide solution (0.025 ml) and water (0.075 ml) were successively added. The obtained mixture was stirred at room temperature for 30 min, filtered through celite, and the filtrate was concentrated under reduced pressure. To a mixture of the obtained residue and acetonitrile (3 ml) were added tetrapropylammonium perruthenate (22 mg), 4-methylmorpholine 4-oxide (112 mg) and molecular sieves 4A (750 mg). The reaction mixture was stirred at room temperature for 4 hr, filtered, and the filtrate was concentrated under reduced pressure. The obtained residue was purified by silica gel column chromatography (hexane/ethyl acetate) to give the title compound (185 mg).

$^1$H NMR (300 MHz, DMSO-$d_6$) δ 0.25-0.35 (2H, m), 0.50-0.61 (2H, m), 1.20-1.28 (1H, m), 1.65-1.84 (2H, m), 2.01-2.14 (2H, m), 3.57-3.72 (2H, m), 3.78 (2H, d, J=6.8 Hz), 3.89-4.01 (2H, m), 4.63-4.76 (1H, m), 6.46-6.62 (3H, m), 7.11-7.22 (1H, m), 7.42 (1H, d, J=8.3 Hz), 7.74-7.81 (1H, m), 7.85 (1H, d, J=1.1 Hz), 9.91 (1H, s).

G) 6-(1-azidoethyl)-2-(4-(3-(cyclopropylmethoxy)phenoxy)piperidin-1-yl)-1,3-benzoxazole To a mixture of 2-(4-(3-(cyclopropylmethoxy)phenoxy)piperidin-1-yl)-1,3-benzoxazole-6-carbaldehyde (185 mg) and THF (3 ml) was added dropwise methylmagnesium bromide (1.0 M THF solution, 0.94 ml) under ice-cooling. The reaction mixture was stirred for 30 min under ice-cooling, 1N hydrochloric acid was added, and the mixture was extracted with ethyl acetate. The obtained organic layer was washed with saturated brine, dried over anhydrous magnesium sulfate, and concentrated under reduced pressure. To a mixture of the obtained residue and toluene (3 ml) were added diphenylphosphoryl azide (259 mg) and DBU (0.21 ml), and the mixture was stirred at room temperature for 2 hr. To the reaction mixture was added water, and the mixture was extracted with toluene. The obtained organic layer was washed with saturated brine, dried over anhydrous magnesium sulfate, and concentrated under reduced pressure. The obtained residue was purified by silica gel column chromatography (hexane/ethyl acetate) to give the title compound (125 mg).

$^1$H NMR (300 MHz, DMSO-$d_6$) δ 0.25-0.35 (2H, m), 0.50-0.62 (2H, m), 1.20-1.27 (1H, m), 1.47 (3H, d, J=6.8 Hz), 1.63-1.80 (2H, m), 2.00-2.12 (2H, m), 3.48-3.63 (2H, m), 3.78 (2H, d, J=6.8 Hz), 3.84-3.97 (2H, m), 4.61-4.74 (1H, m), 4.87 (1H, q, J=6.9 Hz), 6.44-6.61 (3H, m), 7.11-7.23 (2H, m), 7.25-7.32 (1H, m), 7.47 (1H, s).

H) N-(1-(2-(4-(3-(cyclopropylmethoxy)phenoxy)piperidin-1-yl)-1,3-benzoxazol-6-yl)ethyl)acetamide A mixture of 6-(1-azidoethyl)-2-(4-(3-(cyclopropylmethoxy)phenoxy)piperidin-1-yl)-1,3-benzoxazole (125 mg), 10% palladium carbon (containing water (50%), 30.7 mg) and THF (3 ml) was stirred under a hydrogen atmosphere at room temperature for 2 hr. The reaction mixture was filtered through celite, and concentrated under reduced pressure. To the obtained residue were added pyridine (3 ml) and acetic anhydride (0.274 ml), and the mixture was stirred at room temperature for 2 hr. The mixture was concentrated under reduced pressure. The obtained residue was purified by silica gel column chromatography (hexane/ethyl acetate), and crystallized from hexane/ethyl acetate to give the title compound (51.8 mg).

$^1$H NMR (300 MHz, DMSO-$d_6$) δ 0.24-0.35 (2H, m), 0.49-0.61 (2H, m), 1.17-1.27 (1H, m), 1.34 (3H, d, J=7.2 Hz), 1.62-1.76 (2H, m), 1.82 (3H, s), 1.96-2.10 (2H, m), 3.45-3.61 (2H, m), 3.78 (2H, d, J=7.2 Hz), 3.82-3.97 (2H, m), 4.57-4.77 (1H, m), 4.84-5.02 (1H, m), 6.40-6.61 (3H, m), 7.02-7.26 (3H, m), 7.29-7.37 (1H, m), 8.23 (1H, d, J=8.3 Hz).

Example 3

N-(1-(2-(3-(3-butoxyphenoxy)azetidin-1-yl)-1,3-benzoxazol-6-yl)ethyl)acetamide

A) 3-(3-(benzyloxy)phenoxy)-1-(diphenylmethyl)azetidine

To a mixture of 1-(diphenylmethyl)azetidin-3-ol (5.0 g) and toluene (100 ml) were added 3-(benzyloxy)phenol (4.6 g), triphenylphosphine (6.58 g) and diisopropyl azodicarboxylate (4.87 ml) at room temperature. The reaction mixture was stirred at 100° C. for 17 hr. The reaction mixture was cooled to room temperature, and concentrated under reduced pressure. The obtained residue was purified by silica gel column chromatography (hexane/ethyl acetate) to give the title compound (7.65 g).

$^1$H NMR (400 MHz, CDCl$_3$) δ 3.07-3.11 (2H, m), 3.67-3.71 (2H, m), 4.42 (1H, s), 4.72-4.81 (1H, m), 5.00 (2H, s), 6.33-6.38 (2H, m), 6.55 (1H, dd, J=8.0, 2.4 Hz), 7.10-7.42 (16H, m).

B) 3-(azetidin-3-yloxy)phenol hydrochloride

To a mixture of 3-(3-(benzyloxy)phenoxy)-1-(diphenylmethyl)azetidine (7.5 g) and ethyl acetate (60 ml) were added acetic acid (60 ml) and 5% palladium carbon (containing water (50%), 1.89 g). The reaction mixture was stirred under a 10 atm hydrogen atmosphere at room temperature for 14 hr. The reaction mixture was filtered through celite and concentrated under reduced pressure. The obtained residue was dissolved in ethyl acetate, and 4 M hydrogen chloride-dioxane solution (5.34 ml) was added. The reaction mixture was stirred at room temperature for 2 hr. The obtained solid was collected by filtration, and washed with ethyl acetate to give the title compound (3.01 g).

$^1$H NMR (400 MHz, DMSO-$d_6$) δ 3.89-3.97 (2H, m), 4.33-4.41 (2H, m), 4.97-5.03 (1H, m), 6.24-6.27 (2H, m), 6.44 (1H, dd, J=7.8, 1.8 Hz), 7.07 (1H, t, J=8.0 Hz), 9.44-9.65 (3H, m).

C) ethyl 2-(3-(3-hydroxyphenoxy)azetidin-1-yl)-1,3-benzoxazole-6-carboxylate To a mixture of 3-(azetidin-3-yloxy)phenol hydrochloride (3.2 g) and DMF (40 ml) were added 2-chloro-1,3-benzoxazole-6-carboxylate (2.86 g) and N,N-diisopropylethylamine (7.43 ml), and the mixture was stirred at room temperature for 16 hr. The reaction mixture was extracted with ethyl acetate and water. The obtained organic layer was washed with saturated brine, dried over anhydrous sodium sulfate, and concentrated under reduced pressure. The obtained residue was purified by silica gel column chromatography (hexane/ethyl acetate) to give the title compound (4.4 g).

$^1$H NMR (400 MHz, DMSO-$d_6$) δ 1.32 (3H, t, J=7.0 Hz), 4.22 (2H, dd, J=9.6, 4.4 Hz), 4.30 (2H, q, J=7.0 Hz), 4.70 (2H, dd, J=9.6, 6.4 Hz), 5.14-5.21 (1H, m), 6.25-6.31 (2H, m), 6.42 (1H, dd, J=7.8, 1.8 Hz), 7.09 (1H, t, J=8.0 Hz), 7.39 (1H, d, J=8.4 Hz), 7.85 (1H, dd, J=8.4, 1.6 Hz), 7.92 (1H, d, J=1.6 Hz), 9.53 (1H, s).

D) ethyl 2-(3-(3-(benzyloxy)phenoxy)azetidin-1-yl)-1,3-benzoxazole-6-carboxylate To a mixture of ethyl 2-(3-(3-hydroxyphenoxy)azetidin-1-yl)-1,3-benzoxazole-6-carboxylate (2.8 g) and DMF (40 ml) were added benzyl chloride (1.01 ml) and potassium carbonate (1.64 g), and the mixture was stirred at 80° C. for 4 hr. The reaction mixture was cooled to room temperature, and extracted with ethyl acetate and water. The obtained organic layer was washed with saturated brine, dried over anhydrous sodium sulfate, and concentrated under reduced pressure. The obtained residue was purified by silica gel column chromatography (hexane/ethyl acetate) to give the title compound (3.4 g).

$^1$H NMR (400 MHz, CDCl$_3$) 51.37 (3H, t, J=7.2 Hz), 4.34-4.40 (4H, m), 4.66 (2H, dd, J=10.0, 6.4 Hz), 5.05 (2H, s), 5.09-5.13 (1H, m), 6.37 (1H, dd, J=8.0, 2.0 Hz), 6.42 (1H, t, J=2.4 Hz), 6.65 (1H, dd, J=8.4, 2.0 Hz), 7.21 (1H, t, J=8.2 Hz), 7.31-7.45 (6H, m), 7.95-7.97 (2H, m).

E) (2-(3-(3-(benzyloxy)phenoxy)azetidin-1-yl)-1,3-benzoxazol-6-yl)methanol

To a mixture of ethyl 2-(3-(3-(benzyloxy)phenoxy)azetidin-1-yl)-1,3-benzoxazole-6-carboxylate (565 mg) and THF (7 ml) was added lithium aluminum hydride (145 mg) at −78° C. The reaction mixture was stirred at −78° C. for 30 min, and at room temperature for 30 min. To the reaction mixture were successfully added water (0.5 ml), 2N aqueous sodium hydroxide solution (0.5 ml) and water (1 ml), and the mixture was extracted with dichloromethane. The obtained organic layer was washed with water, dried over anhydrous magnesium sulfate, and concentrated under reduced pressure. The obtained residue was purified by silica gel column chromatography (hexane/ethyl acetate) to give the title compound (417 mg).

$^1$H NMR (400 MHz, CDCl$_3$) δ 1.76 (1H, t, J=6.0 Hz), 4.33 (2H, dd, J=10.0, 4.4 Hz), 4.62 (2H, dd, J=9.8, 6.2 Hz), 4.72 (2H, d, J=6.0 Hz), 5.05 (2H, s), 5.06-5.11 (1H, m), 6.37 (1H, dd, J=8.2, 2.2 Hz), 6.42 (1H, t, J=2.4 Hz), 6.65 (1H, dd, J=8.0, 2.4 Hz), 7.17 (1H, dd, J=8.0, 1.6 Hz), 7.20 (1H, t, J=8.2 Hz), 7.32-7.45 (7H, m).

F) 2-(3-(3-(benzyloxy)phenoxy)azetidin-1-yl)-1,3-benzoxazole-6-carbaldehyde

To a mixture of (2-(3-(3-(benzyloxy)phenoxy)azetidin-1-yl)-1,3-benzoxazol-6-yl)methanol (3.6 g) and acetonitrile (56 ml) were added tetrapropylammonium perruthenate (157 mg) and 4-methylmorpholine 4-oxide (1.57 g). The reaction mixture was stirred at room temperature for 2 hr, filtered through celite, and the filtrate was concentrated under reduced pressure. The obtained residue was purified by silica gel column chromatography (hexane/ethyl acetate) to give the title compound (3.3 g).

$^1$H NMR (400 MHz, CDCl$_3$) δ 4.41 (2H, dd, J=10.2, 4.2 Hz), 4.69 (2H, dd, J=10.4, 6.4 Hz), 5.05 (2H, s), 5.11-5.15 (1H, m), 6.37 (1H, dd, J=8.0, 2.4 Hz), 6.42 (1H, t, J=2.4 Hz), 6.66 (1H, dd, J=8.2, 2.2 Hz), 7.22 (1H, t, J=8.2 Hz), 7.33-7.46 (6H, m), 7.74 (1H, dd, J=8.0, 1.6 Hz), 7.79 (1H, d, J=1.2 Hz), 9.95 (1H, s).

G) 1-(2-(3-(3-(benzyloxy)phenoxy)azetidin-1-yl)-1,3-benzoxazol-6-yl)ethanol

To a mixture of 2-(3-(3-(benzyloxy)phenoxy)azetidin-1-yl)-1,3-benzoxazole-6-carbaldehyde (3.3 g) and THF (40 ml) was added methylmagnesium bromide (3.0 M diethyl ether solution, 2.75 ml) under ice-cooling. The reaction mixture was stirred at 0° C. for 1 hr, 1N hydrochloric acid was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (3.3 g).

$^1$H NMR (400 MHz, CDCl$_3$) δ 1.26 (1H, brs), 1.51 (3H, d, J=6.4 Hz), 4.33 (2H, dd, J=9.6, 4.4 Hz), 4.62 (2H, dd, J=9.6, 6.4 Hz), 4.91-4.99 (1H, m), 5.05 (2H, s), 5.07-5.11 (1H, m), 6.37 (1H, dd, J=8.0, 2.0 Hz), 6.42 (1H, t, J=2.4 Hz), 6.65 (1H, dd, J=8.2, 2.2 Hz), 7.16-7.23 (2H, m), 7.31-7.45 (7H, m).

H) 6-(1-azidoethyl)-2-(3-(3-(benzyloxy)phenoxy)azetidin-1-yl)-1,3-benzoxazole To a mixture of 1-(2-(3-(3-(benzyloxy)phenoxy)azetidin-1-yl)-1,3-benzoxazol-6-yl)ethanol (3.3 g) and toluene (40 ml) were added diphenylphosphoryl azide (3.4 ml) and DBU (3.58 ml), and the mixture was stirred at room temperature for 2 hr. The reaction mixture was extracted with ethyl acetate and water. The obtained organic layer was washed with saturated brine, dried over anhydrous sodium sulfate, and concentrated under reduced pressure. The obtained residue was purified by silica gel column chromatography (hexane/ethyl acetate) to give the title compound (2.1 g).

$^1$H NMR (400 MHz, CDCl$_3$) δ 1.54 (3H, d, J=6.8 Hz), 4.34 (2H, dd, J=9.8, 4.2 Hz), 4.60-4.69 (3H, m), 5.05 (2H, s), 5.08-5.11 (1H, m), 6.37 (1H, dd, J=8.2, 2.2 Hz), 6.42 (1H, t, J=2.4 Hz), 6.65 (1H, dd, J=8.0, 2.4 Hz), 7.14 (1H, dd, J=8.2, 1.8 Hz), 7.21 (1H, t, J=8.2 Hz), 7.27 (1H, d, J=1.6 Hz), 7.33-7.44 (6H, m).

I) 1-(2-(3-(3-(benzyloxy)phenoxy)azetidin-1-yl)-1,3-benzoxazol-6-yl)ethanamine To a mixture of 6-(1-azidoethyl)-2-(3-(3-(benzyloxy)phenoxy)azetidin-1-yl)-1,3-benzoxazole (700 mg) and ethyl acetate (30 ml) was added 10% palladium carbon (containing water (50%), 169 mg). The reaction mixture was stirred under a 5 atm hydrogen atmosphere at room temperature for 14 hr. The reaction mixture was filtered through celite and concentrated under reduced pressure to give the title compound (620 mg).

$^1$H NMR (400 MHz, CDCl$_3$) δ 1.39 (3H, d, J=6.4 Hz), 1.67 (2H, brs), 4.11-4.19 (1H, m), 4.33 (2H, dd, J=9.8, 4.2 Hz), 4.61 (2H, dd, J=9.8, 6.6 Hz), 5.05 (2H, s), 5.07-5.11 (1H, m), 6.37 (1H, dd, J=8.2, 2.2 Hz), 6.42 (1H, t, J=2.4 Hz), 6.64 (1H, dd, J=8.2, 2.2 Hz), 7.15 (1H, dd, J=8.4, 1.2 Hz), 7.20 (1H, t, J=8.2 Hz), 7.31-7.45 (7H, m).

J) N-(1-(2-(3-(3-(benzyloxy)phenoxy)azetidin-1-yl)-1,3-benzoxazol-6-yl)ethyl)acetamide To a mixture of 1-(2-(3-(3-(benzyloxy)phenoxy)azetidin-1-yl)-1,3-benzoxazol-6-yl)ethanamine (620 mg) and dichloromethane (15 ml) were added N,N-diisopropylethylamine (0.52 ml) and acetic anhydride (0.16 ml) under ice-cooling. The reaction mixture was stirred at room temperature for 2 hr, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (560 mg).

$^1$H NMR (400 MHz, CDCl$_3$) δ 1.51 (3H, d, J=7.2 Hz), 1.98 (3H, s), 4.33 (2H, dd, J=10.0, 4.4 Hz), 4.61 (2H, dd, J=10.0, 6.4 Hz), 5.05 (2H, s), 5.07-5.11 (1H, m), 5.17 (1H, t, J=7.2 Hz), 5.64 (1H, d, J=7.6 Hz), 6.37 (1H, dd, J=8.0, 2.0 Hz), 6.42 (1H, t, J=2.4 Hz), 6.65 (1H, dd, J=8.2, 2.2 Hz), 7.15 (1H, dd, J=8.0, 1.6 Hz), 7.21 (1H, t, J=8.4 Hz), 7.25-7.45 (7H, m).

K) N-(1-(2-(3-(3-hydroxyphenoxy)azetidin-1-yl)-1,3-benzoxazol-6-yl)ethyl)acetamide To a mixture of N-(1-(2-(3-(3-(benzyloxy)phenoxy)azetidin-1-yl)-1,3-benzoxazol-6-yl)ethyl)acetamide (560 mg) and ethyl acetate (20 ml) was added 10% palladium carbon (containing water (50%), 130 mg). The reaction mixture was stirred under a 5 atm hydrogen atmosphere at room temperature for 14 hr. The reaction mixture was filtered through celite, and concentrated under reduced pressure to give the title compound (422 mg).

$^1$H NMR (400 MHz, CDCl$_3$) δ 1.51 (3H, d, J=7.2 Hz), 1.99 (3H, s), 4.30 (2H, dd, J=9.6, 4.0 Hz), 4.55-4.61 (2H, m), 5.02-5.21 (2H, m), 5.70 (1H, d, J=8.4 Hz), 5.98 (1H, br), 6.26 (1H, t, J=2.4 Hz), 6.32 (1H, dd, J=8.0, 2.0 Hz), 6.49 (1H, dd, J=7.8, 2.2 Hz), 7.11-7.17 (2H, m), 7.22-7.27 (1H, m), 7.34 (1H, d, J=8.0 Hz).

L) N-(1-(2-(3-(3-butoxyphenoxy)azetidin-1-yl)-1,3-benzoxazol-6-yl)ethyl)acetamide To a mixture of N-(1-(2-(3-(3-hydroxyphenoxy)azetidin-1-yl)-1,3-benzoxazol-6-yl)ethyl)acetamide (80 mg) and DMF (1 ml) were added 1-bromobutane (36 mg) and potassium carbonate (60 mg). The reaction mixture was stirred at 80° C. for 2 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (52 mg).

$^1$H NMR (400 MHz, CDCl$_3$) δ 0.97 (3H, t, J=7.6 Hz), 1.45-1.53 (5H, m), 1.74-1.78 (2H, m), 1.98 (3H, s), 3.94 (2H, t, J=6.4 Hz), 4.33 (2H, dd, J=9.6, 4.4 Hz), 4.63 (2H, dd, J=9.6, 6.4 Hz), 5.07-5.18 (2H, m), 5.68 (1H, d, J=7.6 Hz), 6.32-6.35 (2H, m), 6.55-6.57 (1H, m), 7.14-7.21 (2H, m), 7.28-7.29 (1H, m), 7.33 (1H, d, J=8.0 Hz).

Example 8

N-(1-(2-(4-(3-(cyclopropylmethoxy)phenoxy)phenyl)-1,3-benzoxazol-6-yl)ethyl)acetamide

A) ethyl 4-((4-fluorobenzoyl)amino)-3-hydroxybenzoate

A mixture of 4-fluorobenzoic acid (1 g), WSCD (2.05 g), HOBt (1.63 g), triethylamine (1.99 ml), ethyl 4-amino-3-hydroxybenzoate (1.29 g) and DMF (40 ml) was stirred at room temperature for 1 hr. To the reaction mixture was added water (100 ml), and the mixture was stirred at room temperature for 30 min. The obtained solid was collected by filtration to give the title compound (2.08 g).

$^1$H NMR (400 MHz, CDCl$_3$) δ 1.35 (3H, t, J=7.0 Hz), 4.32 (2H, q, J=7.2 Hz), 6.82 (1H, d, J=8.4 Hz), 7.21 (2H, t, J=8.8 Hz), 7.78-7.82 (2H, m), 8.23-8.26 (2H, m).
* The peaks of NH and OH were not observed.

B) ethyl 2-(4-fluorophenyl)-1,3-benzoxazole-6-carboxylate

A mixture of ethyl 4-((4-fluorobenzoyl)amino)-3-hydroxybenzoate (1.0 g), acetic acid (3 ml) and TFA (3 ml) was stirred under microwave radiation at 200° C. for 20 min. The reaction mixture was concentrated under reduced pressure, and the obtained residue was extracted with water and ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (640 mg).

$^1$H NMR (400 MHz, CDCl$_3$) δ 1.43 (3H, t, J=7.0 Hz), 4.43 (2H, q, J=7.2 Hz), 7.23 (2H, d, J=6.8 Hz), 7.78 (1H, d, J=8.4 Hz), 8.11 (1H, dd, J=8.4, 1.6 Hz), 8.27-8.31 (3H, m).

C) ethyl 2-(4-(3-(cyclopropylmethoxy)phenoxy)phenyl)-1,3-benzoxazole-6-carboxylate A mixture of ethyl 2-(4-fluorophenyl)-1,3-benzoxazole-6-carboxylate (174 mg), 3-(cyclopropylmethoxy)phenol (100 mg), potassium carbonate (126 mg) and DMF (5 ml) was stirred under microwave radiation at 120° C. for 4 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (260 mg).

$^1$H NMR (400 MHz, CDCl$_3$) δ 0.35 (2H, dd, J=3.0, 7.4 Hz), 0.62-0.67 (2H, m), 1.25-1.28 (1H, m), 1.43 (3H, t, J=7.2 Hz), 3.79 (2H, d, J=7.2 Hz), 4.43 (2H, q, J=7.0 Hz), 6.65 (1H, t, J=2.4 Hz), 6.67-6.70 (1H, m), 6.74-6.77 (1H, m), 7.12-7.14 (2H, m), 7.29 (1H, t, J=8.2 Hz), 7.76 (1H, d, J=8.4 Hz), 8.10 (1H, dd, J=8.4, 1.6 Hz), 8.22-8.25 (2H, m), 8.26 (1H, d, J=1.6 Hz).

D) (2-(4-(3-(cyclopropylmethyl)oxyphenoxy)phenyl)-1,3-benzoxazol-6-yl)methanol To a mixture of ethyl 2-(4-(3-(cyclopropylmethoxy)phenoxy)phenyl)-1,3-benzoxazole-6-carboxylate (260 mg) and THF (10 ml) was added lithium aluminum hydride (68.9 mg) at −78° C. The reaction mixture was stirred at −78° C. for 20 min, and at room temperature for 1 hr. To the reaction mixture were successively added water (1 ml) and 6N aqueous sodium hydroxide solution (1 ml). The mixture was filtered through celite, and concentrated under reduced pressure to give the title compound (225 mg).

$^1$H NMR (400 MHz, CDCl$_3$) δ 0.32-0.36 (2H, m), 0.62-0.67 (2H, m), 1.24-1.28 (1H, m), 1.77-1.82 (1H, m), 3.78 (2H, d, J=7.2 Hz), 4.84 (2H, d, J=5.2 Hz), 6.64 (1H, t, J=2.4 Hz), 6.66-6.69 (1H, m), 6.73-6.76 (1H, m), 7.11-7.13 (2H, m), 7.29 (1H, d, J=8.4 Hz), 7.34 (1H, dd, J=8.4, 1.4 Hz), 7.61 (1H, d, J=0.8 Hz), 7.71 (1H, d, J=8.0 Hz), 8.20-8.22 (2H, m).

E) 2-(4-(3-(cyclopropylmethoxy)phenoxy)phenyl)-1,3-benzoxazole-6-carbaldehyde To a mixture of (2-(4-(3-(cyclopropylmethyl)oxyphenoxy)phenyl)-1,3-benzoxazol-6-yl)methanol (220 mg) and acetonitrile (10 ml) were added tetrapropylammonium perruthenate (9.98 mg) and 4-methylmorpholine 4-oxide (100 mg). The reaction mixture was stirred at room temperature for 3 hr. The mixture was filtered through celite, and concentrated under reduced pressure. The obtained residue was purified by silica gel column chromatography (hexane/ethyl acetate) to give the title compound (185 mg).

$^1$H NMR (400 MHz, CDCl$_3$) δ 0.33-0.37 (2H, m), 0.63-0.68 (2H, m), 1.24-1.30 (1H, m), 3.79 (2H, d, J=6.8 Hz), 6.65-6.70 (2H, m), 6.76 (1H, dd, J=8.0, 2.0 Hz), 7.13 (2H, d, J=8.8 Hz), 7.29 (1H, t, J=8.8 Hz), 7.86 (1H, d, J=8.4 Hz), 7.91 (1H, dd, J=8.0, 1.2 Hz), 8.09 (1H, s), 8.25 (2H, d, J=8.8 Hz), 10.09 (1H, s).

F) 1-(2-(4-(3-(cyclopropylmethoxy)phenoxy)phenyl)-1,3-benzoxazol-6-yl)ethanol To a mixture of 2-(4-(3-(cyclopropylmethoxy)phenoxy)phenyl)-1,3-benzoxazole-6-carbaldehyde (180 mg) and THF (5 ml) was added methylmagnesium bromide (3.0 M diethyl ether solution, 0.156 ml) under ice-cooling. The reaction mixture was stirred at 0° C. for 1 hr. To the reaction mixture was added 1N hydrochloric acid, and the mixture was extracted with ethyl acetate. The obtained organic layer was washed with saturated brine, dried over anhydrous magnesium sulfate, and concentrated under reduced pressure to give the title compound (187 mg).

$^1$H NMR (400 MHz, CDCl$_3$) δ 0.33-0.37 (2H, m), 0.62-0.67 (2H, m), 1.24-1.27 (1H, m), 2.05 (3H, s), 3.78 (2H, d, J=6.8 Hz), 5.06 (1H, q, J=6.4 Hz), 6.64 (1H, t, J=2.2 Hz), 6.67 (1H, dd, J=8.0, 1.6 Hz), 6.74 (1H, dd, J=8.0, 2.0 Hz), 7.10-7.13 (2H, m), 7.29 (1H, t, J=8.0 Hz), 7.35 (1H, dd, J=1.2, 8.0 Hz), 7.63 (1H, d, J=1.2 Hz), 7.70 (1H, d, J=8.0 Hz), 8.19-8.22 (2H, m).

* The peak of OH was not observed.

G) 6-(1-azidoethyl)-2-(4-(3-(cyclopropylmethoxy) phenoxy)phenyl)-1,3-benzoxazole To a mixture of 1-(2-(4-(3-(cyclopropylmethoxy)phenoxy)phenyl)-1,3-benzoxazol-6-yl)ethanol (185 mg) and toluene (5 ml) were added diphenylphosphoryl azide (254 mg) and DBU (0.208 ml). The reaction mixture was stirred at room temperature for 16 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (110 mg).

$^1$H NMR (400 MHz, CDCl$_3$) δ 0.33-0.37 (2H, m), 0.62-0.67 (2H, m), 1.24-1.28 (1H, m), 1.60 (3H, d, J=6.8 Hz), 3.78 (2H, d, J=6.8 Hz), 5.30 (1H, q, J=6.4 Hz), 6.64 (1H, t, J=2.2 Hz), 6.67 (1H, dd, J=1.6, 8.0 Hz), 6.74 (1H, dd, J=2.0, 8.0 Hz), 7.11-7.13 (2H, m), 7.26-7.33 (2H, m), 7.57 (1H, d, J=1.6 Hz), 7.73 (1H, d, J=8.4 Hz), 8.19-8.22 (2H, m).

H) N-(1-(2-(4-(3-(cyclopropylmethoxy)phenoxy) phenyl)-1,3-benzoxazol-6-yl)ethyl) acetamide A mixture of 6-(1-azidoethyl)-2-(4-(3-(cyclopropylmethoxy)phenoxy)phenyl)-1,3-benzoxazole (110 mg), 5% palladium carbon (containing water (50%), 54.9 mg) and ethyl acetate (5 ml) was stirred under a hydrogen atmosphere at room temperature for 3 hr. The reaction mixture was filtered through celite and concentrated under reduced pressure. To a mixture of the obtained residue, N,N-diisopropylethylamine (0.007 ml) and dichloromethane (5 ml) was added acetic anhydride (0.021 ml). The reaction mixture was stirred at room temperature for 2 hr, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (70 mg).

$^1$H NMR (400 MHz, CDCl$_3$) δ 0.32-0.36 (2H, m), 0.62-0.66 (2H, m), 1.24-1.28 (1H, m), 1.55 (3H, d, J=6.8 Hz), 2.01 (3H, s), 3.78 (2H, d, J=7.2 Hz), 5.22-5.29 (1H, m), 5.85 (1H, d, J=7.6 Hz), 6.64-6.68 (2H, m), 6.74 (1H, dd, J=8.4, 2.0 Hz), 7.09 (2H, d, J=2.0 Hz), 7.26-7.33 (2H, m), 7.53 (1H, s), 7.68 (1H, d, J=8.4 Hz), 8.18 (2H, d, J=2.8 Hz).

Example 9

N-(1-(2-(5-(3-(cyclopropylmethoxy)phenoxy)pyridin-2-yl)-1,3-benzoxazol-6-yl)ethyl) acetamide

A) 5-(3-(cyclopropylmethoxy)phenoxy)pyridine-2-carbonitrile

A mixture of 3-(cyclopropylmethoxy)phenol (12 g), 5-bromopyridine-2-carbonitrile (14.7 g), cesium carbonate (35.7 g) and DMF (120 ml) was stirred at 100° C. overnight. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (19.0 g).

$^1$H NMR (300 MHz, DMSO-d$_6$) δ 0.25-0.35 (2H, m), 0.52-0.62 (2H, m), 1.19-1.27 (1H, m), 3.82 (2H, d, J=7.0 Hz), 6.70-6.81 (2H, m), 6.86 (1H, ddd, J=8.3, 2.4, 0.8 Hz), 7.37 (1H, t, J=8.2 Hz), 7.49 (1H, dd, J=8.6, 2.9 Hz), 8.02 (1H, dd, J=8.7, 0.6 Hz), 8.52 (1H, dd, J=2.9, 0.5 Hz).

B) 5-(3-(cyclopropylmethoxy)phenoxy)pyridine-2-carboxylic acid

A mixture of 5-(3-(cyclopropylmethoxy)phenoxy)pyridine-2-carbonitrile (10 g), 2N aqueous sodium hydroxide solution (94 ml) and ethanol (100 ml) was stirred at 80° C. overnight. The reaction mixture was cooled to room temperature, and acidified with 2N hydrochloric acid. The obtained solid was collected by filtration to give the title compound (8.58 g).

$^1$H NMR (300 MHz, DMSO-d$_6$) δ 0.22-0.37 (2H, m), 0.48-0.65 (2H, m), 1.10-1.30 (1H, m), 3.81 (2H, d, J=7.1 Hz), 6.65-6.78 (2H, m), 6.79-6.87 (1H, m), 7.35 (1H, t, J=8.2 Hz), 7.44 (1H, dd, J=8.6, 2.9 Hz), 8.05 (1H, d, J=8.5 Hz), 8.45 (1H, d, J=2.5 Hz), 12.70-13.29 (1H, m).

C) N-(4-acetyl-2-hydroxyphenyl)-5-(3-(cyclopropylmethoxy)phenoxy)pyridine-2-carboxamide To a mixture of 5-(3-(cyclopropylmethoxy)phenoxy)pyridine-2-carboxylic acid (6 g), DMF (0.08 ml) and THF (50 ml) was added oxalyl chloride (3.68 ml) under ice-cooling. The reaction mixture was stirred at room temperature for 1 hr, and concentrated under reduced pressure. To the obtained residue were added THF (50 ml), 4-amino-3-hydroxyphenylethanone (3.18 g) and triethylamine (8.79 ml), and the mixture was stirred at room temperature overnight. To the reaction mixture was added water, and the mixture was extracted with ethyl acetate. The obtained organic layer was washed with saturated brine, dried over anhydrous magnesium sulfate, and concentrated under reduced pressure. To the obtained residue was added ethanol, and the obtained solid was collected by filtration to give the title compound (7.76 g).

$^1$H NMR (300 MHz, DMSO-d$_6$) δ 0.26-0.36 (2H, m), 0.50-0.61 (2H, m), 1.16-1.28 (1H, m), 2.51 (3H, s), 3.82 (2H, d, J=7.0 Hz), 6.70-6.80 (2H, m), 6.81-6.90 (1H, m), 7.36 (1H, t, J=8.2 Hz), 7.45-7.51 (1H, m), 7.52-7.61 (2H, m), 8.20 (1H, d, J=9.1 Hz), 8.48-8.56 (2H, m), 10.52 (1H, s), 10.76-10.97 (1H, m).

D) 1-(2-(5-(3-(cyclopropylmethoxy)phenoxy)pyridin-2-yl)-1,3-benzoxazol-6-yl)ethanone A mixture of N-(4-acetyl-2-hydroxyphenyl)-5-(3-(cyclopropylmethoxy)phenoxy)pyridine-2-carboxamide (7.76 g), diisopropyl azodicarboxylate (11.7 ml), triphenylphosphine (6.32 g) and THF (50 ml) was stirred at 60° C. for 2 hr. The reaction mixture was cooled to room temperature, and concentrated under reduced pressure. To the obtained residue was added ethanol, and the obtained solid was collected by filtration to give the title compound (3.74 g).

$^1$H NMR (300 MHz, DMSO-$d_6$) δ 0.27-0.35 (2H, m), 0.52-0.61 (2H, m), 1.19-1.28 (1H, m), 2.69 (3H, s), 3.83 (2H, d, J=7.0 Hz), 6.74-6.79 (1H, m), 6.81 (1H, t, J=2.3 Hz), 6.83-6.89 (1H, m), 7.38 (1H, t, J=8.2 Hz), 7.54-7.58 (1H, m), 7.92-7.98 (1H, m), 8.03-8.10 (1H, m), 8.39 (1H, d, J=8.7 Hz), 8.43 (1H, d, J=1.0 Hz), 8.60 (1H, d, J=2.5 Hz).

E) N-(1-(2-(5-(3-(cyclopropylmethoxy)phenoxy)pyridin-2-yl)-1,3-benzoxazol-6-yl)ethyl)acetamide A mixture of 1-(2-(5-(3-(cyclopropylmethoxy)phenoxy)pyridin-2-yl)-1,3-benzoxazol-6-yl)ethanone (3.74 g), ammonium acetate (7.2 g), sodium cyanoborohydride (2.93 g) and methanol (50 ml) was stirred at 60° C. overnight. The reaction mixture was cooled to room temperature, and concentrated to a half amount under reduced pressure. To the obtained residue was added water, and the mixture was extracted with ethyl acetate. The obtained organic layer was washed with saturated brine, dried over anhydrous magnesium sulfate, and concentrated under reduced pressure. To the obtained residue were added pyridine (15 ml) and acetic anhydride (4.41 ml), and the mixture was stirred at room temperature for 30 min. The reaction mixture was concentrated under reduced pressure, and the obtained residue was purified by silica gel column chromatography (NH, hexane/ethyl acetate), and crystallized from hexane/ethyl acetate to give the title compound (2.2 g).

$^1$H NMR (300 MHz, DMSO-$d_6$) δ 0.26-0.35 (2H, m), 0.51-0.61 (2H, m), 1.13-1.29 (1H, m), 1.41 (3H, d, J=7.0 Hz), 1.86 (3H, s), 3.83 (2H, d, J=7.0 Hz), 5.06 (1H, quin, J=7.2 Hz), 6.70-6.81 (2H, m), 6.84 (1H, dt, J=8.3, 1.2 Hz), 7.32-7.43 (2H, m), 7.56 (1H, dd, J=8.8, 2.8 Hz), 7.73 (1H, s), 7.77 (1H, d, J=8.3 Hz), 8.32 (1H, d, J=9.2 Hz), 8.41 (1H, d, J=7.9 Hz), 8.56 (1H, d, J=2.5 Hz)

Example 9a

N-(1-(2-(5-(3-(cyclopropylmethoxy)phenoxy)pyridin-2-yl)-1,3-benzoxazol-6-yl)ethyl)acetamide (optical isomer)

A racemate (1 g) of N-(1-(2-(5-(3-(cyclopropylmethoxy)phenoxy)pyridin-2-yl)-1,3-benzoxazol-6-yl)ethyl)acetamide was fractionated by HPLC (column: CHIRALPAK IA (trade name), 50 mmID×500 mL, Daicel Corporation, mobile phase:hexane/ethanol=400/600(v/v)), and a compound having a shorter retention time was crystallized from hexane/ethyl acetate to give the title compound (434 mg).

$^1$H NMR (300 MHz, DMSO-$d_6$) δ 0.27-0.34 (2H, m), 0.52-0.60 (2H, m), 1.14-1.27 (1H, m), 1.40 (3H, d, J=7.0 Hz), 1.86 (3H, s), 3.83 (2H, d, J=7.1 Hz), 4.99-5.11 (1H, m), 6.72-6.77 (1H, m), 6.77-6.81 (1H, m), 6.81-6.87 (1H, m), 7.33-7.42 (2H, m), 7.56 (1H, dd, J=8.8, 2.8 Hz), 7.71-7.74 (1H, m), 7.77 (1H, d, J=8.3 Hz), 8.32 (1H, d, J=8.8 Hz), 8.41 (1H, d, J=7.9 Hz), 8.56 (1H, d, J=2.6 Hz).

retention time (AD) 12.936 min

Example 9b

N-(1-(2-(5-(3-(cyclopropylmethoxy)phenoxy)pyridin-2-yl)-1,3-benzoxazol-6-yl)ethyl)acetamide (optical isomer)

A racemate (1 g) of N-(1-(2-(5-(3-(cyclopropylmethoxy)phenoxy)pyridin-2-yl)-1,3-benzoxazol-6-yl)ethyl)acetamide was fractionated by HPLC (column: CHIRALPAK IA (trade name), 50 mmID×500 mL, Daicel Corporation, mobile phase:hexane/ethanol=400/600(v/v)), and a compound having a longer retention time was crystallized from hexane/ethyl acetate to give the title compound (416 mg).

$^1$H NMR (300 MHz, DMSO-$d_6$) δ 0.26-0.35 (2H, m), 0.49-0.61 (2H, m), 1.12-1.28 (1H, m), 1.40 (3H, d, J=7.0 Hz), 1.86 (3H, s), 3.83 (2H, d, J=7.0 Hz), 4.99-5.11 (1H, m), 6.72-6.77 (1H, m), 6.77-6.80 (1H, m), 6.82-6.87 (1H, m), 7.32-7.42 (2H, m), 7.56 (1H, dd, J=8.8, 2.8 Hz), 7.71-7.74 (1H, m), 7.77 (1H, d, J=8.3 Hz), 8.32 (1H, d, J=8.4 Hz), 8.41 (1H, d, J=7.6 Hz), 8.56 (1H, d, J=2.5 Hz).

retention time (AD) 17.177 min

Example 10

N-(1-(2-(4-(3-(cyclopropylmethoxy)phenoxy)cyclohexyl)-1,3-benzoxazol-6-yl)ethyl)acetamide

A) ethyl 4-(3-(cyclopropylmethoxy)phenoxy)cyclohexylcarboxylate

A mixture of 3-(cyclopropylmethoxy)phenol (800 mg), ethyl 4-hydroxycyclohexanecarboxylate (0.864 ml), diisopropyl azodicarboxylate (1.14 ml), triphenylphosphine (1.53 g) and toluene (20 ml) was stirred at 80° C. for 12 hr. The reaction mixture was cooled to room temperature, and concentrated under reduced pressure. The obtained residue was purified by silica gel column chromatography (hexane/ethyl acetate), and crystallized from hexane/ethyl acetate to give the title compound (860 mg).

$^1$H NMR (400 MHz, CDCl$_3$) δ 0.32-0.36 (2H, m), 0.62-0.67 (2H, m), 1.26 (4H, t, J=7.2 Hz), 1.41-1.75 (4H, m), 1.95-2.21 (4H, m), 2.30-2.39 (1H, m), 3.77 (2H, d, J=6.8 Hz), 4.11-4.49 (3H, m), 6.47-6.51 (3H, m), 7.15 (1H, t, J=8.2 Hz).

B) 4-(3-(cyclopropylmethoxy)phenoxy)cyclohexanecarboxylic acid

To a mixture of ethyl 4-(3-(cyclopropylmethoxy)phenoxy)cyclohexylcarboxylate (860 mg), THF (15 ml), methanol (7 ml) and water (4 ml) was added sodium hydroxide (432 mg). The reaction mixture was stirred at room temperature for 3 hr, water (15 ml) was added and the mixture was acidified with 6N hydrochloric acid. The obtained mixture was extracted with ethyl acetate. The obtained organic layer was washed with saturated brine, dried over anhydrous magnesium sulfate, and concentrated under reduced pressure to give the title compound (780 mg).

$^1$H NMR (400 MHz, CDCl$_3$) δ 0.32-0.36 (2H, m), 0.62-0.67 (2H, m), 1.23-1.31 (1H, m), 1.43-1.82 (4H, m), 1.94-2.24 (4H, m), 2.36-2.49 (1H, m), 3.77 (2H, d, J=7.2 Hz), 4.15-4.50 (1H, m), 6.47-6.51 (3H, m), 7.15 (1H, t, J=8.0 Hz).

C) ethyl 4-(((4-(3-(cyclopropylmethoxy)phenoxy)cyclohexyl)carbonyl)amino)-3-hydroxybenzoate A mixture of 4-(3-(cyclopropylmethoxy)phenoxy)cyclohexanecarboxylic acid (820 mg), WSCD (596 mg), HOBt (476 mg), triethylamine (2.75 ml), ethyl 4-amino-3-hydroxybenzoate (563 mg) and dichloromethane (30 ml) was stirred at room temperature for 12 hr. To the reaction mixture was added saturated aqueous ammonium chloride solution, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate), and crystallized from hexane/ethyl acetate to give the title compound (705 mg).

$^1$H NMR (400 MHz, DMSO-d$_6$) δ 0.28-0.33 (2H, m), 0.53-0.58 (2H, m), 1.15-1.42 (6H, m), 1.52-1.69 (2H, m), 1.89-1.93 (2H, m), 2.10-2.14 (2H, m), 2.60-2.67 (1H, m), 3.78 (2H, d, J=6.8 Hz), 4.23-4.33 (3H, m), 6.45-6.52 (3H, m), 7.12 (1H, t, J=8.2 Hz), 7.40 (1H, dd, J=8.4, 2.0 Hz), 7.46 (1H, d, J=2.0 Hz), 8.08 (1H, d, J=8.8), 9.17 (1H, s), 10.23 (1H, brs).

D) ethyl 2-(4-(3-(cyclopropylmethoxy)phenoxy)cyclohexyl)-1,3-benzoxazole-6-carboxylate A mixture of ethyl 4-(((4-(3-(cyclopropylmethoxy)phenoxy)cyclohexyl)carbonyl) amino)-3-hydroxybenzoate (700 mg), pyridinium p-toluenesulfonate (966 mg) and acetonitrile (12 ml) was stirred under microwave radiation at 120° C. for 4 hr. The reaction mixture was cooled to room temperature, and concentrated under reduced pressure. The obtained residue was purified by silica gel column chromatography (hexane/ethyl acetate), and crystallized from hexane/ethyl acetate to give the title compound (180 mg).

$^1$H NMR (400 MHz, CDCl$_3$) δ 0.33-0.37 (2H, m), 0.62-0.68 (2H, m), 1.24-1.31 (1H, m), 1.43 (3H, t, J=7.2 Hz), 1.59-1.92 (3H, m), 2.00-2.06 (1H, m), 2.13-2.38 (4H, m), 3.01-3.13 (1H, m), 3.78 (2H, dd, J=7.0, 2.2 Hz), 4.42 (2H, q, J=7.2 Hz), 4.26-4.58 (1H, m), 6.48-6.54 (3H, m), 7.14-7.19 (1H, m), 7.71 (1H, dd, J=8.2, 3.0 Hz), 8.07 (1H, d, J=7.6 Hz), 8.19 (1H, s).

E) 1-(2-(4-(3-(cyclopropylmethoxy)phenoxy)cyclohexyl)-1,3-benzoxazol-6-yl)methanol To a mixture of lithium aluminum hydride (45.2 mg) and THF (7 ml) was added a mixture of ethyl 2-(4-(3-(cyclopropylmethoxy)phenoxy)cyclohexyl)-1,3-benzoxazole-6-carboxylate (173 mg) and THF (2 ml) under ice-cooling. The reaction mixture was stirred at room temperature for 2 hr, and water (5 ml) and 1N aqueous sodium hydroxide solution (1 ml) were successively added. The mixture was stirred for 30 min under ice-cooling, and water (5 ml) was added. The mixture was stirred at room temperature, filtered through celite, and concentrated under reduced pressure. The obtained residue was purified by silica gel column chromatography (hexane/ethyl acetate) to give the title compound (120 mg).

$^1$H NMR (400 MHz, CDCl$_3$) δ 0.32-0.37 (2H, m), 0.62-0.67 (2H, m), 1.24-1.31 (1H, m), 1.61-1.99 (4H, m), 2.00-2.38 (4H, m), 2.98-3.10 (1H, m), 3.78 (2H, dd, J=6.8, 2.4 Hz), 4.25-4.57 (1H, m), 4.82 (2H, d, J=4.4 Hz), 6.48-6.54 (3H, m), 7.13-7.19 (1H, m), 7.30 (1H, d, J=8.4 Hz), 7.54 (1H, s), 7.66 (1H, dd, J=8.0, 2.8 Hz).

* The peak of OH was not observed.

F) 2-(4-(3-(cyclopropylmethoxy) phenoxy)cyclohexyl)-1,3-benzoxazole-6-carbaldehyde To a mixture of (2-(4-(3-(cyclopropylmethoxy)phenoxy)cyclohexyl)-1,3-benzoxazol-6-yl)methanol (120 mg) and acetonitrile (6.1 ml) were added tetrapropylammonium perruthenate (5.36 mg) and 4-methylmorpholine 4-oxide (53.6 mg), and the mixture was stirred at room temperature for 3 hr. The reaction mixture was filtered, and concentrated under reduced pressure. The obtained residue was purified by silica gel column chromatography (hexane/ethyl acetate) to give the title compound (100 mg).

$^1$H NMR (400 MHz, CDCl$_3$) δ 0.32-0.37 (2H, m), 0.62-0.68 (2H, m), 1.22-1.32 (1H, m), 1.60-2.20 (4H, m), 2.21-2.41 (4H, m), 3.04-3.16 (1H, m), 3.78 (2H, dd, J=9.2, 2.4 Hz), 4.26-4.59 (1H, m), 6.48-6.55 (3H, m), 7.14-7.27 (1H, m), 7.81-7.90 (2H, m), 8.03 (1H, s), 10.09 (1H, s).

G) 1-(2-(4-(3-(cyclopropylmethoxy)phenoxy)cyclohexyl)-1,3-benzoxazol-6-yl) ethanol To a mixture of 2-(4-(3-(cyclopropylmethoxy)phenoxy)cyclohexyl)-1,3-benzoxazole-6-carbaldehyde (100 mg) and THF (2.5 ml) was added methylmagnesium bromide (3.0 M diethyl ether solution, 0.128 ml) under ice-cooling, and the mixture was stirred at room temperature for 1 hr. To the reaction mixture was added 1N hydrochloric acid under ice-cooling, and the mixture was extracted with ethyl acetate. The obtained organic layer was washed with saturated brine, dried over anhydrous sodium sulfate, and concentrated under reduced pressure. The obtained residue was purified by silica gel column chromatography (hexane/ethyl acetate) to give the title compound (90 mg).

$^1$H NMR (400 MHz, CDCl$_3$) δ 0.32-0.37 (2H, m), 0.61-0.67 (2H, m), 1.23-1.32 (1H, m), 1.54-1.90 (6H, m), 1.98-2.05 (1H, m), 2.11-2.40 (4H, m), 2.97-3.10 (1H, m), 3.78 (2H, dd, J=6.8, 2.4 Hz), 4.24-4.58 (1H, m), 5.00-5.08 (1H, m), 6.47-6.54 (3H, m), 7.12-7.18 (1H, m), 7.29-7.33 (1H, m), 7.52-7.56 (1H, m), 7.64 (1H, dd, J=7.8, 3.4 Hz).

* The peak of OH was not observed.

H) 6-(1-azidoethyl)-2-(4-(3-(cyclopropylmethoxy)cyclohexyl)cyclohexyl)-1,3-benzoxazole To a mixture of 1-(2-(4-(3-(cyclopropylmethoxy)phenoxy)cyclohexyl)-1,3-benzoxazol-6-yl)ethanol (88 mg) and toluene (1 ml) were added diphenylphosphoryl azide (0.093 ml) and DBU (0.098 ml), and the mixture was stirred at 60° C. for 5 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (hexane/ethyl acetate) to give the title compound (72 mg).

$^1$H NMR (400 MHz, CDCl$_3$) δ 0.32-0.37 (2H, m), 0.62-0.68 (2H, m), 1.24-1.32 (1H, m), 1.56-1.87 (6H, m), 1.89-2.06 (1H, m), 2.10-2.37 (4H, m), 2.99-3.10 (1H, m), 3.78 (2H, dd, J=7.2, 2.4 Hz), 4.25-4.57 (1H, m), 4.75 (1H, q, J=6.8 Hz), 6.47-6.55 (3H, m), 7.13-7.21 (1H, m), 7.26-7.35 (1H, m), 7.49-7.52 (1H, m), 7.68 (1H, dd, J=8.2, 2.6 Hz).

I) N-(1-(2-(4-(3-(cyclopropylmethoxy)phenoxy)cyclohexyl)-1,3-benzoxazol-6-yl)ethyl)acetamide A mixture of ethyl 2-(4-(3-(cyclopropylmethoxy)phenoxy)cyclohexyl)-1,3-benzoxazole-6-carboxylate (72 mg), 5% palladium carbon (7.1 mg) and ethyl acetate (5 ml) was stirred under a hydrogen atmosphere at room temperature for 5 hr. The reaction mixture was filtered through celite, and the residue was washed with methanol, and the filtrate was concentrated under reduced pressure. To the obtained residue were added acetic anhydride (0.017 ml) and dichloromethane (5 ml), and the mixture was stirred at room temperature for 3 hr. The reaction mixture was washed with water and saturated brine, dried over sodium sulfate, and concentrated under reduced pressure. The obtained residue was purified by silica gel column chromatography (dichloromethane/ethyl acetate) to give the title compound (48 mg).

$^1$H NMR (400 MHz, CDCl$_3$) δ 0.32-0.36 (2H, m), 0.62-0.67 (2H, m), 1.24-1.29 (1H, m), 1.54 (3H, d, J=6.8 Hz), 1.59-1.90 (3H, m), 1.96-2.38 (8H, m), 2.97-3.11 (1H, m), 3.78 (2H, dd, J=6.8, 2.0 Hz), 4.25-4.56 (1H, m), 5.19-5.30 (1H, m), 5.68-5.71 (1H, m), 6.48-6.54 (3H, m), 7.13-7.19 (1H, m), 7.26-7.29 (1H, m), 7.46-7.52 (1H, m), 7.64 (1H, dd, J=8.2, 3.0 Hz).

Example 11

N-(1-(2-(3-(3-(cyclopropylmethoxy)phenoxy)cyclobutyl)-1,3-benzoxazol-6-yl)ethyl)acetamide A) 5-(hydroxymethyl)-2-nitrophenol To a mixture of 3-hydroxy-4-nitrobenzoic acid (5 g) and dichloromethane (54.6 ml) were added trimethyl borate (5.18 ml) and boron trifluoride diethyl ether complex (5.88 ml) under ice-cooling. To the reaction mixture was added dropwise borane pyridine complex (4.41 ml) under ice-cooling. The reaction mixture was stirred at room temperature for 4 hr, and methanol (15 ml) was added under ice-cooling. The obtained mixture was concentrated under reduced pressure, and toluene (200 ml) was added. The obtained mixture was extracted 3 times with 1N aqueous sodium hydroxide solution (100 ml), and the combined aqueous layer was acidified with 6N hydrochloric acid. The obtained mixture was extracted with ethyl acetate. The obtained organic layer was washed with saturated brine, dried over anhydrous sodium sulfate, and concentrated under reduced pressure to give the title compound (4.3 g).

$^1$H NMR (400 MHz, DMSO-d$_6$) δ 4.48 (2H, s), 6.85 (1H, dd, J=8.4, 1.6 Hz), 7.05-7.06 (1H, m), 7.83 (1H, d, J=8.4 Hz), 10.87 (1H, brs).

* The peak of OH of —CH$_2$OH was not observed.

B) 5-(((tert-butyl(dimethyl)silyl)oxy)methyl)-2-nitrophenol

To a mixture of 5-(hydroxymethyl)-2-nitrophenol (5.4 g) and dichloromethane (106 ml) were added imidazole (10.9 g) and tert-butylchlorodimethylsilane (5.29 g). The reaction mixture was stirred at room temperature for 3 hr, water was added and the mixture was extracted with ethyl acetate. The obtained organic layer was washed with saturated brine, dried over anhydrous sodium sulfate, and concentrated under reduced pressure. The obtained residue was purified by silica gel column chromatography (hexane/ethyl acetate) to give the title compound (7.05 g).

$^1$H NMR (400 MHz, DMSO-d$_6$) δ 0.10 (6H, s), 0.92 (9H, s), 4.73 (2H, s), 6.86-6.90 (1H, dd, J=8.4, 1.6 Hz), 7.11 (1H, d, J=1.2 Hz), 7.88 (1H, d, J=8.4 Hz), 10.96 (1H, s).

C) 2-amino-5-(((tert-butyl(dimethyl) silyl)oxy)methyl)phenol

A mixture of 5-(((tert-butyl(dimethyl)silyl)oxy)methyl)-2-nitrophenol (7.05 g), 5% palladium carbon (containing water (50%), 1.06 g) and ethyl acetate (100 ml) was stirred under a 10 atm hydrogen atmosphere at 50° C. for 2 hr. The reaction mixture was filtered through celite and concentrated under reduced pressure. The obtained residue was purified by silica gel column chromatography (dichloromethane/ethyl acetate) to give the title compound (4.40 g).

$^1$H NMR (400 MHz, DMSO-d$_6$) δ 0.04 (6H, s), 0.87 (9H, s), 4.40-4.46 (4H, m), 6.45-6.52 (2H, m), 6.62 (1H, d, J=1.2 Hz), 8.94 (1H, brs).

D) N-(4-(((tert-butyl(dimethyl)silyl)oxy)methyl)-2-hydroxyphenyl)-3-oxocyclobutanecarboxamide A mixture of 2-amino-5-(((tert-butyl(dimethyl)silyl)oxy)methyl)phenol (3.17 g), 3-oxocyclobutanecarboxylic acid (1.5 g), WSCD (2.64 g), HOBt (2.11 g), triethylamine (12.2 ml) and dichloromethane (250 ml) was stirred at room temperature for 12 hr. To the reaction mixture was added saturated aqueous ammonium chloride solution, and the mixture was extracted with dichloromethane. The obtained organic layer was washed with saturated brine, dried over anhydrous magnesium sulfate, and concentrated under reduced pressure. The obtained residue was purified by silica gel column chromatography (hexane/ethyl acetate) to give the title compound (1.62 g).

$^1$H NMR (400 MHz, CDCl$_3$) δ 0.10 (6H, s), 0.94 (9H, s), 3.28-3.38 (3H, m), 3.58-3.64 (2H, m), 4.68 (2H, s), 6.86 (1H, dd, J=8.0, 1.6 Hz), 6.98 (1H, s), 7.11 (1H, d, J=8.0 Hz), 7.62 (1H, brs), 8.21 (1H, brs).

E) 3-(6-(((tert-butyl(dimethyl)silyl)oxy)methyl)-1,3-benzoxazol-2-yl)cyclobutanone A mixture of N-(4-(((tert-butyl(dimethyl)silyl)oxy)methyl)-2-hydroxyphenyl)-3-oxocyclobutanecarboxamide (1.62 g), diisopropyl azodicarboxylate (1.08 ml), triphenylphosphine (1.46 g) and THF (77 ml) was stirred at room temperature for 3 hr. The reaction mixture was concentrated under reduced pressure. The obtained residue was purified by silica gel column chromatography (hexane/ethyl acetate) to give the title compound (880 mg).

$^1$H NMR (400 MHz, CDCl$_3$) δ 0.12 (6H, s), 0.96 (9H, s), 3.55-3.73 (4H, s), 3.88-3.95 (1H, m), 4.86 (2H, s), 7.24-7.28 (1H, m), 7.54 (1H, s), 7.63 (1H, d, J=8.0 Hz).

F) 3-(6-(((tert-butyl(dimethyl) silyl)oxy)methyl)-1,3-benzoxazol-2-yl)cyclobutanol To a mixture of 3-(6-(((tert-butyl(dimethyl)silyl)oxy)methyl)-1,3-benzoxazol-2-yl)cyclobutanone (880 mg) and ethanol (10 ml) was added sodium borohydride (121 mg) under ice-cooling. The reaction mixture was stirred at 0° C. for 30 min. To the mixture was added water, and the mixture was extracted with ethyl acetate and saturated aqueous ammonium chloride solution. The obtained organic layer was washed with saturated brine, dried over anhydrous sodium sulfate, and concentrated under reduced pressure to give the title compound (860 mg).

$^1$H NMR (400 MHz, CDCl$_3$) δ 0.12 (6H, s), 0.96 (9H, s), 2.12-2.15 (1H, m), 2.40-2.49 (2H, m), 2.83-2.91 (2H, m), 3.21-3.30 (1H, m), 4.34-4.40 (1H, m), 4.85 (2H, s), 7.21-7.27 (1H, m), 7.51 (1H, s), 7.60 (1H, d, J=8.0 Hz).

G) 6-(((tert-butyl(dimethyl)silyl)oxy)methyl)-2-(3-(3-(cyclopropylmethoxy)phenoxy)cyclobutyl)-1,3-benzoxazole A mixture of 3-(6-(((tert-butyl(dimethyl)silyl)oxy)methyl)-1,3-benzoxazol-2-yl)cyclobutanol (740 mg), 3-(cyclopropylmethoxy)phenol (401 mg), triphenylphosphine (698 mg), diisopropyl azodicarboxylate (0.518 ml) and toluene (14 ml) was stirred at 80° C. for 4 hr. The reaction mixture was cooled to room temperature, and concentrated under reduced pressure. The obtained residue was purified by silica gel column chromatography (hexane/ethyl acetate) to give the title compound (650 mg).

$^1$H NMR (400 MHz, CDCl$_3$) δ 0.14 (6H, s), 0.32-0.36 (2H, m), 0.62-0.67 (2H, m), 1.24-1.29 (1H, m), 0.97 (9H, s), 1.24-1.29 (1H, m), 2.69-2.78 (2H, m), 2.94-3.01 (2H, m), 3.76-3.89 (3H, m), 4.86 (2H, s), 5.02-5.09 (1H, m), 6.40-6.52 (3H, m), 7.14-7.18 (1H, t, J=8.0 Hz), 7.24-7.28 (1H, m), 7.52 (1H, s), 7.63 (1H, d, J=8.0 Hz).

H) (2-(3-(3-(cyclopropylmethoxy)phenoxy)cyclobutyl)-1,3-benzoxazol-6-yl)methanol To a mixture of 6-(((tert-butyl(dimethyl)silyl)oxy)methyl)-2-(3-(3-(cyclopropylmethoxy)phenoxy)cyclobutyl)-1,3-benzoxazole (650 mg) and THF (11 ml) was added tetrabutylammonium fluoride (1.0 M THF solution, 2.71 ml) under ice-cooling. The reaction mixture was stirred at 0° C. for 1 hr, water was added and the mixture was extracted with ethyl acetate. The obtained organic layer was washed with saturated brine, dried over anhydrous sodium sulfate, and concentrated under reduced pressure. The obtained residue was purified by silica gel column chromatography (hexane/ethyl acetate) to give the title compound (460 mg).

$^1$H NMR (400 MHz, CDCl$_3$) δ 0.33-0.36 (2H, m), 0.62-0.67 (2H, m), 1.24-1.30 (1H, m), 1.79-1.80 (1H, m), 2.71-2.78 (2H, m), 2.95-3.01 (2H, m), 3.77-3.89 (3H, m), 4.83-4.84 (2H, m), 5.04-5.07 (1H, m), 6.41-6.52 (3H, m), 7.17 (1H, t, J=8.2 Hz), 7.33 (1H, d, J=8.0 Hz), 7.56 (1H, s), 7.68 (1H, d, J=8.0 Hz).

I) 2-(4-(3-(cyclopropylmethoxy)phenoxy)cyclobutyl)-1,3-benzoxazole-6-carbaldehyde A mixture of (2-(4-(3-(cyclopropylmethoxy)phenoxy)cyclobutyl)-1,3-benzoxazol-6-yl)methanol (460 mg), tetrapropylammonium perruthenate (22.1 mg), 4-methylmorpholine 4-oxide (221 mg) and acetonitrile (11 ml) was stirred at room temperature for 1 hr. The reaction mixture was filtered and concentrated under reduced pressure. The obtained residue was purified by silica gel column chromatography (hexane/ethyl acetate) to give the title compound (298 mg).

$^1$H NMR (400 MHz, CDCl$_3$) δ 0.32-0.37 (2H, m), 0.62-0.68 (2H, m), 1.24-1.29 (1H, m), 2.74-2.82 (2H, m), 2.97-3.04 (2H, m), 3.77-3.94 (3H, m), 5.05-5.09 (1H, m), 6.41-6.53 (3H, m), 7.17 (1H, t, J=8.2 Hz), 7.82-7.92 (2H, m), 8.05 (1H, s), 10.10 (1H, s).

J) 1-(2-(4-(3-(cyclopropylmethoxy)phenoxy)cyclobutyl)-1,3-benzoxazol-6-yl)ethanol To a mixture of 2-(4-(3-(cyclopropylmethoxy)phenoxy)cyclobutyl)-1,3-benzoxazole-6-carbaldehyde (290 mg) and THF (10 ml) was added methylmagnesium bromide (3.0 M diethyl ether solution, 0.798 ml) under ice-cooling, and the mixture was stirred at 0° C. for 2 hr. To the reaction mixture was added 1N hydrochloric acid, and the mixture was extracted with ethyl acetate. The obtained organic layer was washed with saturated brine, dried over anhydrous sodium sulfate, and concentrated under reduced pressure. The obtained residue was purified by silica gel column chromatography (hexane/ethyl acetate) to give the title compound (280 mg).

$^1$H NMR (400 MHz, CDCl$_3$) δ 0.32-0.36 (2H, m), 0.62-0.67 (2H, m), 1.24-1.29 (1H, m), 1.56 (3H, d, J=6.8 Hz), 1.83-1.85 (1H, m), 2.70-2.77 (2H, m), 2.94-3.00 (2H, m), 3.76-3.89 (3H, m), 5.03-5.08 (2H, m), 6.40-6.52 (3H, m), 7.16 (1H, t, J=8.0 Hz), 7.34 (1H, dd, J=8.0, 1.2 Hz), 7.58 (1H, d, J=1.2 Hz), 7.66 (1H, d, J=8.0 Hz).

K) 6-(1-azidoethyl)-2-(4-(3-(cyclopropylmethoxy)cyclobutyl)cyclohexyl)-1,3-benzoxazole To a mixture of 1-(2-(4-(3-(cyclopropylmethoxy)phenoxy)cyclobutyl)-1,3-benzoxazol-6-yl)ethanol (274 mg) and toluene (11 ml) were added diphenylphosphoryl azide (0.311 ml) and DBU (0.327 ml). The reaction mixture was stirred at 60° C. for 3 hr. To the reaction mixture was added water, and the mixture was extracted with toluene. The obtained organic layer was washed with saturated brine, dried over anhydrous sodium sulfate, and concentrated under reduced pressure. The obtained residue was purified by silica gel column chromatography (hexane/ethyl acetate) to give the title compound (180 mg).

$^1$H NMR (400 MHz, CDCl$_3$) δ 0.32-0.36 (2H, m), 0.62-0.67 (2H, m), 1.23-1.30 (1H, m), 1.59 (3H, d, J=6.8 Hz), 2.70-2.78 (2H, m), 2.94-3.01 (2H, m), 3.76-3.90 (3H, m), 4.76 (1H, q, J=6.8 Hz), 5.02-5.09 (1H, m), 6.40-6.52 (3H, m), 7.16 (1H, t, J=8.2 Hz), 7.31 (1H, dd, J=8.0, 1.6 Hz), 7.52 (1H, d, J=1.2 Hz), 7.70 (1H, d, J=8.4 Hz).

L) N-(1-(2-(3-(3-(cyclopropylmethoxy)phenoxy)cyclobutyl)-1,3-benzoxazol-6-yl)ethyl)acetamide A mixture of 6-(1-azidoethyl)-2-(4-(3-(cyclopropylmethoxy)cyclobutyl)cyclohexyl)-1,3-benzoxazole (180 mg), 5% palladium carbon (19 mg) and ethyl acetate (7 ml) was stirred under a hydrogen atmosphere at room temperature for 2 hr. The reaction mixture was filtered through celite, and the residue was washed with methanol, and the filtrate was concentrated under reduced pressure. To the obtained residue were added acetic anhydride (0.12 ml) and dichloromethane (5.5 ml), and the mixture was stirred at room temperature for 5 hr. The reaction mixture was washed with water and saturated brine, dried over anhydrous sodium sulfate, and concentrated under reduced pressure. The obtained residue was purified by silica gel column chromatography (hexane/ethyl acetate) to give the title compound (145 mg).

$^1$H NMR (400 MHz, CDCl$_3$) δ 0.32-0.36 (2H, m), 0.62-0.67 (2H, m), 1.24-1.29 (1H, m), 1.55 (3H, d, J=6.8 Hz), 2.01 (3H, s), 2.69-2.77 (2H, m), 2.92-2.99 (2H, m), 3.76-3.88 (3H, m), 5.00-5.08 (1H, m), 5.20-5.31 (1H, m), 5.74 (1H, d, J=7.6 Hz), 6.40-6.52 (3H, m), 7.16 (1H, t, J=8.0 Hz), 7.30 (1H, dd, J=8.0, 1.6 Hz), 7.49 (1H, d, J=1.2 Hz), 7.66 (1H, d, J=8.0 Hz).

Example 12

N-(1-(2-(5-(3-propoxyphenoxy)pyridin-2-yl)-1,3-benzoxazol-6-yl)ethyl)acetamide

A) 5-(3-(benzyloxy)phenoxy)pyridine-2-carbonitrile

A mixture of 3-(benzyloxy)phenol (15 g), 5-chloropyridine-2-carbonitrile (10.35 g), potassium tert-butoxide (10.08 g) and DMF (50 ml) was stirred at 80° C. overnight. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (14 g).

$^1$H NMR (400 MHz, CDCl$_3$) δ 5.06 (2H, s), 6.66 (2H, d, J=9.2 Hz), 6.88 (1H, d, J=8.4 Hz), 7.23 (1H, d, J=11.2 Hz), 7.32-7.40 (6H, m), 7.60 (1H, d, J=8.4 Hz), 8.44 (1H, s).

B) 5-(3-(benzyloxy)phenoxy)pyridine-2-carboxylic acid

A mixture of 5-(3-(benzyloxy)phenoxy)pyridine-2-carbonitrile (14 g), 3N aqueous sodium hydroxide solution (140 ml) and ethanol (200 ml) was stirred with heating under reflux overnight. The reaction mixture was concentrated under reduced pressure, and the obtained solid was washed with water and diethyl ether. To the obtained residue was added water, and the mixture was acidified with 6N hydrochloric acid. The obtained solid was collected by filtration to give the title compound (12 g).

MS(ESI+): [M+H]$^+$ 322.2.

C) ethyl 4-(((5-(3-(benzyloxy)phenoxy)pyridin-2-yl)carbonyl)amino)-3-hydroxybenzoate To a mixture of 5-(3-(benzyloxy)phenoxy)pyridine-2-carboxylic acid (10 g) and dichloromethane (80 ml) was added oxalyl chloride (7.8 g) under ice-cooling. The reaction mixture was stirred at room temperature for 1 hr, and concentrated under reduced pressure. To the obtained residue was added dichloromethane (50 ml) and the mixture was added to a mixture of ethyl 4-amino-3-hydroxybenzoate (5.61 g), triethylamine (7.84 g) and dichloromethane (30 ml). The reaction mixture was stirred at room temperature overnight, and washed with water. The obtained organic layer was dried, and concentrated under reduced pressure to give the title compound (13 g).

MS(ESI+): [M+H]$^+$ 485.2.

D) ethyl 2-(5-(3-(benzyloxy)phenoxy)pyridin-2-yl)-1,3-benzoxazole-6-carboxylate To a mixture of ethyl 4-(((5-(3-(benzyloxy)phenoxy)pyridin-2-yl)carbonyl)amino)-3-hydroxybenzoate (5 g), triphenylphosphine (4.06 g) and THF (100 ml) was added diisopropyl azodicarboxylate (3.13 g) with heating under reflux. The reaction mixture was concentrated under reduced pressure, and the obtained residue was purified by silica gel column chromatography (petroleum ether/ethyl acetate) to give the title compound (6 g).

$^1$H NMR (400 MHz, CDCl$_3$) δ 1.42 (3H, t, J=6.8 Hz), 4.41 (2H, q, J=6.8 Hz), 5.07 (2H, s), 6.71-6.74 (2H, m), 6.87 (1H, d, J=8.4 Hz), 7.32-7.43 (7H, m), 7.82 (1H, d, J=8.4 Hz), 8.12 (1H, d, J=8.4 Hz), 8.31 (2H, d, J=10.0 Hz), 8.61 (1H, s).

E) 2-(5-(3-(benzyloxy)phenoxy)pyridin-2-yl)-1,3-benzoxazole-6-carboxylic acid To a mixture of ethyl 2-(5-(3-(benzyloxy)phenoxy)pyridin-2-yl)-1,3-benzoxazole-6-carboxylate (6 g) and THF (40 ml) was added a mixture of lithium hydroxide (2.7 g) and water (20 ml). To the reaction mixture was added methanol (20 ml), and the mixture was stirred at room temperature for 30 min. The reaction mixture was concentrated under reduced pressure, and the obtained solid was collected by filtration, and washed with water and diethyl ether. The obtained solid was added with water, and acidified. The obtained solid was collected by filtration to give the title compound (3.5 g).

MS(ESI+): [M+H]$^+$ 439.2.

F) 1-(2-(5-(3-(benzyloxy)phenoxy)pyridin-2-yl)-1,3-benzoxazol-6-yl)ethanone

To a mixture of 2-(5-(3-(benzyloxy)phenoxy)pyridin-2-yl)-1,3-benzoxazole-6-carboxylic acid (3.5 g) and dichloromethane (20 ml) were added triethylamine (3.3 g), HATU (3 g) and N,O-dimethylhydroxylamine hydrochloride (1.55 g). The reaction mixture was stirred at room temperature overnight, and washed with water. The obtained organic layer was dried, and concentrated under reduced pressure. To the obtained residue was added THF (20 ml), and methylmagnesium bromide (3.0 M diethyl ether solution, 4.2 ml) was added at 30° C. The reaction mixture was stirred at room temperature for 1 hr, saturated aqueous ammonium chloride solution was added, and the mixture was concentrated under reduced pressure. The obtained mixture was extracted with ethyl acetate, and the organic layer was washed with water. The obtained organic layer was dried, and concentrated under reduced pressure to give the title compound (1.44 g).

$^1$H NMR (400 MHz, CDCl$_3$) δ 2.70 (3H, s), 5.07 (2H, s), 6.71-6.74 (2H, m), 6.87 (1H, d, J=8.0 Hz), 7.32-7.43 (7H, m), 7.85 (1H, d, J=8.4 Hz), 8.04 (1H, d, J=8.4 Hz), 8.25 (1H, s), 8.31 (1H, d, J=8.4 Hz), 8.61 (1H, s).

G) 1-(2-(5-(3-(benzyloxy)phenoxy)pyridin-2-yl)-1,3-benzoxazol-6-yl)ethanamine To a mixture of 1-(2-(5-(3-(benzyloxy)phenoxy)pyridin-2-yl)-1,3-benzoxazol-6-yl)ethanone (1.4 g) and methanol (10 ml) were added ammonium acetate (2.47 g) and sodium cyanoborohydride (0.3 g). The reaction mixture was stirred with heating under reflux overnight, and concentrated under reduced pressure. To the obtained residue was added dichloromethane, and washed with water. The obtained organic layer was dried, and concentrated under reduced pressure to give the title compound (1.2 g).

MS(ESI+): [M+H]$^+$ 438.2.

H) N-(1-(2-(5-(3-hydroxyphenoxy)pyridin-2-yl)-1,3-benzoxazol-6-yl)ethyl)acetamide To a mixture of 1-(2-(5-(3-(benzyloxy)phenoxy)pyridin-2-yl)-1,3-benzoxazol-6-yl)ethanamine (1.2 g), triethylamine (0.82 g) and dichloromethane (8 ml) was added acetyl chloride (0.43 g) under ice-cooling. The reaction mixture was stirred at room temperature for 1 hr, and washed with water. The obtained organic layer was dried, and concentrated under reduced pressure. To the obtained residue were added methanol (10 ml), acetic acid (5 drops) and palladium carbon (containing water (50%), 0.15 g). The reaction mixture was stirred under a hydrogen atmosphere at room temperature overnight. The catalyst was removed, and the obtained mixture was concentrated under reduced pressure to give the title compound (1 g).

MS(ESI+): [M+H]$^+$ 390.0.

I) N-(1-(2-(5-(3-propoxyphenoxy)pyridin-2-yl)-1,3-benzoxazol-6-yl)ethyl)acetamide To a mixture of N-(1-(2-(5-(3-hydroxyphenoxy)pyridin-2-yl)-1,3-benzoxazol-6-yl)ethyl)acetamide (150 mg), potassium carbonate (160 mg), sodium iodide (174 mg) and acetonitrile (5 ml) was added 1-bromopropane (142 mg). The reaction mixture was stirred with heating under reflux overnight. The reaction mixture was concentrated under reduced pressure, and the obtained residue was purified by HPLC (acetonitrile/water, 1% ammonium carbonate added) to give the title compound (60.4 mg).

$^1$H NMR (400 MHz, CDCl$_3$) δ 1.02-1.40 (3H, m), 1.53-1.60 (3H, m), 1.75-1.90 (2H, m), 2.02 (3H, s), 3.85-3.95 (2H, m), 5.25-5.35 (1H, m), 5.80-5.90 (1H, m), 6.60-6.70 (2H, m), 6.75-6.80 (1H, m), 7.30-7.45 (3H, m), 7.60 (1H, s), 7.70-7.75 (1H, m), 8.30-8.35 (1H, m), 8.53-8.55 (1H, m).

Example 13

N-(1-(2-(5-(3-butoxyphenoxy)pyridin-2-yl)-1,3-benzoxazol-6-yl)ethyl)acetamide

A) N-(1-(2-(5-(3-butoxyphenoxy)pyridin-2-yl)-1,3-benzoxazol-6-yl)ethyl)acetamide To a mixture of N-(1-(2-(5-(3-hydroxyphenoxy)pyridin-2-yl)-1,3-benzoxazol-6-yl)ethyl)acetamide (150 mg), potassium carbonate (160 mg), sodium iodide (174 mg) and acetonitrile (5 ml) was added 1-bromobutane (158 mg). The reaction mixture was stirred with heating under reflux overnight. The reaction mixture was concentrated under reduced pressure, and the obtained residue was purified by HPLC (acetonitrile/water, 1% ammonium carbonate added) to give the title compound (71.3 mg).

$^1$H NMR (400 MHz, CDCl$_3$) δ 0.95-1.00 (3H, m), 1.45-1.57 (5H, m), 1.75-1.79 (2H, m), 2.04 (3H, s), 3.92-3.98 (2H, m), 5.24-5.29 (1H, m), 6.03-6.06 (1H, m), 6.65-6.70 (2H, m), 6.77-6.79 (1H, m), 7.27-7.40 (3H, m), 7.58 (1H, s), 7.73-7.76 (1H, m), 8.26-8.29 (1H, m), 8.58-8.60 (1H, m).

Example 18

N-(1-(2-(5-(3-(2,2-dimethylpropoxy)phenoxy)pyridin-2-yl)-1,3-benzoxazol-6-yl)ethyl)acetamide A) N-(1-(2-(5-(3-(2,2-dimethylpropoxy)phenoxy)pyridin-2-yl)-1,3-benzoxazol-6-yl)ethyl)acetamide To a mixture of N-(1-(2-(5-(3-hydroxyphenoxy)pyridin-2-yl)-1,3-benzoxazol-6-yl)ethyl)acetamide (150 mg), potassium carbonate (266 mg), sodium iodide (174 mg) and DMF (2 ml) was added 1-bromo-2,2-dimethylpropane (175 mg). The reaction mixture was stirred under microwave radiation at 180° C. for 1 hr. The reaction mixture was purified by HPLC (acetonitrile/water, 1% ammonium carbonate added) to give the title compound (71.3 mg).

$^1$H NMR (400 MHz, CDCl$_3$) δ 1.03 (9H, s), 1.55-1.63 (3H, m), 2.02 (3H, s), 3.58 (2H, s), 5.20-5.30 (1H, m), 5.70-5.80 (1H, m), 6.65-6.70 (2H, m), 6.78-6.80 (1H, m), 7.27-7.43 (3H, m), 7.60 (1H, s), 7.75-7.77 (1H, m), 8.27-8.30 (1H, m), 8.59 (1H, s).

Example 19

N-(1-(2-(5-(3-(2-cyclopropylethoxy)phenoxy)pyridin-2-yl)-1,3-benzoxazol-6-yl)ethyl)acetamide A) N-(1-(2-(5-(3-(2-cyclopropylethoxy)phenoxy)pyridin-2-yl)-1,3-benzoxazol-6-yl)ethyl)acetamide To a mixture of N-(1-(2-(5-(3-hydroxyphenoxy)pyridin-2-yl)-1,3-benzoxazol-6-yl)ethyl)acetamide (150 mg), 2-cyclopropylethanol (100 mg), triphenylphosphine (202 mg) and THF (5 ml) was added diisopropyl azodicarboxylate (140 mg) with heating under reflux. The reaction mixture was concentrated under reduced pressure, and the obtained residue was purified by HPLC (acetonitrile/water, 1% ammonium carbonate added) to give the title compound (71.3 mg).

$^1$H NMR (400 MHz, CDCl$_3$) δ 0.11-0.13 (2H, m), 0.47-0.51 (2H, m), 0.82-0.88 (1H, m), 1.54-1.60 (3H, m), 1.65-1.71 (2H, m), 2.02 (3H, s), 4.00-4.05 (2H, m), 5.24-5.29 (1H, m), 5.85-5.90 (1H, m), 6.66-6.69 (2H, m), 6.78-6.81 (1H, m), 7.26-7.42 (3H, m), 7.59 (1H, s), 7.73-7.77 (1H, m), 8.26-8.29 (1H, m), 8.58 (1H, s).

Example 26

N-(1-(2-(4-((3-(cyclopropylmethoxy)phenyl)amino)phenyl)-1,3-benzoxazol-6-yl)ethyl)acetamide A) tert-butyl (3-(cyclopropylmethoxy)phenyl)carbamate A mixture of tert-butyl (3-hydroxyphenyl)carbamate (5 g), (chloromethyl)cyclopropane (3.28 ml), cesium carbonate (14 g) and DMF (150 ml) was stirred at 100° C. for 18 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (6.24 g).

$^1$H NMR (300 MHz, DMSO-d$_6$) δ 0.25-0.37 (2H, m), 0.46-0.64 (2H, m), 1.09-1.30 (1H, m), 1.49 (9H, brs), 3.65-3.85 (2H, m), 6.67-6.86 (1H, m), 6.88-7.03 (1H, m), 7.01-7.19 (2H, m), 9.28 (1H, s).

B) 3-(cyclopropylmethoxy)aniline hydrochloride

A mixture of tert-butyl (3-(cyclopropylmethoxy)phenyl)carbamate (1.26 g) and 4 M hydrogen chloride-ethyl acetate solution (25 ml) was stirred at room temperature for 18 hr. The obtained solid was collected by filtration to give the title compound (800 mg).

$^1$H NMR (300 MHz, DMSO-d$_6$) δ 0.23-0.41 (2H, m), 0.46-0.65 (2H, m), 1.10-1.31 (1H, m), 3.71-3.89 (2H, m), 6.69-6.90 (3H, m), 7.18-7.38 (1H, m), 8.81-10.19 (3H, m).

C) methyl 4-((3-(cyclopropylmethoxy)phenyl)amino)benzoate

A mixture of 3-(cyclopropylmethoxy)aniline hydrochloride (800 mg), palladium acetate (37.5 mg), 2,2'-bis(diphenylphosphino)-1,1'-binaphthyl (208 mg), cesium carbonate (3.26 g) and toluene (16 ml) was stirred under microwave radiation at 130° C. for 1 hr. To the reaction mixture was added saturated aqueous sodium hydrogen carbonate solution, and the mixture was extracted with ethyl acetate. The obtained organic layer was dried over anhydrous magnesium sulfate, and concentrated under reduced pressure. The obtained residue was purified by silica gel column chromatography (hexane/ethyl acetate) to give the title compound (450 mg).

MS (ESI+): [M+H]$^+$ 298.3.

D) 4-((3-(cyclopropylmethoxy)phenyl)amino)benzoic acid

To a mixture of methyl 4-((3-(cyclopropylmethoxy)phenyl)amino)benzoate (450 mg), 1N aqueous sodium hydroxide solution (4.54 ml) and ethanol (50 ml) was added 8N aqueous sodium hydroxide solution (8 ml). The reaction mixture was stirred at 65° C. for 18 hr. To the reaction mixture was acidified with 6N hydrochloric acid, and the obtained solid was collected by filtration to give the title compound (330 mg).
MS (ESI+): [M+H]$^+$ 284.2.

E) tert-butyl (4-acetyl-2-hydroxyphenyl)carbamate

A mixture of 1-(4-amino-3-hydroxyphenyl)ethanone (10.24 g), triethylamine (14.16 ml), di-tert-butyl dicarbonate (17.74 ml), N,N-dimethyl-4-aminopyridine (828 mg) and THF (400 ml) was stirred at 0° C. for 60 min. To the reaction mixture were added water and ethyl acetate, and the mixture was filtered through celite. To the obtained mixture was added saturated aqueous ammonium chloride solution, and the mixture was extracted with ethyl acetate. The obtained organic layer was dried over anhydrous magnesium sulfate, and concentrated under reduced pressure. The obtained residue was purified by silica gel column chromatography (hexane/ethyl acetate) to give the title compound (16 g).
MS (ESI+): [M+H]$^+$ 252.2.

F) tert-butyl (4-(1-acetamidoethyl)-2-hydroxyphenyl)carbamate

A mixture of tert-butyl (4-acetyl-2-hydroxyphenyl)carbamate (8 g), sodium acetate (7.84 g), hydroxyamine hydrochloride (6.64 g), water (30 ml) and ethanol (150 ml) was stirred at 65° C. for 3 hr. To the reaction mixture was added water and the mixture was extracted with ethyl acetate. The obtained organic layer was dried over anhydrous magnesium sulfate, and concentrated under reduced pressure. To the obtained residue were added methanol (200 ml) and 20% palladium hydroxide (containing water (50%), 800 mg), and the mixture was stirred under a hydrogen atmosphere at room temperature for 18 hr. A similar reaction was performed again, and the reaction mixtures were mixed. The catalyst was removed by filtration, and the filtrate was concentrated under reduced pressure. To the obtained residue were added THF (250 ml) and acetic anhydride (7.2 ml), and the mixture was stirred at room temperature for 30 min. To the reaction mixture was added water and the mixture was extracted with ethyl acetate. The obtained organic layer was dried over anhydrous magnesium sulfate, and concentrated under reduced pressure. The obtained residue was purified by silica gel column chromatography (hexane/ethyl acetate), and crystallized from diisopropyl ether/ethyl acetate to give the title compound (9 g).
$^1$H NMR (300 MHz, CDCl$_3$) δ 1.44 (3H, d, J=6.9 Hz), 1.52 (9H, s), 1.98 (3H, s), 4.93-5.12 (1H, m), 5.98 (1H, d, J=8.3 Hz), 6.76 (1H, dd, J=8.3, 1.9 Hz), 6.87 (1H, d, J=1.9 Hz), 6.97 (1H, s), 7.49 (1H, d, J=8.3 Hz), 9.18 (1H, s).

G) N-(4-(1-acetamidoethyl)-2-hydroxyphenyl)-4-((3-(cyclopropylmethoxy)phenyl)amino)benzamide A mixture of tert-butyl (4-(1-acetamidoethyl)-2-hydroxyphenyl)carbamate (366 mg), 4 M hydrogen chloride-ethyl acetate solution (10 ml) and methanol (5 ml) was stirred at room temperature for 18 hr. The reaction mixture was concentrated under reduced pressure. To the obtained residue was added DMF (10 ml), and N,N-diisopropylethylamine (0.541 ml), HATU (283 mg), 4-((3-(cyclopropylmethoxy)phenyl)amino)benzoic acid (176 mg) were added to a half amount (5 ml) of the mixture. The reaction mixture was stirred at 50° C. for 3 hr. To the reaction mixture was added saturated aqueous ammonium chloride solution, and the mixture was extracted with ethyl acetate. The obtained organic layer was washed with saturated aqueous ammonium chloride solution, dried over anhydrous magnesium sulfate, and concentrated under reduced pressure. The obtained residue was purified by silica gel column chromatography (hexane/ethyl acetate), and crystallized from diisopropyl ether/ethyl acetate to give the title compound (165 mg).
MS (ESI+): [M+H]$^+$ 460.3.

H) N-(1-(2-(4-((3-(cyclopropylmethoxy)phenyl)amino)phenyl)-1,3-benzoxazol-6-yl)ethyl)acetamide A mixture of N-(4-(1-acetamidoethyl)-2-hydroxyphenyl)-4-((3-(cyclopropylmethoxy)phenyl)amino)benzamide (60 mg), phosphorus pentaoxide (27.8 mg), p-toluenesulfonic acid monohydrate (37.3 mg) and DMF (8 ml) was stirred at 120° C. for 18 hr. To the reaction mixture was added 1N aqueous sodium hydroxide solution, and the mixture was extracted with ethyl acetate. The obtained organic layer was washed with saturated aqueous ammonium chloride solution, dried over anhydrous magnesium sulfate, and concentrated under reduced pressure. The obtained residue was purified by silica gel column chromatography (NH, hexane/ethyl acetate) to give the title compound (3.2 mg).
$^1$H NMR (300 MHz, CDCl$_3$) δ 0.31-0.40 (2H, m), 0.61-0.70 (2H, m), 1.20-1.34 (1H, m), 1.51-1.62 (3H, m), 2.02 (3H, s), 3.80 (2H, d, J=6.9 Hz), 5.26 (1H, t, J=7.3 Hz), 5.71 (1H, d, J=7.7 Hz), 6.02 (1H, s), 6.57-6.64 (1H, m), 6.72-6.79 (2H, m), 7.08-7.16 (2H, m), 7.26 (2H, s), 7.48-7.54 (1H, m), 7.67 (1H, d, J=8.3 Hz), 8.05-8.15 (2H, m).

Example 28

N-(1-(2-(5-(3-(cyclopropylmethoxy)phenoxy)hexahydrocyclopenta[c]pyrrole-2(1H)-yl)-1,3-benzoxazol-6-yl)ethyl)acetamide A) tert-butyl 5-hydroxyhexahydrocyclopenta[c]pyrrole-2(1H)-carboxylate To a mixture of tert-butyl 5-oxohexahydrocyclopenta[c]pyrrole-2(1H)-carboxylate (250 mg) and methanol (5 ml) was added sodium borohydride (63 mg) under ice-cooling, and the mixture was stirred at 0° C. for 2 hr. To the reaction mixture was added saturated aqueous ammonium chloride solution at 0° C., and the mixture was extracted with ethyl acetate. The obtained organic layer was washed with saturated brine, dried over anhydrous magnesium sulfate, and concentrated under reduced pressure to give the title compound (230 mg).
$^1$H NMR (300 MHz, CDCl$_3$) δ 1.42-1.56 (11H, m), 2.09-2.25 (2H, m), 2.52-2.70 (2H, m), 3.30-3.39 (2H, m), 3.45-3.56 (2H, m), 4.30 (1H, quin, J=6.4 Hz).

B) tert-butyl 5-(3-(cyclopropylmethoxy)phenoxy)hexahydrocyclopenta[c]pyrrole-2(1H)-carboxylate A mixture of tert-butyl 5-hydroxyhexahydrocyclopenta[c]pyrrole-2(1H)-carboxylate (150 mg), 3-(cyclopropylmethoxy)phenol (119 mg), triphenylphosphine (208 mg), diisopropyl azodicarboxylate (0.417 ml) and toluene (5 ml) was stirred at room temperature overnight. To the reaction mixture was added water at 0° C., and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (46 mg).

$^1$H NMR (300 MHz, CDCl$_3$) δ 0.23-0.40 (2H, m), 0.58-0.71 (2H, m), 1.23-1.30 (1H, m), 1.46 (9H, s), 1.72-1.89 (2H, m), 2.09-2.25 (2H, m), 2.74-2.94 (2H, m), 3.12-3.27 (2H, m), 3.45-3.62 (2H, m), 3.77 (2H, d, J=6.9 Hz), 4.82-4.92 (1H, m), 6.38-6.52 (3H, m), 7.09-7.18 (1H, m).

C) 5-(3-(cyclopropylmethoxy) phenoxy) octahydrocyclopenta[c]pyrrole hydrochloride To a mixture of tert-butyl 5-(3-(cyclopropylmethoxy) phenoxy)hexahydrocyclopenta[c]pyrrole-2(1H)-carboxylate (46 mg) and THF (1 ml) was added 4 M hydrogen chloride-cyclopropyl methyl ether solution (5 ml) at 0° C. The reaction mixture was stirred at room temperature overnight, and concentrated under reduced pressure to give the title compound (40 mg).

MS (ESI+): [M+H]$^+$ 274.4.

D) N-(1-(2-sulfanyl-1,3-benzoxazol-6-yl)ethyl)acetamide

A mixture of potassium O-ethyl carbonodithioate (245 mg), N-(1-(4-amino-3-hydroxyphenyl)ethyl)acetamide hydrochloride (235 mg) and pyridine (2 ml) was stirred at 100° C. for 2 hr. The reaction mixture was cooled to room temperature, and 3N hydrochloric acid was added. The mixture was stirred at room temperature for 1 hr, and extracted with water and ethyl acetate. The obtained organic layer was washed with saturated brine, dried over anhydrous magnesium sulfate, and concentrated under reduced pressure to give the title compound (135 mg).

MS (ESI+): [M+H]$^+$ 236.9.

E) N-(1-(2-(methylsulfanyl)-1,3-benzoxazol-6-yl) ethyl)acetamide

A mixture of N-(1-(2-sulfanyl-1,3-benzoxazol-6-yl)ethyl) acetamide (80 mg), methyl iodide (0.023 ml), potassium carbonate (46.8 mg) and DMF (1.6 ml) was stirred at room temperature for 1 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (73 mg).

$^1$H NMR (300 MHz, CDCl$_3$) δ 1.51 (3H, d, J=7.0 Hz), 1.98 (3H, s), 2.74 (3H, s), 5.13-5.26 (1H, m), 5.98 (1H, d, J=7.0 Hz), 7.24 (1H, dd, J=8.2, 1.6 Hz), 7.39 (1H, d, J=1.1 Hz), 7.52 (1H, d, J=8.1 Hz).

F) N-(1-(2-(5-(3-(cyclopropylmethoxy)phenoxy) hexahydrocyclopenta[c]pyrrole-2(1H)-yl)-1,3-benzoxazol-6-yl)ethyl)acetamide To a mixture of N-(1-(2-(methylsulfanyl)-1,3-benzoxazol-6-yl)ethyl)acetamide (60 mg) and THF (1 ml) was added 3-chlorobenzenecarboperoxoic acid (83 mg) under ice-cooling. The reaction mixture was stirred at room temperature for 5 hr. To the reaction mixture was added sodium thiosulfate aqueous solution, and the mixture was extracted with ethyl acetate. The obtained organic layer was washed with water and saturated brine, dried over anhydrous magnesium sulfate, and concentrated under reduced pressure. To a mixture of the obtained residue, triethylamine (0.09 ml) and DMF (1 ml) was added 5-(3-(cyclopropylmethoxy) phenoxy)octahydrocyclopenta[c]pyrrole hydrochloride (40 mg) under ice-cooling. The reaction mixture was stirred at room temperature overnight. To the reaction mixture was added water, and the mixture was extracted with ethyl acetate. The obtained organic layer was washed with saturated brine, dried over anhydrous magnesium sulfate, and concentrated under reduced pressure. The obtained residue was purified by HPLC (acetonitrile/water, 0.1% TFA added) to give the title compound (5 mg).

$^1$H NMR (300 MHz, CD$_3$OD) δ 0.23-0.38 (2H, m), 0.54-0.68 (2H, m), 1.17-1.26 (1H, m), 1.45 (3H, d, J=7.0 Hz), 1.78-2.09 (5H, m), 2.18-2.33 (2H, m), 3.03-3.14 (2H, m), 3.51-3.58 (2H, m), 3.72-3.94 (4H, m), 5.04-5.11 (2H, m), 6.35-6.55 (3H, m), 7.03-7.26 (3H, m), 7.28-7.36 (1H, m).

Example 29

N-(1-(2-(3-(3-pentylphenoxy)azetidin-1-yl)-1,3-benzoxazol-6-yl)ethyl)acetamide

A) ethyl 2-(3-hydroxyazetidin-1-yl)-1,3-benzoxazole-6-carboxylate

A mixture of ethyl 2-chloro-1,3-benzoxazole-6-carboxylate (17.5 g), azetidin-3-ol hydrochloride (9.35 g), N,N-diisopropylethylamine (33.9 ml) and DMF (175 ml) was stirred at room temperature overnight. To the reaction mixture was added water, and the mixture was stirred at room temperature for 30 min. The obtained solid was collected by filtration to give the title compound (19.26 g).

$^1$H NMR (300 MHz, DMSO-d$_6$) δ 1.32 (3H, t, J=7.1 Hz), 3.92-4.05 (2H, m), 4.29 (2H, q, J=7.1 Hz), 4.39-4.49 (2H, m), 4.58-4.73 (1H, m), 5.92 (1H, d, J=6.6 Hz), 7.28-7.38 (1H, m), 7.79-7.86 (1H, m), 7.86-7.93 (1H, m).

B) ethyl 2-(3-((methylsulfonyl)oxy)azetidin-1-yl)-1,3-benzoxazole-6-carboxylate

A mixture of ethyl 2-(3-hydroxyazetidin-1-yl)-1,3-benzoxazole-6-carboxylate (1 g), methanesulfonyl chloride (0.354 ml), triethylamine (0.797 ml) and THF (10 ml) was stirred at room temperature overnight. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ ethyl acetate) to give the title compound (0.8 g).

MS (ESI+): [M+H]$^+$ 340.9.

C) ethyl 2-(3-(3-pentylphenoxy)azetidin-1-yl)-1,3-benzoxazole-6-carboxylate

A mixture of ethyl 2-(3-((methylsulfonyl)oxy)azetidin-1-yl)-1,3-benzoxazole-6-carboxylate (692 mg), 3-pentylphenol (334 mg), cesium carbonate (994 mg) and DMF (5 ml) was stirred at 100° C. for 4 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (700 mg).

$^1$H NMR (300 MHz, DMSO-d$_6$) δ 0.87 (3H, t, J=6.9 Hz), 1.21-1.40 (7H, m), 1.49-1.64 (2H, m), 2.52-2.60 (2H, m), 4.18-4.36 (4H, m), 4.73 (2H, dd, J=9.4, 6.6 Hz), 5.14-5.29 (1H, m), 6.69 (2H, s), 6.79-6.89 (1H, m), 7.22 (1H, t, J=7.8 Hz), 7.39 (1H, d, J=8.2 Hz), 7.85 (1H, dd, J=8.2, 1.6 Hz), 7.92 (1H, d, J=1.1 Hz).

D) (2-(3-(3-pentylphenoxy)azetidin-1-yl)-1,3-benzoxazol-6-yl)methanol

To a mixture of lithium aluminum hydride (65 mg) and THF (7 ml) was added a mixture of ethyl 2-(3-(3-pentylphenoxy)azetidin-1-yl)-1,3-benzoxazole-6-carboxylate (700 mg) and THF (7 ml) under ice-cooling. The reaction mixture was stirred at 0° C. for 30 min, and water (0.07 ml), 1N aqueous sodium hydroxide solution (0.07 ml) and water (0.21 ml) were successively added. The obtained mixture was stirred at room temperature for 30 min, filtered through celite and concentrated under reduced pressure. The obtained residue was purified by silica gel column chromatography (NH, hexane/ethyl acetate) to give the title compound (157 mg).

$^1$H NMR (300 MHz, DMSO-d$_6$) δ 0.80-0.93 (3H, m, J=13.8 Hz), 1.21-1.40 (4H, m), 1.47-1.63 (2H, m), 2.51-2.59 (2H, m), 4.16 (2H, dd, J=9.8, 4.1 Hz), 4.52 (2H, d, J=5.8 Hz), 4.67 (2H, dd, J=9.8, 6.4 Hz), 5.13-5.26 (2H, m), 6.68 (2H, s), 6.83 (1H, d, J=7.6 Hz), 7.14 (1H, d, J=1.5 Hz), 7.17-7.29 (2H, m), 7.36 (1H, d, J=0.8 Hz).

E) N-(1-(2-(3-(3-pentylphenoxy)azetidin-1-yl)-1,3-benzoxazol-6-yl)ethyl)acetamide A mixture of (2-(3-(3-pentylphenoxy)azetidin-1-yl)-1,3-benzoxazol-6-yl)methanol (157 mg), tetrapropylammonium perruthenate (15 mg), 4-methylmorpholine 4-oxide (75 mg), molecular sieves 4A (200 mg) and acetonitrile (5 ml) was stirred at room temperature for 2 hr. The reaction mixture was concentrated under reduced pressure. The obtained residue was passed through a silica gel short column (ethyl acetate), and concentrated under reduced pressure. To the obtained residue was added THF (5 ml), and methylmagnesium bromide (1.0 M THF solution, 0.86 ml) was added under ice-cooling. The reaction mixture was stirred at 0° C. for 1 hr, saturated aqueous ammonium chloride solution was added and the mixture was extracted with ethyl acetate. The obtained organic layer was washed with saturated brine, dried over anhydrous magnesium sulfate, and concentrated under reduced pressure. To the obtained residue was added acetonitrile (3 ml), and concentrated sulfuric acid (0.046 ml) was added under ice-cooling. The reaction mixture was stirred at room temperature for 2 hr, 1N aqueous sodium hydroxide solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (110 mg).

$^1$H NMR (300 MHz, DMSO-d$_6$) δ 0.86 (3H, t, J=6.9 Hz), 1.22-1.31 (4H, m), 1.34 (3H, d, J=7.0 Hz), 1.48-1.64 (2H, m), 1.83 (3H, s), 2.52-2.59 (2H, m), 4.15 (2H, dd, J=9.4, 4.0 Hz), 4.66 (2H, dd, J=9.1, 6.5 Hz), 4.85-5.03 (1H, m), 5.11-5.26 (1H, m), 6.63-6.75 (2H, m), 6.78-6.89 (1H, m), 7.13 (1H, d, J=1.3 Hz), 7.17-7.30 (2H, m), 7.35 (1H, d, J=1.3 Hz), 8.25 (1H, d, J=8.1 Hz).

Example 30

N-(1-(2-(3-(3-(3-methoxypropyl) phenoxy) azetidin-1-yl)-1,3-benzoxazol-6-yl)ethyl)acetamide

A) benzyl 3-(3-(benzyloxy)phenyl)propanoate

A mixture of 3-(3-hydroxyphenyl)propanoic acid (2 g), benzyl bromide (2.86 ml), potassium carbonate (2.16 g) and DMF (30 ml) was stirred at room temperature overnight. To the reaction mixture was added water and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (3.68 g).

$^1$H NMR (300 MHz, DMSO-d$_6$) δ 2.64-2.76 (2H, m), 2.79-2.91 (2H, m), 5.05 (2H, s), 5.08 (2H, s), 6.75-6.86 (2H, m), 6.89 (1H, d, J=1.6 Hz), 7.12-7.22 (1H, m), 7.26-7.48 (10H, m).

B) 3-(3-(benzyloxy)phenyl)propan-1-ol

To a mixture of lithium aluminum hydride (403 mg) and THF (30 ml) was added dropwise a mixture of benzyl 3-(3-(benzyloxy)phenyl)propanoate (3.68 g) and THF (30 ml) under ice-cooling. The reaction mixture was stirred at 0° C. for 30 min, and water (0.5 ml) and 1N aqueous sodium hydroxide solution (0.5 ml) were successively added. Water (1.2 ml) was added to the mixture, and the mixture was stirred at room temperature for 30 min. The mixture was filtered through celite, and concentrated under reduced pressure. The obtained residue was purified by silica gel column chromatography (hexane/ethyl acetate) to give the title compound (2.47 g).

$^1$H NMR (300 MHz, DMSO-d$_6$) δ 1.61-1.78 (2H, m), 2.53-2.62 (2H, m), 3.35-3.45 (2H, m), 4.44 (1H, t, J=5.1 Hz), 5.07 (2H, s), 6.69-6.89 (3H, m), 7.18 (1H, t, J=7.8 Hz), 7.28-7.50 (5H, m).

C) 1-(benzyloxy)-3-(3-methoxypropyl)benzene

To a mixture of sodium hydride (50% in oil, 0.489 g) and DMF (25 ml) was added 3-(3-(benzyloxy)phenyl)propan-1-ol (2.47 g) under ice-cooling. The reaction mixture was stirred at 0° C. for 30 min, and methyl iodide (0.96 ml) was added. The reaction mixture was stirred at room temperature for 2 hr. To the reaction mixture was added water and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (1.28 g).

$^1$H NMR (300 MHz, DMSO-d$_6$) δ 1.70-1.84 (2H, m), 2.53-2.61 (2H, m), 3.22 (3H, s), 3.31 (2H, d, J=5.7 Hz), 5.08 (2H, s), 6.74-6.87 (3H, m), 7.14-7.22 (1H, m), 7.27-7.48 (5H, m).

D) 3-(3-methoxypropyl)phenol

A mixture of 1-(benzyloxy)-3-(3-methoxypropyl)benzene (1.28 g), 10% palladium carbon (containing water (50%), 0.266 g) and methanol (25 ml) was stirred under a hydrogen atmosphere at room temperature for 4 hr. The reaction mixture was filtered through celite, and concentrated under reduced pressure. The obtained residue was purified by silica gel column chromatography (hexane/ethyl acetate) to give the title compound (0.88 g).

$^1$H NMR (300 MHz, DMSO-d$_6$) δ 1.63-1.84 (2H, m), 2.51-2.55 (2H, m), 3.22 (3H, s), 3.26-3.31 (2H, m), 6.49-6.66 (3H, m), 6.97-7.11 (1H, m), 9.22 (1H, s).

E) ethyl 2-(3-(benzyloxy)azetidin-1-yl)-1,3-benzoxazole-6-carboxylate

To a mixture of sodium hydride (60% in oil, 2.99 g) and DMF (150 ml) was added ethyl 2-(3-hydroxyazetidin-1-yl)-1,3-benzoxazole-6-carboxylate (16.34 g). The reaction mixture was stirred at 0° C. for 30 min and (bromomethyl)benzene (8.89 ml) was added. The mixture was stirred at room temperature for 2 hr, and extracted with ethyl acetate and water. The obtained organic layer was washed with saturated brine, dried over anhydrous magnesium sulfate, and concentrated under reduced pressure. The obtained residue was purified by silica gel column chromatography (hexane/ethyl acetate) to give the title compound (20.3 g).

$^1$H NMR (300 MHz, DMSO-d$_6$) δ 1.32 (3H, t, J=7.1 Hz), 4.07-4.15 (2H, m), 4.30 (2H, q, J=7.1 Hz), 4.37-4.48 (2H, m), 4.52 (2H, s), 4.55-4.65 (1H, m), 7.25-7.42 (6H, m), 7.83 (1H, dd, J=8.2, 1.6 Hz), 7.90 (1H, d, J=1.1 Hz).

F) (2-(3-(benzyloxy)azetidin-1-yl)-1,3-benzoxazol-6-yl)methanol

To a mixture of sodium bis(2-methoxyethoxy)aluminum (70% toluene solution, 40 ml) and THF (100 ml) was added a mixture of ethyl 2-(3-(benzyloxy)azetidin-1-yl)-1,3-benzoxazole-6-carboxylate (20.3 g) and THF (100 ml) under ice-cooling. The reaction mixture was stirred at 0° C. for 30 min, 1N hydrochloric acid was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (10 g).

$^1$H NMR (300 MHz, DMSO-d$_6$) δ 4.02-4.08 (2H, m), 4.31-4.42 (2H, m), 4.47-4.53 (4H, m), 4.54-4.62 (1H, m), 5.16 (1H, t, J=5.7 Hz), 7.07-7.15 (1H, m), 7.18-7.26 (1H, m), 7.28-7.43 (6H, m).

G) N-(1-(2-(3-(benzyloxy)azetidin-1-yl)-1,3-benzoxazol-6-yl)ethyl)acetamide

A mixture of (2-(3-(benzyloxy)azetidin-1-yl)-1,3-benzoxazol-6-yl)methanol (10 g), tetrapropylammonium perruthenate (226 mg), 4-methylmorpholine 4-oxide (5.66 g), molecular sieves 4A (15 g) and acetonitrile (100 ml) was stirred at room temperature for 2 hr. The reaction mixture was filtered, and concentrated under reduced pressure. The obtained residue was passed through a silica gel short column (hexane/ethyl acetate), and concentrated under reduced pressure. To the obtained residue was added THF (50 ml), and methylmagnesium bromide (1.0 M THF solution, 48.3 ml) was added under ice-cooling. The reaction mixture was stirred at 0° C. for 1 hr, saturated aqueous ammonium chloride solution was added and the mixture was extracted with ethyl acetate. The obtained organic layer was washed with saturated brine, dried over anhydrous magnesium sulfate, and concentrated under reduced pressure. To the obtained residue was added acetonitrile (50 ml), and concentrated sulfuric acid (3.43 ml) was added under ice-cooling. The reaction mixture was stirred at room temperature for 2 hr, 1N aqueous sodium hydroxide solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (7.29 g).

$^1$H NMR (300 MHz, DMSO-d$_6$) δ 1.33 (3H, d, J=7.0 Hz), 1.82 (3H, s), 3.97-4.10 (2H, m), 4.30-4.42 (2H, m), 4.51 (2H, s), 4.52-4.64 (1H, m), 4.83-5.03 (1H, m), 7.06-7.14 (1H, m), 7.18-7.25 (1H, m), 7.28-7.43 (6H, m), 8.24 (1H, d, J=7.9 Hz).

H) 1-(6-(1-acetamidoethyl)-1,3-benzoxazol-2-yl)azetidin-3-yl methanesulfonate

A mixture of N-(1-(2-(3-(benzyloxy)azetidin-1-yl)-1,3-benzoxazol-6-yl)ethyl)acetamide (7.29 g), 10% palladium carbon (containing water (50%), 1.06 g) and acetic acid (50 ml) was stirred under a 5 atm hydrogen atmosphere at room temperature for 5 days. The reaction mixture was filtered through celite, and concentrated under reduced pressure. To the obtained residue were added THF (100 ml), triethylamine (8.34 ml) and methanesulfonyl chloride (3.09 ml), and the mixture was stirred at room temperature for 2 hr. To the reaction mixture was added water and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (4.8 g).

$^1$H NMR (300 MHz, DMSO-d$_6$) δ 1.34 (3H, d, J=7.0 Hz), 1.83 (3H, s), 3.30 (3H, s), 4.25-4.34 (2H, m), 4.53-4.64 (2H, m), 4.87-5.01 (1H, m), 5.40-5.52 (1H, m), 7.13 (1H, dd, J=8.1, 1.4 Hz), 7.26 (1H, d, J=8.1 Hz), 7.34-7.39 (1H, m), 8.26 (1H, d, J=8.0 Hz).

I) N-(1-(2-(3-(3-(3-methoxypropyl)phenoxy)azetidin-1-yl)-1,3-benzoxazol-6-yl)ethyl)acetamide A mixture of 1-(6-(1-acetamidoethyl)-1,3-benzoxazol-2-yl)azetidin-3-yl methanesulfonate (100 mg), 3-(3-methoxypropyl)phenol (51.7 mg), cesium carbonate (184 mg) and DMF (2 ml) was stirred at 100° C. overnight. The reaction mixture was cooled to room temperature, and extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (100 mg).

$^1$H NMR (300 MHz, DMSO-d$_6$) δ 1.34 (3H, d, J=7.0 Hz), 1.73-1.81 (2H, m), 1.83 (3H, s), 2.54-2.65 (2H, m), 3.23 (3H, s), 3.28-3.31 (2H, m), 4.10-4.21 (2H, m), 4.61-4.71 (2H, m), 4.86-5.01 (1H, m), 5.15-5.25 (1H, m), 6.64-6.75 (2H, m), 6.80-6.88 (1H, m), 7.08-7.16 (1H, m), 7.18-7.29 (2H, m), 7.31-7.40 (1H, m), 8.25 (1H, d, J=8.0 Hz).

Example 31

N-(1-(2-(5-(3-(cyclopropylmethoxy)phenoxy)pyridin-2-yl)-1-benzofuran-5-yl)ethyl)acetamide

A) 5-(3-(cyclopropylmethoxy)phenoxy)pyridine-2-carbaldehyde

To a mixture of 5-(3-(cyclopropylmethoxy)phenoxy)pyridine-2-carbonitrile (1 g) and THF (10 ml) was added diisobutylaluminum hydride (1.5 M toluene solution, 5 ml) under ice-cooling. The reaction mixture was stirred at room temperature for 1 hr, 1N hydrochloric acid was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (0.5 g).
$^1$H NMR (300 MHz, DMSO-$d_6$) δ 0.26-0.34 (2H, m), 0.52-0.61 (2H, m), 1.19-1.27 (1H, m), 3.82 (2H, d, J=7.0 Hz), 6.74 (1H, dd, J=8.0, 0.8 Hz), 6.78 (1H, t, J=2.3 Hz), 6.82-6.90 (1H, m), 7.37 (1H, t, J=8.2 Hz), 7.49 (1H, ddd, J=8.6, 2.8, 0.7 Hz), 7.96 (1H, dd, J=8.6, 0.5 Hz), 8.57 (1H, dd, J=2.7, 0.5 Hz), 9.93 (1H, d, J=0.7 Hz).

B) 5-(3-(cyclopropylmethoxy)phenoxy)-2-ethynylpyridine

A mixture of 5-(3-(cyclopropylmethoxy)phenoxy)pyridine-2-carbaldehyde (0.5 g), potassium carbonate (0.5 g), dimethyl (1-diazo-2-oxopropyl)phosphonate (0.4 ml) and methanol (5 ml) was stirred at room temperature for 2 hr. To the reaction mixture was added water and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (0.35 g).
$^1$H NMR (300 MHz, DMSO-$d_6$) δ 0.26-0.35 (2H, m), 0.51-0.60 (2H, m), 1.18-1.26 (1H, m), 3.80 (2H, d, J=7.0 Hz), 4.27 (1H, s), 6.60-6.72 (2H, m), 6.79 (1H, ddd, J=8.3, 2.4, 0.8 Hz), 7.26-7.42 (2H, m), 7.57 (1H, dd, J=8.6, 0.6 Hz), 8.34 (1H, dd, J=2.9, 0.6 Hz).

C) methyl 2-(5-(3-(cyclopropylmethoxy)phenoxy)pyridin-2-yl)-1-benzofuran-5-carboxylate A mixture of 5-(3-(cyclopropylmethoxy)phenoxy)-2-ethynylpyridine (349 mg), methyl 4-hydroxy-3-iodobenzoate (402 mg), bis(triphenylphosphine)dichloropalladium (46 mg), copper(I) iodide (15 mg), 1,1,3,3-tetramethylguanidine (0.5 ml) and DMF (5 ml) was stirred under an argon atmosphere at 100° C. for 4 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (341 mg).
$^1$H NMR (300 MHz, DMSO-$d_6$) δ 0.22-0.40 (2H, m), 0.48-0.61 (2H, m), 1.08-1.30 (1H, m), 3.82 (2H, d, J=7.0 Hz), 3.89 (3H, s), 6.62-6.75 (2H, m), 6.77-6.87 (1H, m), 7.28-7.39 (1H, m), 7.50-7.58 (1H, m), 7.62 (1H, s), 7.73-7.84 (1H, m), 7.96-8.03 (2H, m), 8.38 (1H, d, J=1.4 Hz), 8.47-8.57 (1H, m).

D) N-(1-(2-(5-(3-(cyclopropylmethoxy)phenoxy)pyridin-2-yl)-1-benzofuran-5-yl)ethyl)acetamide To a mixture of lithium aluminum hydride (31 mg) and THF (3 ml) was added a mixture of methyl 2-(5-(3-(cyclopropylmethoxy)phenoxy)pyridin-2-yl)-1-benzofuran-5-carboxylate (341 mg) and THF (3 ml) under ice-cooling. The reaction mixture was stirred at 0° C. for 30 min, and water (0.03 ml), 1N aqueous sodium hydroxide solution (0.03 ml) and water (0.09 ml) were successively added. The obtained mixture was stirred at room temperature for 30 min, filtered through celite and concentrated under reduced pressure. To the obtained residue was added acetonitrile (3 ml), and tetrapropylammonium perruthenate (14 mg), 4-methylmorpholine 4-oxide (144 mg) and molecular sieves 4A (0.5 g) were added. The reaction mixture was stirred at room temperature for 2 hr, filtered through celite, and concentrated under reduced pressure. The obtained residue was passed through a silica gel short column (ethyl acetate), and concentrated under reduced pressure. To the obtained residue was added THF (5 ml), and methylmagnesium bromide (1.0 M THF solution, 1.6 ml) was added under ice-cooling. The reaction mixture was stirred at 0° C. for 30 min, saturated aqueous ammonium chloride solution was added and the mixture was extracted with ethyl acetate. The obtained organic layer was washed with saturated brine, dried over anhydrous magnesium sulfate, and concentrated under reduced pressure. To the obtained residue was added acetonitrile (5 ml), and concentrated sulfuric acid (0.09 ml) was added under ice-cooling. The reaction mixture was stirred at room temperature for 2 hr, 1N aqueous sodium hydroxide solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (250 mg).
$^1$H NMR (300 MHz, DMSO-$d_6$) δ 0.24-0.35 (2H, m), 0.50-0.61 (2H, m), 1.10-1.27 (1H, m), 1.39 (3H, d, J=7.0 Hz), 1.85 (3H, s), 3.82 (2H, d, J=7.0 Hz), 4.93-5.08 (1H, m), 6.63-6.74 (2H, m), 6.75-6.83 (1H, m), 7.27-7.38 (2H, m), 7.47 (1H, s), 7.49-7.65 (3H, m), 7.95 (1H, d, J=8.7 Hz), 8.33 (1H, d, J=8.0 Hz), 8.48 (1H, d, J=2.4 Hz).

Example 32

N-(1-(2-(5-(3-(cyclopropylmethoxy)phenoxy)pyridin-2-yl)-1H-benzimidazol-6-yl)ethyl)acetamide

A) methyl 2-(5-(3-(cyclopropylmethoxy)phenoxy)pyridin-2-yl)-1H-benzimidazole-6-carboxylate To a mixture of 5-(3-(cyclopropylmethoxy)phenoxy)pyridine-2-carbonitrile (1 g) and methanol (10 ml) was added sodium methoxide (28% methanol solution, 72 mg). The reaction mixture was stirred at room temperature for 30 min, and methyl 3,4-diaminobenzoate (624 mg) and acetic acid (0.43 ml) were added. The reaction mixture was stirred at 60° C. overnight. The reaction mixture was cooled to room temperature, saturated aqueous sodium hydrogen carbonate solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (1.4 g).

$^1$H NMR (300 MHz, DMSO-d$_6$) δ 0.25-0.36 (2H, m), 0.51-0.62 (2H, m), 1.17-1.27 (1H, m), 3.83 (2H, d, J=7.0 Hz), 3.88 (3H, s), 6.68-6.79 (2H, m), 6.79-6.86 (1H, m), 7.36 (1H, t, J=8.2 Hz), 7.58 (1H, dd, J=8.7, 2.8 Hz), 7.63-7.75 (1H, m), 7.81-7.91 (1H, m), 8.17-8.26 (1H, m), 8.37 (1H, d, J=8.7 Hz), 8.56 (1H, d, J=2.4 Hz), 13.42 (1H, brs).

B) (2-(5-(3-(cyclopropylmethoxy)phenoxy)pyridin-2-yl)-1H-benzimidazol-6-yl)methanol To a mixture of lithium aluminum hydride (129 mg) and THF (10 ml) was added dropwise a mixture of methyl 2-(5-(3-(cyclopropylmethoxy)phenoxy)pyridin-2-yl)-1H-benzimidazole-6-carboxylate (1.41 g) and THF (10 ml) under ice-cooling. The reaction mixture was stirred at 0° C. for 30 min, and water (0.13 ml) and 1N aqueous sodium hydroxide solution (0.13 ml) were successively added. Water (0.39 ml) was added to the mixture, and the mixture was stirred at room temperature for 30 min. The mixture was filtered through celite, and concentrated under reduced pressure. The obtained residue was purified by silica gel column chromatography (hexane/ethyl acetate) to give the title compound (330 mg).

$^1$H NMR (300 MHz, DMSO-d$_6$) δ 0.32 (2H, brs), 0.48-0.66 (2H, m), 1.18-1.27 (1H, m), 3.82 (2H, d, J=7.0 Hz), 4.59 (2H, brs), 5.06-5.25 (1H, m), 6.63-6.87 (3H, m), 7.05-7.25 (1H, m), 7.28-7.41 (1H, m), 7.43-7.68 (3H, m), 8.20-8.37 (1H, m), 8.45-8.56 (1H, m), 12.89-13.06 (1H, m).

C) N-(1-(2-(5-(3-(cyclopropylmethoxy)phenoxy)pyridin-2-yl)-1H-benzimidazol-6-yl)ethyl)acetamide A mixture of (2-(5-(3-(cyclopropylmethoxy)phenoxy)pyridin-2-yl)-1H-benzimidazol-6-yl)methanol (330 mg), tetrapropylammonium perruthenate (14.97 mg), 4-methylmorpholine 4-oxide (150 mg), molecular sieves 4A (0.5 g) and acetonitrile (20 ml) was stirred at room temperature for 2 hr. The reaction mixture was concentrated under reduced pressure, the obtained residue was passed through a silica gel short column (hexane/ethyl acetate), and concentrated under reduced pressure. To the obtained residue was added THF (10 ml), and methylmagnesium bromide (1.0 M THF solution, 2.55 ml) was added under ice-cooling. The reaction mixture was stirred at 0° C. for 30 min, saturated aqueous ammonium chloride solution was added and the mixture was extracted with ethyl acetate. The obtained organic layer was washed with saturated brine, dried over anhydrous magnesium sulfate, and concentrated under reduced pressure. To the obtained residue was added acetonitrile (10 ml), and concentrated sulfuric acid (0.091 ml) was added under ice-cooling. The reaction mixture was stirred at room temperature for 2 hr, 1N aqueous sodium hydroxide solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and further purified by HPLC (acetonitrile/water, 0.1% TFA added) to give the title compound (3 mg).

$^1$H NMR (300 MHz, CDCl$_3$) δ 0.29-0.40 (2H, m), 0.56-0.71 (2H, m), 1.27-1.34 (1H, m), 1.57 (3H, d, J=6.7 Hz), 2.00 (3H, d, J=1.1 Hz), 3.79 (2H, d, J=7.0 Hz), 5.19-5.34 (1H, m), 5.67-5.87 (1H, m), 6.61-6.70 (2H, m), 6.72-6.79 (1H, m), 7.26-7.33 (2H, m), 7.38-7.49 (2H, m), 7.73-7.81 (1H, m), 8.35 (1H, d, J=8.7 Hz), 8.40 (1H, d, J=2.3 Hz), 10.38 (1H, d, J=9.5 Hz).

Example 35

N-(1-(2-(5-(3-(cyclopropylmethoxy)phenoxy)pyridin-2-yl)-1-benzofuran-6-yl)ethyl)acetamide A) ethyl 2-(5-(3-(cyclopropylmethoxy)phenoxy)pyridin-2-yl)-1-benzofuran-6-carboxylate A mixture of 5-(3-(cyclopropylmethoxy)phenoxy)-2-ethynylpyridine (0.99 g), ethyl 3-hydroxy-4-iodobenzoate (1.09 g), bis(triphenylphosphine)dichloropalladium (131 mg), copper(I) iodide (43 mg), 1,1,3,3-tetramethylguanidine (1.4 ml) and DMF (10 ml) was stirred under an argon atmosphere at 80° C. for 2 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (1.25 g).

$^1$H NMR (300 MHz, DMSO-d$_6$) δ 0.26-0.35 (2H, m), 0.51-0.60 (2H, m), 1.18-1.27 (1H, m), 1.36 (3H, t, J=7.1 Hz), 3.82 (2H, d, J=7.0 Hz), 4.36 (2H, q, J=7.1 Hz), 6.66-6.75 (2H, m), 6.77-6.86 (1H, m), 7.34 (1H, t, J=8.2 Hz), 7.53-7.62 (2H, m), 7.79-7.86 (1H, m), 7.88-7.95 (1H, m), 8.03 (1H, d, J=8.7 Hz), 8.19 (1H, s), 8.52 (1H, dd, J=2.8, 0.5 Hz).

B) N-(1-(2-(5-(3-(cyclopropylmethoxy)phenoxy)pyridin-2-yl)-1-benzofuran-6-yl)ethyl)acetamide To a mixture of lithium aluminum hydride (110 mg) and THF (10 ml) was added a mixture of ethyl 2-(5-(3-(cyclopropylmethoxy)phenoxy)pyridin-2-yl)-1-benzofuran-6-carboxylate (1.25 g) and THF (10 ml) under ice-cooling. The reaction mixture was stirred at 0° C. for 30 min, water (0.11 ml), 1N aqueous sodium hydroxide solution (0.11 ml) and water (0.33 ml) were successively added. The obtained mixture was stirred at room temperature for 30 min, filtered through celite and concentrated under reduced pressure. To the obtained residue was added acetonitrile (15 ml), and tetrapropylammonium perruthenate (51 mg), 4-methylmorpholine 4-oxide (511 mg) and molecular sieves 4A (1.7 g) were added. The reaction mixture was stirred at room temperature for 2 hr, filtered through celite, and concentrated under reduced pressure. The obtained residue was passed through a silica gel short column (ethyl acetate), and concentrated under reduced pressure. To the obtained residue was added THF (10 ml), and was added methylmagnesium bromide (1.0 M THF solution, 5.8 ml) under ice-cooling. The reaction mixture was stirred at 0° C. for 30 min, saturated aqueous ammonium chloride solution was added and the mixture was extracted with ethyl acetate. The obtained organic layer was washed with saturated brine, dried over anhydrous magnesium sulfate, and concentrated under reduced pressure. To the obtained residue was added acetonitrile (10 ml), and concentrated sulfuric acid (0.31 ml) was added under ice-cooling. The reaction mixture was stirred at room temperature for 2 hr, 1N aqueous sodium hydroxide solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (460 mg).
$^1$H NMR (300 MHz, DMSO-$d_6$) δ 0.25-0.35 (2H, m), 0.50-0.61 (2H, m), 1.13-1.28 (1H, m), 1.35-1.44 (3H, m), 1.86 (3H, s), 3.82 (2H, d, J=7.1 Hz), 4.94-5.10 (1H, m), 6.64-6.73 (2H, m), 6.76-6.83 (1H, m), 7.22-7.27 (1H, m), 7.33 (1H, t, J=8.2 Hz), 7.42-7.46 (1H, m), 7.50-7.59 (2H, m), 7.64 (1H, d, J=8.1 Hz), 7.95 (1H, d, J=8.8 Hz), 8.35 (1H, d, J=7.9 Hz), 8.48 (1H, d, J=2.4 Hz).

Example 36

N-(1-(2-(5-(3-(cyclopropylmethoxy)phenoxy)pyridin-2-yl)-2,3-dihydro-1-benzofuran-5-yl)ethyl)acetamide A) methyl 2-(5-(3-(cyclopropylmethoxy)phenoxy)pyridin-2-yl)-2,3-dihydro-1-benzofuran-5-carboxylate To a mixture of 5-(3-(cyclopropylmethoxy) phenoxy) pyridine-2-carbaldehyde (1 g) and methyl 3-methyl-4-nitrobenzoate (725 mg) and THF (10 ml) was added tetrabutylammonium fluoride (1.0 M THF solution, 5.57 ml). The reaction mixture was stirred at room temperature for 1 hr, and N,N-diisopropylethylamine (1.3 ml) was added. The reaction mixture was stirred at 60° C. overnight. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (370 mg).
$^1$H NMR (300 MHz, DMSO-$d_6$) δ 0.25-0.35 (2H, m), 0.49-0.60 (2H, m), 1.19-1.26 (1H, m), 3.42-3.54 (1H, m), 3.62-3.75 (1H, m), 3.76-3.85 (5H, m), 5.95-6.05 (1H, m), 6.54-6.67 (2H, m), 6.71-6.80 (1H, m), 6.94 (1H, d, J=8.3 Hz), 7.29 (1H, t, J=8.2 Hz), 7.42-7.56 (2H, m), 7.76-7.88 (2H, m), 8.38 (1H, dd, J=2.7, 0.6 Hz).

B) N-(1-(2-(5-(3-(cyclopropylmethoxy)phenoxy)pyridin-2-yl)-2,3-dihydro-1-benzofuran-5-yl)ethyl)acetamide To a mixture of lithium aluminum hydride (33.7 mg) and THF (5 ml) was added a mixture of methyl 2-(5-(3-(cyclopropylmethoxy)phenoxy)pyridin-2-yl)-2,3-dihydro-1-benzofuran-5-carboxylate (370 mg) and THF (5 ml) under ice-cooling. The reaction mixture was stirred at 0° C. for 30 min, and water (0.035 ml), TN aqueous sodium hydroxide solution (0.035 ml) and water (0.105 ml) were successively added. The obtained mixture was stirred at room temperature for 30 min, filtered through celite and concentrated under reduced pressure. To the obtained residue was added acetonitrile (5 ml), and tetrapropylammonium perruthenate (15.6 mg), 4-methylmorpholine 4-oxide (156 mg), molecular sieves 4A (600 mg) were added. The reaction mixture was stirred at room temperature for 4 hr, filtered through celite, and concentrated under reduced pressure. The obtained residue was passed through a silica gel short column (ethyl acetate), and concentrated under reduced pressure. To the obtained residue was added THF (5 ml), and methylmagnesium bromide (1.0 M THF solution, 1.78 ml) was added under ice-cooling. The reaction mixture was stirred at 0° C. for 30 min, saturated aqueous ammonium chloride solution was added and the mixture was extracted with ethyl acetate. The obtained organic layer was washed with saturated brine, dried over anhydrous magnesium sulfate, and concentrated under reduced pressure. To the obtained residue was added acetonitrile (5 ml), and concentrated sulfuric acid (0.095 ml) was added under ice-cooling. The reaction mixture was stirred at room temperature for 2 hr, 1N aqueous sodium hydroxide solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (160 mg).
$^1$H NMR (300 MHz, DMSO-$d_6$) δ 0.25-0.33 (2H, m), 0.50-0.60 (2H, m), 1.19-1.21 (1H, m), 1.30 (3H, d, J=7.0 Hz), 1.81 (3H, d, J=0.9 Hz), 3.33-3.44 (1H, m), 3.56-3.69 (1H, m), 3.79 (2H, d, J=7.0 Hz), 4.77-4.91 (1H, m), 5.84 (1H, dd, J=9.7, 6.7 Hz), 6.55-6.61 (1H, m), 6.61-6.65 (1H, m), 6.71-6.80 (2H, m), 7.01-7.09 (1H, m), 7.13-7.19 (1H, m), 7.28 (1H, t, J=8.2 Hz), 7.40-7.52 (2H, m), 8.12-8.21 (1H, m), 8.37 (1H, d, J=2.4 Hz).

Example 36a

N-(1-(2-(5-(3-(cyclopropylmethoxy)phenoxy)pyridin-2-yl)-2,3-dihydro-1-benzofuran-5-yl)ethyl) acetamide (optical isomer)

A racemate (160 mg) of N-(1-(2-(5-(3-(cyclopropylmethoxy)phenoxy)pyridin-2-yl)-2,3-dihydro-1-benzofuran-5-yl)ethyl)acetamide was fractionated by HPLC (column: CHIRALPAK AD (trade name), 50 mmID×500 mL, Daicel Corporation, mobile phase:hexane/ethanol=700/300(v/v)) to give a compound having the shortest retention time as the title compound (31.5 mg).
$^1$H NMR (300 MHz, DMSO-$d_6$) δ 0.22-0.37 (2H, m), 0.48-0.61 (2H, m), 1.12-1.25 (1H, m), 1.28-1.34 (3H, m), 1.80 (3H, s), 3.37-3.44 (1H, m), 3.55-3.69 (1H, m), 3.74-3.84 (2H, m), 4.77-4.91 (1H, m), 5.77-5.93 (1H, m), 6.52-6.67 (2H, m), 6.70-6.81 (2H, m), 7.00-7.09 (1H, m), 7.12-7.20 (1H, m), 7.23-7.33 (1H, m), 7.39-7.54 (2H, m), 8.10-8.23 (1H, m), 8.32-8.42 (1H, m).
retention time (AD) for 5.760 min Example 36b N-(1-(2-(5-(3-(cyclopropylmethoxy)phenoxy)pyridin-2-yl)-2,3-dihydro-1-benzofuran-5-yl)ethyl)acetamide (optical isomer)

A racemate (160 mg) of N-(1-(2-(5-(3-(cyclopropylmethoxy)phenoxy)pyridin-2-yl)-2,3-dihydro-1-benzofuran-5-yl)ethyl)acetamide was fractionated by HPLC (column: CHIRALPAK AD (trade name), 50 mmID×500 mL, Daicel Corporation, mobile phase:hexane/ethanol=700/300(v/v)) to give a mixture of a compound having the second shortest retention time and a compound having the third shortest retention time, which was further fractionated by HPLC (column: CHIRALPAK IC (trade name), 50 mmID×500 mL, Daicel Corporation, mobile phase:hexane/ethanol=800/200(v/v)) to give a compound having a shorter retention time as the title compound (23 mg).

¹H NMR (300 MHz, DMSO-d₆) δ 0.25-0.34 (2H, m), 0.47-0.61 (2H, m), 1.09-1.22 (1H, m), 1.25-1.33 (3H, m), 1.78-1.85 (3H, m), 3.36-3.46 (1H, m), 3.55-3.70 (1H, m), 3.75-3.84 (2H, m), 4.75-4.93 (1H, m), 5.75-5.90 (1H, m), 6.53-6.66 (2H, m), 6.71-6.81 (2H, m), 7.01-7.09 (1H, m), 7.13-7.20 (1H, m), 7.23-7.33 (1H, m), 7.39-7.55 (2H, m), 8.10-8.22 (1H, m), 8.32-8.41 (1H, m).
  retention time (AD) 7.255 min
  retention time (IC) 9.798 min Example 36c N-(1-(2-(5-(3-(cyclopropylmethoxy)phenoxy)pyridin-2-yl)-2,3-dihydro-1-benzofuran-5-yl)ethyl)acetamide (optical isomer)

A racemate (160 mg) of N-(1-(2-(5-(3-(cyclopropylmethoxy)phenoxy)pyridin-2-yl)-2,3-dihydro-1-benzofuran-5-yl)ethyl)acetamide was fractionated by HPLC (column: CHIRALPAK AD (trade name), 50 mmID×500 mL, Daicel Corporation, mobile phase:hexane/ethanol=700/300(v/v)) to give a mixture of a compound having the second shortest retention time and a compound having the third shortest retention time, which was further fractionated by HPLC (column: CHIRALPAK IC (trade name), 50 mmID×500 mL, Daicel Corporation, mobile phase:hexane/ethanol=800/200(v/v)) to give a compound having a longer retention time as the title compound (36.8 mg).
¹H NMR (300 MHz, DMSO-d₆) δ 0.20-0.35 (2H, m), 0.45-0.63 (2H, m), 1.10-1.24 (1H, m), 1.30 (3H, d, J=7.0 Hz), 1.81 (3H, s), 3.35-3.45 (1H, m), 3.54-3.70 (1H, m), 3.79 (2H, d, J=7.0 Hz), 4.76-4.91 (1H, m), 5.77-5.91 (1H, m), 6.56-6.66 (2H, m), 6.68-6.82 (2H, m), 6.98-7.09 (1H, m), 7.12-7.21 (1H, m), 7.22-7.34 (1H, m), 7.40-7.54 (2H, m), 8.13-8.24 (1H, m), 8.30-8.42 (1H, m).
  retention time (AD) 7.762 min
  retention time (IC) 12.275 min Example 36d N-(1-(2-(5-(3-(cyclopropylmethoxy) phenoxy)pyridin-2-yl)-2,3-dihydro-1-benzofuran-5-yl)ethyl)acetamide (optical isomer)

A racemate (160 mg) of N-(1-(2-(5-(3-(cyclopropylmethoxy)phenoxy)pyridin-2-yl)-2,3-dihydro-1-benzofuran-5-yl)ethyl)acetamide was fractionated by HPLC (column: CHIRALPAK AD (trade name), 50 mmID×500 mL, Daicel Corporation, mobile phase:hexane/ethanol=700/300(v/v)) to give a compound having the longest retention time as the title compound (36.6 mg).
¹H NMR (300 MHz, DMSO-d₆) δ 0.24-0.35 (2H, m), 0.49-0.62 (2H, m), 1.09-1.24 (1H, m), 1.30 (3H, d, J=7.0 Hz), 1.80 (3H, s), 3.34-3.45 (1H, m), 3.56-3.72 (1H, m), 3.79 (2H, d, J=7.0 Hz), 4.75-4.90 (1H, m), 5.78-5.89 (1H, m), 6.52-6.66 (2H, m), 6.71-6.80 (2H, m), 6.99-7.10 (1H, m), 7.12-7.21 (1H, m), 7.24-7.34 (1H, m), 7.37-7.54 (2H, m), 8.11-8.21 (1H, m), 8.31-8.41 (1H, m).
  retention time (AD) 13.005 min Example 37

N-(1-(2-(6-(3-(cyclopropylmethoxy)phenoxy)pyridin-3-yl)-1,3-benzoxazol-6-yl)ethyl)acetamide A) methyl 4-(((6-chloropyridin-3-yl)carbonyl)amino)-3-hydroxybenzoate A mixture of methyl 4-amino-3-hydroxybenzoate (18.13 g), 6-chloronicotinoyl chloride (19.09 g), triethylamine (37.8 ml) and DMF (200 ml) was stirred at room temperature for 2.5 hr. To the reaction mixture was added aqueous ammonium chloride solution, and the obtained solid was collected by filtration to give the title compound (10.25 g).
MS (ESI+): [M+H]⁺ 307.1.

B) methyl 2-(6-chloropyridin-3-yl)-1,3-benzoxazole-6-carboxylate

To a mixture of methyl 4-(((6-chloropyridin-3-yl)carbonyl)amino)-3-hydroxybenzoate (6.57 g), triphenylphosphine (8.43 g) and THF (180 ml) was added diisopropyl azodicarboxylate (1.9 M toluene solution, 16.91 ml). The obtained mixture was stirred at 60° C. for 18 hr, and concentrated under reduced pressure. The obtained solid was washed with ethanol to give the title compound (5.47 g).
¹H NMR (300 MHz, CDCl₃) δ 3.98 (3H, s), 7.54 (1H, dd, J=8.4, 0.7 Hz), 7.82 (1H, dd, J=8.4, 0.4 Hz), 8.14 (1H, dd, J=8.4, 1.5 Hz), 8.30-8.33 (1H, m), 8.49 (1H, dd, J=8.4, 2.4 Hz), 9.28 (1H, dd, J=2.4, 0.7 Hz).

C) methyl 2-(6-(3-(cyclopropylmethoxy)phenoxy)pyridin-3-yl)-1, 3-benzoxazole-6-carboxylate A mixture of methyl 2-(6-chloropyridin-3-yl)-1,3-benzoxazole-6-carboxylate (838 mg), 3-(cyclopropylmethoxy)phenol (506 mg), potassium carbonate (802 mg) and DMF (25 ml) was stirred at 115° C. for 4 hr. To the reaction mixture was added saturated aqueous sodium hydrogen carbonate solution, and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and the obtained solid was washed with hexane/diisopropyl ether to give the title compound (508 mg).
¹H NMR (300 MHz, DMSO-d₆) δ 0.28-0.35 (2H, m), 0.51-0.62 (2H, m), 1.10-1.30 (1H, m), 3.82 (2H, d, J=7.0 Hz), 3.91 (3H, s), 6.90-6.93 (3H, m), 7.25 (1H, d, J=8.7 Hz), 7.35 (1H, t, J=8.1 Hz), 7.93 (1H, d, J=8.4 Hz), 8.02-8.08 (1H, m), 8.32 (1H, d, J=1.1 Hz), 8.59 (1H, dd, J=8.7, 2.5 Hz), 8.99 (1H, d, J=2.2 Hz).

D) (2-(6-(3-(cyclopropylmethoxy)phenoxy)pyridin-3-yl)-1,3-benzoxazol-6-yl)methanol To a mixture of lithium aluminum hydride (114 mg) and THF (50 ml) was added methyl 2-(6-(3-(cyclopropylmethoxy)phenoxy)pyridin-3-yl)-1,3-benzoxazole-6-carboxylate (500 mg) under ice-cooling. The obtained mixture was stirred at 0° C. for 1 hr and water was added. To the obtained mixture were added ethyl acetate and 1N aqueous sodium hydroxide solution, and the mixture was filtered through celite. The organic layer was separated, dried over anhydrous magnesium sulfate and concentrated under reduced pressure to give the title compound (466 mg).
MS (ESI+): [M+H]⁺ 389.2.

E) 2-(6-(3-(cyclopropylmethoxy)phenoxy)pyridin-3-yl)-1,3-benzoxazole-6-carbaldehyde A mixture of (2-(6-(3-(cyclopropylmethoxy)phenoxy)pyridin-3-yl)-1,3-benzoxazol-6-yl)methanol (466 mg), tetrapropylammonium perruthenate (21 mg), 4-methylmorpholine 4-oxide (211 mg), molecular sieves 4A (250 mg) and acetonitrile (35 ml) was stirred at room temperature for 4 hr.

Ethyl acetate was added to the mixture, and the mixture was filtered through celite. The filtrate was concentrated under reduced pressure, and the obtained residue was purified by silica gel column chromatography (hexane/ethyl acetate) to give the title compound (400 mg).

$^1$H NMR (300 MHz, CDCl$_3$) δ 0.31-0.39 (2H, m), 0.61-0.69 (2H, m), 1.20-1.35 (1H, m), 3.81 (2H, d, J=6.9 Hz), 6.73-6.86 (3H, m), 7.07 (1H, dd, J=8.7, 0.6 Hz), 7.34 (1H, t, J=8.3 Hz), 7.84-7.97 (2H, m), 8.11 (1H, d, J=0.6 Hz), 8.53 (1H, dd, J=8.7, 2.4 Hz), 9.10 (1H, dd, J=2.4, 0.6 Hz), 10.10 (1H, s).

F) 6-(1-azidoethyl)-2-(6-(3-(cyclopropylmethoxy)phenoxy)pyridin-3-yl)-1,3-benzoxazole To a solution of 2-(6-(3-(cyclopropylmethoxy)phenoxy)pyridin-3-yl)-1,3-benzoxazole-6-carbaldehyde (400 mg) in THF (35 ml) was added methylmagnesium bromide (1.0 M THF solution, 3.11 ml) under ice-cooling. The obtained mixture was stirred at 0° C. for 3 hr, 1N hydrochloric acid was added and the mixture was extracted with ethyl acetate. The obtained organic layer was dried over anhydrous magnesium sulfate, and concentrated under reduced pressure. To the obtained residue was added toluene (35 ml), and diphenylphosphoryl azide (0.448 ml) and DBU (0.47 ml) were added. The obtained mixture was stirred at room temperature for 2 hr, and stirred at 65° C. for 1 hr. Water was added and the mixture was extracted with ethyl acetate. The obtained organic layer was dried over anhydrous magnesium sulfate, and concentrated under reduced pressure. The obtained residue was purified by silica gel column chromatography (hexane/ethyl acetate) to give the title compound (304 mg).

MS (ESI+): [M+H]$^+$ 428.2.

G) N-(1-(2-(6-(3-(cyclopropylmethoxy)phenoxy)pyridin-3-yl)-1,3-benzoxazol-6-yl)ethyl)acetamide A mixture of 6-(1-azidoethyl)-2-(6-(3-(cyclopropylmethoxy)phenoxy)pyridin-3-yl)-1,3-benzoxazole (304 mg), palladium carbon (containing water (50%), 80 mg) and ethyl acetate (30 ml) was stirred under a hydrogen atmosphere at room temperature for 2 hr. To the reaction mixture was added methanol, and the mixture was filtered through celite. The filtrate was concentrated under reduced pressure, THF (35 ml) was added to the obtained residue, and triethylamine (0.495 ml) and acetic anhydride (0.2 ml) were added. The reaction mixture was stirred at room temperature for 3 hr, water was added and the mixture was extracted with ethyl acetate. The obtained organic layer was dried over anhydrous magnesium sulfate, and concentrated under reduced pressure. The obtained residue was purified by silica gel column chromatography (hexane/ethyl acetate), and crystallized from hexane/ethyl acetate/methanol to give the title compound (150 mg).

$^1$H NMR (300 MHz, DMSO-d$_6$) δ 0.26-0.37 (2H, m), 0.51-0.62 (2H, m), 1.13-1.29 (1H, m), 1.40 (3H, d, J=7.0 Hz), 1.86 (3H, s), 3.82 (2H, d, J=7.0 Hz), 4.97-5.12 (1H, m), 6.72-6.90 (3H, m), 7.22 (1H, d, J=8.7 Hz), 7.30-7.43 (2H, m), 7.66-7.79 (2H, m), 8.39 (1H, d, J=8.3 Hz), 8.54 (1H, dd, J=8.7, 2.4 Hz), 8.94 (1H, d, J=2.4 Hz).

Example 40

N-(1-(2-(3-(3-(cyclopropylmethoxy)phenoxy)azetidin-1-yl)-1,3-benzothiazol-6-yl)ethyl)acetamide

A) 1-(2-amino-1,3-benzothiazol-6-yl)ethanone

To a mixture of 1-(4-aminophenyl)ethanone (3 g), potassium thiocyanate (8.87 g) and acetic acid (35 ml) was slowly added dropwise a mixture of bromine (1.14 ml) and acetic acid (15 ml) at room temperature. The reaction mixture was stirred at room temperature overnight, water was added, and basified with 28% aqueous ammonia. The obtained solid was collected by filtration, and added to heated acetone. Insoluble materials were removed by filtration. The filtrate was concentrated under reduced pressure to give the title compound (3.17 g).

$^1$H NMR (300 MHz, DMSO-d$_6$) δ 2.55 (3H, s), 7.37 (1H, d, J=8.4 Hz), 7.83 (1H, dd, J=8.5, 1.8 Hz), 7.91 (2H, s), 8.32 (1H, d, J=1.6 Hz).

B) 1-(2-bromo-1,3-benzothiazol-6-yl)ethanone

To a mixture of 1-pentyl nitrite (0.199 ml), copper(II) bromide (268 mg) and acetonitrile (5 ml) was added 1-(2-amino-1,3-benzothiazol-6-yl)ethanone (192 mg) under ice-cooling. The reaction mixture was stirred at room temperature overnight. To a mixture of 1-pentyl nitrite (3.01 ml), copper(II) bromide (4.04 g) and acetonitrile (75 ml) was further added 1-(2-amino-1,3-benzothiazol-6-yl)ethanone (2.9 g) under ice-cooling. The reaction mixture was stirred at room temperature overnight. The above-mentioned two reaction mixtures were mixed, water and ethyl acetate were added, and insoluble materials were filtered off through celite. The filtrate was partitioned, and the aqueous layer was extracted with ethyl acetate. The mixed organic layer was washed with saturated brine, dried over anhydrous magnesium sulfate, and concentrated under reduced pressure. The obtained residue was passed through a silica gel short column (ethyl acetate), and concentrated under reduced pressure. The obtained residue was purified by silica gel column chromatography (hexane/ethyl acetate), concentrated under reduced pressure and the obtained solid was collected by filtration, and washed with hexane to give the title compound (2.4 g).

$^1$H NMR (300 MHz, DMSO-d$_6$) δ 2.66 (3H, s), 8.06-8.11 (2H, m), 8.81 (1H, t, J=1.2 Hz)

C) 1-(2-(3-hydroxyazetidin-1-yl)-1,3-benzothiazol-6-yl)ethanone

To a mixture of 1-(2-bromo-1,3-benzothiazol-6-yl)ethanone (700 mg) and DMF (5 ml) were added 3-hydroxyazetidine hydrochloride (359 mg) and N,N-diisopropylethylamine (1.432 ml), and the mixture was stirred at room temperature overnight. To the reaction mixture was added aqueous sodium hydrogen carbonate solution, and the obtained solid was collected by filtration, and washed successively with water and ethyl acetate/diisopropyl ether to give the title compound (621 mg).

$^1$H NMR (300 MHz, DMSO-d$_6$) δ 2.56 (3H, s), 3.94 (2H, dd, J=9.8, 4.5 Hz), 4.32-4.44 (2H, m), 4.63-4.76 (1H, m), 5.95 (1H, d, J=6.6 Hz), 7.50 (1H, d, J=8.5 Hz), 7.89 (1H, dd, J=8.5, 1.7 Hz), 8.44 (1H, d, J=1.7 Hz).

D) 1-(2-(3-((methylsulfonyl)oxy)azetidin-1-yl)-1,3-benzothiazol-6-yl)ethanone To a mixture of 1-(2-(3-hydroxyazetidin-1-yl)-1,3-benzothiazol-6-yl)ethanone (570 mg), triethylamine (0.96 ml) and THF (20 ml) was added methanesulfonyl chloride (0.267 ml) at 0° C. The reaction mixture was stirred at room temperature for 1 hr. The mixture was added to water, and the mixture was extracted with ethyl acetate. The obtained organic layer was washed with saturated brine, dried over anhydrous magnesium sulfate, and concentrated under reduced pressure to give the title compound (782 mg).

$^1$H NMR (300 MHz, DMSO-$d_6$) δ 2.57 (3H, s), 3.32 (3H, s), 4.33 (2H, ddd, J=10.0, 3.8, 1.2 Hz), 4.60 (2H, ddd, J=10.0, 6.6, 1.2 Hz), 5.48-5.58 (1H, m), 7.55 (1H, d, J=8.5 Hz), 7.91 (1H, dd, J=8.5, 1.9 Hz), 8.49 (1H, d, J=1.7 Hz).

E) 1-(2-(3-(3-(cyclopropylmethoxy)phenoxy)azetidin-1-yl)-1,3-benzothiazol-6-yl)ethanone A mixture of 1-(2-(3-((methylsulfonyl)oxy)azetidin-1-yl)-1,3-benzothiazol-6-yl)ethanone (782 mg), 3-(cyclopropylmethoxy)phenol (452 mg), cesium carbonate (1.122 g) and DMF (10 ml) was stirred at 60° C. for 14 hr. To the reaction mixture were added 3-(cyclopropylmethoxy)phenol (302 mg) and cesium carbonate (1.122 g), and the mixture was stirred at 100° C. for 3 hr. The mixture was added to water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (515 mg).

$^1$H NMR (300 MHz, DMSO-$d_6$) δ 0.27-0.36 (2H, m), 0.53-0.61 (2H, m), 1.13-1.29 (1H, m), 2.57 (3H, s), 3.80 (2H, d, J=7.0 Hz), 4.12-4.22 (2H, m), 4.67 (2H, ddd, J=9.5, 6.5, 0.6 Hz), 5.22-5.31 (1H, m), 6.41-6.49 (2H, m), 6.54-6.61 (1H, m), 7.15-7.26 (1H, m), 7.54 (1H, d, J=8.5 Hz), 7.90 (1H, dd, J=8.5, 1.8 Hz), 8.48 (1H, d, J=0.1.6 Hz).

F) 1-(2-(3-(3-(cyclopropylmethoxy)phenoxy)azetidin-1-yl)-1,3-benzothiazol-6-yl)-N-hydroxyethanimine A mixture of 1-(2-(3-(3-(cyclopropylmethoxy)phenoxy)azetidin-1-yl)-1,3-benzothiazol-6-yl)ethanone (500 mg), hydroxylamine hydrochloride (264 mg), sodium acetate (312 mg), water (10 ml) and ethanol (50 ml) was stirred at 60° C. for 1 hr, and then at room temperature for 3 days. To the reaction mixture was added water, and the mixture was extracted with ethyl acetate. The obtained organic layer was washed with saturated brine, dried over anhydrous magnesium sulfate, and concentrated under reduced pressure to give the title compound (548 mg).

$^1$H NMR (300 MHz, DMSO-$d_6$) δ 0.27-0.36 (2H, m), 0.52-0.61 (2H, m), 1.13-1.29 (1H, m), 2.17 (3H, s), 3.80 (2H, d, J=7.0 Hz), 4.11 (2H, dd, J=9.5, 3.7 Hz), 4.62 (2H, dd, J=9.3, 6.5 Hz), 5.20-5.31 (1H, m), 6.41-6.48 (2H, m), 6.54-6.60 (1H, m), 7.15-7.25 (1H, m), 7.47 (1H, d, J=8.5 Hz), 7.63 (1H, dd, J=8.5, 1.8 Hz), 8.07 (1H, d, J=1.6 Hz), 11.07 (1H, s).

G) 1-(2-(3-(3-(cyclopropylmethoxy)phenoxy)azetidin-1-yl)-1,3-benzothiazol-6-yl) ethanamine To a mixture of 1-(2-(3-(3-(cyclopropylmethoxy)phenoxy)azetidin-1-yl)-1,3-benzothiazol-6-yl)-N-hydroxyethanimine (150 mg) and acetic acid (5 ml) was added zinc powder (120 mg). The reaction mixture was stirred at room temperature for 14 hr, and then at 60° C. for 6 hr. Insoluble materials were removed by filtration, and the filtrate was concentrated under reduced pressure. The obtained residue was purified by silica gel column chromatography (NH, hexane/ethyl acetate) to give the title compound (78 mg).

MS (ESI+): [M+H]$^+$ 396.0.

H) N-(1-(2-(3-(3-(cyclopropylmethoxy)phenoxy)azetidin-1-yl)-1,3-benzothiazol-6-yl)ethyl)acetamide To a mixture of 1-(2-(3-(3-(cyclopropylmethoxy)phenoxy) azetidin-1-yl)-1,3-benzothiazol-6-yl)ethanamine (78 mg), triethylamine (0.055 ml) and THF (3 ml) was added acetic anhydride (0.037 ml). The reaction mixture was stirred at room temperature for 1 hr. The reaction mixture was added to saturated aqueous sodium hydrogen carbonate solution, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate), and crystallized from diisopropyl ether/ethyl acetate to give the title compound (41 mg).

$^1$H NMR (300 MHz, DMSO-$d_6$) δ 0.27-0.35 (2H, m), 0.52-0.61 (2H, m), 1.12-1.28 (1H, m), 1.35 (3H, d, J=7.0 Hz), 1.83 (3H, s), 3.80 (2H, d, J=7.0 Hz), 4.08 (2H, dd, J=9.3, 3.8 Hz), 4.59 (2H, dd, J=8.9, 6.7 Hz), 4.87-5.00 (1H, m), 5.19-5.29 (1H, m), 6.40-6.48 (2H, m), 6.53-6.60 (1H, m), 7.14-7.28 (2H, m), 7.44 (1H, d, J=8.3 Hz), 7.70 (1H, d, J=1.7 Hz), 8.25 (1H, d, J=8.0 Hz).

Example 43

N-(1-(2-(4-(3-(cyclopropylmethoxy)benzyl)phenyl)-1,3-benzoxazol-6-yl)ethyl)acetamide

A) methyl 4-(3-(cyclopropylmethoxy)benzyl)benzoate

A mixture of methyl 4-(bromomethyl)benzoate (500 mg), (3-(cyclopropylmethoxy)phenyl)boronic acid (629 mg), 2-(di-tert-butylphosphino)biphenyl (65 mg), palladium acetate (24.5 mg), potassium carbonate (905 mg) and DMF (8 ml) was stirred under microwave radiation at 140° C. for 50 min. To the reaction mixture were added ethyl acetate and saturated brine, and the mixture was filtered through celite. The obtained mixture was partitioned, and the organic layer was washed with saturated brine, dried over anhydrous magnesium sulfate, and concentrated under reduced pressure. The obtained residue was purified by silica gel column chromatography (hexane/ethyl acetate) to give the title compound (320 mg).

$^1$H NMR (300 MHz, CDCl$_3$) δ 0.17-0.41 (2H, m), 0.51-0.71 (2H, m), 1.21-1.36 (1H, m), 3.75 (2H, d, J=6.9 Hz), 3.90 (3H, s), 3.98 (2H, s), 6.65-6.83 (3H, m), 7.12-7.30 (2H, m), 7.12-7.21 (1H, m), 7.76-8.05 (2H, m).

B) 4-(3-(cyclopropylmethoxy)benzyl)benzoic acid

A mixture of methyl 4-(3-(cyclopropylmethoxy)benzyl) benzoate (320 mg), 8N aqueous sodium hydroxide solution (5 ml) and methanol (25 ml) was stirred at 60° C. for 18 hr. The reaction mixture was acidified with 6N hydrochloric acid, and concentrated under reduced pressure. The obtained solid was collected by filtration to give the title compound (260 mg).

MS (ESI Negative): [M–H]$^-$ 281.2.

C) N-(4-(1-acetamidoethyl)-2-hydroxyphenyl)-4-(3-(cyclopropylmethoxy)benzyl)benzamide To a mixture of tert-butyl (4-(1-acetamidoethyl)-2-hydroxyphenyl)carbamate (1 g) and methanol (20 ml) was added 4 M hydrogen chloride-ethyl acetate solution (40 ml), and the mixture was stirred at room temperature for 18 hr. The reaction mixture was concentrated under reduced pressure. To the obtained residue was added DMF (3 ml). To the obtained DMF solution (1 ml) were added N,N-diisopropylethylamine (0.822 ml), HATU (430 mg), 4-(3-(cyclopropylmethoxy)benzyl)benzoic acid (240 mg) and DMF (15 ml). The reaction mixture was stirred at 65° C. for 18 hr. The reaction mixture was extracted with saturated aqueous ammonium chloride solution and ethyl acetate. The obtained organic layer was washed with saturated aqueous ammonium chloride solution, and concentrated under reduced pressure. The obtained residue was dissolved in ethanol (15 ml), 1N aqueous sodium hydroxide solution (10 ml) was added, and the mixture was stirred at room temperature for 1 hr. The mixture was acidified with 6N hydrochloric acid, and extracted with saturated brine and ethyl acetate. The obtained organic layer was dried over anhydrous magnesium sulfate, and concentrated under reduced pressure. The obtained residue was purified by silica gel column chromatography (hexane/ethyl acetate), and the obtained solid was washed with diisopropyl ether to give the title compound (120 mg).

MS (ESI+): [M+H]$^+$ 459.2.

D) N-(1-(2-(4-(3-hydroxybenzyl)phenyl)-1,3-benzoxazol-6-yl)ethyl)acetamide

A mixture of N-(4-(1-acetamidoethyl)-2-hydroxyphenyl)-4-(3-(cyclopropylmethoxy)benzyl)benzamide (53 mg), TFA (2 ml) and acetic acid (2 ml) was stirred under microwave radiation at 120° C. for 40 min. The reaction mixture was concentrated under reduced pressure, and the obtained residue was purified by silica gel column chromatography (hexane/ethyl acetate) to give the title compound (35 mg).

MS (ESI+): [M+H]$^+$ 387.2.

E) N-(1-(2-(4-(3-(cyclopropylmethoxy)benzyl)phenyl)-1,3-benzoxazol-6-yl)ethyl) acetamide A mixture of potassium carbonate (37.6 mg), N-(1-(2-(4-(3-hydroxybenzyl)phenyl)-1,3-benzoxazol-6-yl)ethyl)acetamide (35 mg), (bromomethyl)cyclopropane (0.018 ml) and DMF (5 ml) was stirred at 65° C. for 18 hr. The reaction mixture was extracted with water and ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (12 mg).

$^1$H NMR (300 MHz, CDCl$_3$) δ 0.27-0.37 (2H, m), 0.51-0.69 (2H, m), 1.19-1.32 (1H, m), 1.56 (3H, d, J=7.0 Hz), 2.02 (3H, s), 3.77 (2H, d, J=7.0 Hz), 4.02 (2H, s), 5.18-5.38 (1H, m), 5.78 (1H, d, J=7.3 Hz), 6.58-6.84 (3H, m), 7.12-7.41 (4H, m), 7.54 (1H, s), 7.70 (1H, d, J=8.1 Hz), 8.14 (2H, d, J=8.1 Hz).

Example 44

N-(1-(2-(3-(3-(cyclopropylmethoxy)phenoxy)azetidin-1-yl)-1,3-benzothiazol-5-yl)ethyl)acetamide A) 3-(3-(cyclopropylmethoxy) phenoxy) azetidine A mixture of 3-(3-(cyclopropylmethoxy)phenoxy)-1-(diphenylmethyl)azetidine (2.0 g), 20% palladium hydroxide (containing water (50%), 0.4 g), ethanol (30 ml), THF (3 ml) and 6N hydrochloric acid (1.1 ml) was stirred under a hydrogen atmosphere at room temperature for 3 days. The catalyst was removed by filtration, and the filtrate was concentrated under reduced pressure. To the obtained residue was added 1N hydrochloric acid (25 ml), and the mixture was washed with hexane. The obtained aqueous layer was basified with 8N aqueous sodium hydroxide solution (3 ml) and 10% aqueous sodium carbonate solution (10 ml), and extracted with ethyl acetate. The obtained organic layer was washed with saturated brine, dried over anhydrous magnesium sulfate, and concentrated under reduced pressure to give the title compound (1.17 g).

$^1$H NMR (300 MHz, DMSO-d$_6$) δ 0.26-0.34 (2H, m), 0.51-0.61 (2H, m), 0.90 (1H, s), 1.11-1.26 (1H, m), 3.10-3.81 (4H, m), 3.77 (2H, d, J=7.0 Hz), 4.62-5.06 (1H, m), 6.25-6.43 (2H, m), 6.49 (1H, dd, J=8.1, 2.1 Hz), 7.13 (1H, t, J=8.1 Hz).

B) 1-(3-amino-4-fluorophenyl)ethanone

A mixture of 1-(4-fluoro-3-nitrophenyl)ethanone (5.06 g), 10% palladium carbon (containing water (50%), 500 mg) and ethanol (50 ml) was stirred under a hydrogen atmosphere at room temperature for 2 hr. The catalyst was removed by filtration, and the filtrate was concentrated under reduced pressure. The obtained residue was purified by silica gel column chromatography (hexane/ethyl acetate) to give the title compound (690 mg).

$^1$H NMR (300 MHz, DMSO-d$_6$) δ 2.48 (3H, s), 5.40 (2H, s), 7.05-7.21 (2H, m), 7.36 (1H, dd, J=8.9, 2.2 Hz).

C) N-(5-acetyl-2-fluorophenyl)-3-(3-(cyclopropylmethoxy)phenoxy)azetidine-1-carbothioamide To a mixture of di-1H-imidazol-1-ylmethanethion (349 mg) and acetonitrile (10 ml) was added a mixture of 1-(3-amino-4-fluorophenyl)ethanone (300 mg) and acetonitrile (2 ml) under ice-cooling. The reaction mixture was stirred at room temperature for 8 hr, and a mixture of 3-(3-(cyclopropylmethoxy)phenoxy)azetidine (430 mg) and acetonitrile (2 ml) was added. The reaction mixture was stirred at room temperature overnight and concentrated under reduced pressure. The obtained residue was purified by silica gel column chromatography (hexane/ethyl acetate) to give the title compound (508 mg).

$^1$H NMR (300 MHz, DMSO-d$_6$) δ 0.27-0.35 (2H, m), 0.52-0.62 (2H, m), 1.13-1.29 (1H, m), 2.56 (3H, s), 3.80 (2H, d, J=7.0 Hz), 4.04 (2H, d, J=9.2 Hz), 4.46-4.71 (2H, m), 5.02-5.13 (1H, m), 6.41-6.49 (2H, m), 6.53-6.60 (1H, m), 7.16-7.25 (1H, m), 7.40 (1H, dd, J=9.8, 8.7 Hz), 7.90 (1H, ddd, J=8.6, 4.7, 2.3 Hz), 7.97 (1H, dd, J=7.5, 2.3 Hz), 9.35 (1H, s).

D) 1-(2-(3-(3-(cyclopropylmethoxy)phenoxy)azetidin-1-yl)-1,3-benzothiazol-5-yl)ethanone A mixture of N-(5-acetyl-2-fluorophenyl)-3-(3-(cyclopropylmethoxy)phenoxy) azetidine-1-carbothioamide (490 mg), cesium carbonate (462 mg) and DMF (5 ml) was stirred at 50° C. for 2 hr. The reaction mixture was concentrated under reduced pressure, water was added to the obtained residue and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (458 mg).

¹H NMR (300 MHz, DMSO-d₆) δ 0.28-0.35 (2H, m), 0.53-0.62 (2H, m), 1.13-1.29 (1H, m), 2.61 (3H, s), 3.80 (2H, d, J=7.0 Hz), 4.14 (2H, dd, J=9.9, 3.9 Hz), 4.59-4.69 (2H, m), 5.26 (1H, tt, J=6.4, 3.8 Hz), 6.41-6.49 (2H, m), 6.54-6.61 (1H, m), 7.16-7.25 (1H, m), 7.69 (1H, dd, J=8.3, 1.7 Hz), 7.94 (1H, d, J=8.3 Hz), 8.06 (1H, d, J=1.4 Hz).

E) 1-(2-(3-(3-(cyclopropylmethoxy)phenoxy)azetidin-1-yl)-1,3-benzothiazol-5-yl)ethanol To a mixture of 1-(2-(3-(3-(cyclopropylmethoxy)phenoxy) azetidin-1-yl)-1,3-benzothiazol-5-yl)ethanone (450 mg), methanol (10 ml) and THF (5 ml) was added sodium borohydride (43.2 mg) under ice-cooling. The reaction mixture was stirred at room temperature for 2 hr. To the reaction mixture was added water, and the mixture was extracted with ethyl acetate. The obtained organic layer was washed with saturated brine, dried over anhydrous magnesium sulfate, and concentrated under reduced pressure to give the title compound (472 mg).

¹H NMR (300 MHz, DMSO-d₆) δ 0.27-0.35 (2H, m), 0.52-0.61 (2H, m), 1.13-1.29 (1H, m), 1.33 (3H, d, J=6.4 Hz), 3.80 (2H, d, J=7.0 Hz), 4.08 (2H, dd, J=9.4, 3.8 Hz), 4.59 (2H, dd, J=9.1, 6.5 Hz), 4.70-4.82 (1H, m), 5.15 (1H, d, J=4.2 Hz), 5.19-5.29 (1H, m), 6.40-6.48 (2H, m), 6.53-6.60 (1H, m), 7.10 (1H, dd, J=8.2, 1.5 Hz), 7.15-7.25 (1H, m), 7.46 (1H, d, J=1.5 Hz), 7.70 (1H, d, J=8.2 Hz).

F) 5-(1-azidoethyl)-2-(3-(3-(cyclopropylmethoxy)phenoxy)azetidin-1-yl)-1,3-benzothiazole A mixture of 1-(2-(3-(3-(cyclopropylmethoxy)phenoxy)azetidin-1-yl)-1,3-benzothiazol-5-yl)ethanol (452 mg), diphenylphosphoryl azide (0.491 ml), DBU (0.515 ml) and toluene (10 ml) was stirred at room temperature for 2 hr. To the reaction mixture were added toluene (10 ml) and THF (20 ml). The reaction mixture was stirred at room temperature overnight, and concentrated under reduced pressure. The obtained residue was purified by silica gel column chromatography (hexane/ethyl acetate) to give the title compound (369 mg).

¹H NMR (300 MHz, DMSO-d₆) δ 0.28-0.35 (2H, m), 0.53-0.61 (2H, m), 1.13-1.29 (1H, m), 1.48 (3H, d, J=6.8 Hz), 3.80 (2H, d, J=7.0 Hz), 4.10 (2H, dd, J=9.8, 3.8 Hz), 4.61 (2H, dd, J=9.1, 6.8 Hz), 4.87 (1H, q, J=6.7 Hz), 5.25 (1H, tt, J=6.3, 3.8 Hz), 6.40-6.49 (2H, m), 6.53-6.61 (1H, m), 7.13 (1H, dd, J=8.2, 1.7 Hz), 7.16-7.25 (1H, m), 7.52 (1H, d, J=1.7 Hz), 7.81 (1H, d, J=8.2 Hz).

G) 1-(2-(3-(3-(cyclopropylmethoxy)phenoxy)azetidin-1-yl)-1,3-benzothiazol-5-yl)ethanamine A mixture of 5-(1-azidoethyl)-2-(3-(3-(cyclopropylmethoxy)phenoxy) azetidin-1-yl)-1,3-benzothiazole (340 mg), triphenylphosphine (423 mg), water (0.5 ml) and THF (5 ml) was stirred at room temperature for 3 days. The reaction mixture was concentrated under reduced pressure, and the obtained residue was purified by silica gel column chromatography (NH, hexane/ethyl acetate) to give the title compound (332 mg).

¹H NMR (300 MHz, DMSO-d₆) δ 0.27-0.36 (2H, m), 0.52-0.62 (2H, m), 1.13-1.29 (4H, m), 1.87 (2H, brs), 3.80 (2H, d, J=7.0 Hz), 3.97-4.13 (3H, m), 4.53-4.63 (2H, m), 5.19-5.30 (1H, m), 6.39-6.49 (2H, m), 6.53-6.62 (1H, m), 7.12 (1H, dd, J=8.1, 1.5 Hz), 7.15-7.25 (1H, m), 7.51 (1H, d, J=1.1 Hz), 7.68 (1H, d, J=8.1 Hz).

H) N-(1-(2-(3-(3-(cyclopropylmethoxy)phenoxy)azetidin-1-yl)-1,3-benzothiazol-5-yl)ethyl) acetamide A mixture of 1-(2-(3-(3-(cyclopropylmethoxy)phenoxy) azetidin-1-yl)-1,3-benzothiazol-5-yl)ethanamine (330 mg), acetic anhydride (0.107 ml), triethylamine (0.211 ml) and THF (5 ml) was stirred at room temperature for 1 hr. To the reaction mixture was added saturated aqueous sodium hydrogen carbonate solution, and the mixture was extracted with ethyl acetate. The obtained organic layer was washed with saturated brine, dried over anhydrous magnesium sulfate, and concentrated under reduced pressure. The obtained residue was purified by silica gel column chromatography (ethyl acetate/methanol), and the obtained solid was washed with hexane/acetone to give the title compound (300 mg).

¹H NMR (300 MHz, DMSO-d₆) δ 0.27-0.36 (2H, m), 0.52-0.61 (2H, m), 1.13-1.28 (1H, m), 1.35 (3H, d, J=7.0 Hz), 1.84 (3H, s), 3.80 (2H, d, J=7.0 Hz), 4.08 (2H, dd, J=9.3, 3.8 Hz), 4.59 (2H, dd, J=9.2, 6.4 Hz), 4.87-5.01 (1H, m), 5.24 (1H, tt, J=6.3, 3.8 Hz), 6.40-6.48 (2H, m), 6.54-6.60 (1H, m), 7.05 (1H, dd, J=8.2, 1.7 Hz), 7.16-7.24 (1H, m), 7.43 (1H, d, J=1.6 Hz), 7.70 (1H, d, J=8.2 Hz), 8.28 (1H, d, J=8.2 Hz).

Example 47

N-(1-(2-(5-(3-(cyclopropylmethoxy)phenoxy)-3-methylpyridin-2-yl)-1,3-benzoxazol-6-yl)ethyl)acetamide A) N-(4-acetyl-2-hydroxyphenyl)-5-bromo-3-methylpyridine-2-carboxamide A mixture of 1-(4-amino-3-hydroxyphenyl)ethanone (1.68 g), 5-bromo-3-methylpyridine-2-carboxylic acid (2 g), HATU (4.22 g), N,N-diisopropylethylamine (4.04 ml) and DMF (25 ml) was stirred at room temperature for 18 hr. To the reaction mixture was added saturated aqueous ammonium chloride solution, and the mixture was extracted with ethyl acetate. The obtained organic layer was washed with saturated aqueous ammonium chloride solution, dried over anhydrous magnesium sulfate, and concentrated under reduced pressure. The obtained residue was purified by silica gel column chromatography (hexane/ethyl acetate) to give the title compound (680 mg).

MS (ESI Negative): [M−H]⁻ 347.0, 349.1.

B) 1-(2-(5-bromo-3-methylpyridin-2-yl)-1,3-benzoxazol-6-yl)ethanone

A mixture of N-(4-acetyl-2-hydroxyphenyl)-5-bromo-3-methylpyridine-2-carboxamide (680 mg), TFA (6 ml) and acetic acid (6 ml) was stirred under microwave radiation at 140° C. for 50 min. The reaction mixture was concentrated under reduced pressure. The obtained residue was purified by silica gel column chromatography (NH, hexane/ethyl acetate) to give the title compound (430 mg).

¹H NMR (300 MHz, DMSO-d₆) δ 2.69 (3H, s), 2.80 (3H, s), 7.97-8.11 (2H, m), 8.30 (1H, dd, J=2.3, 0.8 Hz), 8.44 (1H, d, J=0.8 Hz), 8.81 (1H, d, J=2.3 Hz).

C) 1-(2-(5-bromo-3-methylpyridin-2-yl)-1,3-benzoxazol-6-yl)ethanol

A mixture of 1-(2-(5-bromo-3-methylpyridin-2-yl)-1,3-benzoxazol-6-yl)ethanone (400 mg), sodium borohydride (57.7 mg), methanol (8 ml) and THF (8 ml) was stirred at room temperature for 1 hr. To the reaction mixture was added saturated aqueous ammonium chloride solution, and the mixture was extracted with ethyl acetate. The obtained organic layer was dried over anhydrous magnesium sulfate, and concentrated under reduced pressure. The obtained residue was purified by silica gel column chromatography (hexane/ethyl acetate) to give the title compound (300 mg).

$^1$H NMR (300 MHz, CDCl$_3$) δ 1.52-1.65 (3H, m), 1.88-2.07 (1H, m), 2.86 (3H, s), 5.00-5.13 (1H, m), 7.41 (1H, d, J=8.2 Hz), 7.71 (1H, s), 7.80 (1H, d, J=8.2 Hz), 7.88 (1H, s), 8.72 (1H, s).

D) 1-(2-(5-(3-(cyclopropylmethoxy)phenoxy)-3-methylpyridin-2-yl)-1,3-benzoxazol-6-yl)ethanol A mixture of 1-(2-(5-bromo-3-methylpyridin-2-yl)-1,3-benzoxazol-6-yl)ethanol (172 mg), 3-(cyclopropylmethoxy) phenol (85 mg), N,N-dimethylglycine hydrochloride (8.66 mg), copper(I) iodide (9.84 mg), cesium carbonate (505 mg) and DMF (4 ml) was stirred at 120° C. for 18 hr. To the reaction mixture were added saturated aqueous ammonium chloride solution and ethyl acetate, and the mixture was filtered through celite. The organic layer was partitioned, dried over anhydrous magnesium sulfate, and concentrated under reduced pressure. The obtained residue was purified by silica gel column chromatography (hexane/ethyl acetate) to give the title compound (119 mg).

$^1$H NMR (300 MHz, CDCl$_3$) δ 0.18-0.46 (2H, m), 0.55-0.75 (2H, m), 1.03-1.35 (1H, m), 1.56 (3H, d, J=6.0 Hz), 1.91-2.13 (1H, m), 2.82 (3H, s), 3.80 (2H, d, J=7.0 Hz), 5.06 (1H, q, J=6.4 Hz), 6.61-6.71 (2H, m), 6.77 (1H, ddd, J=8.4, 2.3, 0.8 Hz), 7.23 (1H, dd, J=2.7, 0.6 Hz), 7.30 (1H, t, J=8.3 Hz), 7.39 (1H, dd, J=8.4, 1.3 Hz), 7.67-7.70 (1H, m), 7.78 (1H, d, J=8.4 Hz), 8.45 (1H, d, J=2.3 Hz).

E) 6-(1-azidoethyl)-2-(5-(3-(cyclopropylmethoxy) phenoxy)-3-methylpyridin-2-yl)-1,3-benzoxazole A mixture of 1-(2-(5-(3-(cyclopropylmethoxy)phenoxy)-3-methylpyridin-2-yl)-1,3-benzoxazol-6-yl)ethanol (119 mg), diphenylphosphoryl azide (0.123 ml), DBU (0.129 ml) and toluene (15 ml) was stirred at 60° C. for 45 min. To the reaction mixture was added water, and the mixture was extracted with ethyl acetate. The obtained organic layer was dried over anhydrous magnesium sulfate, and concentrated under reduced pressure. The obtained residue was purified by silica gel column chromatography (hexane/ethyl acetate) to give the title compound (64.3 mg).

$^1$H NMR (300 MHz, CDCl$_3$) δ 0.31-0.39 (2H, m), 0.61-0.70 (2H, m), 1.18-1.35 (1H, m), 1.60 (3H, d, J=6.8 Hz), 2.82 (3H, s), 3.80 (2H, d, J=6.8 Hz), 4.78 (1H, q, J=6.8 Hz), 6.62-6.70 (2H, m), 6.77 (1H, ddd, J=8.3, 2.6, 0.8 Hz), 7.16-7.40 (3H, m), 7.64 (1H, d, J=1.6 Hz), 7.82 (1H, d, J=8.3 Hz), 8.46 (1H, d, J=2.6 Hz).

F) N-(1-(2-(5-(3-(cyclopropylmethoxy)phenoxy)-3-methylpyridin-2-yl)-1,3-benzoxazol-6-yl)ethyl) acetamide A mixture of 6-(1-azidoethyl)-2-(5-(3-(cyclopropylmethoxy)phenoxy)-3-methylpyridin-2-yl)-1,3-benzoxazole (64.3 mg), 10% palladium carbon (containing water (50%), 30 mg) and ethyl acetate (8 ml) was stirred under a hydrogen atmosphere at room temperature for 1.5 hr. The catalyst was removed by filtration, and the filtrate was concentrated under reduced pressure. To the obtained residue were added THF (8 ml) and acetic anhydride (0.028 ml). The reaction mixture was stirred at room temperature for 30 min and concentrated under reduced pressure. The obtained residue was purified by silica gel column chromatography (hexane/ethyl acetate), and crystallized from hexane/ethyl acetate to give the title compound (31.7 mg).

$^1$H NMR (300 MHz, CDCl$_3$) δ 0.30-0.40 (2H, m), 0.59-0.70 (2H, m), 1.17-1.34 (1H, m), 1.56 (3H, d, J=7.0 Hz), 2.02 (3H, s), 2.81 (3H, s), 3.80 (2H, d, J=7.0 Hz), 5.27 (1H, t, J=7.0 Hz), 5.78 (1H, d, J=7.2 Hz), 6.60-6.71 (2H, m), 6.77 (1H, ddd, J=8.4, 2.3, 0.8 Hz), 7.18-7.39 (3H, m), 7.61 (1H, d, J=1.5 Hz), 7.77 (1H, d, J=8.2 Hz), 8.45 (1H, d, J=2.6 Hz).

Example 52

N-(1-(5-(4-(3-(cyclopropylmethoxy)phenoxy)phenyl)-1-benzofuran-2-yl)ethyl)acetamide A) 1-(5-bromo-1-benzofuran-2-yl)ethanone To a mixture of potassium hydroxide (5.6 g) and methanol (200 ml) was added 5-bromo-2-hydroxybenzaldehyde (20 g) with heating under reflux. The reaction mixture was cooled, and 1-chloroacetone (11 g) was added under ice-cooling. The reaction mixture was stirred with heating under reflux for 16 hr, and concentrated under reduced pressure. To the obtained residue was added water, and the mixture was extracted with ethyl acetate. The obtained organic layer was washed with saturated brine, dried over anhydrous sodium sulfate, and concentrated under reduced pressure. To the obtained residue was added petroleum ether/ethyl acetate (10/1), and the mixture was stirred at room temperature for 0.5 hr. The obtained solid was collected by filtration, and washed with petroleum ether to give the title compound (13.2 g).

$^1$H NMR (400 MHz, DMSO-d$_6$) δ 2.57 (3H, s), 7.65-7.74 (2H, m), 7.84 (1H, s), 8.06 (1H, d, J=1.6 Hz).

B) N-(1-(5-bromo-1-benzofuran-2-yl)ethyl)acetamide

A mixture of 1-(5-bromo-1-benzofuran-2-yl)ethanone (4 g), ammonium acetate (25.9 g) and methanol (40 ml) was stirred at 70° C. for 3 hr. To the reaction mixture was added sodium cyanoborohydride (2.11 g), and the mixture was stirred with heating under reflux for 16 hr. The reaction mixture was concentrated under reduced pressure, water was added and the mixture was extracted with ethyl acetate. The obtained organic layer was washed with saturated brine, dried over anhydrous sodium sulfate, and concentrated under reduced pressure. To the obtained residue were added THF (50 ml) and acetic anhydride (5.14 g), and the mixture was stirred at room temperature for 5 hr. To the reaction mixture was added water and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (1.39 g).

$^1$H NMR (400 MHz, DMSO-d$_6$) δ 1.44 (3H, d, J=7.2 Hz), 1.87 (3H, s), 5.07-5.20 (1H, m), 6.70 (1H, s), 7.40 (1H, dd, J=8.4, 2.0 Hz), 7.53 (1H, d, J=8.8 Hz), 7.80 (1H, d, J=2.0 Hz), 8.44 (1H, d, J=8.0 Hz).

C) 1-(4-bromophenoxy)-3-(cyclopropylmethoxy)benzene

To a mixture of 3-(cyclopropylmethoxy)phenol (10 g), 1-bromo-4-iodobenzene (17.2 g) and DMSO (120 ml) were added copper(I) iodide (1.16 g), picolinic acid (1.5 g) and potassium phosphate (25.8 g), and the mixture was stirred at 80° C. for 16 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (12.6 g).

$^1$H NMR (400 MHz, CDCl$_3$) δ 0.32-0.42 (2H, m), 0.62-0.71 (2H, m), 1.21-1.35 (1H, m), 3.79 (2H, d, J=6.8 Hz), 6.55-6.69 (2H, m), 6.69 (1H, d, J=8.0 Hz), 6.92 (2H, d, J=8.8 Hz), 7.24 (1H, t, J=8.4 Hz), 6.88-6.96 (2H, m).

D) 2-(4-(3-(cyclopropylmethoxy)phenoxy)phenyl)-4,4,5,5-tetramethyl-1,3,2-dioxaborolane To a mixture of 1-(4-bromophenoxy)-3-(cyclopropylmethoxy)benzene (2 g) and 1,4-dioxane (30 ml) were added 4,4,4',4',5,5,5',5'-octamethyl-2,2'-bi-1,3,2-dioxaborolane (2.39 g), potassium acetate (923 mg) and (bis(1,1'-diphenylphosphino)ferrocene)dichloropalladium (233 mg), and the mixture was stirred at 80° C. for 16 hr. The reaction mixture was cooled to room temperature, water was added and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (1.85 g).

$^1$H NMR (400 MHz, CDCl$_3$) δ 0.32-0.40 (2H, m), 0.62-0.71 (2H, m), 1.32-1.50 (13H, m), 3.77 (2H, d, J=7.2 Hz), 6.55-6.66 (2H, m), 6.68-6.73 (1H, m), 6.98-7.06 (2H, m), 7.24 (1H, t, J=8.0 Hz), 7.80 (2H, d, J=8.4 Hz).

E) N-(1-(5-(4-(3-(cyclopropylmethoxy)phenoxy)phenyl)-1-benzofuran-2-yl)ethyl)acetamide To a mixture of 2-(4-(3-(cyclopropylmethoxy)phenoxy)phenyl)-4,4,5,5-tetramethyl-1,3,2-dioxaborolane (200 mg), N-(1-(5-bromo-1-benzofuran-2-yl)ethyl)acetamide (230 mg), 1,4-dioxane (6 ml) and water (2 ml) were added potassium carbonate (113 mg) and (bis(1,1'-diphenylphosphino) ferrocene)dichloropalladium dichloromethane adduct (22 mg), and the mixture was stirred at 80° C. for 16 hr. To the reaction mixture was added water and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% aqueous ammonia added) to give the title compound (58 mg).

$^1$H NMR (400 MHz, DMSO-d$_6$) δ 0.28-0.37 (2H, m), 0.53-0.61 (2H, m), 1.15-1.23 (1H, m), 1.47 (3H, d, J=7.2 Hz), 1.88 (3H, s), 3.80 (2H, d, J=6.8 Hz), 5.10-5.21 (1H, m), 6.56-6.63 (2H, m), 6.70-6.76 (2H, m), 7.10 (2H, d, J=8.4 Hz), 7.29 (1H, t, J=8.4 Hz), 7.51-7.56 (1H, m), 7.60 (1H, d, J=8.4 Hz), 7.69 (2H, d, J=8.8 Hz), 7.83 (1H, d, J=1.6 Hz), 8.43 (1H, d, J=8.0 Hz).

Example 56

N-(1-(2-(4-(3-(cyclopropylmethoxy)phenoxy)phenyl)-2H-indazol-6-yl)ethyl)acetamide

A) methyl 2-(4-(3-(cyclopropylmethoxy)phenoxy)phenyl)-2H-indazole-6-carboxylate A mixture of 1-(4-bromophenoxy)-3-(cyclopropylmethoxy)benzene (272 mg), methyl 1H-indazole-6-carboxylate (150 mg), copper(I) iodide (81 mg), (+/−)-trans-N,N'-dimethylcyclohexane-1,2-diamine (121 mg), tripotassium phosphate (542 mg) and toluene (10 ml) was stirred under an argon atmosphere and microwave radiation at 200° C. for 4 hr. Furthermore, a mixture of 1-(4-bromophenoxy)-3-(cyclopropylmethoxy)benzene (308 mg), methyl 1H-indazole-6-carboxylate (170 mg), copper(I) iodide (92 mg), (+/−)-trans-N,N'-dimethylcyclohexane-1,2-diamine (137 mg), tripotassium phosphate (614 mg) and toluene (12 ml) was stirred under an argon atmosphere and microwave radiation at 200° C. for 4 hr. The above-mentioned two reaction mixtures were mixed, ethyl acetate was added, and the mixture was filtered through celite. The filtrate was passed through a silica gel short column (ethyl acetate), and concentrated under reduced pressure. The obtained residue was purified by silica gel column chromatography (NH, hexane/ethyl acetate) to give the title compound (48 mg).

$^1$H NMR (300 MHz, DMSO-d$_6$) δ 0.27-0.35 (2H, m), 0.51-0.60 (2H, m), 1.12-1.28 (1H, m), 3.81 (2H, d, J=7.0 Hz), 3.90 (3H, s), 6.61-6.69 (2H, m), 6.77 (1H, ddd, J=8.3, 2.1, 1.0 Hz), 7.19-7.26 (2H, m), 7.28-7.36 (1H, m), 7.63 (1H, dd, J=8.8, 1.3 Hz), 7.90 (1H, dd, J=8.9, 0.8 Hz), 8.08-8.16 (2H, m), 8.37-8.40 (1H, m), 9.18 (1H, d, J=0.9 Hz).

B) (2-(4-(3-(cyclopropylmethoxy)phenoxy)phenyl)-2H-indazol-6-yl)methanol

To a mixture of lithium aluminum hydride (25.6 mg) and THF (5 ml) was added a mixture of methyl 2-(4-(3-(cyclopropylmethoxy)phenoxy)phenyl)-2H-indazole-6-carboxylate (140 mg) and THF (1 ml) under a nitrogen atmosphere and under ice-cooling. The reaction mixture was stirred under a nitrogen atmosphere at 0° C. for 30 min, and water (0.1 m), 15% aqueous sodium hydroxide solution (0.1 ml) and water (0.3 ml) were successively added. The obtained mixture was stirred at room temperature for 30 min, filtered through celite, and the filtrate was concentrated under reduced pressure to give the title compound (139 mg).

$^1$H NMR (300 MHz, DMSO-d$_6$) δ 0.27-0.35 (2H, m), 0.52-0.60 (2H, m), 1.12-1.28 (1H, m), 3.81 (2H, d, J=7.0 Hz), 4.59 (2H, d, J=5.3 Hz), 5.26 (1H, t, J=5.8 Hz), 6.59-6.67 (2H, m), 6.72-6.79 (1H, m), 7.05 (1H, dd, J=8.6, 1.2 Hz), 7.16-7.24 (2H, m), 7.26-7.35 (1H, m), 7.56-7.61 (1H, m), 7.70 (1H, dd, J=8.6, 0.6 Hz), 8.03-8.12 (2H, m), 8.99 (1H, d, J=0.8 Hz).

C) 2-(4-(3-(cyclopropylmethoxy)phenoxy)phenyl)-2H-indazole-6-carbaldehyde

A mixture of (2-(4-(3-(cyclopropylmethoxy) phenoxy) phenyl)-2H-indazol-6-yl) methanol (139 mg), tetrapropylammonium perruthenate (5.94 mg), 4-methylmorpholine 4-oxide (59.4 mg), molecular sieves 4A (150 mg) and acetonitrile (5 ml) was stirred at room temperature for 3 days. The reaction mixture was filtered through celite, and the filtrate was concentrated under reduced pressure. The obtained residue was purified by silica gel column chromatography (hexane/ethyl acetate) to give the title compound (113 mg).

$^1$H NMR (300 MHz, DMSO-d$_6$) δ 0.27-0.35 (2H, m), 0.52-0.60 (2H, m), 1.12-1.28 (1H, m), 3.82 (2H, d, J=7.0 Hz), 6.62-6.69 (2H, m), 6.74-6.81 (1H, m), 7.20-7.28 (2H, m), 7.32 (1H, t, J=8.2 Hz), 7.53 (1H, dd, J=8.7, 1.1 Hz), 7.93

(1H, d, J=8.9 Hz), 8.09-8.18 (2H, m), 8.42-8.49 (1H, m), 9.21 (1H, d, J=0.6 Hz), 10.10 (1H, s).

D) 1-(2-(4-(3-(cyclopropylmethoxy)phenoxy)phenyl)-2H-indazol-6-yl)ethanol

To a mixture of 2-(4-(3-(cyclopropylmethoxy)phenoxy)phenyl)-2H-indazole-6-carbaldehyde (110 mg) and THF (5 ml) was added methylmagnesium bromide (1.0 M THF solution, 0.57 ml) under a nitrogen atmosphere and under ice-cooling. The reaction mixture was stirred under a nitrogen atmosphere at 0° C. for 30 min. To the reaction mixture was added saturated aqueous ammonium chloride solution, and the mixture was extracted with ethyl acetate. The obtained organic layer was washed with saturated brine, dried over anhydrous magnesium sulfate, and concentrated under reduced pressure to give the title compound (120 mg).
$^1$H NMR (300 MHz, DMSO-d$_6$) δ 0.26-0.35 (2H, m), 0.51-0.60 (2H, m), 1.12-1.28 (1H, m), 1.38 (3H, d, J=6.4 Hz), 3.81 (2H, d, J=7.0 Hz), 4.75-4.86 (1H, m), 5.23 (1H, d, J=4.1 Hz), 6.59-6.69 (2H, m), 6.71-6.80 (1H, m), 7.11 (1H, dd, J=8.8, 1.2 Hz), 7.16-7.24 (2H, m), 7.26-7.36 (1H, m), 7.57-7.61 (1H, m), 7.70 (1H, dd, J=8.8, 0.5 Hz), 8.04-8.11 (2H, m), 8.98 (1H, d, J=0.8 Hz).

E) 6-(1-azidoethyl)-2-(4-(3-(cyclopropylmethoxy)phenoxy)phenyl)-2H-indazole

A mixture of 1-(2-(4-(3-(cyclopropylmethoxy)phenoxy)phenyl)-2H-indazol-6-yl)ethanol (120 mg), diphenylphosphoryl azide (0.092 ml), DBU (0.086 ml) and toluene (5 ml) was stirred at 60° C. for 2 hr. To the reaction mixture were added diphenylphosphoryl azide (118 mg) and DBU (0.086 ml), and the mixture was stirred at 60° C. for 1 jo hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (317 mg) containing impurity.
MS (ESI+): [M+H]$^+$ 426.0.

F) N-(1-(2-(4-(3-(cyclopropylmethoxy)phenoxy)phenyl)-2H-indazol-6-yl)ethyl)acetamide A mixture of 6-(1-azidoethyl)-2-(4-(3-(cyclopropylmethoxy)phenoxy)phenyl)-2H-indazole (317 mg) containing impurity, 10% palladium carbon (containing water (50%), 20 mg) and ethyl acetate (10 ml) was stirred under a hydrogen atmosphere at room temperature overnight. The catalyst was removed by filtration, and the obtained filtrate was washed with ethyl acetate (5 ml). To the mixed filtrate was added acetic anhydride (0.081 ml), and the mixture was stirred at room temperature for 30 min. The reaction mixture was concentrated under reduced pressure. To the obtained residue was added toluene, and the insoluble materials were removed by filtration. The filtrate was concentrated under reduced pressure. The obtained residue was purified by silica gel column chromatography (NH, hexane/ethyl acetate), and crystallized from hexane/ethyl acetate to give the title compound (67 mg).
$^1$H NMR (300 MHz, DMSO-d$_6$) δ 0.26-0.36 (2H, m), 0.51-0.61 (2H, m), 1.13-1.28 (1H, m), 1.40 (3H, d, J=7.0 Hz), 1.87 (3H, s), 3.81 (2H, d, J=7.0 Hz), 4.92-5.06 (1H, m), 6.58-6.68 (2H, m), 6.71-6.81 (1H, m), 7.07 (1H, dd, J=8.7, 0.9 Hz), 7.16-7.23 (2H, m), 7.31 (1H, t, J=8.1 Hz), 7.55 (1H, s), 7.71 (1H, d, J=8.7 Hz), 8.02-8.13 (2H, m), 8.34 (1H, d, J=8.1 Hz), 8.99 (1H, s).

Example 60

N-(1-(2-(2-cyano-4-(3-(cyclopropylmethoxy)phenoxy)phenyl)-1,3-benzoxazol-6-yl)ethyl)acetamide A) 2-(6-acetyl-1,3-benzoxazol-2-yl)-5-(3-(cyclopropylmethoxy)phenoxy)benzonitrile A mixture of 1-(2-(2-bromo-4-(3-(cyclopropylmethoxy)phenoxy)phenyl)-1,3-benzoxazol-6-yl)ethanone (350 mg), tetrakis(triphenylphosphine)palladium (85 mg), zinc cyanide (172 mg) and DMF (5 ml) was stirred under microwave radiation at 120° C. for 1 hr. The reaction mixture was cooled to room temperature, saturated aqueous sodium hydrogen carbonate solution was added, and the mixture was extracted with ethyl acetate. The obtained organic layer was washed with water and saturated brine, dried over anhydrous magnesium sulfate, and concentrated under reduced pressure. The obtained residue was purified by silica gel column chromatography (hexane/ethyl acetate) to give the title compound (211 mg).
$^1$H NMR (300 MHz, DMSO-d$_6$) δ 0.17-0.40 (2H, m), 0.45-0.71 (2H, m), 1.02-1.43 (1H, m), 2.69 (3H, s), 3.84 (2H, d, J=7.1 Hz), 6.70-6.83 (2H, m), 6.83-6.95 (1H, m), 7.33-7.43 (1H, m), 7.47 (1H, dd, J=8.9, 2.5 Hz), 7.72 (1H, d, J=2.5 Hz), 7.88-8.11 (2H, m), 8.27-8.45 (2H, m).

B) N-(1-(2-(2-cyano-4-(3-(cyclopropylmethoxy)phenoxy)phenyl)-1,3-benzoxazol-6-yl)ethyl) acetamide To a mixture of 2-(6-acetyl-1,3-benzoxazol-2-yl)-5-(3-(cyclopropylmethoxy)phenoxy)benzonitrile (100 mg), ammonium acetate (182 mg) and methanol (5 ml) was added sodium cyanoborohydride (50 mg), and the mixture was stirred at 60° C. overnight. The reaction mixture was cooled to room temperature, and extracted with saturated aqueous sodium hydrogen carbonate solution and ethyl acetate. The obtained organic layer was washed with saturated brine, dried over anhydrous magnesium sulfate, and concentrated under reduced pressure. To a mixture of the obtained residue, THF (5 ml) and triethylamine (0.065 ml) was added acetic anhydride (0.033 ml), and the mixture was stirred at room temperature for 30 min. The reaction mixture was concentrated under reduced pressure. The obtained residue was purified by silica gel column chromatography (hexane/ethyl acetate) to give the title compound (49.6 mg).
$^1$H NMR (300 MHz, DMSO-d$_6$) δ 0.22-0.38 (2H, m), 0.43-0.66 (2H, m), 1.05-1.28 (1H, m), 1.40 (3H, d, J=7.0 Hz), 1.86 (3H, s), 3.83 (2H, d, J=7.0 Hz), 4.87-5.20 (1H, m), 6.68-6.81 (2H, m), 6.82-6.93 (1H, m), 7.30-7.51 (3H, m), 7.62-7.76 (2H, m), 7.76-7.87 (1H, m), 8.24-8.50 (2H, m).

Example 65

N-(1-(2-(3-(3-(trifluoromethyl)phenoxy)azetidin-1-yl)-1,3-benzoxazol-6-yl)ethyl)acetamide A) tert-butyl 3-(3-(trifluoromethyl)phenoxy)azetidine-1-carboxylate A mixture of 3-(trifluoromethyl)phenol (2 g), tert-butyl 3-iodoazetidine-1-carboxylate (3.48 g), cesium carbonate (6.03 g) and DMF (15 ml) was stirred at 80° C. for 20 hr. The reaction mixture was added to water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (3.1 g).

$^1$H NMR (400 MHz, DMSO-$d_6$) δ 1.40 (9H, s), 3.65-3.90 (2H, m), 4.20-4.45 (2H, m), 5.00-5.20 (1H, m), 7.10-7.21 (2H, m), 7.28-7.40 (1H, m), 7.55 (1H, d, J=8.0 Hz).

B) 3-(3-(trifluoromethyl)phenoxy)azetidine trifluoroacetate

To a mixture of tert-butyl 3-(3-(trifluoromethyl)phenoxy)azetidine-1-carboxylate (1.5 g) and dichloromethane (4 ml) was added TFA (2 ml). The reaction mixture was stirred at room temperature for 2 hr, and concentrated under reduced pressure to give the title compound (1.48 g).

$^1$H NMR (400 MHz, DMSO-$d_6$) δ 3.95-4.13 (2H, m), 4.40-4.60 (2H, m), 5.14-5.30 (1H, m), 7.12-7.25 (2H, m), 7.38 (1H, d, J=8.0 Hz), 7.57 (1H, t, J=8.0 Hz), 9.03 (1H, brs), 9.20 (1H, brs).

C) N-(1-(2-(3-(3-(trifluoromethyl)phenoxy)azetidin-1-yl)-1,3-benzoxazol-6-yl)ethyl)acetamide To a mixture of N-(1-(2-sulfanyl-1,3-benzoxazol-6-yl)ethyl)acetamide (300 mg) and dichloromethane (5 ml) were added (chloromethylene)dimethyliminium chloride (163 mg) and DMF (0.5 ml) under ice-cooling. The reaction mixture was stirred at 0° C. for 5 min, and triethylamine (641 mg) and 3-(3-(trifluoromethyl)phenoxy)azetidine trifluoroacetate (597 mg) were added. The reaction mixture was stirred at room temperature for 1 hr, water was added and the mixture was extracted with dichloromethane. The obtained organic layer was washed with saturated brine, dried over anhydrous sodium sulfate, and concentrated under reduced pressure. The obtained residue was purified by HPLC (water/acetonitrile, 0.1% aqueous ammonia added) to give the title compound (40 mg).

$^1$H NMR (400 MHz, CDCl$_3$) δ 1.51 (3H, d, J=6.8 Hz), 1.98 (3H, s), 4.30-4.40 (2H, m), 4.59-4.71 (2H, m), 5.09-5.25 (2H, m), 5.66 (1H, d, J=7.2 Hz), 6.96 (1H, d, J=8.4 Hz), 7.01 (1H, s), 7.11-7.20 (1H, m), 7.21-7.32 (2H, m), 7.34 (1H, d, J=8.0 Hz), 7.44 (1H, t, J=8.0 Hz).

Example 66

N-(1-(2-(4-(3-(cyclopropylmethoxy)phenoxy)phenyl) imidazo[1,2-a]pyridin-7-yl)ethyl)acetamide

A) 1-(4-(3-(cyclopropylmethoxy)phenoxy)phenyl)ethanone

A mixture of 3-(cyclopropylmethoxy)phenol (10 g), 1-(4-fluorophenyl)ethanone (8.41 g), cesium carbonate (23.8 g) and DMF (60 ml) was stirred at 80° C. for 24 hr. The reaction mixture was added to water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (14.1 g).

$^1$H NMR (400 MHz, DMSO-$d_6$) δ 0.28-0.33 (2H, m), 0.52-0.59 (2H, m), 1.12-1.23 (1H, m), 2.54 (3H, s), 3.81 (2H, d, J=6.8 Hz), 6.62-6.68 (2H, m), 6.80 (1H, dd, J=8.0, 2.0 Hz), 7.05 (2H, d, J=8.8 Hz), 7.33 (1H, t, J=8.0 Hz), 7.98 (2H, d, J=8.8 Hz).

B) 2-bromo-1-(4-(3-(cyclopropylmethoxy)phenoxy)phenyl)ethanone

To a mixture of 1-(4-(3-(cyclopropylmethoxy)phenoxy)phenyl)ethanone (7 g) and acetonitrile (50 ml) was added tetrabutylammonium tribromide (12 g). The reaction mixture was stirred at room temperature for 15 hr. The reaction mixture was concentrated under reduced pressure, water was added and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (2.91 g).

$^1$H NMR (400 MHz, DMSO-$d_6$) δ 0.25-0.35 (2H, m), 0.51-0.60 (2H, m), 1.12-1.23 (1H, m), 3.81 (2H, d, J=6.8 Hz), 4.85-5.12 (2H, m), 6.62-6.72 (2H, m), 6.82 (1H, dd, J=8.4, 1.6 Hz), 7.07 (2H, d, J=8.8 Hz), 7.34 (1H, t, J=8.0 Hz), 8.03 (2H, d, J=8.8 Hz).

C) methyl 2-(4-(3-(cyclopropylmethoxy)phenoxy)phenyl)imidazo[1,2-a]pyridine-7-carboxylate A mixture of 2-bromo-1-(4-(3-(cyclopropylmethoxy)phenoxy)phenyl)ethanone (2.9 g), methyl 2-aminoisonicotinate (1.22 g), triethylamine (244 mg) and ethanol (20 ml) was stirred with heating under reflux for 5 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (1.44 g).

$^1$H NMR (400 MHz, DMSO-$d_6$) δ 0.25-0.35 (2H, m), 0.50-0.60 (2H, m), 1.12-1.23 (1H, m), 3.80 (2H, d, J=6.8 Hz), 3.90 (3H, s), 6.58-6.63 (2H, m), 6.74 (1H, d, J=7.6 Hz), 7.10 (2H, d, J=8.4 Hz), 7.25-7.40 (2H, m), 8.15 (2H, d, J=8.4 Hz), 8.15 (1H, s), 8.57 (1H, s), 8.62 (1H, d, J=6.8 Hz).

D) (2-(4-(3-(cyclopropylmethoxy)phenoxy)phenyl)imidazo[1,2-a]pyridin-7-yl)methanol To a mixture of lithium aluminum hydride (340 mg) and THF (20 ml) was added methyl 2-(4-(3-(cyclopropylmethoxy)phenoxy)phenyl)imidazo[1,2-a]pyridine-7-carboxylate (1.24 g). The reaction mixture was stirred at 20° C. for 1 hr. To the mixture were successively added water (0.34 ml), 15% aqueous sodium hydroxide solution (0.34 ml) and water (1.02 ml). The mixture was filtered, and concentrated under reduced pressure. The obtained residue was purified by silica gel column chromatography (petroleum ether/ethyl acetate) to give the title compound (920 mg).

$^1$H NMR (400 MHz, DMSO-$d_6$) δ 0.25-0.32 (2H, m), 0.50-0.60 (2H, m), 1.12-1.23 (1H, m), 3.79 (2H, d, J=6.8 Hz), 4.54 (2H, d, J=5.6 Hz), 5.41 (1H, t, J=5.6 Hz), 6.56-6.60 (1H, m), 6.70-6.74 (1H, m), 6.83 (1H, dd, J=7.6, 1.6 Hz), 7.07 (2H, d, J=8.8 Hz), 7.25-7.30 (1H, m), 7.43 (1H, s), 7.96 (2H, d, J=8.4 Hz), 8.29 (1H, s), 8.45 (1H, d, J=6.8 Hz).

E) 2-(4-(3-(cyclopropylmethoxy)phenoxy)phenyl) imidazo[1,2-a]pyridine-7-carbaldehyde A mixture of (2-(4-(3-(cyclopropylmethoxy)phenoxy) phenyl)imidazo[1,2-a]pyridin-7-yl)methanol (920 mg), manganese dioxide (1.04 g) and dichloromethane (10 ml) was stirred with heating under reflux for 20 hr. The reaction mixture was concentrated under reduced pressure. The obtained residue was purified by silica gel column chromatography (petroleum ether/ethyl acetate) to give the title compound (770 mg).
$^1$H NMR (400 MHz, DMSO-d$_6$) δ 0.26-0.33 (2H, m), 0.50-0.60 (2H, m), 1.12-1.23 (1H, m), 3.80 (2H, d, J=7.2 Hz), 6.58-6.63 (2H, m), 6.71-6.75 (1H, m), 7.11 (2H, d, J=8.4 Hz), 7.23-7.32 (2H, m), 8.03 (2H, d, J=8.4 Hz), 8.30 (1H, s), 8.60-8.65 (2H, m), 10.00 (1H, s).

F) 1-(2-(4-(3-(cyclopropylmethoxy)phenoxy)phenyl) imidazo[1,2-a]pyridin-7-yl)ethanol To a mixture of 2-(4-(3-(cyclopropylmethoxy) phenoxy) phenyl) imidazo[1,2-a]pyridine-7-carbaldehyde (770 mg) and THF (15 ml) was added methylmagnesium bromide (3.0 M THF solution, 1.33 ml), and the mixture was stirred at 20° C. for 1 hr. To the reaction mixture was added saturated aqueous ammonium chloride solution, the obtained mixture was added to water and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (710 mg).
$^1$H NMR (400 MHz, DMSO-d$_6$) δ 0.30-0.48 (2H, m), 0.53-0.70 (2H, m), 1.20-1.30 (1H, m), 1.43 (3H, d, J=6.4 Hz), 3.86 (2H, d, J=7.2 Hz), 4.70-4.95 (1H, m), 5.43 (1H, d, J=4.4 Hz), 6.59-6.71 (2H, m), 6.74-6.85 (1H, m), 6.95 (1H, d, J=7.2 Hz), 7.14 (2H, d, J=8.4 Hz), 7.34 (1H, t, J=8.0 Hz), 7.50 (1H, s), 8.02 (2H, d, J=8.8 Hz), 8.35 (1H, s), 8.51 (1H, d, J=6.8 Hz).

G) 1-(2-(4-(3-(cyclopropylmethoxy)phenoxy)phenyl)imidazo[1,2-a]pyridin-7-yl)ethanone A mixture of 1-(2-(4-(3-(cyclopropylmethoxy)phenoxy) phenyl)imidazo[1,2-a]pyridin-7-yl)ethanol (610 mg), manganese dioxide (661 mg) and dichloromethane (10 ml) was stirred with heating under reflux for 24 hr. The reaction mixture was concentrated under reduced pressure. The obtained residue was purified by silica gel column chromatography (petroleum ether/ethyl acetate) to give the title compound (500 mg).
$^1$H NMR (400 MHz, DMSO-d$_6$) δ 0.27-0.33 (2H, m), 0.50-0.60 (2H, m), 1.12-1.23 (1H, m), 2.65 (3H, s), 3.80 (2H, d, J=6.8 Hz), 6.58-6.63 (2H, m), 6.71-6.75 (1H, m), 7.10 (2H, d, J=8.4 Hz), 7.25-7.32 (2H, m), 8.02 (2H, d, J=8.4 Hz), 8.34 (1H, s), 8.53-8.60 (2H, m).

H) N-(1-(2-(4-(3-(cyclopropylmethoxy)phenoxy) phenyl)imidazo[1,2-a]pyridin-7-yl)ethyl)acetamide To a mixture of 1-(2-(4-(3-(cyclopropylmethoxy)phenoxy)phenyl)imidazo[1,2-a]pyridin-7-yl)ethanone (80 mg) and methanol (5 ml) were added ammonium acetate (155 mg) and sodium cyanoborohydride (25 mg), and the mixture was stirred at 19-25° C. for 20 hr, and further stirred with heating under reflux for 24 hr. The reaction mixture was added to water, and the mixture was extracted with ethyl acetate. The obtained organic layer was washed with saturated brine, dried over anhydrous sodium sulfate, and concentrated under reduced pressure. To the obtained residue was added THF (5 ml), and acetic anhydride (41 mg) was added at 0° C. The reaction mixture was stirred at 20° C. for 2 hr. The mixture was added to water, and the mixture was extracted with ethyl acetate. The obtained organic layer was washed with saturated brine, dried over anhydrous sodium sulfate, and concentrated under reduced pressure. The obtained residue was purified by HPLC (water/acetonitrile, 0.1% ammonium carbonate added) to give the title compound (24 mg).
$^1$H NMR (400 MHz, DMSO-d$_6$) δ 0.29-0.33 (2H, m), 0.52-0.60 (2H, m), 1.14-1.23 (1H, m), 1.39 (3H, d, J=6.8 Hz), 1.89 (3H, s), 3.80 (2H, d, J=6.8 Hz), 4.90-5.00 (1H, m), 6.58-6.61 (2H, m), 6.71-6.75 (1H, m), 6.92 (1H, d, J=6.8 Hz), 7.09 (2H, d, J=8.4 Hz), 7.29 (1H, t, J=8.0 Hz), 7.42 (1H, s), 7.95 (2H, d, J=8.4 Hz), 8.32 (1H, s), 8.39 (1H, d, J=8.0 Hz), 8.49 (1H, d, J=6.8 Hz).

Example 67

N-(1-(2-(6-(3-(cyclopropylmethoxy)phenoxy)pyridin-3-yl)-1-benzofuran-6-yl)ethyl)acetamide

A) 6-(3-(benzyloxy)phenoxy)nicotinaldehyde

A mixture of 3-(benzyloxy)phenol (5.34 g), 6-chloronicotinaldehyde (3.78 g), potassium carbonate (7.37 g) and DMF (50 ml) was stirred at 60° C. for 2 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (6.72 g).
$^1$H NMR (300 MHz, DMSO-d$_6$) δ 5.11 (2H, s), 6.74-6.83 (1H, m), 6.86-6.99 (2H, m), 7.18 (1H, d, J=8.5 Hz), 7.38-7.48 (6H, m), 8.26 (1H, dd, J=8.6, 2.4 Hz), 8.71 (1H, d, J=1.9 Hz), 10.00 (1H, s)

B) 2-(3-(benzyloxy)phenoxy)-5-ethynylpyridine

A mixture of 6-(3-(benzyloxy)phenoxy)nicotinaldehyde (6.72 g), potassium carbonate (6.08 g), dimethyl (1-diazo-2-oxopropyl)phosphonate (4.95 ml) and methanol (50 ml) was stirred at room temperature for 2 hr. To the reaction mixture was added water and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (3.55 g).
$^1$H NMR (300 MHz, DMSO-d$_6$) δ 4.32 (1H, s), 5.09 (2H, s), 6.73 (1H, dd, J=8.1, 0.8 Hz), 6.83 (1H, t, J=2.3 Hz), 6.89 (1H, dd, J=8.3, 0.8 Hz), 7.02 (1H, dd, J=8.5, 0.7 Hz), 7.28-7.48 (6H, m), 7.94 (1H, dd, J=8.5, 2.4 Hz), 8.29 (1H, dd, J=2.3, 0.5 Hz).

C) ethyl 2-(6-(3-(benzyloxy)phenoxy)pyridin-3-yl)-1-benzofuran-6-carboxylate A mixture of 2-(3-(benzyloxy)phenoxy)-5-ethynylpyridine (3.55 g), ethyl 3-hydroxy-4-iodobenzoate (3.44 g), bis(triphenylphosphine)dichloropalladium (413 mg), copper (I) iodide (135 mg), 1,1,3,3-tetramethylguanidine (4.43 ml) and DMF (40 ml) was stirred under an argon atmosphere at 80° C. for 2 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (5.17 g).

$^1$H NMR (300 MHz, DMSO-$d_6$) δ 1.36 (3H, t, J=7.1 Hz), 4.35 (2H, q, J=7.1 Hz), 5.12 (2H, s), 6.74-6.81 (1H, m), 6.83-6.96 (2H, m), 7.18 (1H, d, J=8.7 Hz), 7.29-7.50 (6H, m), 7.58 (1H, d, J=0.8 Hz), 7.74-7.83 (1H, m), 7.86-7.93 (1H, m), 8.16 (1H, s), 8.39 (1H, dd, J=8.6, 2.5 Hz), 8.78 (1H, d, J=2.1 Hz).

D) 5-(6-(1-azidoethyl)-1-benzofuran-2-yl)-2-(3-(benzyloxy)phenoxy)pyridine

To a mixture of lithium aluminum hydride (843 mg) and THF (40 ml) was added dropwise a mixture of ethyl 2-(6-(3-(benzyloxy)phenoxy)pyridin-3-yl)-1-benzofuran-6-carboxylate (5.17 g) and THF (40 ml) under ice-cooling. The reaction mixture was stirred for 30 min under ice-cooling, and water (0.9 ml), 1N aqueous sodium hydroxide solution (0.9 ml) and water (2.7 ml) were successively added. The obtained mixture was stirred at room temperature for 30 min, filtered through celite, and the filtrate was concentrated under reduced pressure. To a mixture of the obtained residue and acetonitrile (100 ml) were added tetrapropylammonium perruthenate (195 mg), 4-methylmorpholine 4-oxide (1.95 g) and molecular sieves 4A (7 g). The reaction mixture was stirred at room temperature for 2 hr, filtered and concentrated under reduced pressure. To a mixture of the obtained residue and THF (50 ml) was added dropwise methylmagnesium bromide (1.0 M THF solution, 22.2 ml) under ice-cooling. The reaction mixture was stirred for 30 min under ice-cooling, saturated aqueous ammonium chloride solution was added, and the mixture was extracted with ethyl acetate. The obtained organic layer was washed with saturated brine, dried over anhydrous magnesium sulfate, and concentrated under reduced pressure. To a mixture of the obtained residue and toluene (50 ml) were added diphenylphosphoryl azide (6.11 g) and DBU (5.02 ml), and the mixture was stirred at room temperature for 2 hr. To the reaction mixture was added water, and the mixture was extracted with toluene. The obtained organic layer was washed with saturated brine, dried over anhydrous magnesium sulfate, and concentrated under reduced pressure. The obtained residue was purified by silica gel column chromatography (hexane/ethyl acetate) to give the title compound (3 g).

$^1$H NMR (300 MHz, DMSO-$d_6$) δ 1.53 (3H, d, J=6.8 Hz), 4.97 (1H, q, J=6.8 Hz), 5.12 (2H, s), 6.77 (1H, dd, J=7.6, 1.8 Hz), 6.84-6.95 (2H, m), 7.16 (1H, d, J=8.7 Hz), 7.24-7.44 (8H, m), 7.64-7.74 (2H, m), 8.34 (1H, dd, J=8.6, 2.5 Hz), 8.73 (1H, d, J=2.4 Hz).

E) N-(1-(2-(6-(3-hydroxyphenoxy)pyridin-3-yl)-1-benzofuran-6-yl)ethyl)acetamide A mixture of 5-(6-(1-azidoethyl)-1-benzofuran-2-yl)-2-(3-(benzyloxy)phenoxy)pyridine (4.0 g), 10% palladium carbon (containing water (50%), 345 mg) and THF (60 ml) was stirred under a hydrogen atmosphere at room temperature for 4 hr. The 25 reaction mixture was filtered through celite and concentrated under reduced pressure. To the obtained residue were added pyridine (10 ml) and acetic anhydride (3.0 ml), and the mixture was stirred at room temperature for 30 min. The reaction mixture was concentrated under reduced pressure. To the obtained residue were added THF (20 ml) and 2N aqueous sodium hydroxide solution (20 ml), and the mixture was stirred at room temperature for 1 hr. The reaction mixture was acidified with 2N hydrochloric acid, and extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (1.8 g).

$^1$H NMR (300 MHz, DMSO-$d_6$) δ 1.39 (3H, d, J=7.0 Hz), 1.85 (3H, s), 4.95-5.09 (1H, m), 6.51-6.61 (2H, m), 6.61-6.68 (1H, m), 7.12 (1H, d, J=8.7 Hz), 7.18-7.26 (2H, m), 7.42 (1H, s), 7.55 (1H, s), 7.59 (1H, d, J=8.1 Hz), 8.26-8.39 (2H, m), 8.72 (1H, d, J=2.3 Hz), 9.65-9.78 (1H, m).

F) N-(1-(2-(6-(3-(cyclopropylmethoxy)phenoxy)pyridin-3-yl)-1-benzofuran-6-yl)ethyl)acetamide A mixture of N-(1-(2-(6-(3-hydroxyphenoxy)pyridin-3-yl)-1-benzofuran-6-yl)ethyl)acetamide (200 mg), (bromomethyl)cyclopropane (139 mg), potassium carbonate (213 mg) and DMF (3 ml) was stirred at 80° C. for 4 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (138 mg).

$^1$H NMR (300 MHz, DMSO-$d_6$) δ 0.26-0.36 (2H, m), 0.52-0.61 (2H, m), 1.16-1.28 (1H, m), 1.39 (3H, d, J=7.0 Hz), 1.85 (3H, s), 3.81 (2H, d, J=7.1 Hz), 4.95-5.10 (1H, m), 6.69-6.77 (2H, m), 6.77-6.85 (1H, m), 7.11-7.18 (1H, m), 7.19-7.26 (1H, m), 7.27-7.36 (1H, m), 7.39-7.44 (1H, m), 7.52-7.63 (2H, m), 8.28-8.38 (2H, m), 8.68-8.74 (1H, m).

Example 68

N-(1-(2-(6-(3-(((1S)-2,2-difluorocyclopropyl)methoxy)phenoxy)pyridin-3-yl)-1-benzofuran-6-yl)ethyl)acetamide A mixture of N-(1-(2-(6-(3-hydroxyphenoxy)pyridin-3-yl)-1-benzofuran-6-yl)ethyl)acetamide (200 mg), ((1S)-2,2-difluorocyclopropyl)methyl 4-nitrobenzenesulfonate (302 mg), potassium carbonate (213 mg) and DMF (3 ml) was stirred at 80° C. for 4 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (115 mg).

$^1$H NMR (300 MHz, DMSO-$d_6$) δ 1.39 (3H, d, J=7.0 Hz), 1.42-1.54 (1H, m), 1.65-1.80 (1H, m), 1.85 (3H, s), 2.14-2.31 (1H, m), 3.92-4.03 (1H, m), 4.11-4.21 (1H, m), 4.95-5.09 (1H, m), 6.73-6.90 (3H, m), 7.12-7.19 (1H, m), 7.19-7.26 (1H, m), 7.30-7.38 (1H, m), 7.40-7.44 (1H, m), 7.52-7.63 (2H, m), 8.28-8.38 (2H, m), 8.68-8.74 (1H, m).

Example 69

N-(1-(2-(3-((3-(cyclopropylmethoxy)phenyl)amino)azetidin-1-yl)-1,3-benzoxazol-6-yl)ethyl) acetamide

A) tert-butyl 3-((3-(cyclopropylmethoxy)phenyl)amino)azetidine-1-carboxylate A mixture of tert-butyl 3-aminoazetidine-1-carboxylate (3.42 g), 1-bromo-3-(cyclopropylmethoxy)benzene (2.6 g), (dibenzylidene)acetone-palladium(0) (3:2) (690 mg), bis(2,2'-diphenylphosphonyl)-1,1'-binaphthyl (496 mg), cesium carbonate (7.4 g) and toluene (50 ml) was stirred at 110° C. for 15 hr. The reaction mixture was filtered, water was added and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) and purified by HPLC (acetonitrile/water, 0.1% ammonium carbonate added) to give the title compound (835 mg).

$^1$H NMR (400 MHz, DMSO-$d_6$) δ 0.20-0.35 (2H, m), 0.46-0.60 (2H, m), 1.06-1.25 (1H, m), 1.38 (9H, s), 3.50-3.65 (2H, m), 3.71 (2H, d, J=6.8 Hz), 4.02-4.21 (3H, m), 5.95-6.04 (1H, m), 6.07 (1H, dd, J=8.0, 1.6 Hz), 6.15 (1H, dd, J=8.0, 2.0 Hz), 6.21 (1H, d, J=6.4 Hz), 6.96 (1H, t, J=8.0 Hz).

B) N-(3-(cyclopropylmethoxy)phenyl)azetidine-3-amine trifluoroacetate

To a mixture of tert-butyl 3-((3-(cyclopropylmethoxy)phenyl)amino) azetidine-1-carboxylate (835 mg) and dichloromethane (4 ml) was added TFA (2 ml) at 20° C. The reaction mixture was stirred at 19-24° C. for 24 hr. The mixture was concentrated under reduced pressure to give the title compound (1.08 g).

$^1$H NMR (400 MHz, DMSO-$d_6$) δ 0.20-0.40 (2H, m), 0.41-0.64 (2H, m), 1.10-1.30 (1H, m), 3.65-3.90 (4H, m), 4.15-4.40 (3H, m), 6.00-6.90 (3H, m), 7.00 (1H, t, J=8.0 Hz), 8.82 (2H, brs).

C) N-(1-(2-(3-((3-(cyclopropylmethoxy)phenyl)amino)azetidin-1-yl)-1,3-benzoxazol-6-yl)ethyl)acetamide To a mixture of N-(1-(2-sulfanyl-1,3-benzoxazol-6-yl)ethyl)acetamide (300 mg) and dichloromethane (5 ml) were added (chloromethylene)dimethyliminium chloride (163 mg) and DMF (0.5 ml) under ice-cooling. The reaction mixture was stirred at 0° C. for 5 min, and triethylamine (641 mg) and N-(3-(cyclopropylmethoxy)phenyl)azetidine-3-amine trifluoroacetate (536 mg) were added under ice-cooling. The reaction mixture was stirred at room temperature for 1 hr. To the reaction mixture was added water, and the mixture was extracted with dichloromethane. The obtained organic layer was washed with saturated brine, dried over anhydrous sodium sulfate, and concentrated under reduced pressure. The obtained residue was purified by HPLC (acetonitrile/water, 0.1% aqueous ammonia added) to give the title compound (88 mg).

$^1$H NMR (400 MHz, DMSO-$d_6$) δ 0.25-0.40 (2H, m), 0.55-0.70 (2H, m), 1.15-1.35 (1H, m), 1.51 (3H, d, J=6.8 Hz), 1.98 (3H, s), 3.77 (2H, d, J=6.8 Hz), 4.00-4.20 (3H, m), 4.36-4.55 (1H, m), 4.56-4.70 (2H, m), 5.10-5.25 (1H, m), 5.66 (1H, d, J=7.6 Hz), 6.06-6.14 (1H, m), 6.15-6.24 (1H, m), 6.30-6.40 (1H, m), 7.00-7.20 (2H, m), 7.21-7.31 (1H, m), 7.33 (1H, d, J=8.0 Hz).

Example 71

N-(1-(2-(6-(3-(cyclopropylmethoxy)phenoxy)pyridin-3-yl)-1,3-benzoxazol-5-yl)ethyl)acetamide

A) N-(5-acetyl-2-fluorophenyl)-6-chloronicotinamide

To a mixture of 1-(3-amino-4-fluorophenyl)ethanone (1.914 g), triethylamine (3.48 ml) and THF (15 ml) was added 6-chloronicotinoyl chloride (2.2 g), and the mixture was stirred at room temperature for 1 hr. To the reaction mixture was added saturated aqueous sodium hydrogen carbonate solution, and the mixture was extracted with ethyl acetate. The obtained organic layer was washed with water and saturated brine, dried over anhydrous magnesium sulfate, and concentrated under reduced pressure. The obtained residue was purified by silica gel column chromatography (hexane/ethyl acetate) to give the title compound (2 g).

$^1$H NMR (300 MHz, DMSO-$d_6$) δ 2.59 (3H, s), 7.38-7.58 (1H, m), 7.66-7.78 (1H, m), 7.82-8.04 (1H, m), 8.26 (1H, dd, J=7.5, 2.3 Hz), 8.37 (1H, dd, J=8.3, 2.5 Hz), 8.97 (1H, dd, J=2.5, 0.6 Hz), 10.58 (1H, s).

B) 1-(2-(6-(3-(benzyloxy)phenoxy)pyridin-3-yl)-1,3-benzoxazol-5-yl)ethanone

To a mixture of N-(5-acetyl-2-fluorophenyl)-6-chloronicotinamide (400 mg), 3-(benzyloxy)phenol (287 mg) and DMF (5 ml) was added potassium carbonate (378 mg), and the mixture was stirred at 80° C. for 2 hr, and then at 130° C. for 1 hr. The reaction mixture was cooled, added to saturated aqueous sodium hydrogen carbonate solution, and the mixture was extracted with ethyl acetate. The obtained organic layer was washed with water and saturated brine, dried over anhydrous magnesium sulfate, and concentrated under reduced pressure. The obtained residue was purified by silica gel column chromatography (hexane/ethyl acetate) to give the title compound (440 mg).

MS (ESI+): [M+H]$^+$ 437.0.

C) 1-(2-(6-(3-(benzyloxy)phenoxy)pyridin-3-yl)-1,3-benzoxazol-5-yl)ethanamine To a mixture of 1-(2-(6-(3-(benzyloxy)phenoxy)pyridin-3-yl)-1,3-benzoxazol-5-yl)ethanone (435 mg), ammonium acetate (2.3 g), methanol (10 ml) and THF (5 ml) was added borane 2-methylpyridine complex (107 mg) at room temperature. The reaction mixture was stirred with heating under reflux for 3 hr. Sodium cyanoborohydride (130 mg) was added, and the obtained mixture was stirred with heating under reflux for 3 hr. The reaction mixture was allowed to cool to room temperature, added to water and the mixture was extracted with ethyl acetate. The obtained organic layer was washed with water and saturated brine, dried over anhydrous magnesium sulfate, and concentrated under reduced pressure to give the title compound (430 mg).

MS (ESI+): [M+H]$^+$ 438.0.

D) N-(1-(2-(6-(3-(benzyloxy)phenoxy)pyridin-3-yl)-1,3-benzoxazol-5-yl)ethyl) acetamide To a mixture of 1-(2-(6-(3-(benzyloxy)phenoxy)pyridin-3-yl)-1,3-benzoxazol-5-yl)ethanamine (430 mg), triethylamine (0.411 ml) and THF (10 ml) was added acetic anhydride (0.185 ml), and the mixture was stirred at room temperature for 1 hr. The reaction mixture was concentrated under reduced pressure. The obtained residue was purified by silica gel column chromatography (hexane/ethyl acetate) to give the title compound (291 mg).

$^1$H NMR (300 MHz, DMSO-$d_6$) δ 1.40 (3H, d, J=7.0 Hz), 1.86 (3H, s), 4.95-5.08 (1H, m), 5.12 (2H, s), 6.71-6.86 (1H, m), 6.87-7.01 (2H, m), 7.23 (1H, d, J=8.6 Hz), 7.28-7.52 (7H, m), 7.65-7.81 (2H, m), 8.38 (1H, d, J=8.0 Hz), 8.55 (1H, dd, J=8.7, 2.5 Hz), 8.94 (1H, dd, J=2.4, 0.5 Hz).

E) N-(1-(2-(6-(3-hydroxyphenoxy)pyridin-3-yl)-1,3-benzoxazol-5-yl)ethyl)acetamide A mixture of N-(1-(2-(6-(3-(benzyloxy)phenoxy)pyridin-3-yl)-1,3-benzoxazol-5-yl)ethyl)acetamide (280 mg), 10% palladium carbon (containing water (50%), 20 mg), THF (10 ml) and ethyl acetate (10 ml) was stirred under a hydrogen atmosphere at room temperature for 2 hr. To the reaction mixture was added 20% palladium hydroxide (containing water (50%), 25 mg), and the mixture was stirred under a hydrogen atmosphere at room temperature for 3 hr. The catalyst was removed by filtration, and the filtrate was concentrated under reduced pressure to give the title compound (221 mg).

MS (ESI+): [M+H]$^+$ 390.0.

F) N-(1-(2-(6-(3-(cyclopropylmethoxy)phenoxy)pyridin-3-yl)-1,3-benzoxazol-5-yl)ethyl) acetamide A mixture of N-(1-(2-(6-(3-hydroxyphenoxy)pyridin-3-yl)-1,3-benzoxazol-5-yl)ethyl)acetamide (120 mg), (bromomethyl)cyclopropane (0.059 ml), potassium carbonate (128 mg) and DMF (3 ml) was stirred at 100° C. for 2 hr. The reaction mixture was cooled to room temperature, saturated aqueous sodium hydrogen carbonate solution was added and the mixture was extracted with ethyl acetate. The obtained organic layer was washed with water and saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (68.4 mg).

$^1$H NMR (300 MHz, DMSO-$d_6$) δ 0.24-0.38 (2H, m), 0.48-0.66 (2H, m), 1.09-1.29 (1H, m), 1.40 (3H, d, J=7.0 Hz), 1.86 (3H, s), 3.82 (2H, d, J=7.0 Hz), 4.94-5.13 (1H, m), 6.71-6.92 (3H, m), 7.22 (1H, d, J=8.8 Hz), 7.28-7.45 (2H, m), 7.66-7.79 (2H, m), 8.38 (1H, d, J=8.0 Hz), 8.55 (1H, dd, J=8.8, 2.5 Hz), 8.94 (1H, d, J=2.5 Hz).

Example 73

N-(1-(2-(4-(3-(cyclopropylmethoxy)phenoxy)phenyl)-1-benzothiophen-5-yl)ethyl)acetamide A) 1-(1-benzothiophen-5-yl)ethanone A mixture of 5-bromo-1-benzothiophene (2 g), palladium acetate (105 mg), 1,3-bis(diphenylphosphino)propane (387 mg) and ethylene glycol (20 ml) was stirred under a nitrogen atmosphere at 140° C. for 5 min. To the reaction mixture were added butyl vinyl ether (3.64 ml) and triethylamine (3.27 ml). The reaction mixture was stirred under a nitrogen atmosphere at 140° C. for 10 min, and then at 120° C. for 3 hr. The reaction mixture was cooled to room temperature, 1N hydrochloric acid (20 ml) was added, and the mixture was stirred at room temperature for 1 hr. To the reaction mixture was added ethyl acetate, and insoluble materials were removed by filtration. The organic layer of the filtrate was separated, and the aqueous layer was extracted with ethyl acetate. The mixed organic layer was washed successively with saturated aqueous sodium hydrogen carbonate solution and saturated brine, and dried over anhydrous magnesium sulfate. The obtained mixture was passed through a silica gel short column (hexane/ethyl acetate), and concentrated under reduced pressure. To the obtained residue was added toluene, and insoluble materials were removed by filtration. The filtrate was concentrated under reduced pressure and the obtained residue was purified by silica gel column chromatography (hexane/ethyl acetate) to give the title compound (1.49 g).

$^1$H NMR (300 MHz, DMSO-$d_6$) δ 2.66 (3H, s), 7.62 (1H, dd, J=5.5, 0.6 Hz), 7.87-7.94 (2H, m), 8.14 (1H, d, J=8.5 Hz), 8.55 (1H, d, J=1.4 Hz).

B) 1-(1-benzothiophen-5-yl)ethanol

To a mixture of 1-(1-benzothiophen-5-yl)ethanone (530 mg) and methanol (10 ml) was added sodium borohydride (114 mg) under ice-cooling. The reaction mixture was stirred at room temperature for 1 hr. To the reaction mixture was added water, and the mixture was extracted with ethyl acetate. The obtained organic layer was washed with saturated brine, dried over anhydrous magnesium sulfate, and concentrated under reduced pressure to give the title compound (541 mg).

$^1$H NMR (300 MHz, DMSO-$d_6$) δ 1.37 (3H, d, J=6.4 Hz), 4.79-4.91 (1H, m), 5.22 (1H, d, J=4.1 Hz), 7.35 (1H, dd, J=8.4, 1.6 Hz), 7.43 (1H, dd, J=5.5, 0.6 Hz), 7.73 (1H, d, J=5.5 Hz), 7.81-7.86 (1H, m), 7.92 (1H, d, J=8.5 Hz).

C) N-(1-(1-benzothiophen-5-yl)ethyl)acetamide

To a mixture of 1-(1-benzothiophen-5-yl)ethanol (500 mg) and acetonitrile (10 ml) was added concentrated sulfuric acid (0.299 ml). The reaction mixture was stirred at room temperature for 1.5 hr, saturated aqueous sodium hydrogen carbonate solution was added and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (493 mg).

$^1$H NMR (300 MHz, DMSO-$d_6$) δ 1.39 (3H, d, J=7.1 Hz), 1.84 (3H, s), 4.95-5.08 (1H, m), 7.32 (1H, dd, J=8.4, 1.7 Hz), 7.43 (1H, dd, J=5.4, 0.6 Hz), 7.75 (1H, d, J=5.4 Hz), 7.77-7.80 (1H, m), 7.93 (1H, d, J=8.3 Hz), 8.34 (1H, d, J=7.8 Hz).

D) N-(1-(2-(4-(3-(cyclopropylmethoxy)phenoxy)phenyl)-1-benzothiophen-5-yl)ethyl)acetamide A mixture of N-(1-(1-benzothiophen-5-yl)ethyl)acetamide (200 mg), 1-(4-bromophenoxy)-3-(cyclopropylmethoxy)benzene (582 mg), palladium acetate (102 mg), tri(tert-butylphosphonium)tetrafluoroborate (265 mg), lithium tert-butoxide (365 mg) and N,N-dimethylacetamide (10 ml) was stirred under a nitrogen atmosphere at 120° C. overnight. To the reaction mixture were added water and ethyl acetate, and the mixture was filtered through celite and the filtrate was extracted with ethyl acetate. The obtained organic layer was washed with water and saturated brine, dried over anhydrous magnesium sulfate, and concentrated under reduced pressure. The obtained residue was successively purified by silica gel column chromatography (hexane/ethyl acetate), silica gel column chromatography (NH, hexane/ethyl acetate) and HPLC (acetonitrile/water, 0.1% TFA added), and crystallized from diisopropyl ether to give the title compound (36 mg).

$^1$H NMR (300 MHz, DMSO-$d_6$) δ 0.27-0.35 (2H, m), 0.51-0.60 (2H, m), 1.12-1.28 (1H, m), 1.40 (3H, d, J=7.0 Hz), 1.85 (3H, s), 3.80 (2H, d, J=7.0 Hz), 4.94-5.07 (1H, m), 6.58-6.66 (2H, m), 6.75 (1H, ddd, J=8.3, 2.2, 0.8 Hz), 7.07-7.14 (2H, m), 7.26-7.34 (2H, m), 7.70-7.75 (1H, m), 7.75-7.82 (3H, m), 7.89 (1H, d, J=8.3 Hz), 8.36 (1H, d, J=7.9 Hz).

Example 74

N-(1-(2-(6-(3-(((1S)-2,2-difluorocyclopropyl)methoxy)phenoxy)pyridin-3-yl)-1,3-benzoxazol-6-yl)ethyl)acetamide A) methyl 6-(3-(benzyloxy)phenoxy)nicotinate To a mixture of 3-(cyclopropylmethoxy)phenol (2.451 g), methyl 6-chloronicotinate (2 g) and DMF (50 ml) was added potassium carbonate (3.22 g), and the mixture was stirred at 100° C. for 5 hr. The reaction mixture was cooled and extracted with water and ethyl acetate. The obtained organic layer was washed with saturated brine, dried over anhydrous magnesium sulfate, and concentrated under reduced pressure. The obtained residue was successively purified by silica gel column chromatography (hexane/ethyl acetate) and silica gel column chromatography (NH, hexane/ethyl acetate) to give the title compound (2.78 g).

$^1$H NMR (300 MHz, DMSO-$d_6$) δ 3.86 (3H, s), 5.10 (2H, s), 6.70-6.81 (1H, m), 6.82-6.99 (2H, m), 7.10 (1H, d, J=8.7 Hz), 7.20-7.59 (6H, m), 8.30 (1H, dd, J=8.7, 2.5 Hz), 8.59-8.80 (1H, m).

B) 6-(3-(benzyloxy)phenoxy)nicotinic acid

To a mixture of methyl 6-(3-(benzyloxy)phenoxy)nicotinate (2 g), THF (20 ml) and methanol (20 ml) was added 2 M aqueous sodium hydroxide solution (5.96 ml), and the mixture was stirred at room temperature for 2 hr. The reaction mixture was acidified with 2N hydrochloric acid. The obtained solid was collected by filtration, and washed with water to give the title compound (1.9 g).

$^1$H NMR (300 MHz, DMSO-$d_6$) δ 5.10 (2H, s), 6.76 (1H, dd, J=7.9, 1.8 Hz), 6.82-6.98 (2H, m), 7.08 (1H, d, J=8.6 Hz), 7.26-7.55 (6H, m), 8.28 (1H, dd, J=8.6, 2.5 Hz), 8.68 (1H, d, J=2.1 Hz), 13.21 (1H, brs).

C) 2-ethylhexyl 3-((4-acetyl-2-nitrophenyl)sulfanyl)propanoate

A mixture of 1-(4-fluoro-3-nitrophenyl)ethanone (2.5 g), 2-ethylhexyl 3-sulfanylpropanoate (3.09 ml), potassium carbonate (2.83 g) and DMF (30 ml) was stirred at room temperature for 2 hr. To the reaction mixture was added water, and the mixture was extracted with ethyl acetate. The obtained organic layer was washed with water and saturated brine, dried over anhydrous magnesium sulfate, and concentrated under reduced pressure. The obtained residue was purified by silica gel column chromatography (hexane/ethyl acetate) to give the title compound (5.2 g).

$^1$H NMR (300 MHz, DMSO-$d_6$) δ 0.69-0.91 (6H, m), 1.07-1.36 (8H, m), 1.39-1.67 (1H, m), 2.64 (3H, s), 2.77 (2H, t, J=6.8 Hz), 3.37 (2H, t, J=6.8 Hz), 3.97 (2H, d, J=5.8 Hz), 7.81 (1H, d, J=8.6 Hz), 8.20 (1H, dd, J=8.6, 2.0 Hz), 8.64 (1H, d, J=2.0 Hz).

D) 2-ethylhexyl 3-((4-acetyl-2-aminophenyl)sulfanyl)propanoate

To a mixture of 2-ethylhexyl 3-((4-acetyl-2-nitrophenyl)sulfanyl)propanoate (1 g), iron (586 mg) and ethanol (25 ml) was added a mixture of ammonium chloride (1.542 g) and water (25 ml) at 100° C. The reaction mixture was stirred with heating under reflux for 30 min. The reaction mixture was cooled to room temperature, filtered through celite, and the filtrate was concentrated under reduced pressure. To the obtained residue was added saturated aqueous sodium hydrogen carbonate solution, and the mixture was extracted with ethyl acetate. The obtained organic layer was washed with water and saturated brine, dried over anhydrous magnesium sulfate, and concentrated under reduced pressure to give the title compound (920 mg).

MS (ESI+): [M+H]$^+$ 352.0.

E) 2-ethylhexyl 3-((4-acetyl-2-(((6-(3-(benzyloxy)phenoxy)pyridin-3-yl)carbonyl)amino)phenyl)sulfanyl)propanoate To a mixture of 6-(3-(benzyloxy)phenoxy)nicotinic acid (900 mg), thionyl chloride (0.955 ml) and THF (10 ml) was added DMF (3 drops). The reaction mixture was stirred at 60° C. for 30 min. The reaction mixture was cooled to room temperature, and concentrated under reduced pressure. The obtained residue was dissolved in THF (10 ml), and 2-ethylhexyl 3-((4-acetyl-2-aminophenyl)sulfanyl)propanoate (0.92 g) and triethylamine (0.73 ml) were added. The reaction mixture was stirred at room temperature for 30 min. To the reaction mixture was added saturated aqueous sodium hydrogen carbonate solution, and the mixture was extracted with ethyl acetate. The obtained organic layer was washed with water and saturated brine, dried over anhydrous magnesium sulfate, and concentrated under reduced pressure. The obtained residue was purified by silica gel column chromatography (hexane/ethyl acetate) to give the title compound (1.42 g).

$^1$H NMR (300 MHz, DMSO-$d_6$) δ 0.56-0.94 (6H, m), 1.06-1.30 (8H, m), 1.36-1.64 (1H, m), 2.57 (3H, s), 2.62-2.72 (2H, m), 3.23 (2H, t, J=6.8 Hz), 3.92 (2H, d, J=4.9 Hz), 5.11 (2H, s), 6.69-6.81 (1H, m), 6.83-6.89 (1H, m), 6.89-6.98 (1H, m), 7.15 (1H, d, J=8.9 Hz), 7.25-7.50 (6H, m), 7.58 (1H, d, J=8.3 Hz), 7.80-7.97 (2H, m), 8.21-8.49 (1H, m), 8.75 (1H, d, J=2.2 Hz), 10.17 (1H, s).

F) 1-(2-(6-(3-(benzyloxy)phenoxy)pyridin-3-yl)-1,3-benzothiazol-5-yl)ethanone

To a mixture of 2-ethylhexyl 3-((4-acetyl-2-(((6-(3-(benzyloxy)phenoxy)pyridin-3-yl)carbonyl)amino)phenyl)sulfanyl)propanoate (1.15 g) and THF (15 ml) was added sodium methoxide (28% methanol solution, 0.753 ml). The reaction mixture was stirred at room temperature for 30 min, and TFA (2.03 ml) was added under ice-cooling. The reaction mixture was stirred at 60° C. for 20 min. The reaction mixture was cooled to room temperature, saturated aqueous sodium hydrogen carbonate solution was added under ice-cooling, and the mixture was extracted with ethyl acetate. The obtained organic layer was washed with water and saturated brine, passed through a silica gel short column (hexane/ethyl acetate), and concentrated under reduced pressure. To the obtained residue was added a mixture of diisopropyl ether and hexane, and the obtained solid was collected by filtration to give the title compound (680 mg).

$^{1}$H NMR (300 MHz, DMSO-d$_6$) δ 2.71 (3H, s), 5.12 (2H, s), 6.76-6.85 (1H, m), 6.87-7.00 (2H, m), 7.14-7.26 (1H, m), 7.29-7.56 (6H, m), 8.01 (1H, dd, J=8.5, 1.7 Hz), 8.31 (1H, d, J=8.5 Hz), 8.53 (1H, dd, J=8.7, 2.5 Hz), 8.65 (1H, d, J=1.2 Hz), 8.80-9.00 (1H, m).

G) 1-(2-(6-(3-(benzyloxy)phenoxy)pyridin-3-yl)-1,3-benzothiazol-5-yl)ethanamine To a mixture of 1-(2-(6-(3-(benzyloxy)phenoxy)pyridin-3-yl)-1,3-benzothiazol-5-yl)ethanone (600 mg), ammonium acetate (3.066 g), methanol (10 ml) and THF (10 ml) was added sodium cyanoborohydride (170 mg), and the mixture was stirred with heating under reflux for 3 hr. The reaction mixture was cooled, saturated aqueous sodium hydrogen carbonate solution was added, and the mixture was extracted with ethyl acetate. The obtained organic layer was washed with water and saturated brine, dried over anhydrous magnesium sulfate, and concentrated under reduced pressure to give the title compound (603 mg).

MS (ESI+): [M+H]$^+$ 454.0.

H) N-(1-(2-(6-(3-(benzyloxy)phenoxy)pyridin-3-yl)-1,3-benzothiazol-5-yl)ethyl)acetamide To a mixture of 1-(2-(6-(3-(benzyloxy)phenoxy)pyridin-3-yl)-1,3-benzothiazol-5-yl)ethanamine (600 mg), triethylamine (0.553 ml) and THF (10 ml) was added acetic anhydride (0.25 ml), and the mixture was stirred at room temperature for 1 hr. To the reaction mixture was added saturated aqueous sodium hydrogen carbonate solution, and the mixture was extracted with ethyl acetate. The obtained organic layer was washed with water and saturated brine, dried over anhydrous magnesium sulfate, and concentrated under reduced pressure. The obtained residue was purified by silica gel column chromatography (hexane/ethyl acetate) to give the title compound (425 mg).

$^{1}$H NMR (300 MHz, DMSO-d$_6$) δ 1.41 (3H, d, J=7.0 Hz), 1.87 (3H, s), 4.97-5.09 (1H, m), 5.12 (2H, s), 6.73-6.85 (1H, m), 6.86-6.99 (2H, m), 7.20 (1H, d, J=8.7 Hz), 7.29-7.53 (7H, m), 7.98 (1H, d, J=1.5 Hz), 8.09 (1H, d, J=8.3 Hz), 8.33-8.45 (1H, m), 8.49 (1H, dd, J=8.7, 2.5 Hz), 8.86 (1H, d, J=2.0 Hz).

I) N-(1-(2-(6-(3-(((1S)-2,2-difluorocyclopropyl)methoxy)phenoxy)pyridin-3-yl)-1,3-benzothiazol-5-yl)ethyl)acetamide A mixture of N-(1-(2-(6-(3-(benzyloxy)phenoxy)pyridin-3-yl)-1,3-benzothiazol-5-yl)ethyl)acetamide (91 mg), methoxybenzene (0.06 ml) and TFA (2 ml) was stirred at 55° C. for 30 min. The reaction mixture was cooled to room temperature, and concentrated under reduced pressure. To the obtained residue were added ((1S)-2,2-difluorocyclopropyl)methyl 4-nitrobenzenesulfonate (144 mg), potassium carbonate (152 mg) and DMF (3 ml). The reaction mixture was stirred at 50° C. overnight. The reaction mixture was cooled to room temperature, saturated aqueous sodium hydrogen carbonate solution was added, and the mixture was extracted with ethyl acetate. The obtained organic layer was washed with water and saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (28.6 mg).

$^{1}$H NMR (300 MHz, DMSO-d$_6$) δ 1.30-1.57 (4H, m), 1.59-1.81 (1H, m), 1.87 (3H, s), 2.06-2.37 (1H, m), 3.84-4.06 (1H, m), 4.07-4.30 (1H, m), 4.91-5.19 (1H, m), 6.75-6.98 (3H, m), 7.21 (1H, d, J=8.5 Hz), 7.31-7.49 (2H, m), 7.91-8.01 (1H, m), 8.08 (1H, d, J=8.3 Hz), 8.40 (1H, d, J=8.1 Hz), 8.49 (1H, dd, J=8.6, 2.5 Hz), 8.86 (1H, d, J=2.5 Hz).

Example 75

N-(1-(2-(6-(3-(cyclopropylmethoxy)phenoxy)pyridin-3-yl)-1,3-benzothiazol-5-yl)ethyl)acetamide A mixture of N-(1-(2-(6-(3-(benzyloxy)phenoxy)pyridin-3-yl)-1,3-benzothiazol-5-yl)ethyl)acetamide (100 mg), (methylsulfanyl)benzene (0.237 ml) and TFA (2 ml) was stirred at 55° C. for 30 min. The reaction mixture was cooled to room temperature, and concentrated under reduced pressure. To the obtained residue were added (bromomethyl)cyclopropane (0.039 ml), potassium carbonate (152 mg) and DMF (3 ml). The reaction mixture was stirred at 50° C. overnight. The reaction mixture was cooled to room temperature, saturated aqueous sodium hydrogen carbonate solution was added, and the mixture was extracted with ethyl acetate. The obtained organic layer was washed with water and saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (38.4 mg).

$^{1}$H NMR (300 MHz, DMSO-d$_6$) δ 0.21-0.40 (2H, m), 0.46-0.67 (2H, m), 1.07-1.32 (1H, m), 1.41 (3H, d, J=7.0 Hz), 1.87 (3H, s), 3.82 (2H, d, J=7.0 Hz), 4.87-5.19 (1H, m), 6.70-6.93 (3H, m), 7.19 (1H, d, J=8.6 Hz), 7.34 (1H, t, J=8.1 Hz), 7.42 (1H, dd, J=8.4, 1.6 Hz), 7.98 (1H, s), 8.08 (1H, d, J=8.3 Hz), 8.41 (1H, d, J=8.0 Hz), 8.49 (1H, dd, J=8.7, 2.5 Hz), 8.86 (1H, d, J=2.5 Hz).

Example 76

N-(1-(2-(5-(3-(((S)-2,2-difluorocyclopropyl)methoxy)phenoxy)pyridin-2-yl)-1,3-benzoxazol-6-yl)ethyl)acetamide A mixture of N-(1-(2-(5-(3-hydroxyphenoxy)pyridin-2-yl)-1,3-benzoxazol-6-yl)ethyl)acetamide (100 mg), ((1S)-2,2-difluorocyclopropyl)methyl 4-nitrobenzenesulfonate (377 mg), potassium carbonate (177 mg) and DMF (1 ml) was stirred at 80° C. for 4 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (30 mg).

$^{1}$H NMR (300 MHz, DMSO-d$_6$) δ 1.41 (3H, d, J=7.0 Hz), 1.44-1.53 (1H, m), 1.64-1.78 (1H, m), 1.86 (3H, s), 2.12-2.32 (1H, m), 3.93-4.05 (1H, m), 4.12-4.24 (1H, m), 4.99-5.12 (1H, m), 6.76-6.82 (1H, m), 6.83-6.92 (2H, m), 7.33-7.44 (2H, m), 7.58 (1H, dd, J=8.8, 2.8 Hz), 7.70-7.81 (2H, m), 8.33 (1H, d, J=9.3 Hz), 8.41 (1H, d, J=7.9 Hz), 8.57 (1H, d, J=2.4 Hz).

Example 79

N-(1-(2-(4-((6-(cyclopropylmethoxy)pyridin-2-yl) oxy)phenyl)-1,3-benzoxazol-6-yl)ethyl)acetamide

A) N-(1-(4-amino-3-hydroxyphenyl)ethyl)acetamide hydrochloride

To a mixture of tert-butyl (4-(1-acetamidoethyl)-2-hydroxyphenyl)carbamate (2 g) and dioxane (100 ml) was added saturated hydrogen chloride-dioxane solution (50 ml) under ice-cooling. The reaction mixture was stirred at room temperature for 16 hr. The reaction mixture was concentrated under reduced pressure to give the title compound (1.4 g).

$^1$H NMR (400 MHz, DMSO-$d_6$) δ 1.29 (3H, d, J=7.0 Hz), 1.83 (3H, s), 4.79 (1H, m), 6.81 (1H, dd, J=1.3, 6.8 Hz), 6.92 (1H, d, J=1.3 Hz), 7.24 (1H, d, J=8.1 Hz), 8.32 (1H, d, J=7.8 Hz), 9.80 (2H, brs), 10.63 (1H, s).

B) N-(4-(1-acetamidoethyl)-2-hydroxyphenyl)-4-(benzyloxy)benzamide

To a mixture of N-(1-(4-amino-3-hydroxyphenyl)ethyl) acetamide hydrochloride (500 mg), 4-(benzyloxy)benzoic acid (588 mg) and dichloroethane (10 ml) was added N,N-diisopropylethylamine (2.24 ml). The reaction mixture was stirred at room temperature for 15 min, HATU (1 g) was added, and the mixture was stirred at room temperature for 15 min. To the reaction mixture was added water, and the mixture was extracted with ethyl acetate. The obtained organic layer was washed successively with water and saturated brine, dried over sodium sulfate, and concentrated under reduced pressure. The obtained residue was purified by silica gel column chromatography (dichloromethane/methanol) to give the title compound (400 mg).

MS (ESI+): [M+H]$^+$ 405.4.

C) N-(1-(2-(4-(benzyloxy)phenyl)-1,3-benzoxazol-6-yl)ethyl)acetamide

To a mixture of N-(4-(1-acetamidoethyl)-2-hydroxyphenyl)-4-(benzyloxy)benzamide (120 mg), hexachloroethane (175.7 mg), triphenylphosphine (195 mg) and acetonitrile (2 ml) was added triethylamine (0.124 ml). The reaction mixture was stirred with heating under reflux for 4 hr. The reaction mixture was concentrated under reduced pressure, and the obtained residue was purified by silica gel column chromatography (dichloromethane/methanol) to give the title compound (80 mg).

MS (ESI+): [M+H]$^+$ 387.0.

D) N-(1-(2-(4-hydroxyphenyl)-1,3-benzoxazol-6-yl)ethyl)acetamide

To a mixture of N-(1-(2-(4-(benzyloxy)phenyl)-1,3-benzoxazol-6-yl)ethyl)acetamide (80 mg) and methanol (10 ml) was added 10% palladium carbon (8 mg), and the mixture was stirred under a hydrogen atmosphere at room temperature for 4 hr. The reaction mixture was filtered through celite, and concentrated under reduced pressure to give the title compound (25 mg).

MS (ESI+): [M+H]$^+$ 297.2.

E) N-(1-(2-(4-((6-(cyclopropylmethoxy)pyridin-2-yl)oxy)phenyl)-1,3-benzoxazol-6-yl)ethyl) acetamide To a mixture of N-(1-(2-(4-hydroxyphenyl)-1,3-benzoxazol-6-yl)ethyl)acetamide (60 mg), 2-chloro-6-(cyclopropylmethoxy)pyridine (93.3 mg) and DMF (2 ml) was added cesium carbonate (132 mg), and the mixture was stirred at 110° C. for 12 hr. The reaction mixture was cooled to room temperature, and insoluble materials were removed by filtration. The obtained organic layer was concentrated under reduced pressure. A similar reaction was performed again, and the mixed residue was purified by HPLC (acetonitrile/water, 0.1% TFA added) to give the title compound (15 mg).

$^1$H NMR (400 MHz, CD$_3$OD) δ 0.03-0.22 (2H, m), 0.43-0.49 (2H, m), 1.15-1.27 (1H, m), 1.50 (3H, d, J=7.0 Hz), 1.94 (1H, s), 1.97 (3H, s), 3.90 (2H, d, J=7.1 Hz), 5.10-5.19 (1H, m), 6.53 (2H, dd, J=7.7, 10.8 Hz), 7.29 (2H, d, J=8.7 Hz), 7.38 (1H, dd, J=1.2, 8.2 Hz), 7.63-7.72 (3H, m), 8.24 (2H, d, J=8.7 Hz).

Example 80

N-(1-(2-(6-(3-(((1S)-2,2-difluorocyclopropyl) methoxy)phenoxy)pyridin-3-yl)-1,3-benzoxazol-6-yl)ethyl) acetamide

A) methyl 2-(6-(3-(benzyloxy)phenoxy)pyridin-3-yl)-1,3-benzoxazole-6-carboxylate A mixture of methyl 2-(6-chloropyridin-3-yl)-1,3-benzoxazole-6-carboxylate (650 mg), 3-(benzyloxy)phenol (496 mg), potassium carbonate (622 mg) and DMF (35 ml) was stirred at 115° C. for 18 hr. To the reaction mixture was added saturated aqueous sodium hydrogen carbonate solution, and the mixture was extracted with ethyl acetate. The obtained organic layer was washed with saturated brine, dried over anhydrous magnesium sulfate, and concentrated under reduced pressure. The obtained residue was passed through a silica gel short column (NH, hexane/ethyl acetate), and concentrated under reduced pressure. To the obtained residue were added diisopropyl ether and ethyl acetate, and the obtained solid was collected by filtration to give the title compound (560 mg).

$^1$H NMR (300 MHz, CDCl$_3$) δ 3.97 (3H, s), 5.08 (2H, s), 6.76-6.85 (2H, m), 6.90 (1H, ddd, J=8.4, 2.4, 0.8 Hz), 7.05 (1H, dd, J=8.7, 0.6 Hz), 7.29-7.48 (6H, m), 7.78 (1H, dd, J=8.4, 0.6 Hz), 8.11 (1H, dd, J=8.4, 1.5 Hz), 8.22-8.33 (1H, m), 8.51 (1H, dd, J=8.7, 2.4 Hz), 9.08 (1H, dd, J=2.5, 0.6 Hz).

B) (2-(6-(3-(benzyloxy)phenoxy)pyridin-3-yl)-1,3-benzoxazol-6-yl)methanol

To a mixture of lithium aluminum hydride (33.6 mg) and THF (20 ml) was added methyl 2-(6-(3-(benzyloxy)phenoxy)pyridin-3-yl)-1,3-benzoxazole-6-carboxylate (200 mg) under ice-cooling. The reaction mixture was stirred at 0° C. for 1 hr and water, ethyl acetate and 1N aqueous sodium hydroxide solution were successively added. The obtained mixture was filtered through celite, and the organic layer was partitioned. The obtained organic layer was dried over anhydrous magnesium sulfate, and concentrated under reduced pressure to give the title compound (125 mg).

$^1$H NMR (300 MHz, CDCl$_3$) δ 1.83 (1H, brs), 4.85 (2H, brs), 5.07 (2H, s), 6.74-6.94 (3H, m), 7.03 (1H, d, J=8.6 Hz), 7.29-7.50 (7H, m), 7.64 (1H, s), 7.73 (1H, d, J=8.2 Hz), 8.49 (1H, dd, J=8.6, 1.9 Hz), 9.05 (1H, d, J=1.9 Hz).

C) 2-(6-(3-(benzyloxy)phenoxy)pyridin-3-yl)-1,3-benzoxazole-6-carbaldehyde

A mixture of (2-(6-(3-(benzyloxy)phenoxy)pyridin-3-yl)-1,3-benzoxazol-6-yl)methanol (245 mg), tetrapropylammonium perruthenate (10 mg), 4-methylmorpholine 4-oxide (101 mg), molecular sieves 4A (125 mg) and acetonitrile (35 ml) was stirred at room temperature for 18 hr. To the reaction mixture was added ethyl acetate, and the mixture was filtered through celite. The filtrate was concentrated, and the obtained residue was purified by silica gel column chromatography (hexane/ethyl acetate) to give the title compound (210 mg).
$^1$H NMR (300 MHz, CDCl$_3$) δ 5.08 (2H, s), 6.77-6.86 (2H, m), 6.87-6.95 (1H, m), 7.07 (1H, d, J=8.7 Hz), 7.30-7.51 (6H, m), 7.83-7.98 (2H, m), 8.12 (1H, s), 8.53 (1H, dd, J=8.7, 2.4 Hz), 9.10 (1H, d, J=1.8 Hz), 10.11 (1H, s).

D) 6-(1-azidoethyl)-2-(6-(3-(benzyloxy)phenoxy) pyridin-3-yl)-1,3-benzoxazole

To a mixture of 2-(6-(3-(benzyloxy)phenoxy)pyridin-3-yl)-1,3-benzoxazole-6-carbaldehyde (210 mg) and THF (35 ml) was added methylmagnesium bromide (1.0 M THF solution, 1.49 ml) under ice-cooling. The reaction mixture was stirred at 0° C. for 3 hr, 1N hydrochloric acid was added and the mixture was extracted with ethyl acetate. The obtained organic layer was dried over anhydrous magnesium sulfate, and concentrated under reduced pressure. To the obtained residue were added toluene (35 ml), diphenylphosphoryl azide (0.216 ml) and DBU (0.226 ml). The reaction mixture was stirred at room temperature for 2 hr, and then at 65° C. for 1 hr. Water was added and the mixture was extracted with ethyl acetate. The obtained organic layer was dried over anhydrous magnesium sulfate, and concentrated under reduced pressure. The obtained residue was purified by silica gel column chromatography (hexane/ethyl acetate) to give the title compound (228 mg).
MS (ESI+): [M+H]$^+$ 464.2.

E) N-(1-(2-(6-(3-hydroxyphenoxy)pyridin-3-yl)-1,3-benzoxazol-6-yl)ethyl)acetamide A mixture of 6-(1-azidoethyl)-2-(6-(3-(benzyloxy)phenoxy)pyridin-3-yl)-1,3-benzoxazole (228 mg), 10% palladium carbon (containing water (50%), 80 mg) and ethyl acetate (30 ml) was stirred under a hydrogen atmosphere at room temperature for 18 hr. To the reaction mixture was added methanol, and the mixture was filtered through celite. The filtrate was concentrated under reduced pressure, and to the obtained residue were added THF (35 ml), triethylamine (0.341 ml) and acetic anhydride (0.139 ml). The reaction mixture was stirred at room temperature for 3 hr, 1N aqueous sodium hydroxide solution was added, and the mixture was stirred at room temperature for 1 hr. To the reaction mixture was added 1N hydrochloric acid, and the mixture was extracted with ethyl acetate. The obtained organic layer was dried over anhydrous magnesium sulfate, and concentrated under reduced pressure. The obtained residue was purified by silica gel column chromatography (hexane/ethyl acetate) to give the title compound (162.7 mg).
MS (ESI+): [M+H]$^+$ 390.2.

F) N-(1-(2-(6-(3-(((1S)-2,2-difluorocyclopropyl) methoxy)phenoxy)pyridin-3-yl)-1,3-benzoxazol-6-yl)ethyl)acetamide A mixture of N-(1-(2-(6-(3-hydroxyphenoxy)pyridin-3-yl)-1,3-benzoxazol-6-yl)ethyl)acetamide (162 mg), ((1S)-2,2-difluorocyclopropyl)methyl 4-nitrobenzenesulfonate (244 mg), potassium carbonate (172 mg) and DMF (35 ml) was stirred at 115° C. for 2 hr. To the reaction mixture were further added ((1S)-2,2-difluorocyclopropyl)methyl 4-nitrobenzenesulfonate (400 mg) and potassium carbonate (288 mg), and the mixture was stirred at 115° C. for 5 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate), and crystallized from diisopropyl ether/THF to give the title compound (32 mg).
$^1$H NMR (300 MHz, DMSO-d$_6$) δ 1.29-1.56 (4H, m), 1.63-1.81 (1H, m), 1.86 (3H, s), 2.13-2.31 (1H, m), 3.92-4.05 (1H, m), 4.11-4.23 (1H, m), 4.98-5.12 (1H, m), 6.78-6.92 (3H, m), 7.24 (1H, d, J=9.1 Hz), 7.32-7.42 (2H, m), 7.67-7.78 (2H, m), 8.39 (1H, d, J=8.0 Hz), 8.55 (1H, dd, J=8.7, 2.5 Hz), 8.94 (1H, d, J=2.1 Hz).

Example 82

N-(1-(2-(4-((4-(cyclopropylmethoxy)pyridin-2-yl) oxy)phenyl)-1,3-benzoxazol-6-yl)ethyl)acetamide A mixture of N-(1-(2-(4-hydroxyphenyl)-1,3-benzoxazol-6-yl)ethyl)acetamide (80 mg), 2-chloro-4-(cyclopropylmethoxy)pyridine (123.8 mg), cesium carbonate (220 mg) and DMF (2 ml) was stirred at 110° C. for 12 hr. The reaction mixture was cooled to room temperature, filtered, and concentrated under reduced pressure. A similar reaction was performed again, and the mixed residue was purified by HPLC (acetonitrile/water, 0.05% TFA added) to give the title compound (10 mg).
$^1$H NMR (400 MHz, CD$_3$OD) δ 0.36-0.38 (2H, m), 0.61-0.64 (2H, m), 1.25-1.27 (1H, m), 1.50 (3H, d, J=7.0 Hz), 1.97 (3H, s), 3.92 (2H, d, J=7.0 Hz), 5.12-5.14 (1H, m), 6.56 (1H, d, J=2.1 Hz), 6.76 (1H, dd, J=2.1, 5.9 Hz), 7.25-7.28 (2H, m), 7.34-7.39 (1H, m), 7.62-7.67 (2H, m), 7.96 (1H, d, J=5.9 Hz), 8.00-8.06 (1H, m), 8.25 (2H, d, J=8.7 Hz).

Example 84

N-(1-(2-(5-(4-(cyclopropylmethoxy)phenoxy)-1-methyl-1H-pyrazol-3-yl)-1,3-benzoxazol-6-yl)ethyl) acetamide A) methyl 5-(4-((tert-butyl(dimethyl)silyl)oxy)phenoxy)-1-methyl-1H-pyrazole-3-carboxylate A mixture of methyl 5-hydroxy-1-methyl-1H-pyrazole-3-carboxylate (2.68 g), (4-((tert-butyl(dimethyl)silyl)oxy)phenyl)boronic acid (4.33 g), copper(II) acetate (4.69 g), triethylamine (3.90 ml), molecular sieves 4A (5.5 g) and dichloromethane (60 ml) was stirred at room temperature for 15 hr. The reaction mixture was filtered, and the filtrate was concentrated under reduced pressure. The obtained residue was purified by silica gel column chromatography (petroleum ether/ethyl acetate) to give the title compound (600 mg).
$^1$H NMR (400 MHz, CDCl$_3$) δ 0.20 (6H, s), 0.99 (9H, s), 3.83 (3H, s), 3.89 (3H, s), 6.03 (1H, s), 6.75-6.86 (2H, m), 6.95-7.05 (2H, m).

B) 5-(4-hydroxyphenoxy)-1-methyl-1H-pyrazole-3-carboxylic acid

To a mixture of methyl 5-(4-((tert-butyl(dimethyl)silyl) oxy)phenoxy)-1-methyl-1H-pyrazole-3-carboxylate (600 mg) and THF (15 ml) was added a mixture of sodium hydroxide (480 mg) and water (30 ml). The reaction mixture was stirred at room temperature for 2 hr. The reaction mixture was adjusted to pH=4-5 with 1N hydrochloric acid and extracted with ethyl acetate. The obtained organic layer was dried over anhydrous sodium sulfate, and concentrated under reduced pressure to give the title compound (388 mg).

$^1$H NMR (400 MHz, DMSO-d$_6$) δ 3.74 (3H, s), 5.85 (1H, s), 6.79 (2H, d, J=8.8 Hz), 7.04 (2H, d, J=8.8 Hz), 9.49 (1H, brs), 12.66 (1H, brs).

C) N-(4-(1-acetamidoethyl)-2-hydroxyphenyl)-5-(4-hydroxyphenoxy)-1-methyl-1H-pyrazole-3-carboxamide A mixture of 5-(4-hydroxyphenoxy)-1-methyl-1H-pyrazole-3-carboxylic acid (388 mg), N-(1-(4-amino-3-hydroxyphenyl)ethyl)acetamide hydrochloride (459 mg), WSCD (640 mg) and pyridine (10 ml) was stirred at room temperature for 12 hr. The reaction mixture was concentrated under reduced pressure, water was added to the obtained residue and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate/methanol) to give the title compound (370 mg).

$^1$H NMR (400 MHz, DMSO-d$_6$) δ 1.30 (3H, d, J=7.2 Hz), 1.82 (3H, s), 3.80 (3H, s), 4.70-4.85 (1H, m), 5.93 (1H, s), 6.69-6.85 (4H, m), 7.00-7.13 (2H, m), 8.07 (1H, d, J=8.4 Hz), 8.22 (1H, d, J=7.6 Hz), 9.20 (1H, brs), 9.53 (1H, brs), 10.14 (1H, brs).

D) N-(1-(2-(5-(4-hydroxyphenoxy)-1-methyl-1H-pyrazol-3-yl)-1,3-benzoxazol-6-yl)ethyl)acetamide To a mixture of N-(4-(1-acetamidoethyl)-2-hydroxyphenyl)-5-(4-hydroxyphenoxy)-1-methyl-1H-pyrazole-3-carboxamide (320 mg) and TFA (2 ml) was added acetic acid (2 ml), and the mixture was stirred under microwave radiation at 100° C. for 45 min. The reaction mixture was concentrated under reduced pressure, saturated aqueous sodium hydrogen carbonate solution was added, and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate) to give the title compound (180 mg).

MS (ESI+): [M+H]$^+$ 392.9.

E) N-(1-(2-(5-(4-(cyclopropylmethoxy)phenoxy)-1-methyl-1H-pyrazol-3-yl)-1,3-benzoxazol-6-yl)ethyl)acetamide A mixture of N-(1-(2-(5-(4-hydroxyphenoxy)-1-methyl-1H-pyrazol-3-yl)-1,3-benzoxazol-6-yl)ethyl)acetamide (180 mg), (bromomethyl)cyclopropane (60 mg), cesium carbonate (120 mg) and DMF (2 ml) was stirred at room temperature for 15 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% TFA added) to give the title compound (50 mg).

$^1$H NMR (400 MHz, DMSO-d$_6$) δ 0.24-0.36 (2H, m), 0.50-0.63 (2H, m), 1.12-1.30 (1H, m), 1.38 (3H, d, J=7.2 Hz), 1.85 (3H, s), 3.75-3.85 (5H, m), 4.91-5.08 (1H, m), 6.18 (1H, s), 6.94-7.06 (2H, m), 7.15-7.27 (2H, m), 7.30-7.40 (1H, m), 7.60-7.72 (2H, m), 8.40 (1H, d, J=8.0 Hz).

Example 86

N-(1-(2-(4-(3-(cyclopropylmethoxy)phenoxy)phenyl)pyrazolo[1,5-a]pyridin-6-yl)ethyl)acetamide

A) 2-(5-bromopyridin-2-yl)-1-(4-(3-(cyclopropylmethoxy)phenoxy)phenyl)-N-hydroxyethanimine To a mixture of ethyl 4-(3-(cyclopropylmethoxy)phenoxy)benzoate (3.34 g), 5-bromo-2-methylpyridine (1.84 g) and THF (40 ml) was added lithium bis(trimethylsilyl)amide (1.0 M THF solution, 21.4 ml) under a nitrogen atmosphere under ice-cooling over 0.5 hr. The reaction mixture was stirred at 30° C. for 16 hr. To the reaction mixture was added water, and the mixture was extracted with methyl tert-butyl ether. The obtained organic layer was washed with saturated aqueous ammonium chloride solution and saturated brine, dried over anhydrous sodium sulfate, and concentrated under reduced pressure. To the obtained residue were added methanol (40 ml), hydroxylamine hydrochloride (2.36 g) and 10% aqueous sodium hydroxide solution (13.6 ml). The reaction mixture was stirred with heating under reflux for 16 hr, and concentrated under reduced pressure. To the obtained residue was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (1.4 g).

$^1$H NMR (400 MHz, DMSO-d$_6$) δ 0.26-0.36 (2H, m), 0.51-0.62 (2H, m), 1.15-1.30 (1H, m), 3.78 (2H, d, J=7.2 Hz), 4.23 (2H, s), 6.51-6.58 (2H, m), 6.72 (1H, dd, J=8.4, 2.4 Hz), 6.97 (2H, d, J=8.8 Hz), 7.21-7.32 (2H, m), 7.71 (2H, d, J=8.8 Hz), 7.95 (1H, dd, J=8.4, 2.4 Hz), 8.57 (1H, d, J=2.4 Hz), 11.46 (1H, brs).

B) 6-bromo-2-(4-(3-(cyclopropylmethoxy)phenoxy)phenyl)pyrazolo[1,5-a]pyridine To a mixture of 2-(5-bromopyridin-2-yl)-1-(4-(3-(cyclopropylmethoxy)phenoxy)phenyl)-N-hydroxyethanimine (1.2 g) and 1,2-dimethoxyethane (12 ml) was added under ice-cooling trifluoroacetic anhydride (1.11 g). The reaction mixture was stirred at room temperature for 7 hr. To the reaction mixture was added triethylamine (535 mg) under ice-cooling, and the mixture was stirred at room temperature for 10 min. Iron(II) chloride (34 mg) was added and the mixture was stirred at 70° C. for 16 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (210 mg).

$^1$H NMR (400 MHz, DMSO-d$_6$) δ 0.26-0.37 (2H, m), 0.52-0.61 (2H, m), 1.14-1.27 (1H, m), 3.80 (2H, d, J=6.8 Hz), 6.55-6.64 (2H, m), 6.71-6.80 (1H, m), 7.05-7.15 (3H, m), 7.27-7.42 (2H, m), 7.68 (1H, d, J=9.6 Hz), 7.99 (2H, d, J=8.8 Hz), 9.08 (1H, s).

C) 1-(2-(4-(3-(cyclopropylmethoxy)phenoxy)phenyl)pyrazolo[1,5-a]pyridin-6-yl)ethanone A mixture of 6-bromo-2-(4-(3-(cyclopropylmethoxy)phenoxy)phenyl)pyrazolo[1,5-a]pyridine (210 mg), tributyl(1-ethoxyvinyl)tin (192 mg), bis(triphenylphosphine)dichloropalladium (7 mg) and DMF (5 ml) was stirred under a nitrogen atmosphere at 70° C. for 16 hr. To the reaction mixture was added 2N potassium fluoride aqueous solution (10 ml), and the mixture was stirred at room temperature for 1 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (120 mg).
$^1$H NMR (400 MHz, CDCl$_3$) δ 0.32-0.41 (2H, m), 0.62-0.71 (2H, m), 1.22-1.33 (1H, m), 2.65 (3H, s), 3.80 (2H, d, J=6.8 Hz), 6.62-6.74 (3H, m), 6.84 (1H, s), 7.14 (2H, d, J=8.8 Hz), 7.23-7.31 (1H, m), 7.54 (1H, d, J=9.2 Hz), 7.69 (1H, dd, J=9.2, 1.6 Hz), 7.96 (2H, d, J=8.8 Hz), 9.14 (1H, s).

D) 1-(2-(4-(3-(cyclopropylmethoxy)phenoxy)phenyl)pyrazolo[1,5-a]pyridin-6-yl)ethanol To a mixture of 1-(2-(4-(3-(cyclopropylmethoxy)phenoxy)phenyl)pyrazolo[1,5-a]pyridin-6-yl)ethanone (130 mg), methanol (4 ml) and THF (4 ml) was added sodium borohydride (19 mg) under ice-cooling. The reaction mixture was stirred at room temperature for 1 hr. The reaction mixture was neutralized with 1N hydrochloric acid and extracted with ethyl acetate. The obtained organic layer was washed with saturated brine, dried over anhydrous sodium sulfate, and concentrated under reduced pressure to give the title compound (125 mg)
$^1$H NMR (400 MHz, DMSO-d$_6$) δ 0.25-0.35 (2H, m), 0.49-0.61 (2H, m), 1.21-1.28 (1H, m), 1.40 (3H, d, J=6.4 Hz), 3.80 (2H, d, J=6.8 Hz), 4.70-4.86 (1H, m), 5.37 (1H, d, J=4.4 Hz), 6.55-6.67 (2H, m), 6.69-6.78 (1H, m), 6.98 (1H, s), 7.10 (2H, d, J=8.8 Hz), 7.22-7.37 (2H, m), 7.64 (1H, d, J=9.2 Hz), 7.98 (2H, d, J=8.4 Hz), 8.54 (1H, s).

E) N-(1-(2-(4-(3-(cyclopropylmethoxy)phenoxy)phenyl)pyrazolo[1,5-a]pyridin-6-yl)ethyl)acetamide To a mixture of 1-(2-(4-(3-(cyclopropylmethoxy)phenoxy)phenyl)pyrazolo[1,5-a]pyridin-6-yl)ethanol (125 mg), triethylamine (95 mg) and dichloromethane (8 ml) was added methanesulfonyl chloride (71 mg) under ice-cooling. The reaction mixture was stirred at room temperature for 2 hr. To the reaction mixture was added water, and the mixture was extracted with dichloromethane. The obtained organic layer was washed with saturated brine, dried over anhydrous sodium sulfate, and concentrated under reduced pressure. To the obtained residue were added DMF (8 ml) and sodium azide (101 mg), and the mixture was stirred at room temperature for 2 hr. To the reaction mixture was added water, and the mixture was extracted with ethyl acetate. The obtained organic layer was washed with saturated brine, dried over anhydrous sodium sulfate, and concentrated under reduced pressure. To the obtained residue were added triphenylphosphine (164 mg), water (2 ml) and THF (8 ml), and the mixture was stirred with heating under reflux for 24 hr. To the reaction mixture was added acetic anhydride (64 mg) under ice-cooling, and the mixture was stirred at 0° C. for 1 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% ammonium carbonate added) to give the title compound (50 mg).
$^1$H NMR (400 MHz, DMSO-d$_6$) δ 0.25-0.35 (2H, m), 0.51-0.60 (2H, m), 1.15-1.25 (1H, m), 1.40 (3H, d, J=6.8 Hz), 1.86 (3H, s), 3.80 (2H, d, J=7.2 Hz), 4.84-4.97 (1H, m), 6.58-6.65 (2H, m), 6.70-6.78 (1H, m), 6.98 (1H, s), 7.09 (2H, d, J=8.8 Hz), 7.20 (1H, dd, J=9.2, 1.2 Hz), 7.29 (1H, t, J=8.0 Hz), 7.64 (1H, d, J=9.2 Hz), 7.98 (2H, d, J=8.8 Hz), 8.36 (1H, d, J=8.0 Hz), 8.52 (1H, s).

Example 90

N-(1-(2-(4-(3-(cyclopropylmethoxy)phenoxy)phenyl)-7-fluoro-1,3-benzoxazol-6-yl)ethyl)acetamide A) 7-fluoro-1,3-benzoxazol-2(3H)-one To a mixture of 6-amino-2-fluorophenol (16.1 g) and THF (100 ml) were added carbonyldiimidazole (41.1 g) and triethylamine (25.7 g). The reaction mixture was stirred at room temperature for 15 hr. The reaction mixture was added to water, and the mixture was extracted with ethyl acetate. The obtained organic layer was washed with saturated brine, dried over anhydrous sodium sulfate, and concentrated under reduced pressure to give the title compound (16.9 g).
$^1$H NMR (400 MHz, DMSO-d$_6$) δ 6.90-7.00 (1H, m), 7.01-7.05 (1H, m), 7.09-7.18 (1H, m), 11.96 (1H, brs).

B) 6-bromo-7-fluoro-1,3-benzoxazol-2(3H)-one

A mixture of 7-fluoro-1,3-benzoxazol-2(3H)-one (4.26 g), N-bromosuccinimide (4.95 g) and DMF (50 ml) was stirred at room temperature for 1 hr. To the reaction mixture were added saturated aqueous sodium hydrogen carbonate solution and ethyl acetate. The obtained mixture was neutralized with 1N hydrochloric acid, and the mixture was extracted with ethyl acetate. The obtained organic layer was washed with saturated aqueous ammonium chloride solution, dried over anhydrous magnesium sulfate, and concentrated under reduced pressure. The obtained residue was purified by silica gel column chromatography (petroleum ether/ethyl acetate) to give the title compound (3.58 g).
$^1$H NMR (400 MHz, DMSO-d$_6$) δ 6.92 (1H, d, J=8.4 Hz), 7.43 (1H, dd, J=8.4, 6.4 Hz), 12.13 (1H, brs).

C) 6-amino-3-bromo-2-fluorophenol

A mixture of 6-bromo-7-fluoro-1,3-benzoxazol-2(3H)-one (3.58 g), sodium hydroxide (9.24 g) and water (80 ml) was stirred at 100° C. for 6 hr. The reaction mixture was neutralized with 6N hydrochloric acid, and the obtained solid was collected by filtration to give the title compound (2.63 g)
$^1$H NMR (400 MHz, DMSO-d$_6$) δ 5.03 (2H, brs), 6.39 (1H, dd, J=8.8, 1.6 Hz), 6.78 (1H, dd, J=8.4, 7.2 Hz), 9.38 (1H, brs).

D) N-(4-bromo-3-fluoro-2-hydroxyphenyl)-4-fluorobenzamide

A mixture of 6-amino-3-bromo-2-fluorophenol (2.63 g), 4-fluorobenzoic acid (2.17 g), WSCD (2.97 g) and pyridine (30 ml) was stirred at room temperature for 7 hr. To the reaction mixture was added water, and the mixture was extracted with ethyl acetate. The obtained organic layer was washed with saturated brine, dried over anhydrous sodium sulfate, and concentrated under reduced pressure. To the obtained residue were added potassium carbonate (5.31 g) and methanol (100 ml), and the mixture was stirred at room temperature for 1 hr. The reaction mixture was concentrated under reduced pressure, to the obtained residue was added water and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (1.79 g).

$^1$H NMR (400 MHz, DMSO-$d_6$) δ 7.14 (1H, dd, J=8.8, 7.2 Hz), 7.32-7.43 (3H, m), 8.06 (2H, dd, J=9.2, 5.6 Hz), 9.87 (1H, brs), 10.35 (1H, brs).

E) 6-bromo-7-fluoro-2-(4-fluorophenyl)-1,3-benzoxazole

A mixture of N-(4-bromo-3-fluoro-2-hydroxyphenyl)-4-fluorobenzamide (1.79 g), TFA (6 ml) and acetic acid (6 ml) was stirred under microwave radiation at 135° C. for 40 min. To the reaction mixture was added saturated aqueous sodium carbonate solution, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (1.42 g).

$^1$H NMR (400 MHz, DMSO-$d_6$) δ 7.40-7.58 (2H, m), 7.65 (1H, d, J=8.8 Hz), 7.69-7.75 (1H, m), 8.29 (2H, dd, J=8.8, 5.2 Hz).

F) 6-bromo-2-(4-(3-(cyclopropylmethoxy)phenoxy) phenyl)-7-fluoro-1,3-benzoxazole A mixture of 6-bromo-7-fluoro-2-(4-fluorophenyl)-1,3-benzoxazole (1.42 g), 3-(cyclopropylmethoxy)phenol (751 mg), potassium carbonate (950 mg) and DMF (15 ml) was stirred under microwave radiation at 135° C. for 3 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% ammonium carbonate added) to give the title compound (750 mg).

$^1$H NMR (400 MHz, DMSO-$d_6$) δ 0.25-0.35 (2H, m), 0.50-0.60 (2H, m), 1.15-1.25 (1H, m), 3.82 (2H, d, J=7.2 Hz), 6.66-6.74 (2H, m), 6.80-6.85 (1H, m), 7.18 (2H, dd, J=7.2, 2.4 Hz), 7.35 (1H, t, J=8.0 Hz), 7.60 (1H, d, J=8.8 Hz), 7.68 (1H, dd, J=8.4, 6.0 Hz), 8.20 (2H, d, J=8.8 Hz).

G) 1-(2-(4-(3-(cyclopropylmethoxy)phenoxy)phenyl)-7-fluoro-1,3-benzoxazol-6-yl)ethanone A mixture of 6-bromo-2-(4-(3-(cyclopropylmethoxy)phenoxy)phenyl)-7-fluoro-1,3-benzoxazole (750 mg), tributyl (1-ethoxyvinyl)tin (715 mg), bis(triphenylphosphine)dichloropalladium (23 mg) and DMF (10 ml) was stirred under a nitrogen atmosphere at 70° C. for 15 hr. To the reaction mixture was added 2N potassium fluoride aqueous solution (50 ml), and the obtained mixture was stirred at room temperature for 2 hr. The reaction mixture was added to water, and the mixture was extracted with ethyl acetate. The obtained organic layer was washed with saturated brine, dried over anhydrous sodium sulfate, and concentrated under reduced pressure. To the obtained residue were added 1N hydrochloric acid and acetone, and the mixture was stirred at room temperature for 2 hr. To the reaction mixture was added water, and the mixture was neutralized with 6N aqueous sodium hydroxide solution and extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (620 mg).

$^1$H NMR (400 MHz, DMSO-$d_6$) δ 0.20-0.35 (2H, m), 0.45-0.60 (2H, m), 1.15-1.25 (1H, m), 2.64 (3H, d, J=4.0 Hz), 3.79 (2H, d, J=6.8 Hz), 6.64-6.72 (2H, m), 6.79-6.83 (1H, m), 7.17 (2H, d, J=8.8 Hz), 7.31 (1H, t, J=8.0 Hz), 7.67 (1H, d, J=8.4 Hz), 7.80-7.90 (1H, m), 8.22 (2H, d, J=8.8 Hz).

H) N-(1-(2-(4-(3-(cyclopropylmethoxy)phenoxy) phenyl)-7-fluoro-1, 3-benzoxazol-6-yl)ethyl) acetamide A mixture of 1-(2-(4-(3-(cyclopropylmethoxy)phenoxy) phenyl)-7-fluoro-1,3-benzoxazol-6-yl)ethanone (300 mg), ammonium acetate (554 mg), sodium cyanoborohydride (90 mg) and methanol (10 ml) was stirred with heating under reflux for 24 hr. The reaction mixture was added to water, and the mixture was extracted with ethyl acetate. The obtained organic layer was washed with saturated brine, dried over anhydrous sodium sulfate, and concentrated under reduced pressure. To the obtained residue was added THF (10 ml), and acetic anhydride (147 mg) was added under ice-cooling. The reaction mixture was stirred at 0° C. for 1 hr. The reaction mixture was added to water, and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% ammonium carbonate added) to give the title compound (127 mg).

$^1$H NMR (400 MHz, DMSO-$d_6$) δ 0.25-0.35 (2H, m), 0.52-0.62 (2H, m), 1.15-1.25 (1H, m), 1.41 (3H, d, J=7.2 Hz), 1.85 (3H, s), 3.83 (2H, d, J=7.2 Hz), 5.72-5.82 (1H, m), 6.68-6.73 (2H, m), 6.83 (1H, dd, J=8.0, 1.6 Hz), 7.19 (2H, d, J=8.8 Hz), 7.32-7.45 (2H, m), 7.61 (1H, d, J=8.4 Hz), 8.21 (2H, d, J=8.8 Hz), 8.49 (1H, d, J=7.6 Hz).

Example 93

N-(1-(2-(4-(3-(cyclopropylmethoxy)phenoxy)phenyl)-7-methyl-1,3-benzoxazol-6-yl)ethyl)acetamide A) 6-bromo-7-methyl-1,3-benzoxazol-2(3H)-one A mixture of 7-methyl-1,3-benzoxazol-2(3H)-one (7.56 g), N-bromosuccinimide (8.97 g) and THF (90 ml) was stirred at room temperature for 2 hr. To the reaction mixture were added water and ethyl acetate, and the obtained solid was collected by filtration. The obtained solid was washed with petroleum ether to give the title compound (7 g).

$^1$H NMR (400 MHz, DMSO-$d_6$) δ 2.31 (3H, s), 6.89 (1H, dd, J=8.0, 0.4 Hz), 7.36 (1H, d, J=8.0 Hz), 11.74 (1H, brs).

B) 6-amino-3-bromo-2-methylphenol

A mixture of 6-bromo-7-methyl-1,3-benzoxazol-2(3H)-one (9.9 g), sodium hydroxide (8.68 g) and water (100 ml)

was stirred with heating under reflux for 27 hr. The mixture was further stirred with heating under reflux for 15 hr. The reaction mixture was neutralized with 2N hydrochloric acid, and extracted with ethyl acetate. The obtained organic layer was washed with saturated brine, dried over anhydrous sodium sulfate, and concentrated under reduced pressure to give the title compound (6.64 g).

$^1$H NMR (400 MHz, DMSO-$d_6$) δ 2.18 (3H, s), 4.80 (2H, brs), 6.43 (1H, d, J=8.8 Hz), 6.80 (1H, d, J=8.4 Hz).

* A peak of one proton was not observed.

C) N-(4-bromo-2-hydroxy-3-methylphenyl)-4-fluorobenzamide

A mixture of 6-amino-3-bromo-2-methylphenol (530 mg), 4-fluorobenzoic acid (433 mg), WSCD (985 mg) and pyridine (10 ml) was stirred at room temperature for 2 hr. To the reaction mixture was added water, and the mixture was extracted with ethyl acetate. The obtained organic layer was washed with saturated brine, dried over anhydrous sodium sulfate, and concentrated under reduced pressure. To the obtained residue were added potassium carbonate (500 mg) and methanol (10 ml), and the mixture was stirred at room temperature for 0.5 hr. The reaction mixture was concentrated under reduced pressure. To the obtained residue was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (460 mg).

$^1$H NMR (400 MHz, DMSO-$d_6$) δ 2.29 (3H, s), 7.12 (1H, d, J=8.8 Hz), 7.23 (1H, d, J=8.4 Hz), 7.30-7.43 (2H, m), 8.08 (2H, dd, J=8.8, 5.2 Hz), 9.43 (1H, brs), 9.99 (1H, brs).

D) 6-bromo-2-(4-fluorophenyl)-7-methyl-1,3-benzoxazole

A mixture of N-(4-bromo-2-hydroxy-3-methylphenyl)-4-fluorobenzamide (460 mg), TFA (2 ml) and acetic acid (2 ml) was stirred under microwave radiation at 135° C. for 40 min. The reaction mixture was concentrated under reduced pressure, saturated aqueous sodium hydrogen carbonate solution was added, and the mixture was extracted with ethyl acetate. The obtained organic layer was washed with saturated brine, dried over anhydrous sodium sulfate, and concentrated under reduced pressure to give the title compound (434 mg).

$^1$H NMR (400 MHz, CDCl$_3$) δ 2.62 (3H, s), 7.15-7.28 (2H, m), 7.45 (1H, dd, J=8.4, 0.4 Hz), 7.52 (1H, d, J=8.4 Hz), 8.15-8.30 (2H, m).

E) 6-bromo-2-(4-(3-(cyclopropylmethoxy)phenoxy)phenyl)-7-methyl-1,3-benzoxazole A mixture of 6-bromo-2-(4-fluorophenyl)-7-methyl-1,3-benzoxazole (434 mg), 3-(cyclopropylmethoxy)phenol (279 mg), potassium carbonate (294 mg) and DMF (5 ml) was stirred under microwave radiation at 135° C. for 11 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (550 mg).

$^1$H NMR (400 MHz, DMSO-$d_6$) δ 0.22-0.38 (2H, m), 0.48-0.62 (2H, m), 1.10-1.28 (1H, m), 2.57 (3H, s), 3.81 (2H, d, J=6.8 Hz), 6.61-6.73 (2H, m), 6.75-6.89 (1H, m), 7.18 (2H, d, J=8.8 Hz), 7.34 (1H, t, J=8.0 Hz), 7.50-7.65 (2H, m), 8.21 (2H, d, J=8.8 Hz).

F) 1-(2-(4-(3-(cyclopropylmethoxy)phenoxy)phenyl)-7-methyl-1,3-benzoxazol-6-yl)ethanone A mixture of 6-bromo-2-(4-(3-(cyclopropylmethoxy)phenoxy)phenyl)-7-methyl-1,3-benzoxazole (550 mg), tributyl (1-ethoxyvinyl)tin (485 mg), bis(triphenylphosphine)dichloropalladium (17 mg) and DMF (5 ml) was stirred at 70° C. for 2 hr. To the reaction mixture was added saturated potassium fluoride aqueous solution (20 ml), and the mixture was stirred at room temperature for 1 hr. The reaction mixture was extracted with ethyl acetate. The obtained organic layer was washed with saturated brine, dried over anhydrous sodium sulfate, and concentrated under reduced pressure. To the obtained residue were added acetone (10 ml) and 1N hydrochloric acid (15 ml), and the mixture was stirred at room temperature for 1 hr. The reaction mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (430 mg).

$^1$H NMR (400 MHz, CDCl$_3$) δ 0.25-0.40 (2H, m), 0.57-0.70 (2H, m), 1.20-1.32 (1H, m), 2.67 (3H, s), 2.80 (3H, s), 3.79 (2H, d, J=7.2 Hz), 6.60-6.71 (2H, m), 6.75 (1H, dd, J=8.4, 1.6 Hz), 7.13 (2H, d, J=8.4 Hz), 7.20-7.33 (1H, m), 7.60 (1H, d, J=8.4 Hz), 7.80 (1H, d, J=8.4 Hz), 8.24 (2H, d, J=8.8 Hz).

G) N-(1-(2-(4-(3-(cyclopropylmethoxy)phenoxy)phenyl)-7-methyl-1,3-benzoxazol-6-yl)ethyl)acetamide A mixture of 1-(2-(4-(3-(cyclopropylmethoxy)phenoxy)phenyl)-7-methyl-1,3-benzoxazol-6-yl)ethanone (430 mg), ammonium acetate (1.15 g) and methanol (15 ml) was stirred with heating under reflux for 0.5 hr. To the reaction mixture was added sodium cyanoborohydride (131 mg), and the mixture was stirred with heating under reflux for 12 hr. The reaction mixture was concentrated under reduced pressure. To the obtained residue was added water, and the mixture was extracted with ethyl acetate. The obtained organic layer was washed with saturated brine, dried over anhydrous sodium sulfate, and concentrated under reduced pressure. To the obtained residue were added THF (20 ml) and acetic anhydride (204 mg), and the mixture was stirred at room temperature for 2 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% ammonium carbonate added) to give the title compound (52 mg).

$^1$H NMR (400 MHz, DMSO-$d_6$) δ 0.23-0.35 (2H, m), 0.49-0.61 (2H, m), 1.11-1.29 (1H, m), 1.36 (3H, d, J=7.2 Hz), 1.82 (3H, s), 2.55 (3H, s), 3.82 (2H, d, J=6.8 Hz), 5.10-5.25 (1H, m), 6.63-6.73 (2H, m), 6.81 (1H, dd, J=8.0, 1.6 Hz), 7.18 (2H, d, J=8.8 Hz), 7.31-7.43 (2H, m), 7.58 (1H, d, J=8.0 Hz), 8.21 (2H, d, J=8.8 Hz), 8.42 (1H, d, J=7.6 Hz).

Example 95

N-(1-(2-(4-(3-(cyclopropylmethoxy)phenoxy)phenyl)-4,5,6,7-tetrahydro-1,3-benzoxazol-6-yl)ethyl)acetamide

A) ethyl 3-bromo-4-oxocyclohexanecarboxylate

A mixture of ethyl 4-oxocyclohexanecarboxylate (10 g), N-bromosuccinimide (10.5 g), 4-methylbenzenesulfonic acid (1.01 g) and toluene (100 ml) was stirred with heating under reflux for 2 hr. The reaction mixture was concentrated under reduced pressure. To the obtained residue was added saturated aqueous sodium hydrogen carbonate solution, and the mixture was extracted with ethyl acetate. The obtained organic layer was washed with saturated brine, dried over anhydrous sodium sulfate, and concentrated under reduced pressure to give the title compound (14.9 g).

$^1$H NMR (400 MHz, CDCl$_3$) δ 1.27-1.32 (3H, m), 1.90-2.01 (1H, m), 2.27-2.33 (1H, m), 2.43-2.51 (3H, m), 2.85-2.95 (1H, m), 3.15-3.25 (1H, m), 4.15-4.24 (2H, m), 4.43-4.52 (1H, m).

B) 4-(3-(cyclopropylmethoxy)phenoxy)benzamide

A mixture of ethyl 4-(3-(cyclopropylmethoxy)phenoxy)benzoate (2 g) and ammonia (8.0 M methanol solution, 20 ml) was stirred in a sealed tube reaction apparatus at 80° C. for 24 hr. The reaction mixture was concentrated under reduced pressure. The obtained residue was purified by silica gel column chromatography (petroleum ether/ethyl acetate) to give the title compound (390 mg).

$^1$H NMR (400 MHz, DMSO-d$_6$) δ 0.25-0.36 (2H, m), 0.50-0.60 (2H, m), 1.15-1.25 (1H, m), 3.80 (2H, d, J=7.2 Hz), 6.57-6.67 (2H, m), 6.77 (1H, dd, J=8.4, 1.6 Hz), 7.02 (2H, d, J=8.4 Hz), 7.27-7.37 (2H, m), 7.85-7.99 (3H, m).

C) ethyl 2-(4-(3-(cyclopropylmethoxy)phenoxy)phenyl)-4,5,6,7-tetrahydro-1,3-benzoxazole-6-carboxylate A mixture of 4-(3-(cyclopropylmethoxy)phenoxy)benzamide (800 mg), ethyl 3-bromo-4-oxocyclohexanecarboxylate (2.11 g) and 1,2-dichloroethane (15 ml) was stirred under microwave radiation at 120° C. for 4 hr. The reaction mixture was concentrated under reduced pressure. The obtained residue was purified by silica gel column chromatography (petroleum ether/ethyl acetate) to give the title compound (1.1 g).

MS (ESI+): [M+H]$^+$ 434.1.

D) (2-(4-(3-(cyclopropylmethoxy)phenoxy)phenyl)-4,5,6,7-tetrahydro-1,3-benzoxazol-6-yl)methanol To a mixture of ethyl 2-(4-(3-(cyclopropylmethoxy)phenoxy)phenyl)-4,5,6,7-tetrahydro-1,3-benzoxazole-6-carboxylate (1.1 g) and THF (20 ml) was added lithium aluminum hydride (289 mg) under ice-cooling. The reaction mixture was stirred at 0° C. for 1 hr, and water (5 ml) and 10% aqueous sodium hydroxide solution (50 ml) were added. Insoluble materials were removed by filtration, and the filtrate was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (670 mg).

$^1$H NMR (400 MHz, DMSO-d$_6$) δ 0.25-0.35 (2H, m), 0.50-0.60 (2H, m), 1.18-1.25 (1H, m), 1.40-1.55 (1H, m), 1.85-1.97 (2H, m), 2.33-2.45 (1H, m), 2.46-2.52 (2H, m), 2.70-2.81 (1H, m), 3.43 (2H, t, J=5.6 Hz), 3.80 (2H, d, J=6.8 Hz), 4.71 (1H, t, J=5.2 Hz), 6.60-6.70 (2H, m), 6.78 (1H, dd, J=8.0, 1.6 Hz), 7.08 (2H, d, J=8.8 Hz), 7.31 (1H, t, J=8.4 Hz), 7.91 (2H, d, J=8.8 Hz).

E) 2-(4-(3-(cyclopropylmethoxy)phenoxy)phenyl)-4,5,6,7-tetrahydro-1,3-benzoxazole-6-carbaldehyde A mixture of (2-(4-(3-(cyclopropylmethoxy)phenoxy)phenyl)-4,5,6,7-tetrahydro-1,3-benzoxazol-6-yl)methanol (670 mg), Dess-Martin periodinane (1.09 g) and dichloromethane (20 ml) was stirred at room temperature for 2 hr. The reaction mixture was neutralized with saturated aqueous sodium hydrogen carbonate solution, water was added and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (402 mg).

$^1$H NMR (400 MHz, CDCl$_3$) δ 0.26-0.39 (2H, m), 0.60-0.70 (2H, m), 1.20-1.30 (1H, m), 1.90-2.05 (1H, m), 2.23-2.36 (1H, m), 2.65-2.75 (2H, m), 2.80-2.93 (2H, m), 2.95-3.10 (1H, m), 3.77 (2H, d, J=6.8 Hz), 6.55-6.65 (2H, m), 6.70 (1H, dd, J=8.4, 2.4 Hz), 7.05 (2H, d, J=8.8 Hz), 7.20-7.30 (1H, m), 7.95 (2H, d, J=8.4 Hz), 9.80 (1H, s).

F) 1-(2-(4-(3-(cyclopropylmethoxy)phenoxy)phenyl)-4,5,6,7-tetrahydro-1,3-benzoxazol-6-yl)ethanol To a mixture of 2-(4-(3-(cyclopropylmethoxy)phenoxy)phenyl)-4,5,6,7-tetrahydro-1,3-benzoxazole-6-carbaldehyde (402 mg) and THF (10 ml) was added methylmagnesium bromide (3.0 M diethyl ether solution, 0.7 ml) under ice-cooling. The reaction mixture was stirred at 0° C. for 1 hr, water was added and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (290 mg).

$^1$H NMR (400 MHz, DMSO-d$_6$) δ 0.25-0.35 (2H, m), 0.50-0.60 (2H, m), 1.12-1.25 (4H, m), 1.30-1.60 (1H, m), 1.68-1.82 (1H, m), 1.83-2.18 (1H, m), 2.40-2.52 (3H, m), 2.65-2.80 (1H, m), 3.52-3.65 (1H, m), 3.81 (2H, d, J=7.2 Hz), 4.55-4.65 (1H, m), 6.55-6.70 (2H, m), 6.72-6.82 (1H, m), 7.08 (2H, d, J=8.8 Hz), 7.31 (1H, t, J=8.0 Hz), 7.91 (2H, d, J=8.8 Hz).

G) 6-(1-azidoethyl)-2-(4-(3-(cyclopropylmethoxy)phenoxy)phenyl)-4,5,6,7-tetrahydro-1,3-benzoxazole To a mixture of 1-(2-(4-(3-(cyclopropylmethoxy)phenoxy)phenyl)-4,5,6,7-tetrahydro-1,3-benzoxazol-6-yl)ethanol (190 mg), triethylamine (143 mg) and dichloromethane (10 ml) was added methanesulfonyl chloride (107 mg). The reaction mixture was stirred at room temperature for 1 hr, and concentrated under reduced pressure. To the obtained residue were added sodium azide (153 mg) and DMF (10 ml), and the mixture was stirred at 80° C. for 12 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (160 mg).

$^1$H NMR (400 MHz, CDCl$_3$) δ 0.27-0.38 (2H, m), 0.58-0.68 (2H, m), 1.18-1.32 (1H, m), 1.35-1.45 (3H, m), 1.50-1.75 (1H, m), 1.98-2.18 (2H, m), 2.45-2.90 (4H, m), 3.50-3.65 (1H, m), 3.77 (2H, d, J=6.8 Hz), 6.55-6.66 (2H, m), 6.67-6.75 (1H, m), 7.04 (2H, d, J=8.8 Hz), 7.20-7.30 (1H, m), 7.94 (2H, d, J=8.8 Hz).

H) N-(1-(2-(4-(3-(cyclopropylmethoxy)phenoxy)phenyl)-4,5,6,7-tetrahydro-1,3-benzoxazol-6-yl)ethyl)acetamide A mixture of 6-(1-azidoethyl)-2-(4-(3-(cyclopropylmethoxy)phenoxy)phenyl)-4,5,6,7-tetrahydro-1,3-benzoxazole (122 mg), triphenylphosphine (79 mg), water (1 ml) and THF (10 ml) was stirred with heating under reflux for 12 hr. To the reaction mixture was added acetic anhydride (38 mg) at room temperature, and the mixture was stirred at room temperature for 1 hr. To the reaction mixture was added water, and the mixture was extracted with ethyl acetate. The obtained organic layer was washed with saturated brine, dried over anhydrous sodium sulfate, and concentrated under reduced pressure. Further, a mixture of 6-(1-azidoethyl)-2-(4-(3-(cyclopropylmethoxy)phenoxy)phenyl)-4,5,6,7-tetrahydro-1,3-benzoxazole (160 mg), triphenylphosphine (117 mg), water (1 ml) and THF (10 ml) was stirred with heating under reflux for 12 hr. To the reaction mixture was added acetic anhydride (57 mg) at room temperature, and the mixture was stirred at room temperature for 1 hr. To the reaction mixture was added water, and the mixture was extracted with ethyl acetate. The obtained organic layer was washed with saturated brine, dried over anhydrous sodium sulfate, and concentrated under reduced pressure. The above-mentioned two residues were mixed and purified by HPLC (acetonitrile/water, 0.1% ammonium carbonate added) to give the title compound (116 mg).

$^1$H NMR (400 MHz, DMSO-d$_6$) δ 0.25-0.35 (2H, m), 0.51-0.62 (2H, m), 1.02-1.12 (3H, m), 1.15-1.27 (1H, m), 1.35-1.50 (1H, m), 1.83 (3H, s), 1.86-2.00 (2H, m), 2.35-2.49 (3H, m), 2.70-2.80 (1H, m), 3.80 (2H, d, J=6.8 Hz), 3.81-3.95 (1H, m), 6.60-6.68 (2H, m), 6.78 (1H, dd, J=8.0, 1.6 Hz), 7.08 (2H, d, J=8.4 Hz), 7.31 (1H, t, J=8.0 Hz), 7.80 (1H, d, J=8.4 Hz), 7.90 (2H, d, J=8.8 Hz).

Example 95a

N-(1-(2-(4-(3-(cyclopropylmethoxy)phenoxy)phenyl)-4,5,6,7-tetrahydro-1,3-benzoxazol-6-yl)ethyl)acetamide (optical isomer)

A racemate (70 mg) of N-(1-(2-(4-(3-(cyclopropylmethoxy)phenoxy)phenyl)-4,5,6,7-tetrahydro-1,3-benzoxazol-6-yl)ethyl)acetamide was fractionated by HPLC (column: CHIRALCEL OD (trade name), 50 mmID×500 mL, Daicel Corporation, mobile phase:hexane/ethanol=800/200 (v/v)) to give a compound having the shortest retention time as the title compound (8.7 mg).

retention time (AD) 5.202 min

Example 95b

N-(1-(2-(4-(3-(cyclopropylmethoxy)phenoxy)phenyl)-4,5,6,7-tetrahydro-1,3-benzoxazol-6-yl)ethyl)acetamide (optical isomer)

A racemate (70 mg) of N-(1-(2-(4-(3-(cyclopropylmethoxy)phenoxy)phenyl)-4,5,6,7-tetrahydro-1,3-benzoxazol-6-yl)ethyl)acetamide was fractionated by HPLC (column: CHIRALCEL OD (trade name), 50 mmID×500 mL, Daicel Corporation, mobile phase:hexane/ethanol=800/200 (v/v)) to give a compound having the second shortest retention time as the title compound (9.0 mg).

$^1$H NMR (300 MHz, DMSO-d$_6$) δ 0.23-0.37 (2H, m), 0.49-0.61 (2H, m), 1.09 (3H, d, J=6.7 Hz), 1.15-1.21 (1H, m), 1.47 (2H, d, J=7.9 Hz), 1.82 (3H, s), 1.86-1.99 (2H, m), 2.37-2.49 (2H, m), 2.67-2.80 (1H, m), 3.80 (2H, d, J=7.0 Hz), 3.84-3.97 (1H, m), 6.55-6.69 (2H, m), 6.72-6.82 (1H, m), 7.08 (2H, d, J=8.8 Hz), 7.31 (1H, t, J=8.1 Hz), 7.76 (1H, d, J=8.8 Hz), 7.90 (2H, d, J=8.8 Hz).

retention time (AD) 8.524 min

Example 95c

N-(1-(2-(4-(3-(cyclopropylmethoxy)phenoxy)phenyl)-4,5,6,7-tetrahydro-1,3-benzoxazol-6-yl)ethyl)acetamide (optical isomer)

A racemate (70 mg) of N-(1-(2-(4-(3-(cyclopropylmethoxy)phenoxy)phenyl)-4,5,6,7-tetrahydro-1,3-benzoxazol-6-yl)ethyl)acetamide was fractionated by HPLC (column: CHIRALCEL OD (trade name), 50 mmID×500 mL, Daicel Corporation, mobile phase:hexane/ethanol=800/200 (v/v)) to give a compound having the third shortest retention time as the title compound (15.3 mg).

retention time (AD) 12.291 min

Example 95d

N-(1-(2-(4-(3-(cyclopropylmethoxy)phenoxy)phenyl)-4,5,6,7-tetrahydro-1,3-benzoxazol-6-yl)ethyl)acetamide (optical isomer)

A racemate (70 mg) of N-(1-(2-(4-(3-25 (cyclopropylmethoxy)phenoxy)phenyl)-4,5,6,7-tetrahydro-1,3-benzoxazol-6-yl)ethyl)acetamide was fractionated by HPLC (column: CHIRALCEL OD (trade name), 50 mmID×500 mL, Daicel Corporation, mobile phase:hexane/ethanol=800/200 (v/v)) to give a compound having the longest retention time as the title compound (15.3 mg).

retention time (AD) 17.264 min

Example 96

N-(1-(2-(6-(3-(cyclopropylmethoxy)phenoxy)pyridazin-3-yl)-1,3-benzoxazol-6-yl)ethyl)acetamide A) 6-(3-(cyclopropylmethoxy)phenoxy)pyridazine-3-carboxylic acid To a mixture of 3-(cyclopropylmethoxy)phenol (328 mg) and DMF (6 ml) were added 6-chloropyridazine-3-carboxylic acid (317 mg) and cesium carbonate (1.30 g), and the mixture was stirred at 80° C. for 48 hr. Further, to a mixture of 3-(cyclopropylmethoxy)phenol (985 mg) and DMF (15 ml) were added 6-chloropyridazine-3-carboxylic acid (951 mg) and cesium carbonate (3.91 g), and the mixture was stirred at 80° C. for 15 hr. The above-mentioned two mixtures were each cooled to room temperature and mixed, water was added and the mixture was extracted with ethyl acetate. The obtained aqueous layer was acidified with 1N hydrochloric acid, and extracted with ethyl acetate. The obtained organic layer was washed with saturated brine, dried over anhydrous sodium sulfate, and concentrated under reduced pressure to give the title compound (1.6 g).

$^1$H NMR (400 MHz, DMSO-d$_6$) δ 0.25-0.35 (2H, m), 0.47-0.62 (2H, m), 1.13-1.30 (1H, m), 3.81 (2H, d, J=6.8 Hz), 6.76-6.94 (3H, m), 7.36 (1H, t, J=8.4 Hz), 7.50 (1H, d, J=9.2 Hz), 8.21 (1H, d, J=9.2 Hz).

B) N-(4-acetyl-2-hydroxyphenyl)-6-(3-(cyclopropylmethoxy)phenoxy)pyridazine-3-carboxamide To a mixture of 6-(3-(cyclopropylmethoxy)phenoxy)pyridazine-3-carboxylic acid (400 mg) and pyridine (10 ml) were added 1-(4-amino-3-hydroxyphenyl)ethanone (197 mg) and WSCD (374 mg), and the mixture was stirred at 15° C. for 1 hr. Further, to a mixture of 6-(3-(cyclopropylmethoxy)phenoxy)pyridazine-3-carboxylic acid (1.2 g) and pyridine (30 ml) were added 1-(4-amino-3-hydroxyphenyl)ethanone (591 mg) and WSCD (1.12 g), and the mixture was stirred at 15° C. for 1 hr. The above-mentioned two mixtures were mixed, water was added and the mixture was extracted with ethyl acetate. The obtained organic layer was dried over anhydrous sodium sulfate, and concentrated under reduced pressure. To the obtained residue were added methanol (30 ml) and potassium carbonate (2.4 g), and the mixture was stirred at 15° C. for 0.5 hr. The reaction mixture was concentrated, saturated aqueous sodium hydrogen carbonate solution was added, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (950 mg).

$^1$H NMR (400 MHz, DMSO-d$_6$) δ 0.25-0.39 (2H, m), 0.50-0.65 (2H, m), 1.10-1.30 (1H, m), 2.50 (3H, s), 3.83 (2H, d, J=6.8 Hz), 6.80-6.95 (3H, m), 7.38 (1H, t, J=8.8 Hz), 7.41-7.57 (1H, m), 7.58 (1H, d, J=8.4 Hz), 7.67 (1H, d, J=9.2 Hz), 8.39 (1H, d, J=8.8 Hz), 8.47 (1H, d, J=8.4 Hz), 10.49 (1H, brs), 10.92 (1H, brs).

C) 1-(2-(6-(3-(cyclopropylmethoxy)phenoxy)pyridazin-3-yl)-1,3-benzoxazol-6-yl)ethanone To a mixture of N-(4-acetyl-2-hydroxyphenyl)-6-(3-(cyclopropylmethoxy)phenoxy)pyridazine-3-carboxamide (200 mg) and THF (10 ml) were added triphenylphosphine (187 mg) and diisopropyl azodicarboxylate (114 mg), and the mixture was stirred under a nitrogen atmosphere with heating under reflux for 2 hr. Further, to a mixture of N-(4-acetyl-2-hydroxyphenyl)-6-(3-(cyclopropylmethoxy)phenoxy)pyridazine-3-carboxamide (750 mg) and THF (20 ml) were added triphenylphosphine (701 mg) and diisopropyl azodicarboxylate (540 mg), and the mixture was stirred under a nitrogen atmosphere with heating under reflux for 2 hr. The above-mentioned two mixtures were each cooled to room temperature and mixed, and concentrated under reduced pressure. To the obtained residue was added ethanol (20 ml) and the mixture was stirred at 15° C. for 5 min and filtered. The obtained solid was washed with petroleum ether to give the title compound (520 mg).

$^1$H NMR (400 MHz, DMSO-d$_6$) δ 0.23-0.45 (2H, m), 0.49-0.65 (2H, m), 1.12-1.30 (1H, m), 2.70 (3H, s), 3.84 (2H, d, J=7.2 Hz), 6.81-6.96 (3H, m), 7.40 (1H, t, J=8.4 Hz), 7.66 (1H, d, J=9.2 Hz), 8.02 (1H, d, J=8.4 Hz), 8.08 (1H, dd, J=8.8, 1.6 Hz), 8.51 (1H, d, J=1.2 Hz), 8.57 (1H, d, J=9.2 Hz).

D) N-(1-(2-(6-(3-(cyclopropylmethoxy)phenoxy)pyridazin-3-yl)-1,3-benzoxazol-6-yl)ethyl)acetamide To a mixture of 1-(2-(6-(3-(cyclopropylmethoxy)phenoxy)pyridazin-3-yl)-1,3-benzoxazol-6-yl)ethanone (300 mg) and methanol (20 ml) were added ammonium acetate (576 mg) and sodium cyanoborohydride (140 mg), and the mixture was stirred with heating under reflux for 2 hr. The reaction mixture was cooled to room temperature, acetic anhydride (152 mg) was added and the mixture was stirred at 15° C. for 0.5 hr. The reaction mixture was concentrated under reduced pressure, water was added to the obtained residue and the mixture was extracted with ethyl acetate. The obtained organic layer was washed with saturated brine, dried over anhydrous sodium sulfate, and concentrated under reduced pressure. The obtained residue was purified by silica gel column chromatography (ethyl acetate), and further purified by HPLC (acetonitrile/water, 0.1% ammonium carbonate added) to give the title compound (62 mg).

$^1$H NMR (400 MHz, DMSO-d$_6$) δ 0.25-0.35 (2H, m), 0.50-0.62 (2H, m), 1.15-1.30 (1H, m), 1.41 (3H, d, J=6.8 Hz), 1.86 (3H, s), 3.83 (2H, d, J=7.2 Hz), 4.98-5.14 (1H, m), 6.80-6.95 (3H, m), 7.33-7.46 (2H, m), 7.63 (1H, d, J=9.2 Hz), 7.80 (1H, s), 7.84 (1H, d, J=8.4 Hz), 8.72 (1H, d, J=7.6 Hz), 8.52 (1H, d, J=9.2 Hz).

Example 97

N-(1-(2-(6-(3-(cyclopropylmethoxy)phenoxy)-4-methylpyridin-3-yl)-1,3-benzoxazol-6-yl)ethyl)acetamide A) N-(4-acetyl-2-hydroxyphenyl)-2-chloro-4-methylpyridine-5-carboxamide A mixture of 1-(4-amino-3-hydroxyphenyl)ethanone (529 mg), 6-chloro-4-methylnicotinic acid (600 mg), HATU (1.60 g), triethylamine (1.42 g) and DMF (10 ml) was stirred at room temperature for 15 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (600 mg).

$^1$H NMR (400 MHz, DMSO-d$_6$) δ 2.42 (3H, s), 2.63 (3H, s), 6.16 (2H, brs), 6.80 (1H, d, J=8.4 Hz), 7.62-7.71 (3H, m), 9.08 (1H, s).

B) 1-(2-(6-chloro-4-methylpyridin-3-yl)-1,3-benzoxazol-6-yl)ethanone

A mixture of N-(4-acetyl-2-hydroxyphenyl)-2-chloro-4-methylpyridine-5-carboxamide (600 mg), triphenylphosphine (876 mg), diisopropyl azodicarboxylate (675 mg) and THF (15 ml) was stirred under a nitrogen atmosphere with heating under reflux for 3 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (320 mg).

$^1$H NMR (400 MHz, DMSO-d$_6$) δ 2.72 (3H, s), 2.87 (3H, s), 7.38 (1H, s), 7.87 (1H, d, J=8.0 Hz), 8.06 (1H, dd, J=8.0, 1.6 Hz), 8.26 (1H, s), 9.08 (1H, s).

C) 1-(2-(6-(3-(cyclopropylmethoxy)phenoxy)-4-methylpyridin-3-yl)-1,3-benzoxazol-6-yl)ethanone A mixture of 1-(2-(6-chloro-4-methylpyridin-3-yl)-1,3-benzoxazol-6-yl)ethanone (345 mg), 3-(cyclopropylmethoxy)phenol (197 mg), cesium carbonate (782 mg) and DMF (10 ml) was stirred at 80° C. for 15 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (120 mg).

$^1$H NMR (400 MHz, CDCl$_3$) δ 0.30-0.38 (2H, m), 0.62-0.69 (2H, m), 1.25-1.32 (1H, m), 2.71 (3H, s), 2.84 (3H, s), 3.82 (2H, d, J=6.8 Hz), 6.70-6.80 (2H, m), 6.80-6.85 (1H, m), 6.88 (1H, s), 7.34 (1H, t, J=8.0 Hz), 7.83 (1H, d, J=8.4 Hz), 8.00-8.05 (1H, m), 8.22 (1H, d, J=1.2 Hz), 9.03 (1H, s).

D) N-(1-(2-(6-(3-(cyclopropylmethoxy)phenoxy)-4-methylpyridin-3-yl)-1,3-benzoxazol-6-yl)ethyl)acetamide A mixture of 1-(2-(6-(3-(cyclopropylmethoxy)phenoxy)-4-methylpyridin-3-yl)-1,3-benzoxazol-6-yl)ethanone (120 mg), ammonium acetate (224 mg), sodium cyanoborohydride (36 mg) and methanol (10 ml) was stirred with heating under reflux for 15 hr. To the reaction mixture was added acetic anhydride (59 mg) and the mixture was stirred at 14° C. for 1 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% ammonium carbonate added) to give the title compound (52 mg).

$^1$H NMR (400 MHz, DMSO-d$_6$) δ 0.27-0.35 (2H, m), 0.51-0.59 (2H, m), 1.15-1.25 (1H, m), 1.39 (3H, d, J=7.2 Hz), 1.86 (3H, s), 2.76 (3H, s), 3.82 (2H, d, J=7.2 Hz), 5.00-5.10 (1H, m), 6.70-6.78 (2H, m), 6.82 (1H, d, J=7.6 Hz), 7.12 (1H, s), 7.30-7.39 (2H, m), 7.70 (1H, s), 7.76 (1H, d, J=8.0 Hz), 8.39 (1H, d, J=8.0 Hz), 8.83 (1H, s).

Example 98

1-(1-(2-(6-(3-(cyclopropylmethoxy)phenoxy)pyridin-3-yl)-1,3-benzoxazol-6-yl)ethyl)urea

A) N-(4-acetyl-2-hydroxyphenyl)-6-chloronicotinamide

To a mixture of 1-(4-amino-3-hydroxyphenyl)ethanone (2.9 g), triethylamine (4 ml) and THF (40 ml) was added 6-chloronicotinoyl chloride (3.38 g) under ice-cooling. The reaction mixture was stirred at room temperature overnight and extracted with water and ethyl acetate. The obtained organic layer was washed with saturated brine, dried over anhydrous magnesium sulfate, and concentrated under reduced pressure. To the obtained residue was added ethanol, and the obtained solid was collected by filtration to give the title compound (3.5 g).

$^1$H NMR (300 MHz, DMSO-d$_6$) δ 2.53 (3H, s), 7.43-7.55 (2H, m), 7.70 (1H, dd, J=8.4, 0.5 Hz), 7.94 (1H, d, J=8.2 Hz), 8.35 (1H, dd, J=8.3, 2.5 Hz), 8.94 (1H, d, J=2.0 Hz), 9.92-10.33 (2H, m).

B) 1-(2-(6-chloropyridin-3-yl)-1,3-benzoxazol-6-yl)ethanone

A mixture of N-(4-acetyl-2-hydroxyphenyl)-6-chloronicotinamide (3.5 g), triphenylphosphine (4.74 g), diisopropyl azodicarboxylate (40% toluene solution, 8.8 ml) and THF (40 ml) was stirred at 60° C. for 2 hr. The reaction mixture was cooled to room temperature, and concentrated under reduced pressure. To the obtained residue was added ethanol, and the obtained solid was collected by filtration to give the title compound (1.68 g).

$^1$H NMR (300 MHz, DMSO-d$_6$) δ 2.69 (3H, s), 7.78-7.87 (1H, m), 7.99 (1H, s), 8.03-8.13 (1H, m), 8.40-8.45 (1H, m), 8.61 (1H, dd, J=8.4, 2.5 Hz), 9.14-9.31 (1H, m).

C) 1-(2-(6-(3-(cyclopropylmethoxy)phenoxy)pyridin-3-yl)-1,3-benzoxazol-6-yl)ethanone A mixture of 1-(2-(6-chloropyridin-3-yl)-1,3-benzoxazol-6-yl)ethanone (25 g), 3-(cyclopropylmethoxy)phenol (16.63 g), cesium carbonate (45 g) and DMF (200 ml) was stirred at 100° C. for 4 hr. The reaction mixture was cooled to room temperature, water was added and the mixture was extracted with ethyl acetate. The obtained organic layer was washed with saturated brine, dried over anhydrous magnesium sulfate, and concentrated under reduced pressure. To the obtained residue was added ethanol, and the obtained solid was collected by filtration to give the title compound (28.3 g).

$^1$H NMR (300 MHz, DMSO-d$_6$) δ 0.26-0.36 (2H, m), 0.51-0.62 (2H, m), 1.14-1.28 (1H, m), 2.68 (3H, s), 3.83 (2H, d, J=7.0 Hz), 6.71-6.90 (3H, m), 7.26 (1H, d, J=8.7 Hz), 7.36 (1H, t, J=8.1 Hz), 7.92 (1H, d, J=8.3 Hz), 8.00-8.08 (1H, m), 8.40 (1H, d, J=1.1 Hz), 8.59 (1H, dd, J=8.7, 2.4 Hz), 9.00 (1H, d, J=2.4 Hz).

D) 1-(2-(6-(3-(cyclopropylmethoxy)phenoxy)pyridin-3-yl)-1,3-benzoxazol-6-yl)ethanol To a mixture of 1-(2-(6-(3-(cyclopropylmethoxy)phenoxy)pyridin-3-yl)-1,3-benzoxazol-6-yl)ethanone (28.3 g), THF (200 ml) and ethanol (200 ml) was added sodium borohydride (2.67 g) under ice-cooling. The reaction mixture was stirred at room temperature for 2 hr, 1N hydrochloric acid (100 ml) was added at 0° C., and the mixture was extracted with ethyl acetate. The obtained organic layer was washed with saturated brine, dried over anhydrous magnesium sulfate, and concentrated under reduced pressure. The obtained residue was passed through a short column (hexane/ethyl acetate) of NH silica gel column to give the title compound (28 g).

$^1$H NMR (300 MHz, DMSO-d$_6$) δ 0.27-0.37 (2H, m), 0.49-0.61 (2H, m), 1.20-1.29 (1H, m), 1.38 (3H, d, J=6.4 Hz), 3.82 (2H, d, J=7.0 Hz), 4.81-4.95 (1H, m), 5.35 (1H, d, J=4.2 Hz), 6.72-6.91 (3H, m), 7.22 (1H, dd, J=8.7, 0.7 Hz), 7.29-7.45 (2H, m), 7.67-7.78 (2H, m), 8.55 (1H, dd, J=8.7, 2.5 Hz), 8.94 (1H, dd, J=2.5, 0.7 Hz).

E) 6-(1-azidoethyl)-2-(6-(3-(cyclopropylmethoxy)phenoxy)pyridin-3-yl)-1,3-benzoxazole A mixture of 1-(2-(6-(3-(cyclopropylmethoxy)phenoxy)pyridin-3-yl)-1,3-benzoxazol-6-yl)ethanol (28 g), diphenylphosphoryl azide (25 g), DBU (20 ml) and toluene (200 ml) was stirred at room temperature for 2 hr. The reaction mixture was extracted with toluene and water. The obtained organic layer was washed with saturated brine, dried over anhydrous magnesium sulfate, and concentrated under reduced pressure. The obtained residue was purified by silica gel column chromatography (hexane/ethyl acetate) to give the title compound (21.06 g).

$^1$H NMR (300 MHz, DMSO-$d_6$) δ 0.27-0.35 (2H, m), 0.53-0.62 (2H, m), 1.20-1.29 (1H, m), 1.54 (3H, d, J=6.8 Hz), 3.82 (2H, d, J=7.1 Hz), 5.03 (1H, q, J=6.7 Hz), 6.73-6.89 (3H, m), 7.31-7.40 (1H, m), 7.42-7.51 (2H, m), 7.81-7.89 (2H, m), 8.56 (1H, dd, J=8.7, 2.5 Hz), 8.95 (1H, dd, J=2.5, 0.7 Hz).

F) tert-butyl (1-(2-(6-(3-(cyclopropylmethoxy)phenoxy)pyridin-3-yl)-1,3-benzoxazol-6-yl)ethyl)carbamate A mixture of 6-(1-azidoethyl)-2-(6-(3-(cyclopropylmethoxy)phenoxy)pyridin-3-yl)-1,3-benzoxazole (21 g), 10% palladium carbon (containing water (50%), 2.7 g) and THF (300 ml) was stirred under a hydrogen atmosphere at room temperature for 2 hr. The reaction mixture was filtered through celite, and concentrated under reduced pressure. The obtained residue was dissolved in THF (200 ml). To the obtained mixture were added di-tert-butyl dicarbonate (15 ml) and triethylamine (14 ml), and the mixture was stirred at room temperature for 2 hr. The reaction mixture was extracted with ethyl acetate and water. The obtained organic layer was washed with saturated brine, dried over anhydrous magnesium sulfate, and concentrated under reduced pressure. The obtained residue was crystallized from ethyl acetate/hexane to give the title compound (10.81 g).

$^1$H NMR (300 MHz, DMSO-$d_6$) δ 0.26-0.35 (2H, m), 0.51-0.61 (2H, m), 1.18-1.23 (1H, m), 1.26-1.42 (12H, m), 3.82 (2H, d, J=7.0 Hz), 4.67-4.84 (1H, m), 6.70-6.89 (3H, m), 7.22 (1H, dd, J=8.7, 0.7 Hz), 7.30-7.42 (2H, m), 7.51 (1H, d, J=7.7 Hz), 7.69 (1H, s), 7.74 (1H, d, J=8.2 Hz), 8.55 (1H, dd, J=8.7, 2.5 Hz), 8.94 (1H, dd, J=2.5, 0.7 Hz).

G) 1-(1-(2-(6-(3-(cyclopropylmethoxy)phenoxy)pyridin-3-yl)-1,3-benzoxazol-6-yl)ethyl)urea A mixture of tert-butyl (1-(2-(6-(3-(cyclopropylmethoxy)phenoxy)pyridin-3-yl)-1,3-benzoxazol-6-yl)ethyl)carbamate (27 g) and 4N hydrogen chloride-ethyl acetate solution (150 ml) was stirred at room temperature for 1 hr. The obtained solid was collected by filtration, and suspended in THF (200 ml). To the obtained mixture were added triethylamine (25 ml) and 4-nitrophenyl carbonochloridate (15 g) at 0° C. The reaction mixture was stirred at 0° C. for 1 hr and 28% aqueous ammonia (50 ml) was added. The mixture was stirred at room temperature for 30 min and extracted with ethyl acetate. The obtained organic layer was washed with saturated brine, and dried over anhydrous magnesium sulfate. The organic layer was passed through a NH silica gel short column (ethyl acetate), and concentrated under reduced pressure. To the obtained residue was added ethyl acetate/hexane, and the obtained solid was crystallized from ethanol/water to give the title compound (13.94 g).

$^1$H NMR (300 MHz, DMSO-$d_6$) δ 0.25-0.38 (2H, m), 0.50-0.62 (2H, m), 1.13-1.29 (1H, m), 1.37 (3H, d, J=7.0 Hz), 3.82 (2H, d, J=7.0 Hz), 4.85 (1H, quin, J=7.2 Hz), 5.46 (2H, s), 6.56 (1H, d, J=8.1 Hz), 6.72-6.87 (3H, m), 7.22 (1H, d, J=9.3 Hz), 7.29-7.40 (2H, m), 7.68 (1H, s), 7.74 (1H, d, J=8.2 Hz), 8.54 (1H, dd, J=8.6, 2.5 Hz), 8.89-8.98 (1H, m).

Example 98a 1-((1R)-1-(2-(6-(3-(cyclopropylmethoxy)phenoxy)pyridin-3-yl)-1,3-benzoxazol-6-yl)ethyl)urea A) tert-butyl ((1R)-1-(2-(6-(3-(cyclopropylmethoxy)phenoxy)pyridin-3-yl)-1,3-benzoxazol-6-yl)ethyl)carbamate A racemate (2.2 g) of tert-butyl (1-(2-(6-(3-(cyclopropylmethoxy)phenoxy)pyridin-3-yl)-1,3-benzoxazol-6-yl)ethyl)carbamate was fractionated by HPLC (column: CHIRALPAK IA (trade name), 50 mmIDx500 mL, Daicel Corporation, mobile phase:hexane/ethanol=50/50(v/v)) to give a compound having a shorter retention time as the title compound (925.2 mg).

MS (ESI+): [M+H]$^+$ 502.3.
retention time (IA) 13.864 min

B) 1-((1R)-1-(2-(6-(3-(cyclopropylmethoxy)phenoxy)pyridin-3-yl)-1,3-benzoxazol-6-yl)ethyl)urea A mixture of tert-butyl ((1R)-1-(2-(6-(3-(cyclopropylmethoxy)phenoxy)pyridin-3-yl)-1,3-benzoxazol-6-yl)ethyl)carbamate (1 g) and 4N hydrogen chloride-ethyl acetate solution (5 ml) was stirred at room temperature for 1 hr. The reaction mixture was concentrated under reduced pressure. To a mixture of the obtained residue and THF (5 ml) were added 4-nitrophenyl carbonochloridate (0.5 g) and triethylamine (1 ml) under ice-cooling. The reaction mixture was stirred at room temperature for 1 hr, and 28% aqueous ammonia solution (5 ml) was added. The reaction mixture was stirred at room temperature for 30 min, and extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (315 mg).

$^1$H NMR (300 MHz, DMSO-$d_6$) δ 0.25-0.37 (2H, m), 0.50-0.62 (2H, m), 1.20-1.28 (1H, m), 1.37 (3H, d, J=7.2 Hz), 3.82 (2H, d, J=7.0 Hz), 4.78-4.92 (1H, m), 5.47 (2H, s), 6.58 (1H, d, J=8.2 Hz), 6.72-6.89 (3H, m), 7.22 (1H, dd, J=8.7, 0.7 Hz), 7.29-7.40 (2H, m), 7.68 (1H, s), 7.74 (1H, d, J=8.2 Hz), 8.55 (1H, dd, J=8.7, 2.5 Hz), 8.94 (1H, dd, J=2.5, 0.7 Hz).

Example 98b 1-((1S)-1-(2-(6-(3-(cyclopropylmethoxy)phenoxy)pyridin-3-yl)-1,3-benzoxazol-6-yl)ethyl)urea A) tert-butyl ((1S)-1-(2-(6-(3-(cyclopropylmethoxy)phenoxy)pyridin-3-yl)-1,3-benzoxazol-6-yl)ethyl)carbamate A racemate (2.2 g) of tert-butyl (1-(2-(6-(3-(cyclopropylmethoxy)phenoxy)pyridin-3-yl)-1,3-benzoxazol-6-yl)ethyl)carbamate was fractionated by HPLC (column: CHIRALPAK IA (trade name), 50 mmIDx500 mL, Daicel Corporation, mobile phase:hexane/ethanol=50/50(v/v)) to give a compound having a longer retention time as the title compound (910.2 mg).

MS (ESI+): [M+H]$^+$ 502.3.
retention time (IA) 20.494 min

B) 1-((1S)-1-(2-(6-(3-(cyclopropylmethoxy)phenoxy)pyridin-3-yl)-1,3-benzoxazol-6-yl)ethyl)urea A mixture of tert-butyl ((1S)-1-(2-(6-(3-(cyclopropylmethoxy)phenoxy)pyridin-3-yl)-1,3-benzoxazol-6-yl)ethyl) carbamate (1 g) and 4N hydrogen chloride-ethyl acetate solution (5 ml) was stirred at room temperature for 1 hr. The reaction mixture was concentrated under reduced pressure. To a mixture of the obtained residue and THF (5 ml) were added 4-nitrophenyl carbonochloridate (0.5 g) and triethylamine (1 ml) under ice-cooling. The reaction mixture was stirred at room temperature for 1 hr, and 28% aqueous ammonia solution (5 ml) was added. The reaction mixture was stirred at room temperature for 30 min and extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from hexane/ethyl acetate to give the title compound (345 mg).

$^1$H NMR (300 MHz, DMSO-$d_6$) δ 0.27-0.35 (2H, m), 0.51-0.61 (2H, m), 1.21-1.24 (1H, m), 1.37 (3H, d, J=7.0 Hz), 3.82 (2H, d, J=7.1 Hz), 4.85 (1H, t, J=7.4 Hz), 5.47 (2H, s), 6.58 (1H, d, J=8.1 Hz), 6.73-6.88 (3H, m), 7.18-7.26 (1H, m), 7.30-7.39 (2H, m), 7.68 (1H, s), 7.74 (1H, d, J=8.3 Hz), 8.55 (1H, dd, J=8.7, 2.5 Hz), 8.94 (1H, dd, J=2.5, 0.7 Hz).

The compound of Example 98b can also be produced by the following method.

C) N—(S)-((1E)-1-(2-(6-(3-(cyclopropylmethoxy)phenoxy)pyridin-3-yl)-1,3-benzoxazol-6-yl)ethylidene)-2-methylpropane-2-sulfinamide To a mixture of 1-(2-(6-(3-(cyclopropylmethoxy) phenoxy)pyridin-3-yl)-1,3-benzoxazol-6-yl)ethanone (7.86 g), titanium (IV) tetraethanolate (6.9 g) and THF (150 ml) was added (S)-2-methylpropane-2-sulfinamide (2.3 g), and the mixture was stirred with heating under reflux for 15 hr. The mixture was added to water, and the mixture was extracted with ethyl acetate. The organic layer was washed with saturated brine, dried over anhydrous sodium sulfate, and concentrated under reduced pressure. The obtained residue was purified by silica gel column chromatography (petroleum ether/ethyl acetate) to give the title compound (7.8 g).

$^1$HNMR (400 MHz, DMSO-$d_6$) δ 0.28-0.38 (2H, m), 0.52-0.63 (2H, m), 1.20-1.30 (10H, m), 2.81 (3H, s), 3.82 (2H, d, J=6.8 Hz), 6.75-6.82 (2H, m), 6.85 (1H, d, J=8.0 Hz), 7.24 (1H, d, J=8.8 Hz), 7.35 (1H, t, J=8.0 Hz), 7.89 (1H, d, J=8.8 Hz), 8.03 (1H, d, J=8.8 Hz), 8.32 (1H, s), 8.58 (1H, dd, J=8.8, 2.4 Hz), 8.98 (1H, d, J=2.4 Hz).

D) N—(S)-((1S)-1-(2-(6-(3-(cyclopropylmethoxy)phenoxy)pyridin-3-yl)-1,3-benzoxazol-6-yl)ethyl)-2-methylpropane-2-sulfinamide To a mixture of N—(S)-((1E)-1-(2-(6-(3-(cyclopropylmethoxy)phenoxy)pyridin-3-yl)-1,3-benzoxazol-6-yl)ethylidene)-2-methylpropane-2-sulfinamide (3.8 g) and THF (50 ml) was added diisobutylaluminum hydride (1 M toluene solution, 22.6 ml) at −78° C., and the mixture was stirred at −78° C. for 2 hr. The mixture was added to water, and the mixture was extracted with ethyl acetate. The organic layer was washed with saturated brine, dried over anhydrous sodium sulfate, and concentrated under reduced pressure. The obtained residue was purified by silica gel column chromatography (petroleum ether/ethyl acetate) to give the title compound (3.4 g).

$^1$HNMR (400 MHz, DMSO-$d_6$) δ 0.27-0.38 (2H, m), 0.53-0.61 (2H, m), 1.13 (9H, s), 1.20-1.28 (1H, m), 1.46 (3H, d, J=7.2 Hz), 3.82 (2H, d, J=7.2 Hz), 4.49-4.59 (1H, m), 5.79 (1H, d, J=7.6 Hz), 6.75-6.82 (2H, m), 6.84 (1H, d, J=8.0 Hz), 7.22 (1H, d, J=8.8 Hz), 7.34 (1H, t, J=8.4 Hz), 7.45 (1H, d, J=8.4 Hz), 7.74 (1H, d, J=8.0 Hz), 7.83 (1H, s), 8.55 (1H, dd, J=8.8, 2.8 Hz), 8.94 (1H, d, J=2.4 Hz).

E) (1S)-1-(2-(6-(3-(cyclopropylmethoxy)phenoxy)pyridin-3-yl)-1,3-benzoxazol-6-yl)ethanamine To a mixture of N-((1S)-1-(2-(6-(3-(cyclopropylmethoxy)phenoxy)pyridin-3-yl)-1,3-benzoxazol-6-yl)ethyl)-2-methylpropane-2-sulfinamide (3.4 g), methanol (30 ml) and 1,4-dioxane (30 ml) was added hydrogen chloride (4 M 1,4-dioxane solution, 6 ml), and the mixture was stirred at room temperature for 0.5 hr. The mixture was added to water, and the mixture was neutralized with 2N aqueous sodium hydroxide solution and extracted with ethyl acetate. The organic layer was washed with saturated brine, dried over anhydrous sodium sulfate, and concentrated under reduced pressure. The obtained residue was purified by HPLC (water/acetonitrile, 0.1% aqueous ammonia added) and freeze-dried to give the title compound (1.39 g).

F) 1-((1S)-1-(2-(6-(3-(cyclopropylmethoxy)phenoxy)pyridin-3-yl)-1,3-benzoxazol-6-yl)ethyl)urea To a mixture of 4-nitrophenyl carbonochloridate (0.6 g) and THF (10 ml) was added a mixture of (1S)-1-(2-(6-(3-(cyclopropylmethoxy)phenoxy)pyridin-3-yl)-1,3-benzoxazol-6-yl)ethanamine (1 g), triethylamine (0.5 ml) and THF (10 ml) under ice-cooling. The mixture was stirred at 0° C. for 30 min, and 28% aqueous ammonia solution (2 ml) was added. To a mixture of 4-nitrophenyl carbonochloridate (1.3 g) and THF (15 ml) was added a mixture of (1S)-1-(2-(6-(3-(cyclopropylmethoxy)phenoxy)pyridin-3-yl)-1,3-benzoxazol-6-yl)ethanamine (2.15 g), triethylamine (1.2 ml) and THF (15 ml) under ice-cooling. The mixture was stirred at room temperature for 30 min, and 28% aqueous ammonia solution (5 ml) was added. The above-mentioned two reaction mixtures were mixed and extracted with ethyl acetate and water. The organic layer was washed with saturated brine, dried over magnesium sulfate, and concentrated under reduced pressure. The obtained residue was purified by silica gel column chromatography (NH, ethyl acetate/methanol), and crystallized from hexane/ethyl acetate to give the title compound (2.4 g).

Example 99 methyl (1-(2-(6-(3-(cyclopropylmethoxy)phenoxy)pyridin-3-yl)-1,3-benzoxazol-6-yl)ethyl)carbamate

A) 1-(2-(6-(3-(cyclopropylmethoxy)phenoxy)pyridin-3-yl)-1,3-benzoxazol-6-yl)ethanamine A mixture of 6-(1-azidoethyl)-2-(6-(3-(cyclopropylmethoxy)phenoxy)pyridin-3-yl)-1,3-benzoxazole (20 g), palladium carbon (1.4 g), methanol (100 ml) and ethyl acetate (300 ml) was stirred under a hydrogen atmosphere at room temperature for 4 hr. The reaction mixture was filtered, and concentrated under reduced pressure. The obtained residue was purified by silica gel column chromatography (NH, hexane/ethyl acetate) to give the title compound (7.5 g).

MS (ESI+): [M+H]$^+$ 402.2.

B) methyl (1-(2-(6-(3-(cyclopropylmethoxy)phenoxy)pyridin-3-yl)-1,3-benzoxazol-6-yl)ethyl)carbamate A mixture of 1-(2-(6-(3-(cyclopropylmethoxy)phenoxy)pyridin-3-yl)-1,3-benzoxazol-6-yl)ethanamine (430 mg), triethylamine (0.597 ml), methyl chloroformate (153 mg) and THF (35 ml) was stirred at room temperature 3 days. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate), and crystallized from diisopropyl ether/ethyl acetate to give the title compound (353 mg).

$^1$H NMR (300 MHz, DMSO-$d_6$) δ 0.26-0.36 (2H, m), 0.49-0.62 (2H, m), 1.13-1.29 (1H, m), 1.40 (3H, d, J=7.0 Hz), 3.51 (3H, s), 3.82 (2H, d, J=7.0 Hz), 4.73-4.89 (1H, m), 6.71-6.89 (3H, m), 7.22 (1H, d, J=8.7 Hz), 7.27-7.45 (2H, m), 7.65-7.86 (3H, m), 8.54 (1H, dd, J=8.7, 2.5 Hz), 8.94 (1H, d, J=2.1 Hz).

Example 100

1-(1-(2-(6-(3-(cyclopropylmethoxy)phenoxy)pyridin-3-yl)-1,3-benzoxazol-6-yl)ethyl)-3-methylurea To a mixture of 1-(2-(6-(3-(cyclopropylmethoxy) phenoxy)pyridin-3-yl)-1,3-benzoxazol-6-yl)ethanamine (811 mg) and THF (45 ml) were added N,N-diisopropylethylamine (1.058 ml) and carbonyldiimidazole (345 mg). The reaction mixture was stirred at room temperature for 30 min, methylamine (2.0 M THF solution, 2.02 ml) was added, and the mixture was stirred at room temperature for 3.5 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (ethyl acetate/methanol), and crystallized from hexane/ethyl acetate/methanol to give the title compound (228 mg).

$^1$H NMR (300 MHz, DMSO-$d_6$) δ 0.28-0.36 (2H, m), 0.52-0.61 (2H, m), 1.14-1.29 (1H, m), 1.37 (3H, d, J=7.0 Hz), 2.53 (3H, d, J=4.7 Hz), 3.82 (2H, d, J=7.0 Hz), 4.80-4.96 (1H, m), 5.70 (1H, q, J=4.5 Hz), 6.47 (1H, d, J=8.2 Hz), 6.72-6.89 (3H, m), 7.22 (1H, d, J=8.6 Hz), 7.28-7.40 (2H, m), 7.67 (1H, s), 7.73 (1H, d, J=8.2 Hz), 8.54 (1H, dd, J=8.6, 2.4 Hz), 8.94 (1H, d, J=2.4 Hz).

Example 101

1-(1-(2-(6-(3-(cyclopropylmethoxy)phenoxy)pyridin-3-yl)-1,3-benzoxazol-6-yl)ethyl)-3,3-dimethylurea To a mixture of 1-(2-(6-(3-(cyclopropylmethoxy)phenoxy)pyridin-3-yl)-1,3-benzoxazol-6-yl)ethylamine (950 mg) and THF (45 ml) were added N,N-diisopropylethylamine (1.24 ml) and carbonyldiimidazole (404 mg). The reaction mixture was stirred at room temperature for 30 min, dimethylamine (2.0 M methanol solution, 2.366 ml) was added, and the mixture was stirred at room temperature for 3.5 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (ethyl acetate/methanol), and crystallized from hexane/ethyl acetate to give the title compound (170 mg).

$^1$H NMR (300 MHz, DMSO-$d_6$) δ 0.26-0.38 (2H, m), 0.49-0.62 (2H, m), 1.13-1.29 (1H, m), 1.43 (3H, d, J=7.1 Hz), 2.81 (6H, s), 3.82 (2H, d, J=7.0 Hz), 4.95 (1H, quin, J=7.3 Hz), 6.61 (1H, d, J=7.8 Hz), 6.72-6.90 (3H, m), 7.22 (1H, d, J=8.6 Hz), 7.29-7.43 (2H, m), 7.65-7.76 (2H, m), 8.54 (1H, dd, J=8.6, 2.2 Hz), 8.94 (1H, d, J=2.2 Hz).

Example 102

N-(1-(2-(6-((6-oxo-1-propyl-1,6-dihydropyridin-3-yl)oxy)pyridin-3-yl)-1,3-benzoxazol-6-yl)ethyl)acetamide A) N-(4-(1-acetamidoethyl)-2-hydroxyphenyl)-6-chloronicotinamide To a solution of N-(1-(4-amino-3-hydroxyphenyl)ethyl)acetamide (13.2 g) in pyridine (150 ml) were added 6-chloronicotinic acid (13.5 g) and WSCD (21.9 g), and the mixture was stirred at room temperature for 2 hr. To the reaction mixture was added water, and the mixture was extracted with ethyl acetate. The obtained organic layer was washed with saturated brine, dried over anhydrous sodium sulfate, and concentrated under reduced pressure. To the obtained residue were added methanol (120 ml) and potassium carbonate (15 g), and the mixture was stirred at room temperature for 0.5 hr. The reaction mixture was concentrated under reduced pressure, and saturated aqueous sodium hydrogen carbonate solution and ethyl acetate were added to the obtained residue. The mixture was filtered, and the obtained solid was washed with petroleum ether to give the title compound (11.8 g).

$^1$H NMR (400 MHz, DMSO-$d_6$) δ 1.30 (3H, d, J=7.2 Hz), 1.83 (3H, s), 4.70-4.90 (1H, m), 6.68 (1H, d, J=8.0 Hz), 6.78 (1H, s), 7.50 (1H, d, J=8.0 Hz), 7.63 (1H, d, J=8.4 Hz), 8.20 (1H, d, J=7.6 Hz), 8.32 (1H, d, J=6.4 Hz), 8.92 (1H, s).

B) N-(1-(2-(6-chloropyridin-3-yl)-1,3-benzoxazol-6-yl)ethyl)acetamide

To a suspension of N-(4-(1-acetamidoethyl)-2-hydroxyphenyl)-6-chloronicotinamide (1.8 g) in THF (20 ml) were added triphenylphosphine (2.12 g) and diisopropyl azodicarboxylate (1.64 g), and the mixture was stirred under a nitrogen atmosphere with heating under reflux for 2 hr. Furthermore, to a suspension of N-(4-(1-acetamidoethyl)-2-hydroxyphenyl)-6-chloropyridin-3-ylamide (10 g) in THF (100 ml) were added triphenylphosphine (11.8 g) and diisopropyl azodicarboxylate (9.1 g), and the mixture was stirred under a nitrogen atmosphere with heating under reflux for 2 hr. The above-mentioned two mixtures were each cooled to room temperature and mixed, and concentrated under reduced pressure. To the obtained residue was added ethanol (80 ml) and the mixture was stirred at room temperature for 5 min. The obtained solid was collected by filtration, and washed with petroleum ether to give the title compound (7.77 g).

$^1$H NMR (400 MHz, DMSO-$d_6$) δ 1.40 (3H, d, J=6.8 Hz), 1.86 (3H, s), 4.96-5.15 (1H, m), 7.40 (1H, d, J=8.0 Hz), 7.73

(1H, s), 7.78 (2H, d, J=8.0 Hz), 8.42 (1H, d, J=8.0 Hz), 8.54 (1H, dd, J=8.4, 2.4 Hz), 9.16 (1H, d, J=2.0 Hz).

C) 5-bromo-1-propylpyridin-2(1H)-one

A mixture of 5-bromopyridin-2(1H)-one (2.92 g), 1-bromopropane (1.82 ml), potassium carbonate (3.48 g) and DMF (85 ml) was stirred at 60° C. for 18 hr. To the obtained mixture was added brine, and the mixture was extracted with ethyl acetate. The obtained organic layer was washed with brine, dried over anhydrous magnesium sulfate, and concentrated under reduced pressure. The obtained residue was purified by silica gel column chromatography (hexane/ethyl acetate) to give the title compound (1.98 g).
$^1$H NMR (300 MHz, DMSO-d$_6$) δ 0.84 (3H, t, J=7.4 Hz), 1.63 (2H, sxt, J=7.4 Hz), 3.81 (2H, t, J=7.3 Hz), 6.36 (1H, d, J=9.6 Hz), 7.50 (1H, dd, J=9.6, 2.8 Hz), 8.02 (1H, d, J=2.8 Hz).

D) 1-propyl-5-(4,4,5,5-tetramethyl-1,3,2-dioxaborolan-2-yl)pyridin-2 (1H)-one

A mixture of 5-bromo-1-propylpyridin-2(1H)-one (514 mg), 4,4,4',4',5,5,5',5'-octamethyl-2,2'-bi-1,3,2-dioxaborolane (725 mg), (bis(1,1'-diphenylphosphino)ferrocene)dichloropalladium dichloromethane adduct (97 mg), potassium acetate (700 mg) and acetonitrile (12 ml) was stirred under microwave radiation at 125° C. for 45 min. Furthermore, a mixture of 5-bromo-1-propylpyridin-2(1H)-one (586 mg), 4,4,4',4',5,5,5',5'-octamethyl-2,2'-bi-1,3,2-dioxaborolane (826 mg), (bis(1,1'-diphenylphosphino)ferrocene) dichloropalladium dichloromethane adduct (111 mg), potassium acetate (798 mg) and acetonitrile (12 ml) was stirred under microwave radiation at 125° C. for 45 min. The above-mentioned two mixtures were mixed, and water and ethyl acetate were added. The mixture was filtered through celite, and the organic layer was separated. The obtained organic layer was dried over anhydrous magnesium sulfate, and concentrated under reduced pressure. The obtained residue was purified by silica gel column chromatography (hexane/ethyl acetate) to give the title compound (1.38 g).
MS (ESI+): [M+H]$^+$ 264.2.

E) 5-hydroxy-1-propylpyridin-2(1H)-one

To a solution of 1-propyl-5-(4,4,5,5-tetramethyl-1,3,2-dioxaborolan-2-yl)pyridin-2(1H)-one (1.38 g) in THF (20 ml) were added 2N aqueous sodium hydroxide solution (5.24 ml) and 30% hydrogen peroxide water (1.07 ml). The reaction mixture was stirred at room temperature for 3 hr, 1N hydrochloric acid was added, and the mixture was extracted with water and ethyl acetate. The obtained organic layer was dried over anhydrous magnesium sulfate, and concentrated under reduced pressure. The obtained residue was purified by silica gel column chromatography (hexane/ethyl acetate/ methanol) to give the title compound (210 mg).
MS (ESI+): [M+H]$^+$ 154.1.

F) N-(1-(2-(6-((6-oxo-1-propyl-1,6-dihydropyridin-3-yl)oxy)pyridin-3-yl)-1,3-benzoxazol-6-yl)ethyl) acetamide To a mixture of N-(1-(2-(6-chloropyridin-3-yl)-1,3-benzoxazol-6-yl)ethyl)acetamide (216 mg), potassium carbonate (237 mg) and DMF (20 ml) was added a solution of 5-hydroxy-1-propylpyridin-2(1H)-one (210 mg) in DMF (5 ml) at 120° C., and the mixture was stirred at 120° C. for 30 min. The reaction mixture was extracted with water and ethyl acetate. The obtained organic layer was washed with saturated brine, dried over anhydrous magnesium sulfate, and concentrated under reduced pressure. The obtained residue was purified by silica gel column chromatography (hexane/ethyl acetate/methanol), and crystallized from hexane/diisopropyl ether/ethyl acetate to give the title compound (64 mg).
$^1$H NMR (300 MHz, DMSO-d$_6$) δ 0.88 (3H, t, J=7.2 Hz), 1.40 (3H, d, J=7.2 Hz), 1.59-1.75 (2H, m), 1.86 (3H, s), 3.83 (2H, t, J=7.2 Hz), 4.97-5.11 (1H, m), 6.45 (1H, d, J=9.8 Hz), 7.29 (1H, d, J=9.2 Hz), 7.37 (1H, dd, J=8.4, 1.5 Hz), 7.47 (1H, dd, J=9.8, 3.1 Hz), 7.65-7.78 (2H, m), 7.85 (1H, d, J=3.0 Hz), 8.38 (1H, d, J=7.9 Hz), 8.55 (1H, dd, J=8.7, 2.5 Hz), 8.94 (1H, d, J=1.9 Hz).

Example 103

N-(1-(5-(5-(3-(cyclopropylmethoxy)phenoxy) pyrazin-2-yl)-1-benzofuran-2-yl)ethyl)acetamide A) 1-(5-bromo-1-benzofuran-2-yl)ethanone To a mixture of potassium hydroxide (11.2 g) and methanol (400 ml) was added 5-bromo-2-hydroxybenzaldehyde (40 g) with heating under reflux. The reaction mixture was cooled to 0° C., and 1-chloroacetone (22 g) was added. The reaction mixture was stirred with heating under reflux for 16 hr, and concentrated under reduced pressure. To the obtained residue was added water, and the mixture was extracted with ethyl acetate. The obtained organic layer was dried over anhydrous sodium sulfate, and concentrated under reduced pressure. To the obtained residue was added petroleum ether/ethyl acetate (10/1), and the mixture was stirred at room temperature for 0.5 hr. The reaction mixture was filtered, and the obtained solid was washed with petroleum ether. The filtrate was concentrated and the residue was purified by silica gel column chromatography (petroleum ether/ethyl acetate) and combined with the solid obtained earlier to give the title compound (36 g).
$^1$H NMR (400 MHz, CDCl$_3$) δ 2.62 (3H, s), 7.44 (1H, s), 7.47 (1H, d, J=9.2 Hz), 7.57 (1H, dd, J=8.8, 2.0 Hz), 7.85 (1H, d, J=2.0 Hz).

B) N-(1-(5-bromo-1-benzofuran-2-yl)ethyl)acetamide

Ammonia gas was blown into a mixture of 1-(5-bromo-1-benzofuran-2-yl)ethanone (20 g) and methanol (200 ml) at 0° C. for 1 hr. The reaction mixture was stirred at room temperature for 3 hr, and sodium cyanoborohydride (10.5 g) was added. The reaction mixture was stirred at room temperature for 16 hr, and concentrated under reduced pressure. To the obtained residue were added THF (200 ml) and acetic anhydride (26 g). The reaction mixture was stirred at room temperature for 3 hr, and concentrated under reduced pressure. The obtained residue was purified by silica gel column chromatography (petroleum ether/ethyl acetate) to give the title compound (5.26 g).
$^1$H NMR (400 MHz, CDCl$_3$) δ 1.56 (3H, d, J=6.8 Hz), 2.03 (3H, s), 5.30-5.85 (1H, m), 5.82 (1H, d, J=7.6 Hz), 6.51 (1H, s), 7.23 (1H, d, J=8.8 Hz), 7.35 (1H, dd, J=8.8, 2.0 Hz), 7.64 (1H, d, J=1.6 Hz).

C) N-(1-(5-(4,4,5,5-tetramethyl-1,3,2-dioxaborolan-2-yl)-1-benzofuran-2-yl)ethyl)acetamide A mixture of N-(1-(5-bromo-1-benzofuran-2-yl)acetamide (2 g), 4,4,4',4',5,5,5',5'-octamethyl-2,2'-bi-1,3,2-dioxaborolane (2.16 g), (bis(1,1'-diphenylphosphino)ferrocene)dichloropalladium (520 mg), potassium acetate (1.4 g) and 1,4-dioxane (20 ml) was stirred under a nitrogen atmosphere at 90° C. for 16 hr. The reaction mixture was concentrated under reduced pressure, and the obtained residue was purified by silica gel column chromatography (petroleum ether/ethyl acetate) to give the title compound (1.8 g).

$^1$H NMR (400 MHz, CDCl$_3$) δ 1.36 (12H, s), 1.56 (3H, d, J=6.8 Hz), 2.02 (3H, s), 5.30-5.840 (1H, m), 5.84 (1H, d, J=8.4 Hz, brs), 6.55 (1H, s), 7.42 (1H, d, J=8.0 Hz), 7.72 (1H, d, J=8.4 Hz), 8.0 (1H, s).

D) 2-bromo-5-(3-(cyclopropylmethoxy)phenoxy)pyrazine

To a mixture of 3-(cyclopropylmethoxy)phenol (500 mg), 2,5-dibromopyrazine (719 mg), copper(I) iodide (577 mg), picolinic acid (74 mg) and DMSO (15 ml) was added tripotassium phosphate (1.28 g). The reaction mixture was stirred under a nitrogen atmosphere at 80° C. for 16 hr. To the reaction mixture was added water, and the mixture was extracted with ethyl acetate. The obtained organic layer was dried over anhydrous sodium sulfate, and concentrated under reduced pressure. The obtained residue was purified by silica gel column chromatography (petroleum ether/ethyl acetate) to give the title compound (500 mg).

$^1$H NMR (400 MHz, DMSO-d$_6$) δ 0.25-0.35 (2H, m), 0.50-0.60 (2H, m), 1.15-1.25 (1H, m), 3.79 (2H, d, J=6.8 Hz), 6.65-6.85 (3H, m), 7.25-7.35 (1H, m), 8.38 (1H, d, J=1.6 Hz), 8.42 (1H, d, J=1.2 Hz).

E) N-(1-(5-(5-(3-(cyclopropylmethoxy)phenoxy)pyrazin-2-yl)-1-benzofuran-2-yl)ethyl)acetamide A mixture of 2-bromo-5-(3-(cyclopropylmethoxy)phenoxy)pyrazine (300 mg), N-(1-(5-(4,4,5,5-tetramethyl-1,3,2-dioxaborolan-2-yl)-1-benzofuran-2-yl)ethyl)acetamide (340 mg), potassium carbonate (200 mg), (bis(1,1'-diphenylphosphino)ferrocene)dichloropalladium (70 mg), 1,4-dioxane/water (5/1) (10 ml) was stirred under a nitrogen atmosphere at 90° C. for 16 hr. The reaction mixture was concentrated under reduced pressure. The obtained residue was purified by silica gel column chromatography (petroleum ether/ethyl acetate), and the obtained solid was washed with hexane/ethyl acetate to give the title compound (200 mg).

$^1$H NMR (400 MHz, CDCl$_3$) δ 0.30-0.40 (2H, m), 0.60-0.70 (2H, m), 1.20-1.35 (1H, m), 1.60 (3H, d, J=7.2 Hz), 2.04 (3H, s), 3.81 (2H, d, J=6.8 Hz), 5.35-5.45 (1H, m), 5.85 (1H, d, J=8.4 Hz, brs), 6.64 (1H, s), 6.75-6.85 (3H, m), 7.32 (1H, t, J=8.0 Hz), 7.52 (1H, d, J=8.4 Hz), 7.84 (1H, dd, J=8.4, 1.6 Hz), 8.07 (1H, s), 8.44 (1H, d, J=0.8 Hz), 8.55 (1H, s).

Example 104

N-(1-(2-(4-(3-(cyclopropylmethoxy)phenoxy)phenyl) [1,3]oxazolo[5,4-b]pyridin-5-yl)ethyl)acetamide

A) N-(2-chloro-6-methylpyridin-3-yl)-4-fluorobenzamide

To a mixture of 2-chloro-6-methylpyridine-3-amine (10 g), 4-fluorobenzoyl chloride (11 g) and THF (100 ml) was added triethylamine (21.3 g), and the mixture was stirred at room temperature for 16 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (16.3 g).

$^1$H NMR (400 MHz, DMSO-d$_6$) δ 2.51 (3H, s), 7.34-7.46 (3H, m), 7.91 (1H, d, J=8.0 Hz), 8.08 (2H, dd, J=8.8, 5.6 Hz), 10.19 (1H, brs).

B) 2-(4-fluorophenyl)-5-methyl[1,3]oxazolo[5,4-b]pyridine

A mixture of phosphorus pentaoxide (4.71 g), hexamethyldisiloxane (21.1 g) and dichlorobenzene (8 ml) was stirred at 180° C. for 1 hr. To the reaction mixture was added N-(2-chloro-6-methylpyridin-3-yl)-4-fluorobenzamide (8 g), and the mixture was stirred at 180° C. for 20 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (3.4 g).

$^1$H NMR (400 MHz, CDCl$_3$) δ 2.68 (3H, s), 7.20-7.28 (3H, s), 7.93 (1H, d, J=8.4 Hz), 8.26 (2H, dd, J=9.2, 5.6 Hz).

C) 5-(dibromomethyl)-2-(4-fluorophenyl)[1,3]oxazolo[5,4-b]pyridine

To a mixture of 2-(4-fluorophenyl)-5-methyl[1,3]oxazolo[5,4-b]pyridine (3.2 g) and carbon tetrachloride (100 ml) were added N-bromosuccinimide (12.5 g) and benzoylperoxide (1.69 g), and the mixture was stirred with heating under reflux for 16 hr. The reaction mixture was cooled to room temperature, water was added and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (4.45 g).

MS (ESI+): [M+H]$^+$ 386.8.

D) 2-(4-fluorophenyl) [1,3]oxazolo[5,4-b]pyridine-5-carbaldehyde

To a mixture of 5-(dibromomethyl)-2-(4-fluorophenyl)[1,3]oxazolo[5,4-b]pyridine (4.45 g), ethanol (30 ml) and water (20 ml) was added silver nitrate (3.92 g), and the mixture was stirred at room temperature for 16 hr. To the reaction mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (620 mg).

$^1$H NMR (400 MHz, CDCl$_3$) 57.23-7.32 (2H, m), 8.12 (1H, d, J=8.0 Hz), 8.19 (1H, d, J=8.0 Hz), 8.35 (2H, dd, J=9.2, 5.2 Hz), 10.11 (1H, s).

E) 1-(2-(4-fluorophenyl) [1, 3]oxazolo[5,4-b]pyridin-5-yl)ethanol

To a mixture of 2-(4-fluorophenyl) [1,3]oxazolo[5,4-b]pyridine-5-carbaldehyde (470 mg) and THF (8 ml) was added methylmagnesium bromide (3.0 M diethyl ether solution, 0.97 ml) at 0° C., and the mixture was stirred at 0° C. for 1 hr. To the mixture was added saturated aqueous ammonium chloride solution, and the mixture was extracted with ethyl acetate. The obtained organic layer was washed with saturated brine, dried over anhydrous sodium sulfate, and concentrated under reduced pressure to give the title compound (424 mg).

$^1$H NMR (400 MHz, DMSO-d$_6$) δ 1.42 (3H, d, J=6.4 Hz), 4.77-4.83 (1H, m), 5.55 (1H, d, J=4.4 Hz), 7.46-7.50 (2H, m), 7.61 (1H, d, J=8.0 Hz), 8.21-8.28 (3H, m).

F) 1-(2-(4-(3-(cyclopropylmethoxy)phenoxy)phenyl) [1,3]oxazolo[5,4-b]pyridin-5-yl)ethanol To a mixture of 1-(2-(4-fluorophenyl) [1, 3]oxazolo[5, 4-b]pyridin-5-yl)ethanol (424 mg), 3-(cyclopropylmethoxy) phenol (404 mg) and DMF (10 ml) was added cesium carbonate (1.07 g), and the mixture was stirred at 80-85° C. for 40 hr. To the mixture was added water, and the mixture was extracted with ethyl acetate. The obtained organic layer was washed with saturated brine, dried over anhydrous sodium sulfate, and concentrated under reduced pressure. The obtained residue was purified by silica gel column chromatography (petroleum ether/ethyl acetate) to give the title compound (530 mg).

MS (ESI+): [M+H]$^+$ 403.0.

G) 1-(2-(4-(3-(cyclopropylmethoxy)phenoxy)phenyl) [1,3]oxazolo[5,4-b]pyridin-5-yl)ethyl methanesulfonate To a mixture of 1-(2-(4-(3-(cyclopropylmethoxy)phenoxy)phenyl) [1,3]oxazolo[5,4-b]pyridin-5-yl)ethanol (530 mg), triethylamine (400 mg) and dichloromethane (6 ml) was added methanesulfonyl chloride (302 mg), and the mixture was stirred at room temperature for 2 hr. To the reaction mixture was added water, and the mixture was extracted with dichloromethane. The obtained organic layer was washed with saturated brine, dried over anhydrous sodium sulfate, and concentrated under reduced pressure to give the title compound (530 mg).

MS (ESI+): [M+H]$^+$ 480.9.

H) 5-(1-azidoethyl)-2-(4-(3-(cyclopropylmethoxy) phenoxy)phenyl) [1,3]oxazolo[5, 4-b]pyridine To a mixture of 1-(2-(4-(3-(cyclopropylmethoxy)phenoxy)phenyl) [1,3]oxazolo[5, 4-b]pyridin-5-yl)ethyl methanesulfonate (480 mg) and DMF (5 ml) was added sodium azide (428 mg), and the mixture was stirred at 60° C. for 16 hr. To the reaction mixture was added water, and the mixture was basified with saturated aqueous sodium hydrogen carbonate solution and extracted with ethyl acetate. The obtained organic layer was washed with water and saturated brine, dried over anhydrous sodium sulfate, and concentrated under reduced pressure. The obtained residue was purified by silica gel column chromatography (petroleum ether/ethyl acetate) to give the title compound (111 mg).

$^1$H NMR (400 MHz, CDCl$_3$) δ 0.32-0.39 (2H, m), 0.63-0.70 (2H, m), 1.20-1.26 (1H, m), 1.69 (3H, d, J=6.8 Hz), 3.79 (2H, d, J=6.8 Hz), 4.73-4.82 (1H, m), 6.62-6.69 (2H, m), 6.76 (1H, d, J=8.4 Hz), 7.12 (2H, d, J=9.2 Hz), 7.29 (1H, t, J=8.0 Hz), 7.40 (1H, d, J=8.0 Hz), 8.03 (1H, d, J=8.0 Hz), 8.23 (2H, d, J=8.8 Hz).

I) N-(1-(2-(4-(3-(cyclopropylmethoxy)phenoxy) phenyl) [1,3]oxazolo[5,4-b]pyridin-5-yl)ethyl)acetamide A mixture of 5-(1-azidoethyl)-2-(4-(3-(cyclopropylmethoxy)phenoxy)phenyl) [1,3]oxazolo[5, 4-b]pyridine (111 mg), triphenylphosphine (83 mg), THF (3 ml) and water (2 ml) was stirred with heating under reflux for 3 hr. The reaction mixture was cooled to room temperature, acetic anhydride (80 mg) was added, and the mixture was stirred at room temperature for 2 hr. To the mixture was added water, and the mixture was extracted with ethyl acetate. The obtained organic layer was washed with saturated aqueous sodium hydrogen carbonate solution and saturated brine, dried over anhydrous sodium sulfate, and concentrated under reduced pressure. The obtained residue was purified by HPLC (acetonitrile/water, 0.1% aqueous ammonia added) to give the title compound (60 mg).

$^1$H NMR (400 MHz, DMSO-d$_6$) δ 0.28-0.33 (2H, m), 0.53-0.60 (2H, m), 1.16-1.25 (1H, m), 1.42 (3H, d, J=6.8 Hz), 1.87 (3H, s), 3.82 (2H, d, J=6.8 Hz), 5.02-5.11 (1H, m), 6.67-6.75 (2H, m), 6.83 (1H, dd, J=8.4, 2.0 Hz), 7.19 (2H, d, J=8.8 Hz), 7.36 (1H, t, J=8.0 Hz), 7.44 (1H, d, J=8.0 Hz), 8.14-8.27 (3H, m), 8.46 (1H, d, J=8.0 Hz).

Example 105

N-(1-(2-(6-((1-butyl-6-oxo-1, 6-dihydropyridin-3-yl) oxy)pyridin-3-yl)-1,3-benzoxazol-6-yl)ethyl)acetamide A) 5-bromo-1-butylpyridin-2(1H)-one To a mixture of 5-bromopyridin-2(1H)-one (5 g) and DMF (50 ml) were added 1-bromobutane (4.14 g) and potassium carbonate (7.93 g), and the mixture was stirred at room temperature for 12 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (petroleum ether/ethyl acetate) to give the title compound (3.9 g).

$^1$H NMR (400 MHz, CDCl$_3$) δ 0.95 (3H, t, J=7.2 Hz), 1.30-1.45 (2H, m), 1.61-1.76 (2H, m), 3.89 (2H, t, J=7.2 Hz), 6.47 (1H, d, J=9.6 Hz), 7.32 (1H, dd, J=9.6, 2.8 Hz), 7.37 (1H, d, J=2.4 Hz).

B) 1-butyl-5-hydroxypyridin-2(1H)-one

To a mixture of 5-bromo-1-butylpyridin-2(1H)-one (2 g) and 1,4-dioxane (20 ml) were added 4,4,4',4',5,5,5',5'-octamethyl-2,2'-bi-1,3,2-dioxaborolane (3.48 g), (bis(1,1'-diphenylphosphino)ferrocene)dichloropalladium (252 mg) and potassium acetate (1.34 g), and the mixture was stirred at 80° C. for 6 hr. The reaction mixture was cooled to room temperature, sodium hydroxide (400 mg), ethanol (10 ml) and 30% hydrogen peroxide water (1 g) were added, and the mixture was stirred at 10° C. for 2 hr. The mixture was warmed to room temperature, aqueous saturated sodium sulfite solution was added, and the mixture was extracted with ethyl acetate. The obtained organic layer was dried over anhydrous sodium sulfate, and concentrated under reduced pressure. The obtained residue was purified by silica gel column chromatography (ethyl acetate/methanol) to give the title compound (350 mg).

¹H NMR (400 MHz, CDCl₃) δ 0.93 (3H, t, J=7.2 Hz), 1.25-1.40 (2H, m), 1.50-1.80 (2H, m), 3.89 (2H, t, J=7.2 Hz), 6.48 (1H, d, J=9.2 Hz), 7.00 (1H, d, J=2.4 Hz), 7.20-7.35 (1H, m), 8.86 (1H, brs).

C) N-(1-(2-(6-((1-butyl-6-oxo-1,6-dihydropyridin-3-yl)oxy)pyridin-3-yl)-1,3-benzoxazol-6-yl)ethyl) acetamide To a mixture of 1-butyl-5-hydroxypyridin-2(1H)-one (200 mg) and DMF (5 ml) were added N-(1-(2-(6-chloropyridin-3-yl)-1,3-benzoxazol-6-yl)ethyl)acetamide (127 mg) and cesium carbonate (414 mg), and the mixture was stirred at 60° C. for 12 hr. The reaction mixture was cooled to room temperature, water was added and the mixture was extracted with ethyl acetate. The obtained organic layer was washed with saturated brine, dried over anhydrous sodium sulfate, and concentrated under reduced pressure. The obtained residue was purified by HPLC (acetonitrile/water, 0.1% aqueous ammonia added) to give the title compound (48 mg).
¹H NMR (400 MHz, DMSO-d₆) δ 0.90 (3H, t, J=7.2 Hz), 1.20-1.37 (2H, m), 1.39 (3H, d, J=6.8 Hz), 1.55-1.70 (2H, m), 1.86 (3H, s), 3.87 (2H, t, J=7.2 Hz), 4.95-5.10 (1H, m), 6.45 (1H, d, J=10.0 Hz), 7.29 (1H, d, J=8.8 Hz), 7.36 (1H, dd, J=9.6, 1.6 Hz), 7.47 (1H, dd, J=9.6, 3.2 Hz), 7.70 (1H, s), 7.74 (1H, d, J=8.0 Hz), 7.85 (1H, d, J=3.2 Hz), 8.39 (1H, d, J=8.0 Hz), 8.55 (1H, dd, J=8.8, 2.4 Hz), 8.94 (1H, d, J=2.0 Hz).

Example 106

1-(1-(2-(6-((5-(cyclopropylmethoxy)pyridin-3-yl)oxy)pyridin-3-yl)-1,3-benzoxazol-6-yl)ethyl)urea A) 3-bromo-5-(cyclopropylmethoxy)pyridine A mixture of 5-bromopyridin-3-ol (15 g), (bromomethyl)cyclopropane (10.87 ml), potassium carbonate (17.87 g) and DMF (200 ml) was stirred at 80° C. for 2 hr. The reaction mixture was cooled to room temperature and extracted with ethyl acetate and water. The obtained organic layer was washed with saturated brine, dried over anhydrous magnesium sulfate, and concentrated under reduced pressure. The obtained residue was purified by silica gel column chromatography (hexane/ethyl acetate) to give the title compound (14.31 g).
¹H NMR (300 MHz, DMSO-d₆) δ 0.26-0.39 (2H, m), 0.49-0.69 (2H, m), 1.09-1.31 (1H, m), 3.93 (2H, d, J=7.1 Hz), 7.68 (1H, t, J=2.1 Hz), 8.26 (1H, d, J=1.8 Hz), 8.29 (1H, d, J=2.5 Hz).

B) 5-(cyclopropylmethoxy)pyridin-3-ol

To a mixture of 3-bromo-5-(cyclopropylmethoxy)pyridine (14.31 g) and toluene (200 ml) was added dropwise n-butyllithium (1.6 M hexane solution, 47.1 ml) at −78° C. The mixture was stirred at −78° C. for 1 hr and trimethyl borate (10.69 ml) was added. The reaction mixture was warmed to room temperature, and 8N aqueous sodium hydroxide solution (54.9 ml) and 35% hydrogen peroxide water (19.23 ml) were added. The reaction mixture was stirred at room temperature for 30 min, neutralized with 6N hydrochloric acid, and extracted with toluene. The obtained organic layer was washed with saturated brine, dried over anhydrous magnesium sulfate, and concentrated under reduced pressure. The obtained residue was purified by silica gel column chromatography (hexane/ethyl acetate) to give the title compound (5.53 g).
¹H NMR (300 MHz, DMSO-d₆) δ 0.25-0.39 (2H, m), 0.48-0.64 (2H, m), 1.07-1.32 (1H, m), 3.82 (2H, d, J=7.0 Hz), 6.70 (1H, t, J=2.4 Hz), 7.74 (2H, dd, J=5.5, 2.4 Hz), 9.93 (1H, brs).

C) 1-(2-(6-((5-(cyclopropylmethoxy)pyridin-3-yl)-1,3-benzoxazol-6-yl)ethanone

A mixture of 5-(cyclopropylmethoxy)pyridin-3-ol (1.212 g), 1-(2-(6-chloropyridin-3-yl)-1,3-benzoxazol-6-yl)ethanone (2 g), cesium carbonate (4.78 g) and DMF (20 ml) was stirred at 100° C. for 2 hr. The reaction mixture was cooled to room temperature, and the mixture was extracted with ethyl acetate and water. The obtained organic layer was washed with saturated brine, dried over anhydrous magnesium sulfate, and concentrated under reduced pressure. To the obtained residue was added ethanol, and the obtained solid was collected by filtration to give the title compound (0.9 g).
¹H NMR (300 MHz, DMSO-d₆) δ 0.30-0.38 (2H, m), 0.53-0.65 (2H, m), 1.17-1.31 (1H, m), 2.68 (3H, s), 3.92 (2H, d, J=7.1 Hz), 7.34-7.42 (2H, m), 7.89-7.97 (1H, m), 8.01-8.09 (1H, m, J=1.5 Hz), 8.14 (1H, d, J=2.1 Hz), 8.24 (1H, d, J=2.5 Hz), 8.40 (1H, d, J=1.0 Hz), 8.63 (1H, dd, J=8.7, 2.5 Hz), 8.99 (1H, d, J=1.9 Hz).

D) 1-(2-(6-((5-(cyclopropylmethoxy)pyridin-3-yl)oxy)pyridin-3-yl)-1,3-benzoxazol-6-yl)ethanamine A mixture of 1-(2-(6-((5-(cyclopropylmethoxy)pyridin-3-yl)oxy)pyridin-3-yl)-1,3-benzoxazol-6-yl)ethanone (0.9 g), sodium cyanoborohydride (423 mg), ammonium acetate (864 mg), methanol (50 ml) and THF (50 ml) was stirred at 60° C. overnight. The reaction mixture was cooled to room temperature, and concentrated under reduced pressure. The obtained residue was extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (256 mg).
¹H NMR (300 MHz, DMSO-d₆) δ 0.29-0.37 (2H, m), 0.53-0.63 (2H, m), 1.21-1.27 (1H, m), 1.30 (3H, d, J=6.6 Hz), 3.92 (2H, d, J=7.1 Hz), 4.10-4.20 (1H, m), 7.32-7.39 (2H, m), 7.40-7.46 (1H, m), 7.67-7.75 (1H, m), 7.77-7.82 (1H, m), 8.10-8.15 (1H, m), 8.20-8.24 (1H, m), 8.55-8.62 (1H, m), 8.90-8.94 (1H, m).
* The peak of NH₂ was not observed.

E) 1-(1-(2-(6-((5-(cyclopropylmethoxy)pyridin-3-yl)oxy)pyridin-3-yl)-1,3-benzoxazol-6-yl)ethyl)urea A mixture of 1-(2-(6-((5-(cyclopropylmethoxy)pyridin-3-yl)oxy)pyridin-3-yl)-1,3-benzoxazol-6-yl)ethanamine (256 mg), trimethylsilyl isocyanate (0.215 ml), triethylamine (0.266 ml) and THF (5 ml) was stirred at room temperature overnight. The reaction mixture was extracted with ethyl acetate and water. The obtained organic layer was washed with saturated brine, dried over anhydrous magnesium sulfate, and concentrated under reduced pressure. The obtained residue was purified by silica gel column chromatography (NH, ethyl acetate/methanol), and crystallized from ethanol/hexane to give the title compound (100 mg).

$^1$H NMR (300 MHz, DMSO-d$_6$) δ 0.29-0.38 (2H, m), 0.54-0.63 (2H, m), 1.18-1.31 (1H, m), 1.37 (3H, d, J=7.0 Hz), 3.92 (2H, d, J=7.1 Hz), 4.77-4.92 (1H, m), 5.47 (2H, s), 6.57 (1H, d, J=7.8 Hz), 7.32-7.41 (3H, m), 7.68 (1H, s), 7.74 (1H, d, J=8.2 Hz), 8.13 (1H, d, J=2.2 Hz), 8.23 (1H, d, J=2.5 Hz), 8.59 (1H, dd, J=8.7, 2.5 Hz), 8.93 (1H, d, J=1.9 Hz).

Example 107

1-(1-(2-(6-(3-(2,2-difluoropropoxy)phenoxy)pyridin-3-yl)-1,3-benzoxazol-6-yl)ethyl)urea A) 1-(2-(6-(3-(benzyloxy)phenoxy)pyridin-3-yl)-1,3-benzoxazol-6-yl) ethanone A mixture of 1-(2-(6-chloropyridin-3-yl)-1,3-benzoxazol-6-yl)ethanone (5 g), 3-(benzyloxy)phenol (4.41 g), cesium carbonate (11.95 g) and DMF (50 ml) was stirred at 100° C. for 2 hr. The reaction mixture was cooled to room temperature, and extracted with ethyl acetate and water. The obtained organic layer was washed with saturated brine, dried over anhydrous magnesium sulfate, and concentrated under reduced pressure. To the obtained residue was added ethanol, and the obtained solid was collected by filtration to give the title compound (6 g).
$^1$H NMR (300 MHz, DMSO-d$_6$) δ 2.68 (3H, s), 5.12 (2H, s), 6.77-6.85 (1H, m), 6.90-6.99 (2H, m), 7.22-7.29 (1H, m), 7.32-7.50 (6H, m), 7.88-7.96 (1H, m), 8.01-8.09 (1H, m), 8.37-8.42 (1H, m), 8.53-8.63 (1H, m), 8.95-9.02 (1H, m).

B) 6-(1-azidoethyl)-2-(6-(3-(benzyloxy)phenoxy)pyridin-3-yl)-1,3-benzoxazole

To a mixture of 1-(2-(6-(3-(benzyloxy)phenoxy)pyridin-3-yl)-1,3-benzoxazol-6-yl)ethanone (6 g), ethanol (50 ml) and THF (50 ml) was added sodium borohydride (0.6 g) under ice-cooling. The reaction mixture was stirred at room temperature for 2 hr, and extracted with ethyl acetate and 1N hydrochloric acid. The obtained organic layer was washed with saturated brine, dried over anhydrous magnesium sulfate, and concentrated under reduced pressure. To the obtained residue were added toluene (50 ml), diphenylphosphoryl azide (7.5 g) and DBU (4 ml). The reaction mixture was stirred at room temperature for 2 hr, and extracted with ethyl acetate and water. The obtained organic layer was washed with saturated brine, dried over anhydrous magnesium sulfate, and concentrated under reduced pressure. The obtained residue was purified by silica gel column chromatography (hexane/ethyl acetate) to give the title compound (4.68 g).
$^1$H NMR (300 MHz, DMSO-d$_6$) δ 1.54 (3H, d, J=6.8 Hz), 4.96-5.08 (1H, m), 5.12 (2H, s), 6.78-6.86 (1H, m), 6.89-6.99 (2H, m), 7.22-7.26 (1H, m), 7.31-7.46 (7H, m), 7.79-7.90 (2H, m), 8.56 (1H, dd, J=8.6, 2.5 Hz), 8.95 (1H, dd, J=2.5, 0.7 Hz).

C) 1-(2-(6-(3-(benzyloxy)phenoxy)pyridin-3-yl)-1,3-benzoxazol-6-yl)ethanamine

A mixture of 6-(1-azidoethyl)-2-(6-(3-(benzyloxy)phenoxy)pyridin-3-yl)-1,3-benzoxazole (4.68 g), triphenylphosphine (5.3 g), THF (40 ml) and water (20 ml) was stirred at 60° C. for 2 hr. The reaction mixture was cooled to room temperature, and extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (3.69 g).
$^1$H NMR (300 MHz, DMSO-d$_6$) δ 1.30 (3H, d, J=6.6 Hz), 1.95 (2H, s), 4.14 (1H, d, J=6.6 Hz), 5.12 (2H, s), 6.77-6.84 (1H, m), 6.88-6.98 (2H, m), 7.22 (1H, dd, J=8.6, 0.7 Hz), 7.31-7.49 (7H, m), 7.71 (1H, d, J=8.2 Hz), 7.77-7.82 (1H, m), 8.54 (1H, dd, J=8.7, 2.5 Hz), 8.93 (1H, dd, J=2.4, 0.7 Hz).

D) tert-butyl (1-(2-(6-(3-(benzyloxy)phenoxy)pyridin-3-yl)-1,3-benzoxazol-6-yl)ethyl)carbamate A mixture of 1-(2-(6-(3-(benzyloxy)phenoxy)pyridin-3-yl)-1,3-benzoxazol-6-yl)ethanamine (3.69 g), di-tert-butyl dicarbonate (2.94 ml), triethylamine (2.351 ml) and THF (30 ml) was stirred at room temperature for 2 hr. The reaction mixture was extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (3.25 g).
$^1$H NMR (300 MHz, DMSO-d$_6$) δ 1.37 (12H, brs), 4.68-4.83 (1H, m), 5.05-5.14 (2H, m), 6.76-6.85 (1H, m), 6.88-6.98 (2H, m), 7.18-7.27 (1H, m), 7.30-7.56 (8H, m), 7.65-7.77 (2H, m), 8.49-8.59 (1H, m), 8.90-8.97 (1H, m).

E) tert-butyl (1-(2-(6-(3-(2-oxopropoxy)phenoxy)pyridin-3-yl)-1,3-benzoxazol-6-yl)ethyl)carbamate A mixture of tert-butyl (1-(2-(6-(3-(benzyloxy)phenoxy)pyridin-3-yl)-1,3-benzoxazol-6-yl)ethyl)carbamate (3.25 g), 10% Pd/C (containing water (50%), 650 mg), THF (100 ml) and methanol (50 ml) was stirred under a hydrogen atmosphere at room temperature for 4 hr. The reaction mixture was filtered through celite, and concentrated under reduced pressure. To the obtained residue were added DMF (30 ml), potassium carbonate (2 g) and 1-bromoacetone (1 ml). The reaction mixture was stirred at room temperature for 2 hr, and extracted with ethyl acetate and water. The obtained organic layer was washed with saturated brine, dried over anhydrous magnesium sulfate, and concentrated under reduced pressure. The obtained residue was purified by silica gel column chromatography (hexane/ethyl acetate) to give the title compound (2.19 g).
$^1$H NMR (300 MHz, DMSO-d$_6$) δ 1.28-1.45 (12H, m), 2.15 (3H, s), 4.70-4.82 (1H, m), 4.85 (2H, s), 6.77-6.85 (3H, m), 7.19-7.26 (1H, m), 7.30-7.40 (2H, m), 7.46-7.55 (1H, m), 7.66-7.70 (1H, m), 7.71-7.78 (11H, m), 8.50-8.59 (1H, m), 8.91-8.97 (1H, m).

F) tert-butyl (1-(2-(6-(3-(2,2-difluoropropoxy)phenoxy)pyridin-3-yl)-1,3-benzoxazol-6-yl)ethyl)carbamate To a mixture of tert-butyl (1-(2-(6-(3-(2-oxopropoxy)phenoxy)pyridin-3-yl)-1,3-benzoxazol-6-yl)ethyl)carbamate (2.19 g) and toluene (150 ml) was added [bis(2-methoxyethyl)amino]sulfur trifluoride (2.4 ml) and the mixture was stirred at room temperature overnight. Furthermore, [bis(2-methoxyethyl)amino]sulfur trifluoride (1.5 ml) was added, and the mixture was stirred at 40° C. for 2 hr. The reaction mixture was cooled to room temperature, and extracted with toluene and saturated aqueous sodium hydrogen carbonate solution. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (1.98 g).

$^1$H NMR (300 MHz, DMSO-d$_6$) δ 1.29-1.43 (12H, m), 1.73 (3H, t, J=19.3 Hz), 4.24-4.37 (2H, m), 4.70-4.83 (1H, m), 6.78-6.89 (1H, m), 6.90-6.99 (2H, m), 7.22-7.28 (1H, m), 7.33-7.44 (2H, m), 7.47-7.55 (1H, m), 7.65-7.70 (1H, m), 7.71-7.77 (1H, m), 8.52-8.60 (1H, m), 8.91-8.97 (1H, m).

G) 1-(2-(6-(3-(2,2-difluoropropoxy)phenoxy)pyridin-3-yl)-1,3-benzoxazol-6-yl)ethanamine hydrochloride A mixture of tert-butyl (1-(2-(6-(3-(2,2-difluoropropoxy) phenoxy)pyridin-3-yl)-1,3-benzoxazol-6-yl)ethyl)carbamate (1.98 g) and 4N hydrogen chloride-ethyl acetate solution (20 ml) was stirred at room temperature for 1 hr. The precipitated solid was collected by filtration to give the title compound (1.7 g).

$^1$H NMR (300 MHz, DMSO-d$_6$) δ 1.59 (3H, d, J=6.8 Hz), 1.74 (3H, t, J=19.3 Hz), 4.32 (2H, t, J=12.7 Hz), 4.53-4.65 (1H, m), 6.86 (1H, d, J=8.8 Hz), 6.91-7.00 (2H, m), 7.27 (1H, dd, J=8.7, 0.6 Hz), 7.40 (1H, t, J=8.4 Hz), 7.59 (1H, dd, J=8.4, 1.5 Hz), 7.87 (1H, d, J=8.2 Hz), 8.03 (1H, d, J=1.0 Hz), 8.59 (1H, dd, J=8.7, 2.5 Hz), 8.66 (3H, brs), 8.98 (1H, dd, J=2.5, 0.7 Hz).

H) 1-(1-(2-(6-(3-(2,2-difluoropropoxy)phenoxy) pyridin-3-yl)-1,3-benzoxazol-6-yl)ethyl)urea A mixture of 1-(2-(6-(3-(2,2-difluoropropoxy)phenoxy) pyridin-3-yl)-1,3-benzoxazol-6-yl)ethanamine hydrochloride (0.85 g), 4-nitrophenyl carbonochloridate (0.5 g), triethylamine (0.8 ml) and THF (10 ml) was stirred at 0° C. for 30 min. To the reaction mixture was added 28% aqueous ammonia (0.6 ml), and the mixture was stirred at room temperature for 30 min. The reaction mixture was extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from acetone/water to give the title compound (385 mg).

$^1$H NMR (300 MHz, DMSO-d$_6$) δ 1.37 (3H, d, J=6.9 Hz), 1.74 (3H, t, J=19.3 Hz), 4.31 (2H, t, J=12.7 Hz), 4.77-4.92 (1H, m), 5.47 (2H, s), 6.56 (1H, d, J=8.1 Hz), 6.81-6.89 (1H, m), 6.91-6.99 (2H, m), 7.25 (1H, dd, J=8.7, 0.6 Hz), 7.31-7.44 (2H, m), 7.68 (1H, s), 7.74 (1H, d, J=8.3 Hz), 8.56 (1H, dd, J=8.7, 2.5 Hz), 8.95 (1H, dd, J=2.5, 0.7 Hz).

Example 108

1-(1-(2-(6-(3-(cyclopropylmethoxy)phenoxy)pyridin-3-yl)-7-fluoro-1,3-benzoxazol-6-yl)ethyl)urea A) N-(4-bromo-3-fluoro-2-hydroxyphenyl)-6-chloronicotinamide A mixture of 6-amino-3-bromo-2-fluorophenol (500 mg), 6-chloronicotinoyl chloride (470 mg), triethylamine (0.507 ml) and THF (35 ml) was stirred at room temperature for 18 hr. To the reaction mixture was added water, and the mixture was extracted with ethyl acetate. The obtained organic layer was washed with saturated brine, dried over anhydrous magnesium sulfate, and concentrated under reduced pressure. To the obtained residue was added diisopropyl ether, and the obtained solid was collected by filtration to give the title compound (512 mg).

MS (ESI+): [M−H]$^+$403.0.

B) 6-bromo-2-(6-chloropyridin-3-yl)-7-fluoro-1,3-benzoxazole

A mixture of N-(4-bromo-3-fluoro-2-hydroxyphenyl)-6-chloronicotinamide (578 mg), triphenylphosphine (288 mg), azodiisopropyl azodicarboxylate (578 mg) and THF (25 ml) was stirred with heating under reflux for 4 hr. To the reaction mixture was added water, and the mixture was extracted with ethyl acetate. The obtained organic layer was washed with saturated brine, dried over anhydrous magnesium sulfate, and concentrated under reduced pressure. To the obtained residue was added ethanol, and the obtained solid was collected by filtration to give the title compound (136.6 mg).

$^1$H NMR (300 MHz, DMSO-d$_6$) δ 7.65-7.84 (3H, m), 8.60 (1H, dd, J=8.4, 2.5 Hz), 9.21 (1H, dd, J=2.5, 0.7 Hz).

C) 6-bromo-2-(6-(3-(cyclopropylmethoxy)phenoxy) pyridin-3-yl)-7-fluoro-1,3-benzoxazole A mixture of 6-bromo-2-(6-chloropyridin-3-yl)-7-fluoro-1,3-benzoxazole (136 mg), 3-(cyclopropylmethoxy)phenol (82 mg), cesium carbonate (271 mg) and DMF (20 ml) was stirred at 110° C. for 2 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (115.5 mg).

$^1$H NMR (300 MHz, DMSO-d$_6$) δ 0.26-0.36 (2H, m), 0.49-0.62 (2H, m), 1.13-1.30 (1H, m), 3.82 (2H, d, J=7.1 Hz), 6.72-6.91 (3H, m), 7.23 (1H, dd, J=8.7, 0.7 Hz), 7.35 (1H, t, J=8.1 Hz), 7.59-7.77 (2H, m), 8.58 (1H, dd, J=8.7, 2.5 Hz), 8.97 (1H, dd, J=2.5, 0.6 Hz).

D) 1-(2-(6-(3-(cyclopropylmethoxy)phenoxy)pyridin-3-yl)-7-fluoro-1,3-benzoxazol-6-yl)ethanone A mixture of 6-bromo-2-(6-(3-(cyclopropylmethoxy)phenoxy)pyridin-3-yl)-7-fluoro-1,3-benzoxazole (115 mg), (bis(1,1'-diphenylphosphino)ferrocene)dichloropalladium (8.86 mg), (1-ethoxyvinyl)tributyltin (0.115 ml) and DMF (12 ml) was stirred at 120° C. for 18 hr. To the reaction mixture was added 1N hydrochloric acid (5 ml), and the mixture was stirred at room temperature for 1 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ ethyl acetate) to give the title compound (65 mg).

MS (ESI+): [M+H]$^+$ 419.2.

E) 1-(2-(6-(3-(cyclopropylmethoxy)phenoxy)pyridin-3-yl)-7-fluoro-1,3-benzoxazol-6-yl)ethanol A mixture of 1-(2-(6-(3-(cyclopropylmethoxy)phenoxy) pyridin-3-yl)-7-fluoro-1,3-benzoxazol-6-yl)ethanone (65 mg), sodium borohydride (23 mg), THF (10 ml) and ethanol (10 ml) was stirred at room temperature for 1 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (55.5 mg).

MS (ESI+): [M+H]+ 421.1.

F) 6-(1-azidoethyl)-2-(6-(3-(cyclopropylmethoxy)phenoxy)pyridin-3-yl)-7-fluoro-1,3-benzoxazole A mixture of 1-(2-(6-(3-(cyclopropylmethoxy)phenoxy)pyridin-3-yl)-7-fluoro-1,3-benzoxazol-6-yl)ethanol (55.5 mg), DBU (0.109 ml), diphenylphosphoryl azide (0.114 ml) and toluene (20 ml) was stirred at 65° C. for 18 hr. To the reaction mixture was added water, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (130 mg).

MS (ESI+): [M+H]+ 446.2.

G) 1-(2-(6-(3-(cyclopropylmethoxy)phenoxy)pyridin-3-yl)-7-fluoro-1,3-benzoxazol-6-yl)ethanamine A mixture of 6-(1-azidoethyl)-2-(6-(3-(cyclopropylmethoxy)phenoxy)pyridin-3-yl)-7-fluoro-1,3-benzoxazole (57.9 mg), 10% Pd/C (containing water (50%), 35 mg), methanol (5 ml) and ethyl acetate (5 ml) was stirred under a hydrogen atmosphere at room temperature for 1 hr. The reaction mixture was filtered, and concentrated under reduced pressure to give the title compound (28 mg).

MS (ESI+): [M+H]+ 420.2.

H) 1-(1-(2-(6-(3-(cyclopropylmethoxy)phenoxy)pyridin-3-yl)-7-fluoro-1,3-benzoxazol-6-yl)ethyl)urea A mixture of 1-(2-(6-(3-(cyclopropylmethoxy)phenoxy)pyridin-3-yl)-7-fluoro-1,3-benzoxazol-6-yl)ethanamine (14 mg), 4-nitrophenyl carbonochloridate (9.42 mg), triethylamine (9.3 µl) and THF (35 ml) was stirred at room temperature for 2 hr. To the reaction mixture was added 28% aqueous ammonia (0.023 ml), and the mixture was stirred at room temperature for 1 hr. To the reaction mixture was added 1N aqueous sodium hydroxide solution, and the mixture was extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate), and crystallized from ethyl acetate/hexane to give the title compound (1.8 mg).

$^1$H NMR (300 MHz, CDCl$_3$) δ 0.30-0.39 (2H, m), 0.60-0.70 (2H, m), 1.20-1.35 (1H, m), 1.51-1.62 (3H, m), 3.81 (2H, d, J=7.0 Hz), 4.33 (2H, brs), 4.98 (1H, brs), 5.20 (1H, quin, J=7.2 Hz), 6.72-6.86 (3H, m), 7.04 (1H, dd, J=8.6, 0.7 Hz), 7.28-7.38 (2H, m), 7.50 (1H, d, J=8.2 Hz), 8.48 (1H, dd, J=8.6, 2.5 Hz), 9.05 (1H, d, J=2.5 Hz).

Example 109

1-(1-(2-(5-(3-(cyclopropylmethoxy)phenoxy)pyrazin-2-yl)-1,3-benzoxazol-6-yl)ethyl)urea A) methyl 5-(3-(cyclopropylmethoxy)phenoxy)pyrazine-2-carboxylate A mixture of methyl 5-chloropyrazine-2-carboxylate (5 g), 3-(cyclopropylmethoxy)phenol (5.23 g), cesium carbonate (18.88 g) and DMF (50 ml) was stirred at 60° C. for 2 hr. The reaction mixture was cooled to room temperature, and extracted with ethyl acetate and saturated aqueous ammonium chloride solution. The obtained organic layer was washed with saturated brine, dried over anhydrous magnesium sulfate, and concentrated under reduced pressure. The obtained residue was purified by silica gel column chromatography (hexane/ethyl acetate) to give the title compound (8.7 g).

$^1$H NMR (300 MHz, DMSO-d$_6$) δ 0.25-0.35 (2H, m), 0.50-0.61 (2H, m), 1.20-1.28 (1H, m), 3.81 (2H, d, J=7.1 Hz), 3.89 (3H, s), 6.77-6.90 (3H, m), 7.29-7.40 (1H, m), 8.62 (1H, d, J=1.3 Hz), 8.78 (1H, d, J=1.3 Hz).

B) 5-(3-(cyclopropylmethoxy)phenoxy)pyrazine-2-carboxylic acid

A mixture of methyl 5-(3-(cyclopropylmethoxy)phenoxy)pyrazine-2-carboxylate (8.7 g), 2N aqueous sodium hydroxide solution (72.4 ml), THF (50 ml) and methanol (50 ml) was stirred at room temperature for 4 hr. The reaction mixture was acidified with 2N hydrochloric acid and extracted with ethyl acetate. The obtained organic layer was washed with saturated brine, dried over anhydrous magnesium sulfate, and concentrated under reduced pressure. The obtained residue was purified by silica gel column chromatography (hexane/ethyl acetate) to give the title compound (4.8 g).

$^1$H NMR (300 MHz, DMSO-d$_6$) δ 0.25-0.35 (2H, m), 0.50-0.61 (2H, m), 1.19-1.27 (1H, m), 3.81 (2H, d, J=7.0 Hz), 6.76-6.90 (3H, m), 7.35 (1H, t, J=8.5 Hz), 8.59 (1H, d, J=1.2 Hz), 8.76 (1H, d, J=1.3 Hz), 13.42 (1H, brs)

C) N-(4-acetyl-2-hydroxyphenyl)-5-(3-(cyclopropylmethoxy)phenoxy) pyrazine-2-carboxamide To a mixture of 5-(3-(cyclopropylmethoxy)phenoxy)pyrazine-2-carboxylic acid (4.8 g), DMF (0.065 ml) and THF (50 ml) was added oxalyl chloride (2.2 ml) under ice-cooling. The reaction mixture was stirred at room temperature for 1 hr, and concentrated under reduced pressure. The obtained residue was dissolved in THF (50 ml), and 1-(4-amino-3-hydroxyphenyl)ethanone (2.53 g) and triethylamine (3.51 ml) were added under ice-cooling. The reaction mixture was stirred at room temperature overnight, and extracted with ethyl acetate and water. The obtained organic layer was washed with saturated brine, dried over anhydrous magnesium sulfate, and concentrated under reduced pressure. To the obtained residue was added diisopropyl ether, and the precipitated solid was collected by filtration to give the title compound (3.27 g).

$^1$H NMR (300 MHz, DMSO-d) δ 0.31 (2H, dd, J=4.8, 1.5 Hz), 0.57 (2H, dd, J=8.1, 1.8 Hz), 1.16-1.29 (1H, m), 2.52 (3H, s), 3.82 (2H, d, J=7.1 Hz), 6.78-6.91 (3H, m), 7.30-7.41 (1H, m), 7.49 (1H, d, J=2.0 Hz), 7.56 (1H, s), 8.48-8.52 (1H, m), 8.66 (1H, d, J=1.3 Hz), 8.89 (1H, d, J=1.3 Hz), 10.23 (1H, s), 10.82-10.88 (1H, m).

D) 1-(2-(5-(3-(cyclopropylmethoxy)phenoxy)pyrazin-2-yl)-1,3-benzoxazol-6-yl)ethanone A mixture of N-(4-acetyl-2-hydroxyphenyl)-5-(3-(cyclopropylmethoxy)phenoxy)pyrazine-2-carboxamide (3.27 g), diisopropyl azodicarboxylate (1.9 M toluene solution, 5.33 ml), triphenylphosphine (2.66 g) and THF (50 ml) was stirred at 60° C. for 1 hr. The reaction mixture was cooled to room temperature, and concentrated under reduced pressure. To the obtained residue was added ethanol, and the obtained solid was collected by filtration to give the title compound (2.52 g).

$^1$H NMR (300 MHz, DMSO-d$_6$) δ 0.27-0.36 (2H, m), 0.50-0.62 (2H, m), 1.13-1.31 (1H, m), 2.69 (3H, s), 3.83 (2H, d, J=7.0 Hz), 6.81-6.94 (3H, m), 7.38 (1H, t, J=8.2 Hz), 7.95 (1H, d, J=5.6 Hz), 8.09 (1H, t, J=1.7 Hz), 8.43 (1H, d, J=1.0 Hz), 8.55 (1H, d, J=1.3 Hz), 9.11 (1H, d, J=1.3 Hz).

E) 1-(2-(5-(3-(cyclopropylmethoxy)phenoxy)pyrazin-2-yl)-1,3-benzoxazol-6-yl)ethanol To a mixture of 1-(2-(5-(3-(cyclopropylmethoxy) phenoxy) pyrazin-2-yl)-1,3-benzoxazol-6-yl)ethanone (2.52 g), THF (50 ml) and ethanol (25 ml) was added sodium borohydride (238 mg) under ice-cooling. The reaction mixture was stirred at room temperature for 2 hr, and 1N hydrochloric acid was added. The obtained mixture was extracted with ethyl acetate and water. The obtained organic layer was washed with saturated brine, dried over anhydrous magnesium sulfate, and concentrated under reduced pressure. The obtained residue was purified by silica gel column chromatography (hexane/ethyl acetate) to give the title compound (1.84 g).

$^1$H NMR (300 MHz, DMSO-d$_6$) δ 0.24-0.38 (2H, m), 0.48-0.62 (2H, m), 1.21-1.28 (1H, m), 1.39 (3H, d, J=6.3 Hz), 3.83 (2H, d, J=7.0 Hz), 4.81-4.96 (1H, m), 5.37 (1H, d, J=4.2 Hz), 6.75-6.95 (3H, m), 7.29-7.50 (2H, m), 7.73-7.86 (2H, m), 8.71 (1H, d, J=1.3 Hz), 9.05 (1H, d, J=1.3 Hz).

F) 6-(1-azidoethyl)-2-(5-(3-(cyclopropylmethoxy)phenoxy)pyrazin-2-yl)-1,3-benzoxazole A mixture of 1-(2-(5-(3-(cyclopropylmethoxy) phenoxy) pyrazin-2-yl)-1,3-benzoxazol-6-yl)ethanol (1.84 g), DBU (2.062 ml), diphenylphosphoryl azide (2.51 g) and toluene (20 ml) was stirred at room temperature overnight. The reaction mixture was extracted with toluene and water. The obtained organic layer was washed with saturated brine, dried over anhydrous magnesium sulfate, and concentrated under reduced pressure. The obtained residue was purified by silica gel column chromatography (hexane/ethyl acetate) to give the title compound (1.17 g).

$^1$H NMR (300 MHz, DMSO-d$_6$) δ 0.27-0.36 (2H, m), 0.52-0.61 (2H, m), 1.20-1.29 (1H, m), 1.55 (3H, d, J=6.8 Hz), 3.83 (2H, d, J=7.0 Hz), 5.00-5.11 (1H, m), 6.81-6.94 (3H, m), 7.37 (1H, t, J=8.3 Hz), 7.47-7.54 (1H, m), 7.84-7.95 (2H, m), 8.73 (1H, d, J=1.3 Hz), 9.07 (1H, d, J=1.3 Hz).

G) 1-(1-(2-(5-(3-(cyclopropylmethoxy)phenoxy)pyrazin-2-yl)-1,3-benzoxazol-6-yl)ethyl)urea A mixture of 6-(1-azidoethyl)-2-(5-(3-(cyclopropylmethoxy)phenoxy)pyrazin-2-yl)-1,3-benzoxazole (1.17 g), 10% palladium carbon (containing water (50%), 291 mg) and THF (20 ml) was stirred under a hydrogen atmosphere at room temperature for 2 hr. The reaction mixture was filtered through celite, and concentrated under reduced pressure. To the obtained residue were added THF (10 ml), triethylamine (0.761 ml) and trimethylsilyl isocyanate (0.555 ml), and the mixture was stirred at room temperature overnight. The reaction mixture was extracted with THF and saturated brine. The obtained organic layer was washed with saturated brine, dried over anhydrous magnesium sulfate, and concentrated under reduced pressure. The obtained residue was purified by silica gel column chromatography (NH, ethyl acetate/methanol), and crystallized from acetone/water to give the title compound (456 mg).

$^1$H NMR (300 MHz, DMSO-d$_6$) δ 0.27-0.35 (2H, m), 0.51-0.61 (2H, m), 1.14-1.29 (1H, m), 1.38 (3H, d, J=7.0 Hz), 3.82 (2H, d, J=7.0 Hz), 4.79-4.94 (1H, m), 5.47 (2H, s), 6.59 (1H, d, J=8.0 Hz), 6.80-6.92 (3H, m), 7.32-7.44 (2H, m), 7.73 (1H, s), 7.80 (1H, d, J=8.3 Hz), 8.71 (1H, d, J=1.3 Hz), 9.05 (1H, d, J=1.3 Hz).

Example 110

1-(1-(2-(6-(3-(cyclopropylmethoxy)phenoxy)pyridazin-3-yl)-1,3-benzoxazol-6-yl)ethyl)urea A) N-(4-acetyl-2-hydroxyphenyl)-6-chloro-pyridazine-3-carboxamide To a mixture of 6-chloropyridazine-3-carboxylic acid (5 g), DMF (0.122 ml) and THF (70 ml) was added dropwise oxalyl chloride (4.14 ml) under ice-cooling. The reaction mixture was stirred at room temperature for 1 hr, and concentrated under reduced pressure. To the obtained residue were added THF (70 ml), 1-(4-amino-3-hydroxyphenyl)ethanone (4.77 g) and triethylamine (13.19 ml), and the mixture was stirred at room temperature overnight. The reaction mixture was filtered through celite, and the obtained solid was washed with ethyl acetate. The combined organic layer was washed with saturated brine, dried over anhydrous magnesium sulfate, and concentrated under reduced pressure. To the obtained residue was added diisopropyl ether, and the obtained solid was collected by filtration to give the title compound (2.47 g).

$^1$H NMR (300 MHz, DMSO-d$_6$) δ 2.53 (3H, s), 7.51 (1H, s), 7.55-7.63 (1H, m), 8.21 (1H, d, J=8.9 Hz), 8.43 (2H, dd, J=14.8, 8.6 Hz), 10.54 (1H, brs), 10.80-11.07 (1H, m).

B) 1-(2-(6-chloropyridazin-3-yl)-1,3-benzoxazol-6-yl)ethanone

A mixture of N-(4-acetyl-2-hydroxyphenyl)-6-chloropyridazine-3-carboxamide (2.47 g), triphenylphosphine (2.89 g), diisopropyl azodicarboxylate (40% toluene solution, 5.35 ml) and THF (30 ml) was stirred at 60° C. for 2 hr. The reaction mixture was cooled to room temperature, and concentrated under reduced pressure. To the obtained residue was added ethanol, and the obtained solid was collected by filtration to give the title compound (1.79 g).

$^1$H NMR (300 MHz, DMSO-d$_6$) δ 2.71 (3H, s), 8.01-8.15 (2H, m), 8.19-8.26 (1H, m), 8.54 (1H, s), 8.61 (1H, d, J=9.1 Hz).

C) 1-(2-(6-(3-(cyclopropylmethoxy)phenoxy)pyridazin-3-yl)-1,3-benzoxazol-6-yl)ethanone A mixture of 1-(2-(6-chloropyridazin-3-yl)-1,3-benzoxazol-6-yl)ethanone (1.79 g), (3-cyclopropylmethoxy)phenol (1.289 g), cesium carbonate (4.26 g) and DMF (20 ml) was stirred at 100° C. for 2 hr. The reaction mixture was cooled to room temperature, and concentrated under reduced pressure. To the obtained residue was added diisopropyl ether, and the obtained solid was collected by filtration to give the title compound (1.74 g).

$^1$H NMR (300 MHz, DMSO-d$_6$) δ 0.28-0.35 (2H, m), 0.53-0.61 (2H, m), 1.17-1.30 (1H, m), 2.70 (3H, s), 3.84 (2H, d, J=7.0 Hz), 6.83-6.94 (3H, m), 7.35-7.43 (1H, m), 7.66 (1H, d, J=9.3 Hz), 8.00-8.05 (1H, m), 8.06-8.12 (1H, m), 8.52 (1H, d, J=0.8 Hz), 8.58 (1H, d, J=9.2 Hz).

D) 1-(2-(6-(3-(cyclopropylmethoxy)phenoxy) pyridazin-3-yl)-1,3-benzoxazol-6-yl)ethanamine A mixture of 1-(2-(6-(3-(cyclopropylmethoxy)phenoxy) pyridazin-3-yl)-1,3-benzoxazol-6-yl)ethanone (1.74 g), ammonium acetate (2.67 g), sodium cyanoborohydride (1.09 g) and methanol (20 ml) was stirred at 60° C. overnight. The reaction mixture was cooled to room temperature, and concentrated under reduced pressure to about half amount. The mixture was extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate) to give the title compound (900 mg).

$^1$H NMR (300 MHz, DMSO-$d_6$) δ 0.28-0.36 (2H, m), 0.52-0.61 (2H, m), 1.20-1.27 (1H, m), 1.31 (3H, d, J=6.6 Hz), 1.99-2.05 (2H, m), 3.84 (2H, d, J=7.0 Hz), 4.17 (1H, q, J=6.6 Hz), 6.81-6.94 (3H, m), 7.34-7.43 (1H, m), 7.45-7.53 (1H, m), 7.62 (1H, d, J=9.3 Hz), 7.81 (1H, d, J=8.2 Hz), 7.88 (1H, s), 8.52 (1H, d, J=9.3 Hz).

E) 1-(1-(2-(6-(3-(cyclopropylmethoxy)phenoxy) pyridazin-3-yl)-1, 3-benzoxazol-6-yl)ethyl)urea A mixture of 1-(2-(6-(3-(cyclopropylmethoxy)phenoxy) pyridazin-3-yl)-1,3-benzoxazol-6-yl)ethanamine (900 mg), trimethylsilyl isocyanate (0.757 ml), triethylamine (0.935 ml) and THF (10 ml) was stirred at room temperature overnight. The reaction mixture was extracted with ethyl acetate and water. The obtained organic layer was washed with saturated brine, dried over anhydrous magnesium sulfate, and concentrated under reduced pressure. The obtained residue was purified by silica gel column chromatography (NH, hexane/ethyl acetate), and crystallized from ethanol/water to give the title compound (675 mg).

$^1$H NMR (300 MHz, DMSO-$d_6$) δ 0.27-0.36 (2H, m), 0.50-0.63 (2H, m), 1.15-1.30 (1H, m), 1.38 (3H, d, J=7.0 Hz), 3.84 (2H, d, J=7.0 Hz), 4.79-4.96 (1H, m), 5.48 (2H, s), 6.59 (1H, d, J=8.1 Hz), 6.79-6.97 (3H, m), 7.33-7.48 (2H, m), 7.63 (1H, d, J=9.3 Hz), 7.77 (1H, s), 7.84 (1H, d, J=8.3 Hz), 8.53 (1H, d, J=9.3 Hz).

Examples 4-7, 14-17, 20-25, 27, 33, 34, 38, 39, 41, 42, 45, 46, 48-51, 53-55, 57-59, 61-64, 70, 72, 77, 78, 81, 83, 85, 87-89, 91, 92 and 94 were produced according to the methods shown in the above-mentioned Examples or a method analogous thereto.

The compound names, structural formulas and measured values of MS of the Example compounds are shown in the following Table 1-1 to Table 1-14.

TABLE 1-1

| Ex. No. | IUPAC name | Structure | MS |
|---|---|---|---|
| 1 | N-(1-(2-(3-(3-(cyclopropylmethoxy)-phenoxy)azetidin-1-yl)-1,3-benzoxazol-6-yl)ethyl)acetamide | 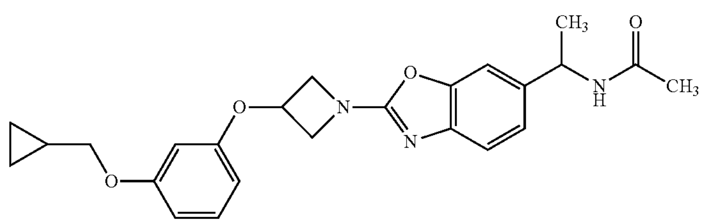 [SMILES: CC(=O)NC(C)c1ccc2nc(N3CC(Oc4cccc(OCC5CC5)c4)C3)oc2c1] | 422.2 |
| 1a | N-(1-(2-(3-(3-(cyclopropylmethoxy)-phenoxy)azetidin-1-yl)-1,3-benzoxazol-6-yl)ethyl)acetamide | 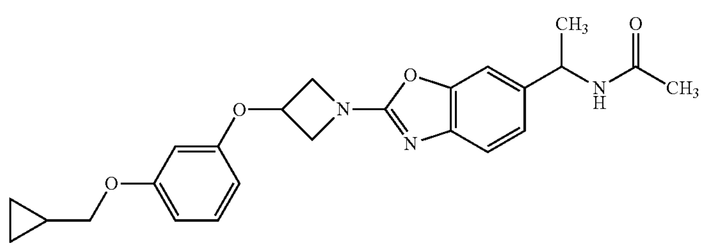 [SMILES: CC(=O)NC(C)c1ccc2nc(N3CC(Oc4cccc(OCC5CC5)c4)C3)oc2c1] | 422.2 |
| 1b | N-(1-(2-(3-(3-(cyclopropylmethoxy)-phenoxy)azetidin-1-yl)-1,3-benzoxazol-6-yl)ethyl)acetamide | 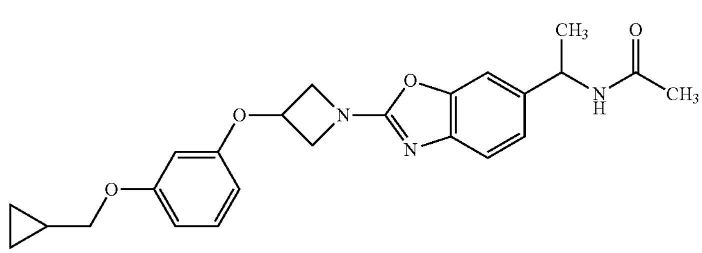 | 422.2 |

TABLE 1-1-continued

| Ex. No. | IUPAC name | Structure | MS |
|---|---|---|---|
| 2 | N-(1-(2-(4-(3-(cyclopropylmethoxy)-phenoxy)piperidin-1-yl)-1,3-benzoxazol-6-yl)-ethyl)acetamide | 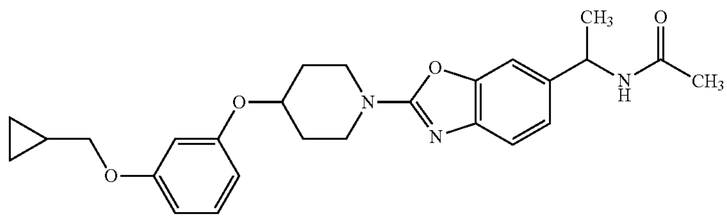 [SMILES: CC(=O)NC(C)c1ccc2nc(N3CCC(Oc4cccc(OCC5CC5)c4)CC3)oc2c1] | 450.2 |
| 3 | N-(1-(2-(3-(3-butoxyphenoxy)azetidin-1-yl)-1,3-benzoxazol-6-yl)ethyl)acetamide | 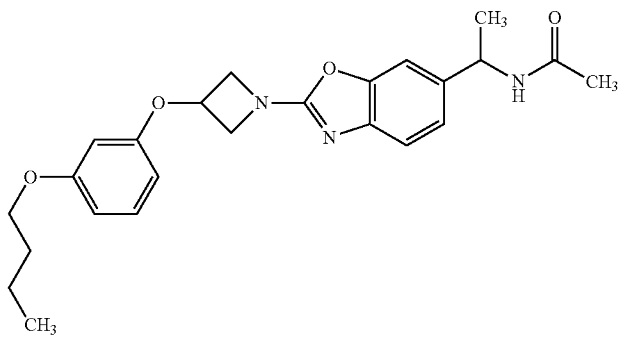 [SMILES: CCCCOc1cccc(OC2CN(c3nc4ccc(C(C)NC(C)=O)cc4o3)C2)c1] | 424.2 |
| 4 | N-(1-(2-(3-(3-(2-methoxyethoxy)phenoxy)-azetidin-1-yl)-1,3-benzoxazol-6-yl)ethyl)acetamide | 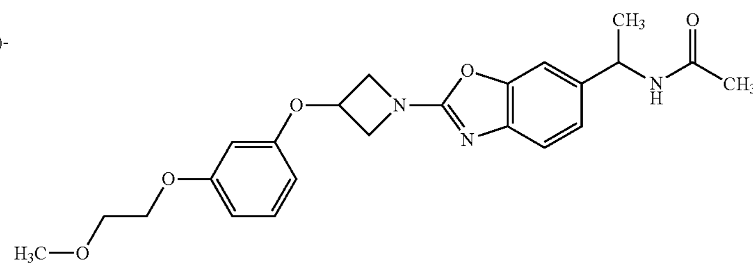 | 426.1 |
| 5 | N-(1-(2-(3-(3-(cyclobutylmethoxy)-phenoxy)azetidin-1-yl)-1,3-benzoxazol-6-yl)ethyl)acetamide | 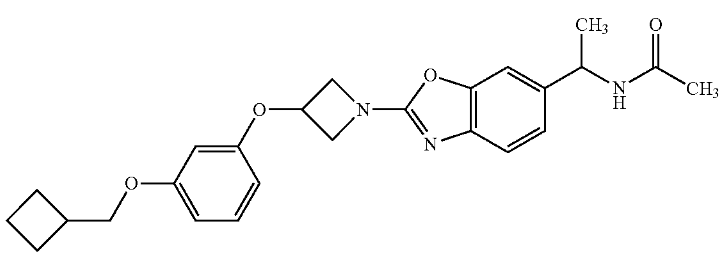 [SMILES: CC(=O)NC(C)c1ccc2nc(N3CC(Oc4cccc(OCC5CCC5)c4)C3)oc2c1] | 436.2 |
| 6 | N-(1-(2-(3-(3-(cyclobutyloxy)-phenoxy)azetidin-1-yl)-1,3-benzoxazol-6-yl)ethyl)acetamide | 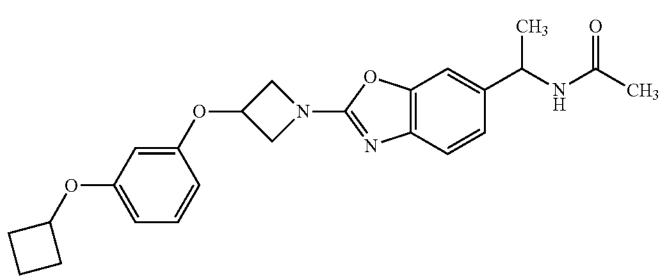 [SMILES: CC(=O)NC(C)c1ccc2nc(N3CC(Oc4cccc(OC5CCC5)c4)C3)oc2c1] | 422.2 |

TABLE 1-1-continued

| Ex. No. | IUPAC name | Structure | MS |
|---|---|---|---|
| 7 | N-(1-(2-(3-(3-(benzyloxy)phenoxy)-azetidin-1-yl)-1,3-benzoxazol-6-yl)ethyl)acetamide | 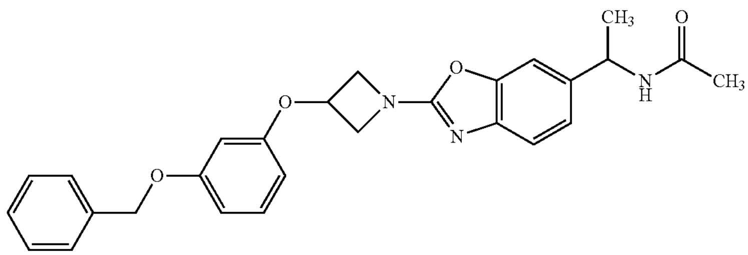 [SMILES: CC(=O)NC(C)c1ccc2nc(N3CC(Oc4cccc(OCc5ccccc5)c4)C3)oc2c1] | 458.3 |

TABLE 1-2

| Ex. No. | IUPAC name | Structure | MS |
|---|---|---|---|
| 8 | N-(1-(2-(4-(3-(cyclopropylmethoxy)-phenoxy)phenyl)-1,3-benzoxazol-6-yl)ethyl)acetamide | 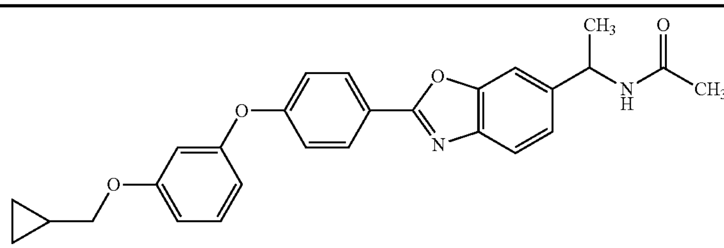 | 443.2 |
| 9 | N-(1-(2-(5-(3-(cyclopropylmethoxy)-phenoxy)pyridin-2-yl)-1,3-benzoxazol-6-yl)ethyl)acetamide | 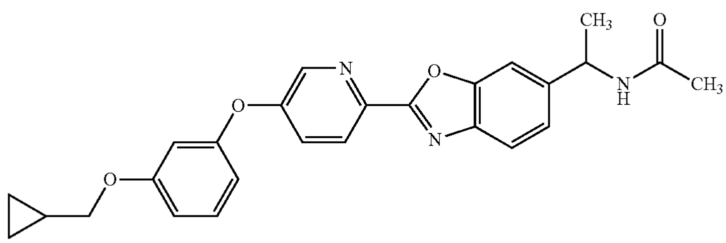 [SMILES: CC(=O)NC(C)c1ccc2nc(-c3ccc(Oc4cccc(OCC5CC5)c4)cn3)oc2c1] | 444.2 |
| 9a | N-(1-(2-(5-(3-(cyclopropylmethoxy)-phenoxy)pyridin-2-yl)-1,3-benzoxazol-6-yl)ethyl)acetamide | 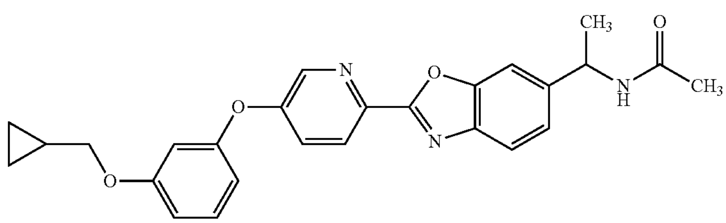 [SMILES: CC(=O)NC(C)c1ccc2nc(-c3ccc(Oc4cccc(OCC5CC5)c4)cn3)oc2c1] | 444.2 |
| 9b | N-(1-(2-(5-(3-(cyclopropylmethoxy)-phenoxy)pyridin-2-yl)-1,3-benzoxazol-6-yl)ethyl)acetamide | 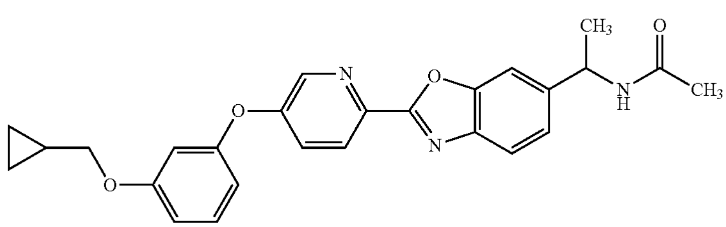 [SMILES: CC(=O)NC(C)c1ccc2nc(-c3ccc(Oc4cccc(OCC5CC5)c4)cn3)oc2c1] | 444.2 |
| 10 | N-(1-(2-(4-(3-(cyclopropylmethoxy)-phenoxy)cyclohexyl)-1,3-benzoxazol-6-yl)ethyl)acetamide | 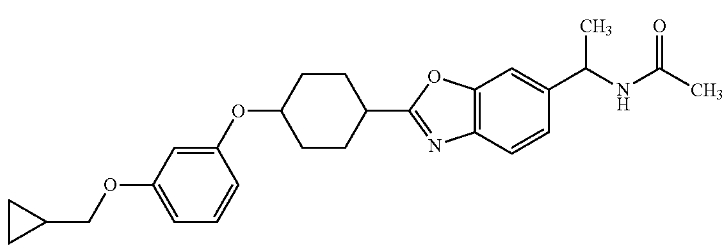 [SMILES: CC(=O)NC(C)c1ccc2nc(C3CCC(Oc4cccc(OCC5CC5)c4)CC3)oc2c1] | 449.2 |

TABLE 1-2-continued

| Ex. No. | IUPAC name | Structure | MS |
|---|---|---|---|
| 11 | N-(1-(2-(3-(3-(cyclopropylmethoxy)-phenoxy)cyclobutyl)-1,3-benzoxazol-6-yl)ethyl)acetamide | 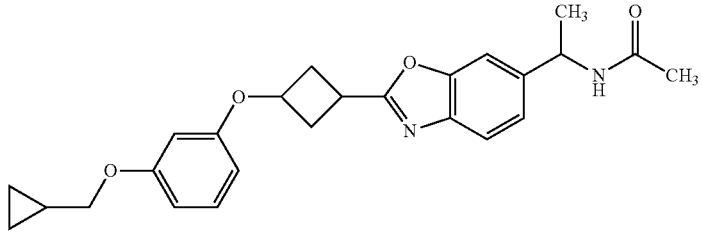 [SMILES: CC(=O)NC(C)c1ccc2nc(C3CC(Oc4cccc(OCC5CC5)c4)C3)oc2c1] | 421.2 |
| 12 | N-(1-(2-(5-(3-propoxyphenoxy)pyridin-2-yl)-1,3-benzoxazol-6-yl)ethyl)acetamide | 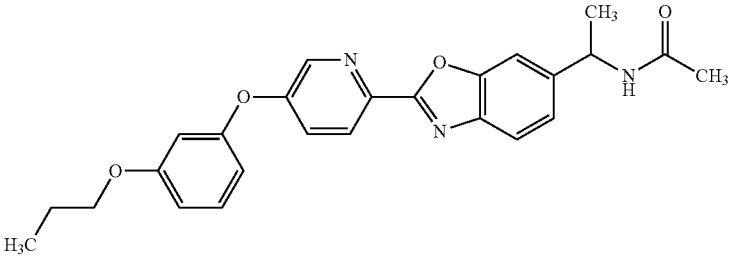 [SMILES: CCCOc1cccc(Oc2ccc(-c3nc4ccc(C(C)NC(C)=O)cc4o3)nc2)c1] | 432.1 |
| 13 | N-(1-(2-(5-(3-butoxyphenoxy)pyridin-2-yl)-1,3-benzoxazol-6-yl)ethyl)acetamide | 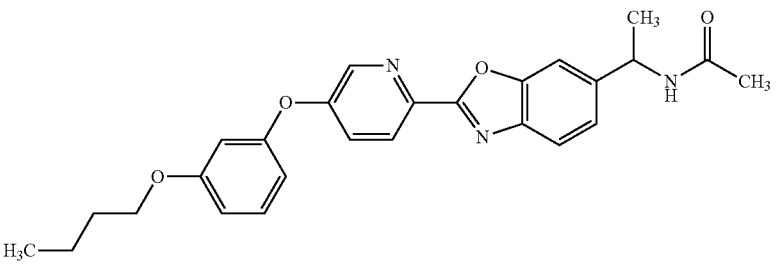 [SMILES: CCCCOc1cccc(Oc2ccc(-c3nc4ccc(C(C)NC(C)=O)cc4o3)nc2)c1] | 446.2 |
| 14 | N-(1-(2-(5-(3-(2-methoxyethoxy)phenoxy)-pyridin-2-yl)-1,3-benzoxazol-6-yl)ethyl)acetamide | 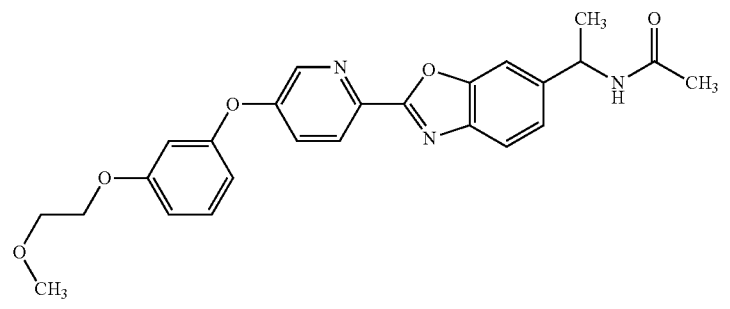 [SMILES: COCCOc1cccc(Oc2ccc(-c3nc4ccc(C(C)NC(C)=O)cc4o3)nc2)c1] | 448.1 |

TABLE 1-3

| Ex. No. | IUPAC name | Structure | MS |
|---|---|---|---|
| 15 | N-(1-(2-(5-(3-(2-ethoxyethoxy)phenoxy)-pyridin-2-yl)-1,3-benzoxazol-6-yl)ethyl)acetamide | 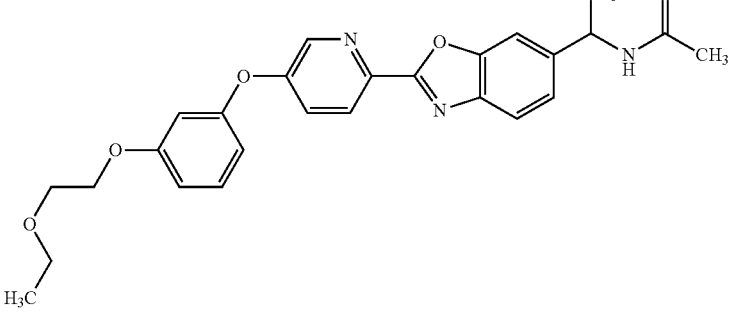 | 462.2 |

TABLE 1-3-continued

| Ex. No. | IUPAC name | Structure | MS |
|---|---|---|---|
| 16 | N-(1-(2-(5-(3-(3-methoxypropoxy)phenoxy)-pyridin-2-yl)-1,3-benzoxazol-6-yl)ethyl)acetamide | 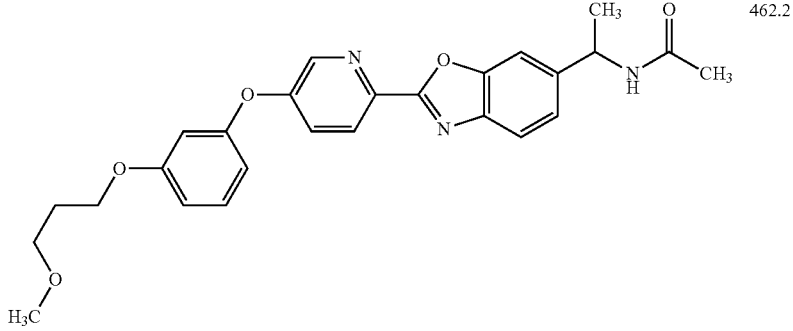 | 462.2 |
| 17 | N-(1-(2-(5-(3-isobutoxy-phenoxy)pyridin-2-yl)-1,3-benzoxazol-6-yl)ethyl)acetamide | 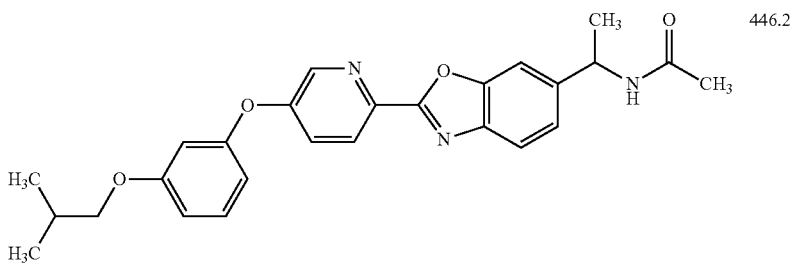 | 446.2 |
| 18 | N-(1-(2-(5-(3-(2,2-dimethylpro-poxy)phenoxy)pyridin-2-yl)-1,3-benzoxazol-6-yl)ethyl)acetamide | 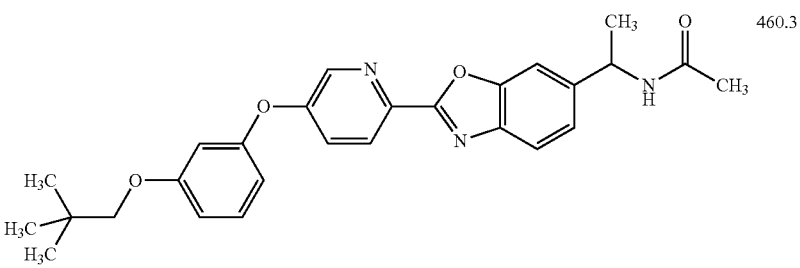 | 460.3 |
| 19 | N-(1-(2-(5-(3-(2-cyclopropylethoxy)-phenoxy)pyridin-2-yl)-1,3-benzoxazol-6-yl)ethyl)acetamide | 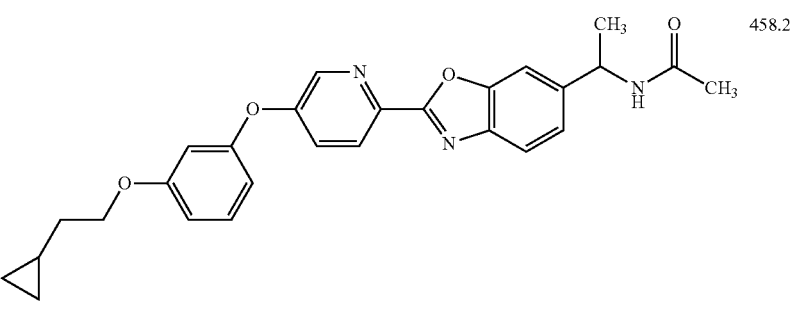 | 458.2 |
| 20 | N-(1-(2-(5-(3-(oxetan-2-ylmethoxy)phenoxy)-pyridin-2-yl)-1,3-benzoxazol-6-yl)ethyl)acetamide | 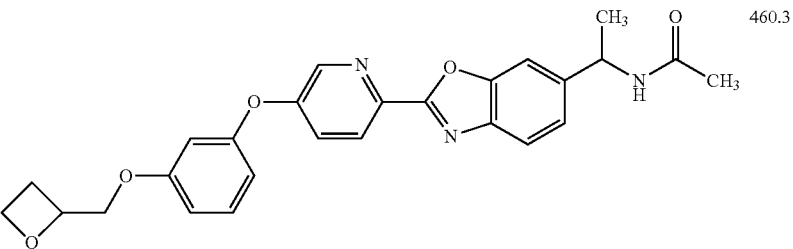 | 460.3 |

TABLE 1-3-continued

| Ex. No. | IUPAC name | Structure | MS |
|---|---|---|---|
| 21 | N-(1-(2-(5-(3-((3-methyloxetan-3-yl)-methoxy)phenoxy)pyridin-2-yl)-1,3-benzoxazol-6-yl)ethyl)acetamide | 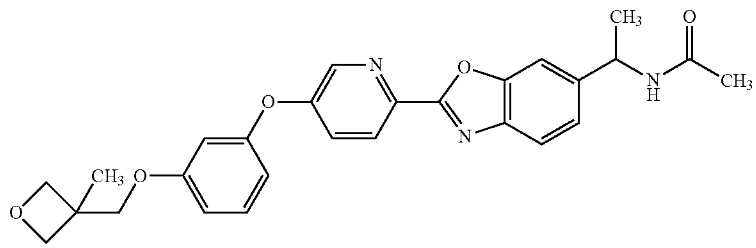 [SMILES: CC(=O)NC(C)c1ccc2nc(-c3ccc(Oc4cccc(OCC5(C)COC5)c4)cn3)oc2c1] | 474.2 |
| 22 | N-(1-(2-(5-(3-(tetrahydrofuran-2-ylmethoxy)phenoxy)-pyridin-2-yl)-1,3-benzoxazol-6-yl)-ethyl)acetamide | 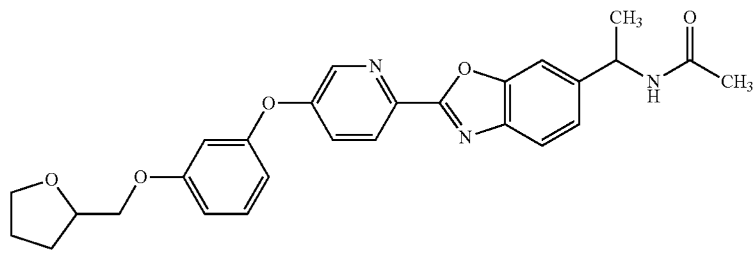 [SMILES: CC(=O)NC(C)c1ccc2nc(-c3ccc(Oc4cccc(OCC5CCCO5)c4)cn3)oc2c1] | 474.2 |
| 23 | N-(1-(2-(5-(3-((1-methylcyclopropyl)-methoxy)phenoxy)pyridin-2-yl)-1,3-benzoxazol-6-yl)ethyl)acetamide | 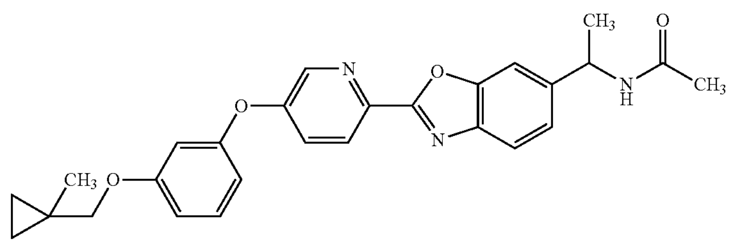 [SMILES: CC(=O)NC(C)c1ccc2nc(-c3ccc(Oc4cccc(OCC5(C)CC5)c4)cn3)oc2c1] | 458.2 |

TABLE 1-4

| Ex. No. | IUPAC name | Structure | MS |
|---|---|---|---|
| 24 | N-(1-(2-(5-(3-(2-(morpholin-4-yl)-ethoxy)phenoxy)pyridin-2-yl)-1,3-benzoxazol-6-yl)ethyl)acetamide | 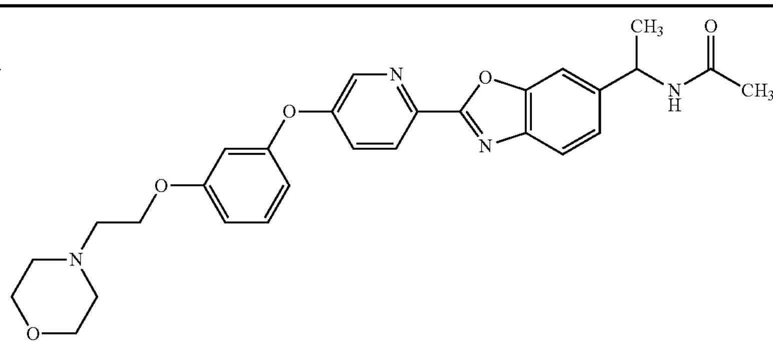 | 503.2 |
| 25 | N-(1-(2-(3-(3-(cyclopropylmethoxy)-phenoxy)azetidin-1-yl)-1,3-benzoxazol-5-yl)ethyl)acetamide | 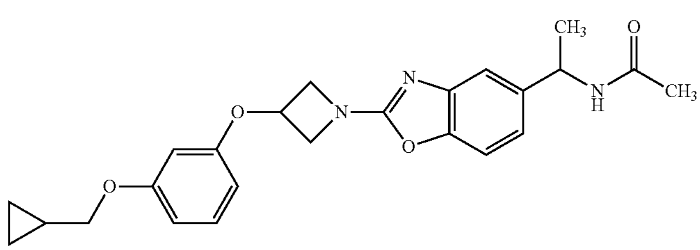 [SMILES: CC(=O)NC(C)c1ccc2oc(N3CC(Oc4cccc(OCC5CC5)c4)C3)nc2c1] | 422.2 |

TABLE 1-4-continued

| Ex. No. | IUPAC name | Structure | MS |
|---|---|---|---|
| 26 | N-(1-(2-(4-((3-(cyclopropylmethoxy)-phenyl)amino)phenyl)-1,3-benzoxazol-6-yl)ethyl)acetamide | 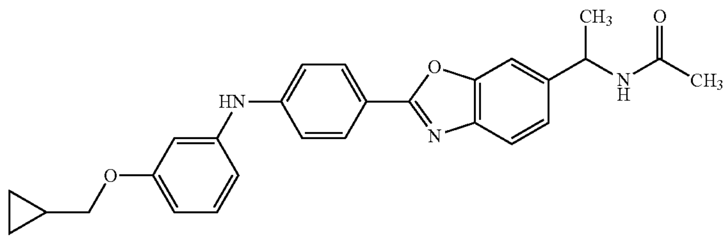 [SMILES: CC(=O)NC(C)c1ccc2nc(-c3ccc(Nc4cccc(OCC5CC5)c4)cc3)oc2c1] | 442.2 |
| 27 | N-(1-(2-(4-((3-(cyclopropylmethoxy)-phenyl)(methyl)-amino)phenyl)-1,3-benzoxazol-6-yl)ethyl)acetamide | 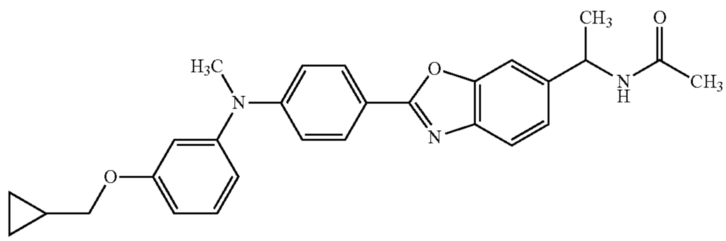 [SMILES: CC(=O)NC(C)c1ccc2nc(-c3ccc(N(C)c4cccc(OCC5CC5)c4)cc3)oc2c1] | 456.2 |
| 28 | N-(1-(2-(5-(3-(cyclopropylmethoxy)-phenoxy)hexahydro-cyclopenta[c]pyrrol-2(1H)-yl)-1,3-benzoxazol-6-yl)ethyl)acetamide | 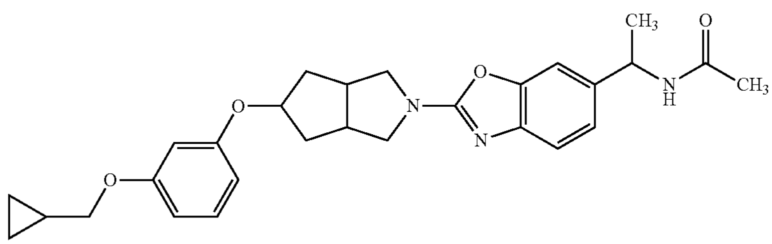 [SMILES: CC(=O)NC(C)c1ccc2nc(N3CC4CC(Oc5cccc(OCC6CC6)c5)CC4C3)oc2c1] | 476.3 |
| 29 | N-(1-(2-(3-(3-pentylphenoxy)azetidin-1-yl)-1,3-benzoxazol-6-yl)ethyl)acetamide | 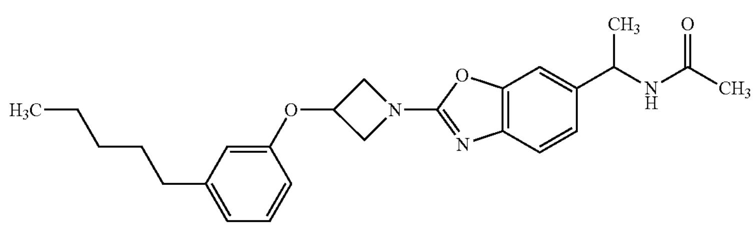 [SMILES: CCCCCc1cccc(OC2CN(c3nc4ccc(C(C)NC(C)=O)cc4o3)C2)c1] | 422.2 |
| 30 | N-(1-(2-(3-(3-(3-methoxypropyl)phenoxy)-azetidin-1-yl)-1,3-benzoxazol-6-yl)ethyl)acetamide | 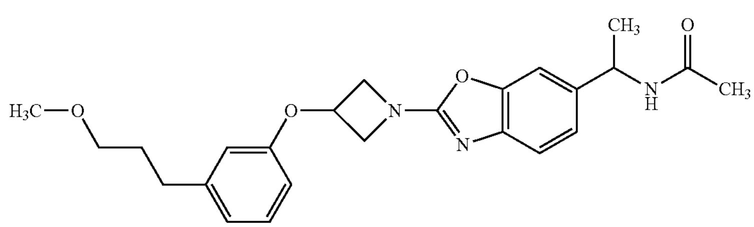 [SMILES: COCCCc1cccc(OC2CN(c3nc4ccc(C(C)NC(C)=O)cc4o3)C2)c1] | 424.1 |
| 31 | N-(1-(2-(5-(3-(cyclopropylmethoxy)-phenoxy)pyridin-2-yl)-1-benzofuran-5-yl)ethyl)acetamide | 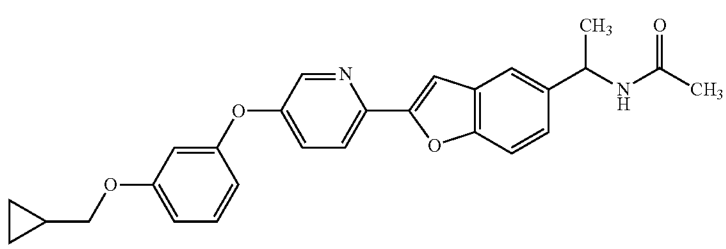 [SMILES: CC(=O)NC(C)c1ccc2oc(-c3ccc(Oc4cccc(OCC5CC5)c4)cn3)cc2c1] | 443.2 |

TABLE 1-4-continued

| Ex. No. | IUPAC name | Structure | MS |
|---|---|---|---|
| 32 | N-(1-(2-(5-(3-(cyclopropylmethoxy)-phenoxy)pyridin-2-yl)-1H-benzimidazol-6-yl)ethyl)acetamide | 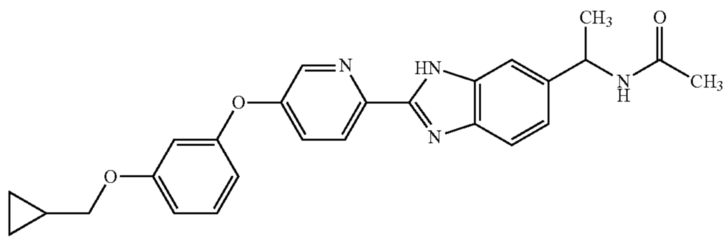 [SMILES: CC(=O)NC(C)c1ccc2nc(-c3ccc(Oc4cccc(OCC5CC5)c4)cn3)[nH]c2c1] | 443.2 |

TABLE 1-5

| Ex. No. | IUPAC name | Structure | MS |
|---|---|---|---|
| 33 | N-(1-(2-(5-(3-(cyclopropylmethoxy)-phenoxy)pyridin-2-yl)-1-methyl-1H-benzimidazol-6-yl)ethyl)acetamide | 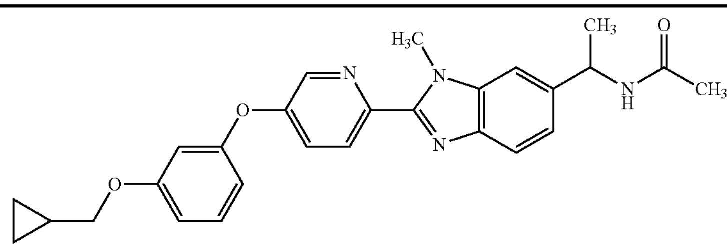 | 457.2 |
| 34 | N-(1-(2-(5-(3-(cyclopropylmethoxy)-phenoxy)pyridin-2-yl)-1-methyl-1H-benzimidazol-5-yl)ethyl)acetamide | 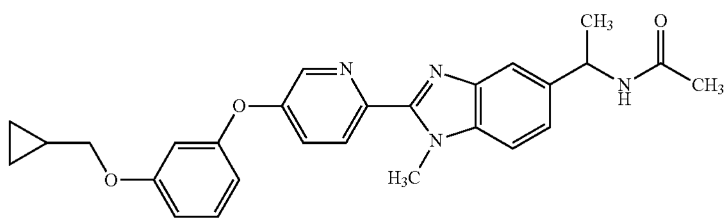 [SMILES: CC(=O)NC(C)c1ccc2c(c1)nc(-c1ccc(Oc3cccc(OCC4CC4)c3)cn1)n2C] | 457.2 |
| 35 | N-(1-(2-(5-(3-(cyclopropylmethoxy)-phenoxy)pyridin-2-yl)-1-benzofuran-6-yl)ethyl)acetamide | 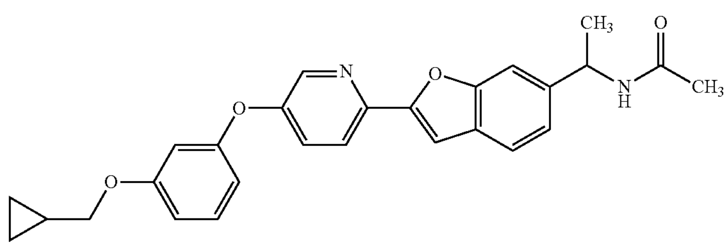 | 443.2 |
| 36 | N-(1-(2-(5-(3-(cyclopropylmethoxy)-phenoxy)pyridin-2-yl)-2,3-dihydro-1-benzofuran-5-yl)ethyl)-acetamide | 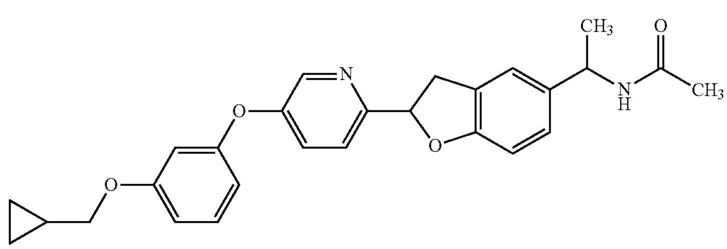 [SMILES: CC(=O)NC(C)c1ccc2c(c1)CC(c1ccc(Oc3cccc(OCC4CC4)c3)cn1)O2] | 445.2 |
| 36a | N-(1-(2-(5-(3-(cyclopropylmethoxy)-phenoxy)pyridin-2-yl)-2,3-dihydro-1-benzofuran-5-yl)ethyl)-acetamide | 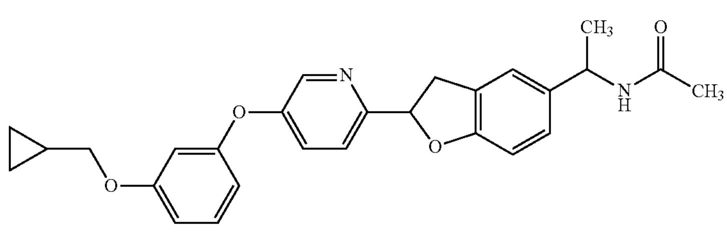 [SMILES: CC(=O)NC(C)c1ccc2c(c1)CC(c1ccc(Oc3cccc(OCC4CC4)c3)cn1)O2] | 445.2 |

TABLE 1-5-continued

| Ex. No. | IUPAC name | Structure | MS |
|---|---|---|---|
| 36b | N-(1-(2-(5-(3-(cyclo-propylmethoxy)phenoxy)-pyridin-2-yl)-2,3-dihydro-1-benzofuran-5-yl)ethyl)acetamide | 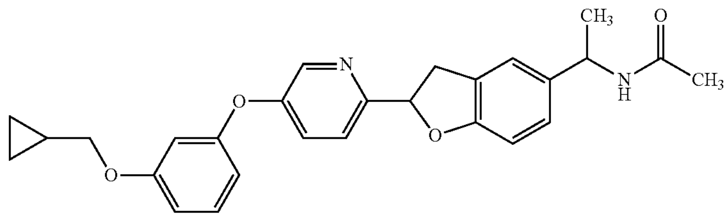 [SMILES: CC(=O)NC(C)c1ccc2c(c1)CC(c1ccc(Oc3cccc(OCC4CC4)c3)cn1)O2] | 445.2 |
| 36c | N-(1-(2-(5-(3-(cyclo-propylmethoxy)phenoxy)-pyridin-2-yl)-2,3-dihydro-1-benzofuran-5-yl)ethyl)acetamide | 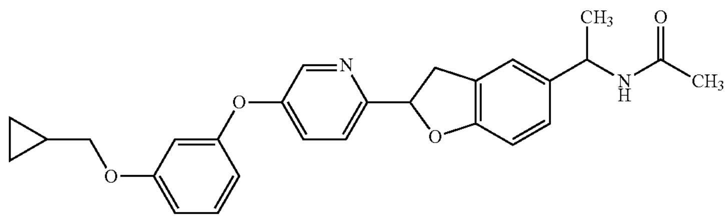 | 445.2 |
| 36d | N-(1-(2-(5-(3-(cyclo-propylmethoxy)phenoxy)-pyridin-2-yl)-2,3-dihydro-1-benzofuran-5-yl)ethyl)acetamide | 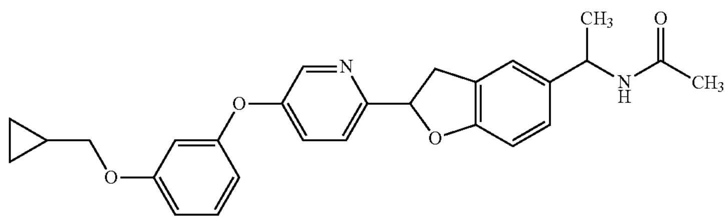 [SMILES: CC(=O)NC(C)c1ccc2c(c1)CC(c1ccc(Oc3cccc(OCC4CC4)c3)cn1)O2] | 445.2 |
| 37 | N-(1-(2-(6-(3-(cyclopropylmethoxy)-phenoxy)pyridin-3-yl)-1,3-benzoxazol-6-yl)ethyl)acetamide | 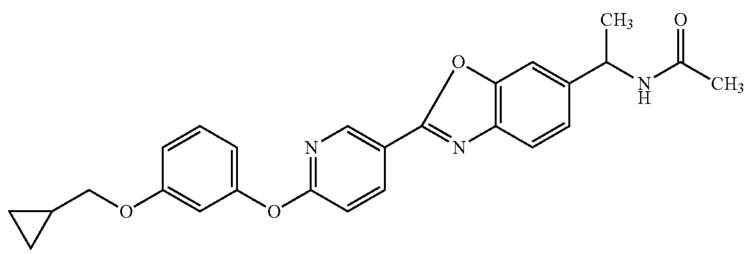 [SMILES: CC(=O)NC(C)c1ccc2nc(-c3ccc(Oc4cccc(OCC5CC5)c4)nc3)oc2c1] | 444.2 |

TABLE 1-6

| Ex. No. | IUPAC name | Structure | MS |
|---|---|---|---|
| 38 | N-(1-(2-(3-(3-(cyclopropylmethoxy)-phenoxy)phenyl)-1,3-benzoxazol-6-yl)ethyl)acetamide | 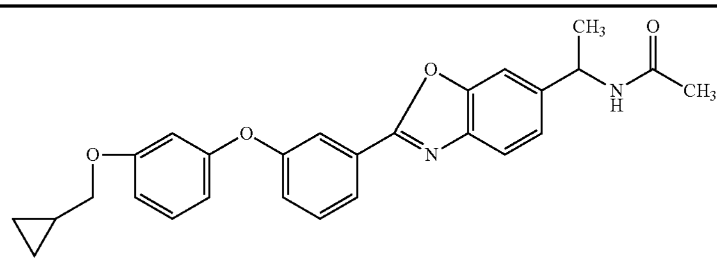 | 443.2 |
| 39 | N-(1-(2-(3-(4-(cyclopropylmethoxy)-phenoxy)phenyl)-1,3-benzoxazol-6-yl)ethyl)acetamide | 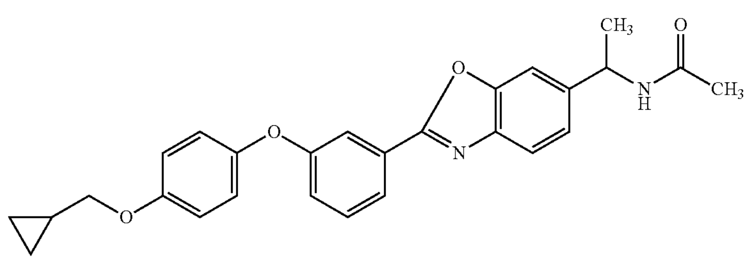 [SMILES: CC(=O)NC(C)c1ccc2nc(-c3cccc(Oc4ccc(OCC5CC5)cc4)c3)oc2c1] | 443.2 |

TABLE 1-6-continued

| Ex. No. | IUPAC name | Structure | MS |
|---|---|---|---|
| 40 | N-(1-(2-(3-(3-(cyclopropylmethoxy)-phenoxy)azetidin-1-yl)-1,3-benzothiazol-6-yl)ethyl)acetamide | 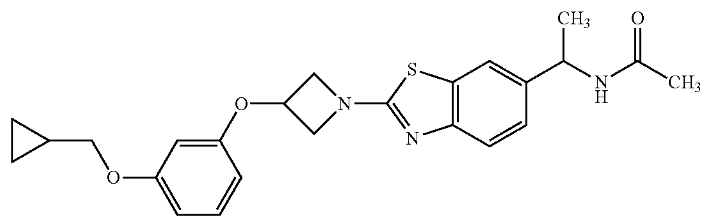 [SMILES: CC(=O)NC(C)c1ccc2nc(N3CC(Oc4cccc(OCC5CC5)c4)C3)sc2c1] | 438.1 |
| 41 | N-(1-(2-(4-(3-(cyclopropylmethoxy)-phenoxy)-2-methylphenyl)-1,3-benzoxazol-6-yl)ethyl)acetamide | 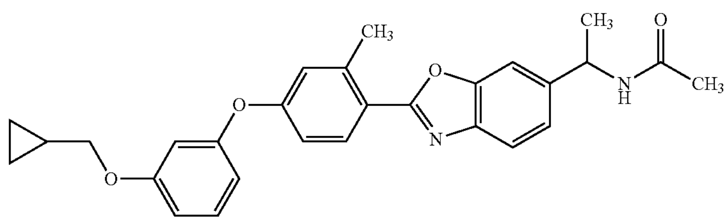 [SMILES: CC(=O)NC(C)c1ccc2nc(-c3ccc(Oc4cccc(OCC5CC5)c4)cc3C)oc2c1] | 457.2 |
| 42 | N-(1-(2-(3-(3-(cyclopropylmethoxy)-phenoxy)-3-methylazetidin-1-yl)-1,3-benzoxazol-6-yl)ethyl)acetamide | 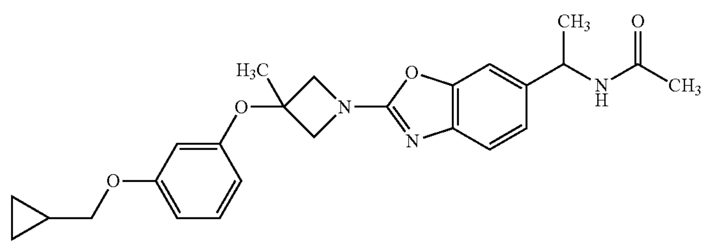 [SMILES: CC(=O)NC(C)c1ccc2nc(N3CC(C)(Oc4cccc(OCC5CC5)c4)C3)oc2c1] | 436.3 |
| 43 | N-(1-(2-(4-(3-(cyclopropylmethoxy)-benzyl)phenyl)-1,3-benzoxazol-6-yl)ethyl)acetamide | 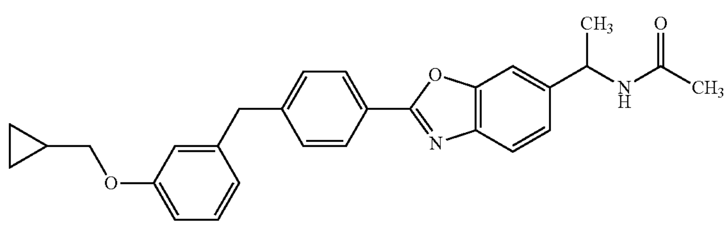 [SMILES: CC(=O)NC(C)c1ccc2nc(-c3ccc(Cc4cccc(OCC5CC5)c4)cc3)oc2c1] | 441.2 |
| 44 | N-(1-(2-(3-(3-(cyclopropylmethoxy)-phenoxy)azetidin-1-yl)-1,3-benzothiazol-5-yl)ethyl)acetamide | 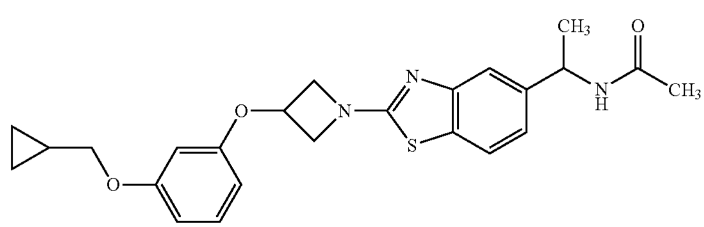 | 438.1 |
| 45 | N-(1-(2-(5-(3-(cyclopropylmethoxy)-phenoxy)pyridin-2-yl)-1-ethyl-1H-benzimidazol-5-yl)ethyl)acetamide | 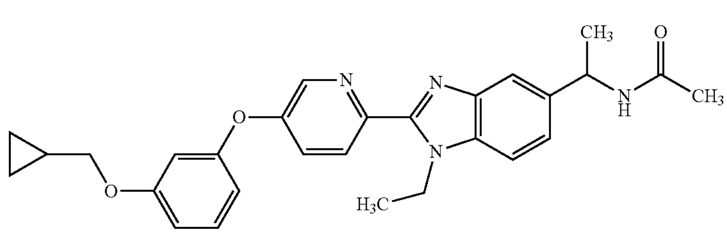 [SMILES: CCn1c(-c2ccc(Oc3cccc(OCC4CC4)c3)cn2)nc2cc(C(C)NC(C)=O)ccc21] | 471.3 |

TABLE 1-6-continued

| Ex. No. | IUPAC name | Structure | MS |
|---|---|---|---|
| 46 | N-(1-(2-(3-(3-methylphenoxy)azetidin-1-yl)-1,3-benzoxazol-6-yl)ethyl)acetamide | 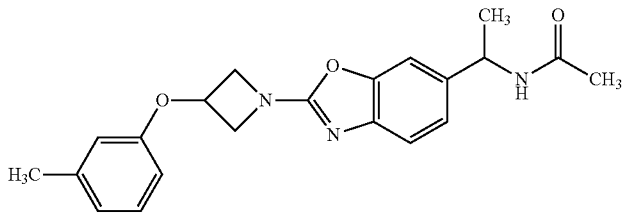 [SMILES: CC(=O)NC(C)c1ccc2nc(N3CC(Oc4cccc(C)c4)C3)oc2c1] | 366.2 |

TABLE 1-7

| Ex. No. | IUPAC name | Structure | MS |
|---|---|---|---|
| 47 | N-(1-(2-(5-(3-(cyclopropylmethoxy)phenoxy)-3-methylpyridin-2-yl)-1,3-benzoxazol-6-yl)ethyl)acetamide | 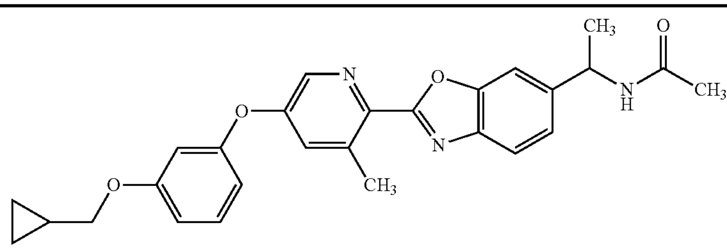 | 458.2 |
| 48 | N-(1-(2-(4-(3-(cyclopropylmethoxy)phenoxy)phenyl)-2H-indazol-5-yl)ethyl)acetamide | 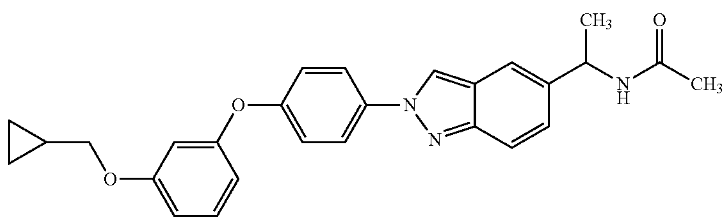 [SMILES: CC(=O)NC(C)c1ccc2nn(-c3ccc(Oc4cccc(OCC5CC5)c4)cc3)cc2c1] | 442.2 |
| 49 | N-(1-(2-(4-(3-(cyclopropylmethoxy)phenoxy)-2-ethylphenyl)-1,3-benzoxazol-6-yl)ethyl)acetamide | 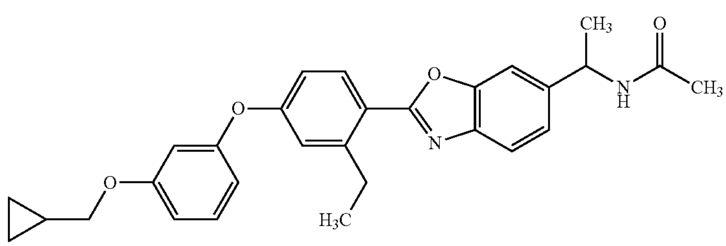 [SMILES: CCc1cc(Oc2cccc(OCC3CC3)c2)ccc1-c1nc2ccc(C(C)NC(C)=O)cc2o1] | 471.2 |
| 50 | N-(1-(2-(3-(3-(((1R)-2,2-difluorocyclopropyl)methoxy)phenoxy)azetidin-1-yl)-1,3-benzoxazol-6-yl)ethyl)-acetamide | 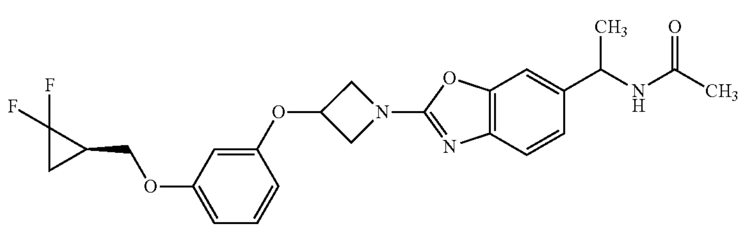 [SMILES: CC(=O)NC(C)c1ccc2nc(N3CC(Oc4cccc(OC[C@H]5CC5(F)F)c4)C3)oc2c1] | 458.2 |
| 51 | N-(1-(2-(3-(3-(((1S)-2,2-difluorocyclopropyl)methoxy)phenoxy)azetidin-1-yl)-1,3-benzoxazol-6-yl)ethyl)acetamide | 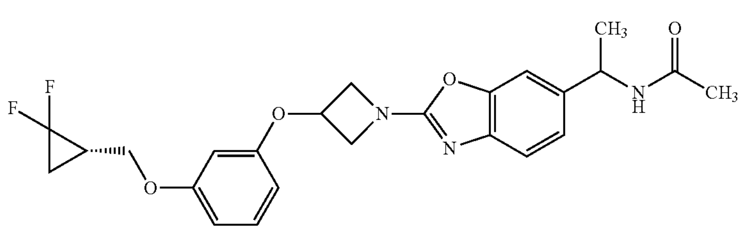 [SMILES: CC(=O)NC(C)c1ccc2nc(N3CC(Oc4cccc(OC[C@@H]5CC5(F)F)c4)C3)oc2c1] | 458.2 |

TABLE 1-7-continued

| Ex. No. | IUPAC name | Structure | MS |
|---|---|---|---|
| 52 | N-(1-(5-(4-(3-(cyclopropylmethoxy)-phenoxy)phenyl)-1-benzofuran-2-yl)ethyl)-acetamide | 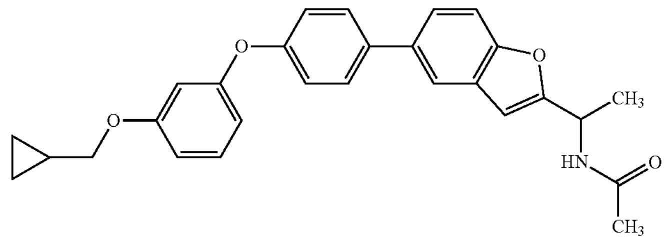 [SMILES: CC(=O)NC(C)c1cc2cc(-c3ccc(Oc4cccc(OCC5CC5)c4)cc3)ccc2o1] | 442.1 |
| 53 | N-(1-(2-(3-(3-(2,2,3,3,3-pentafluoro-propoxy)phenoxy)-azetidin-1-yl)-1,3-benzoxazol-6-yl)ethyl)-acetamide | 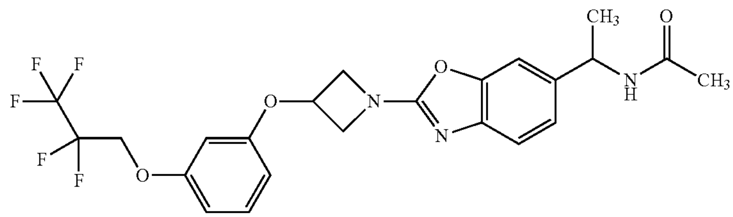 [SMILES: CC(=O)NC(C)c1ccc2nc(N3CC(Oc4cccc(OCC(F)(F)C(F)(F)F)c4)C3)oc2c1] | 500.1 |
| 54 | N-(1-(2-(4-(3-(cyclopropylmethoxy)-phenoxy)phenyl)-5-fluoro-1,3-benzoxazol-6-yl)ethyl)acetamide | 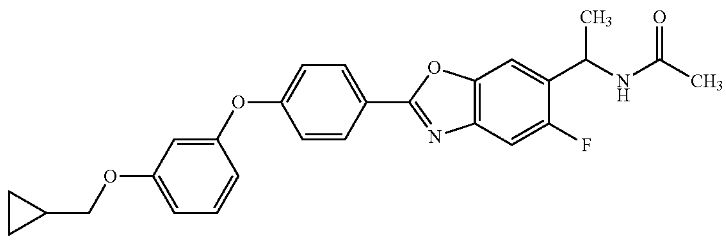 [SMILES: CC(=O)NC(C)c1cc2oc(-c3ccc(Oc4cccc(OCC5CC5)c4)cc3)nc2cc1F] | 461.2 |
| 55 | N-(1-(2-(3-(3-(cyclopropylmethoxy)-phenoxy)azetidin-1-yl)-1,3-benzoxazol-6-yl)propyl)acetamide | 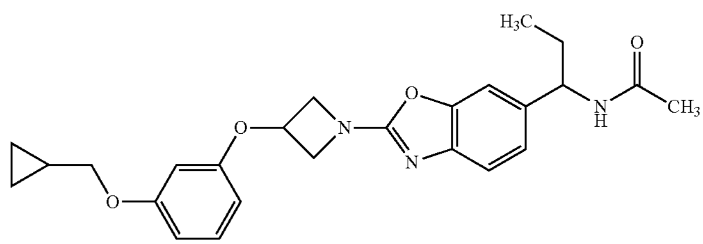 [SMILES: CCC(NC(C)=O)c1ccc2nc(N3CC(Oc4cccc(OCC5CC5)c4)C3)oc2c1] | 436.2 |

TABLE 1-8

| Ex. No. | IUPAC name | Structure | MS |
|---|---|---|---|
| 56 | N-(1-(2-(4-(3-(cyclopropylmethoxy)-phenoxy)phenyl)-2H-indazol-6-yl)ethyl)-acetamide | 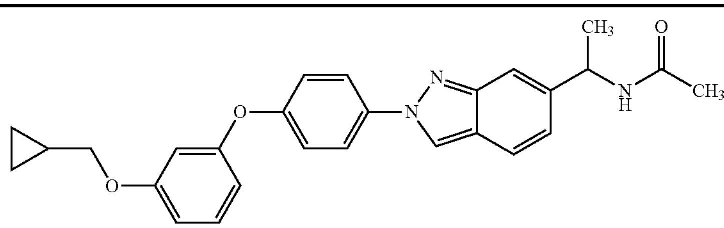 | 442.2 |
| 57 | N-(1-(2-(3-(3-(cyclopropylmethoxy)-phenoxy)azetidin-1-yl)-1,3-benzoxazol-6-yl)ethyl)propanamide | 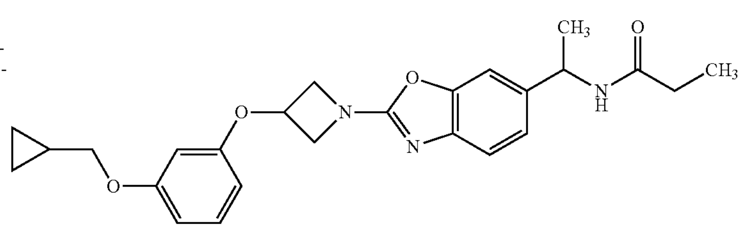 | 436.2 |

TABLE 1-8-continued

| Ex. No. | IUPAC name | Structure | MS |
|---|---|---|---|
| 58 | N-(1-(2-(3-(3-(dimethylamino)-phenoxy)azetidin-1-yl)-1,3-benzoxazol-6-yl)ethyl)acetamide | 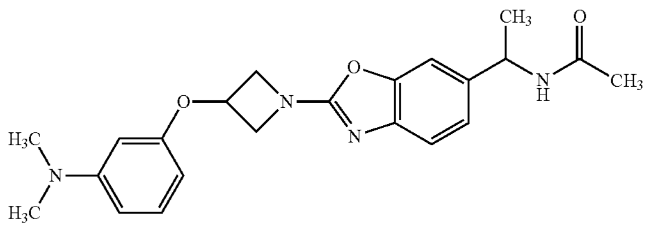 [SMILES: CC(=O)NC(C)c1ccc2nc(N3CC(Oc4cccc(N(C)C)c4)C3)oc2c1] | 395.3 |
| 59 | N-(1-(2-(2-bromo-4-(3-(cyclopropylmethoxy)-phenoxy)phenyl)-1,3-benzoxazol-6-yl)ethyl)-acetamide | 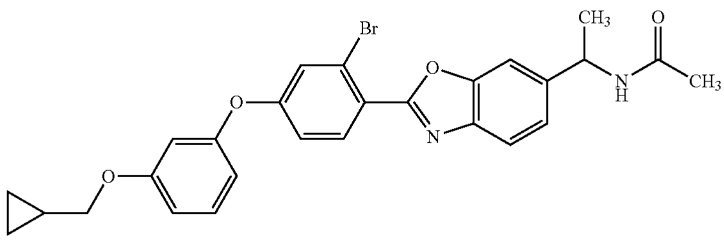 [SMILES: CC(=O)NC(C)c1ccc2nc(-c3ccc(Oc4cccc(OCC5CC5)c4)cc3Br)oc2c1] | 521.1 |
| 60 | N-(1-(2-(2-cyano-4-(3-(cyclopropylmethoxy)-phenoxy)phenyl)-1,3-benzoxazol-6-yl)ethyl)-acetamide | 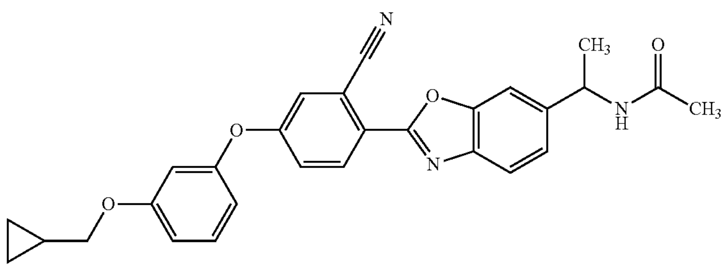 [SMILES: CC(=O)NC(C)c1ccc2nc(-c3ccc(Oc4cccc(OCC5CC5)c4)cc3C#N)oc2c1] | 468.2 |
| 61 | N-(1-(2-(3-(3-(cyclopropylmethoxy)-phenoxy)azetidin-1-yl)-1,3-benzoxazol-6-yl)ethyl)-2,2,2-trifluoroacetamide | 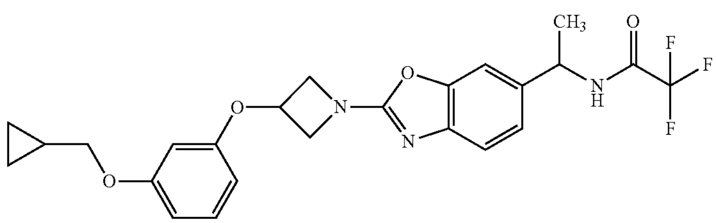 [SMILES: CC(NC(=O)C(F)(F)F)c1ccc2nc(N3CC(Oc4cccc(OCC5CC5)c4)C3)oc2c1] | 474.1 |
| 62 | N-(1-(2-(3-(3-(cyclopropylmethoxy)-phenoxy)azetidin-1-yl)-1,3-benzoxazol-6-yl)ethyl)-2,2-difluoroacetamide | 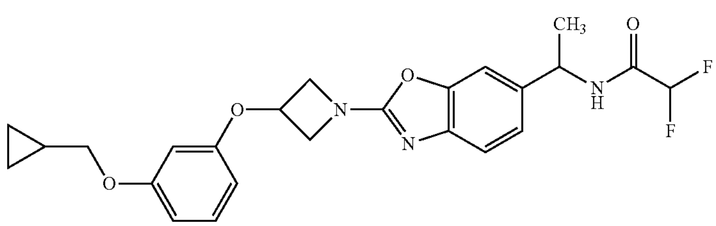 [SMILES: CC(NC(=O)C(F)F)c1ccc2nc(N3CC(Oc4cccc(OCC5CC5)c4)C3)oc2c1] | 458.2 |
| 63 | methyl (1-(2-(3-(3-(cyclopropylmethoxy)-phenoxy)azetidin-1-yl)-1,3-benzoxazol-6-yl)ethyl)carbamate | 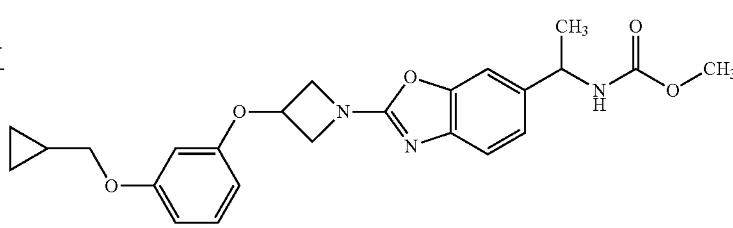 | 438.1 |

TABLE 1-8-continued

| Ex. No. | IUPAC name | Structure | MS |
|---|---|---|---|
| 64 | N-(1-(2-(2-chloro-4-(3-(cyclopropylmethoxy)phenoxy)phenyl)-1,3-benzoxazol-6-yl)ethyl)acetamide | 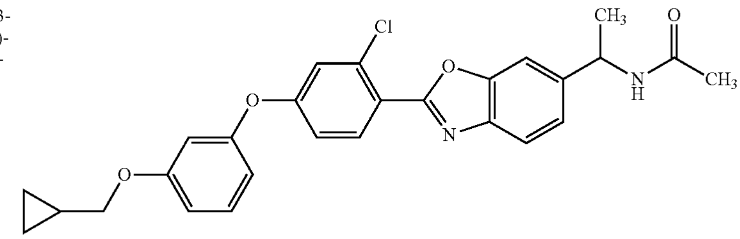 | 477.2 |

TABLE 1-9

| Ex. No. | IUPAC name | Structure | MS |
|---|---|---|---|
| 65 | N-(1-(2-(3-(3-(trifluoromethyl)phenoxy)azetidin-1-yl)-1,3-benzoxazol-6-yl)ethyl)acetamide | 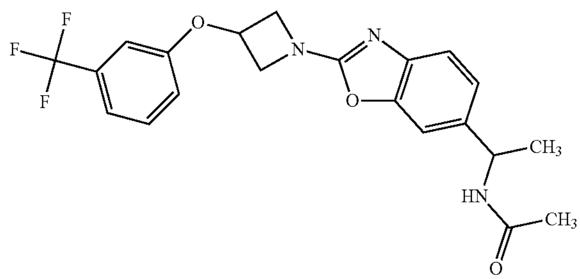 [SMILES: CC(=O)NC(C)c1ccc2nc(N3CC(Oc4cccc(C(F)(F)F)c4)C3)oc2c1] | 420.1 |
| 66 | N-(1-(2-(4-(3-(cyclopropylmethoxy)phenoxy)phenyl)-imidazo[1,2-a]pyridin-7-yl)ethyl)acetamide | 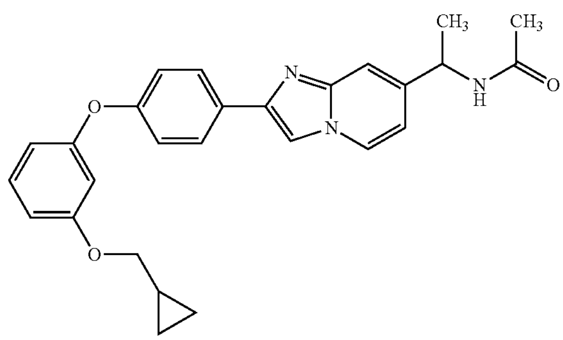 [SMILES: CC(=O)NC(C)c1ccn2cc(-c3ccc(Oc4cccc(OCC5CC5)c4)cc3)nc2c1] | 442.1 |
| 67 | N-(1-(2-(6-(3-(cyclopropylmethoxy)phenoxy)pyridin-3-yl)-1-benzofuran-6-yl)ethyl)-acetamide | 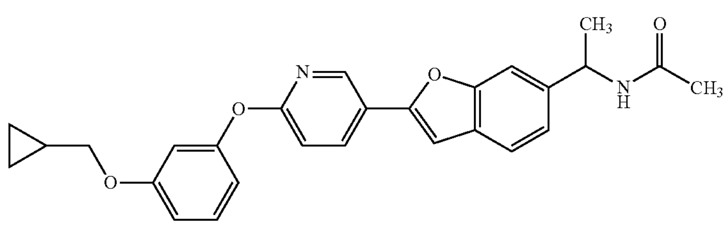 [SMILES: CC(=O)NC(C)c1ccc2cc(-c3ccc(Oc4cccc(OCC5CC5)c4)nc3)oc2c1] | 443.2 |
| 68 | N-(1-(2-(6-(3-(((1S)-2,2-difluorocyclopropyl)methoxy)phenoxy)pyridin-3-yl)-1-benzofuran-6-yl)ethyl)-acetamide | 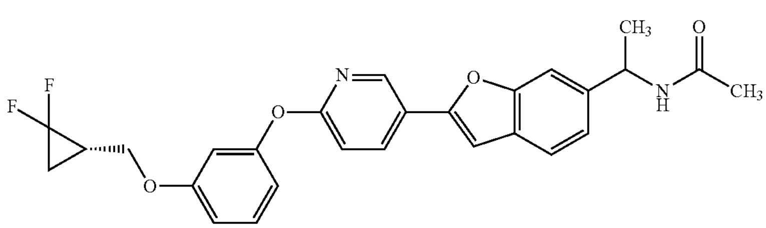 [SMILES: CC(=O)NC(C)c1ccc2cc(-c3ccc(Oc4cccc(OC[C@@H]5CC5(F)F)c4)nc3)oc2c1] | 479.1 |

TABLE 1-9-continued

| Ex. No. | IUPAC name | Structure | MS |
|---|---|---|---|
| 69 | N-(1-(2-(3-((3-(cyclopropylmethoxy)-phenyl)amino)azetidin-1-yl)-1,3-benzoxazol-6-yl)ethyl)acetamide | 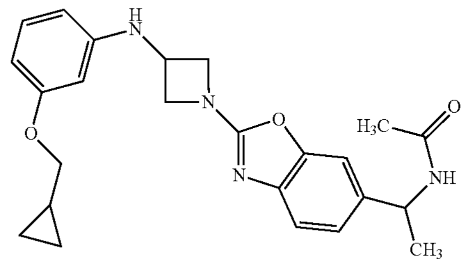 [SMILES: CC(=O)NC(C)c1ccc2nc(N3CC(Nc4cccc(OCC5CC5)c4)C3)oc2c1] | 421.2 |
| 70 | N-(1-(2-(6-(3-(((1S)-2,2-difluoro-cyclopropyl)methoxy)-phenoxy)pyridin-3-yl)-1,3-benzoxazol-5-yl)ethyl)acetamide | 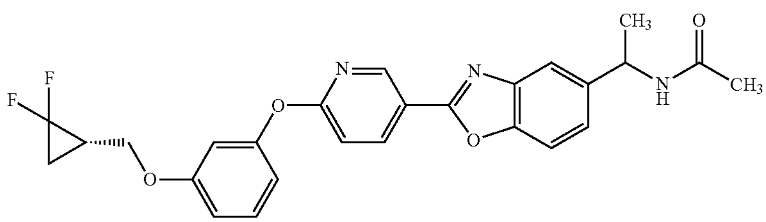 | 480.1 |
| 71 | N-(1-(2-(6-(3-(cyclopropylmethoxy)-phenoxy)pyridin-3-yl)-1,3-benzoxazol-5-yl)ethyl)acetamide | 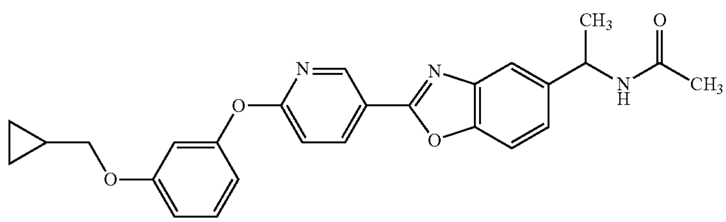 [SMILES: CC(=O)NC(C)c1ccc2oc(-c3ccc(Oc4cccc(OCC5CC5)c4)nc3)nc2c1] | 444.2 |
| 72 | N-(1-(2-(3-(3-(3,3,3-trifluoropropoxy)-phenoxy)azetidin-1-yl)-1,3-benzoxazol-6-yl)ethyl)acetamide | 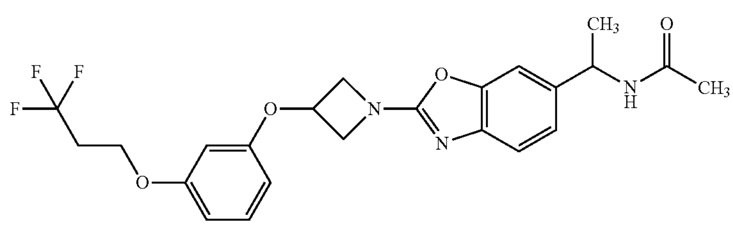 [SMILES: CC(=O)NC(C)c1ccc2nc(N3CC(Oc4cccc(OCCC(F)(F)F)c4)C3)oc2c1] | 464.1 |
| 73 | N-(1-(2-(4-(3-(cyclopropylmethoxy)-phenoxy)phenyl)-1-benzothiophen-5-yl)ethyl)acetamide | 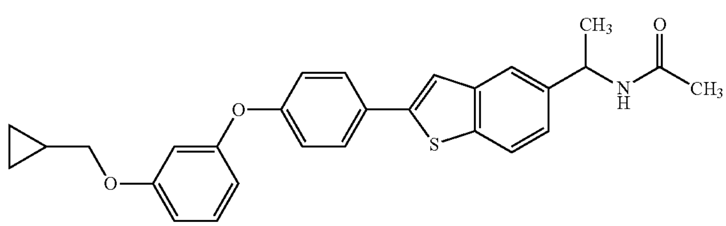 [SMILES: CC(=O)NC(C)c1ccc2sc(-c3ccc(Oc4cccc(OCC5CC5)c4)cc3)cc2c1] | 458.1 |

TABLE 1-10

| Ex. No. | IUPAC name | Structure | MS |
|---|---|---|---|
| 74 | N-(1-(2-(6-(3-(((1S)-2,2-difluoro-cyclopropyl)methoxy)-phenoxy)pyridin-3-yl)-1,3-benzothiazol-5-yl)ethyl)acetamide | 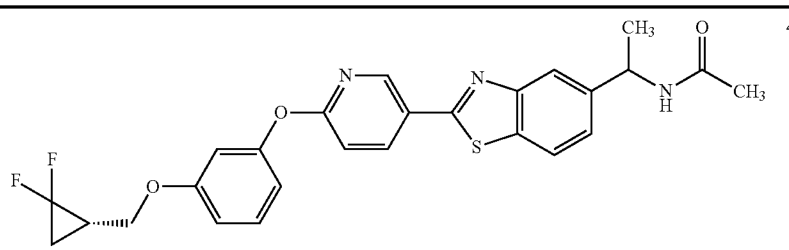 | 496.1 |

TABLE 1-10-continued

| Ex. No. | IUPAC name | Structure | MS |
|---|---|---|---|
| 75 | N-(1-(2-(6-(3-(cyclopropylmethoxy)-phenoxy)pyridin-3-yl)-1,3-benzothiazol-5-yl)ethyl)acetamide | 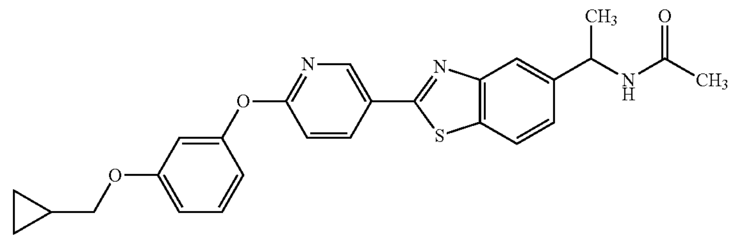 [SMILES: CC(=O)NC(C)c1ccc2sc(-c3ccc(Oc4cccc(OCC5CC5)c4)nc3)nc2c1] | 460.2 |
| 76 | N-(1-(2-(5-(3-(((1S)-2,2-difluoro-cyclopropyl)methoxy)-phenoxy)pyridin-2-yl)-1,3-benzoxazol-6-yl)ethyl)acetamide | 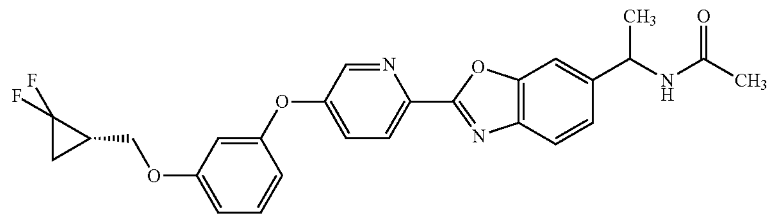 [SMILES: CC(=O)NC(C)c1ccc2nc(-c3ccc(Oc4cccc(OC[C@@H]5CC5(F)F)c4)cn3)oc2c1] | 480.1 |
| 77 | N-(1-(2-(4-(3-(cyclopropylmethoxy)-phenoxy)phenyl)-imidazo[1,2-a]pyridin-6-yl)ethyl)acetamide | 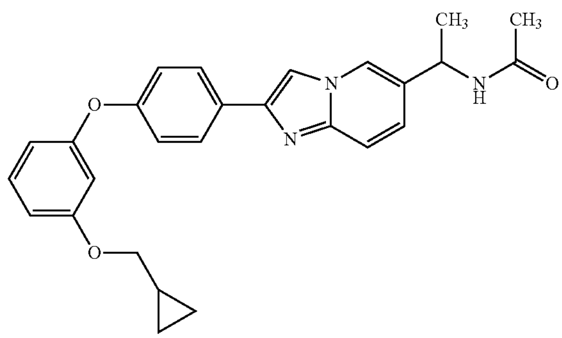 [SMILES: CC(=O)NC(C)c1ccc2nc(-c3ccc(Oc4cccc(OCC5CC5)c4)cc3)cn2c1] | 442.1 |
| 78 | N-(1-(2-(4-(3-(cyclopropylmethoxy)-phenoxy)phenyl)-1-benzothiophen-6-yl)ethyl)acetamide | 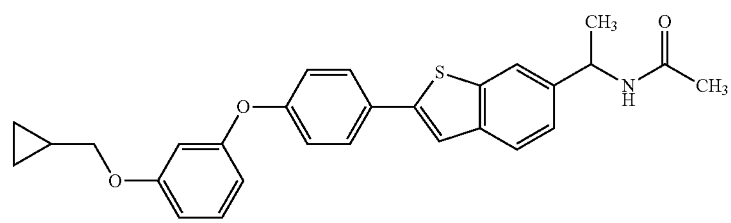 | 458.1 |
| 79 | N-(1-(2-(4-((6-(cyclopropylmethoxy)-pyridin-2-yl)oxy)-phenyl)-1,3-benzoxazol-6-yl)ethyl)acetamide | 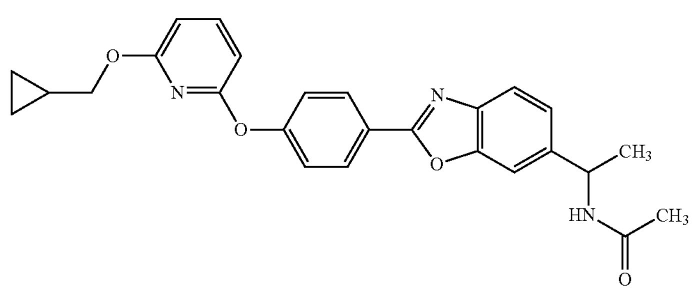 [SMILES: CC(=O)NC(C)c1ccc2nc(-c3ccc(Oc4cccc(OCC5CC5)n4)cc3)oc2c1] | 444.2 |
| 80 | N-(1-(2-(6-(3-(((1S)-2,2-difluoro-cyclopropyl)methoxy)-phenoxy)pyridin-3-yl)-1,3-benzoxazol-6-yl)ethyl)acetamide | 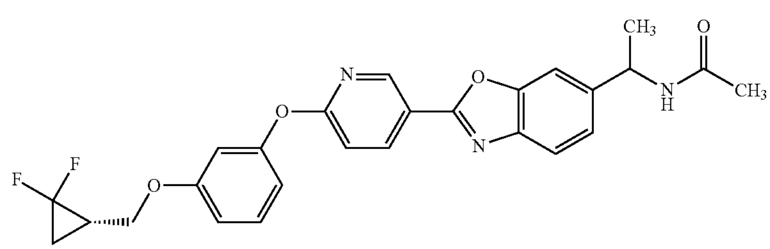 [SMILES: CC(=O)NC(C)c1ccc2nc(-c3ccc(Oc4cccc(OC[C@@H]5CC5(F)F)c4)nc3)oc2c1] | 480.1 |

TABLE 1-10-continued

| Ex. No. | IUPAC name | Structure | MS |
|---|---|---|---|
| 81 | N-(1-(2-(6-(3-(2-methoxyethoxy)phenoxy)-pyridin-3-yl)-1-benzofuran-6-yl)ethyl)acetamide | 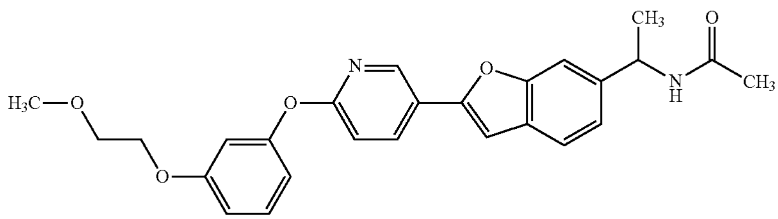 [SMILES: COCCOc1cccc(Oc2ccc(-c3cc4ccc(C(C)NC(C)=O)cc4o3)cn2)c1] | 447.1 |
| 82 | N-(1-(2-(4-((4-(cyclopropylmethoxy)-pyridin-2-yl)oxy)phenyl)-1,3-benzoxazol-6-yl)ethyl)-acetamide | 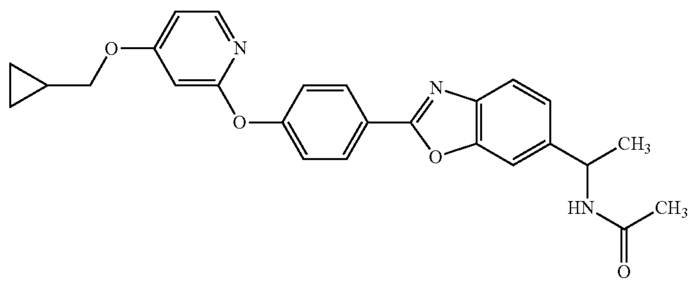 [SMILES: CC(=O)NC(C)c1ccc2nc(-c3ccc(Oc4cc(OCC5CC5)ccn4)cc3)oc2c1] | 444.2 |

TABLE 1-11

| Ex. No. | IUPAC name | Structure | MS |
|---|---|---|---|
| 83 | N-(1-(2-(3-(3-(cyclopropylmethoxy)-phenoxy)azetidin-1-yl)quinazolin-7-yl)ethyl)acetamide | 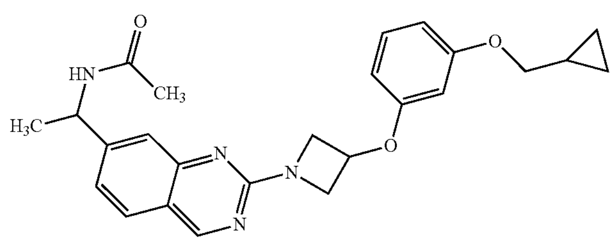 [SMILES: CC(=O)NC(C)c1ccc2cnc(N3CC(Oc4cccc(OCC5CC5)c4)C3)nc2c1] | 433.1 |
| 84 | N-(1-(2-(5-(4-(cyclopropylmethoxy)-phenoxy)-1-methyl-1H-pyrazol-3-yl)-1,3-benzoxazol-6-yl)ethyl)acetamide | 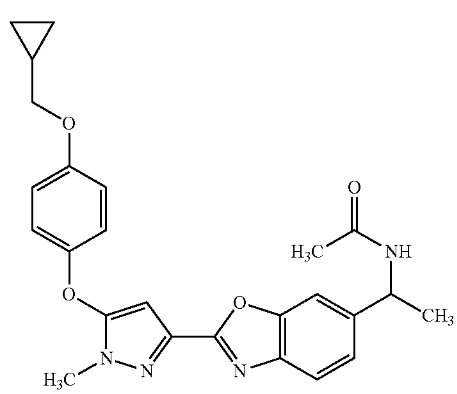 [SMILES: CC(=O)NC(C)c1ccc2nc(-c3cc(Oc4ccc(OCC5CC5)cc4)n(C)n3)oc2c1] | 447.1 |

TABLE 1-11-continued

| Ex. No. | IUPAC name | Structure | MS |
|---|---|---|---|
| 85 | N-(1-(2-(4-(3-(cyclopropylmethoxy)-phenoxy)phenyl)-pyrazolo[1,5-a]pyridin-5-yl)ethyl)acetamide | 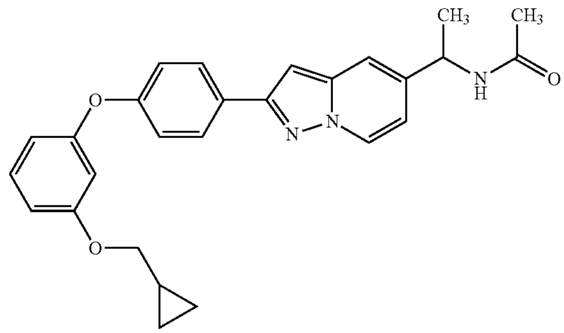 [SMILES: CC(=O)NC(C)c1ccn2nc(-c3ccc(Oc4cccc(OCC5CC5)c4)cc3)cc2c1] | 442.2 |
| 86 | N-(1-(2-(4-(3-(cyclopropylmethoxy)-phenoxy)phenyl)-pyrazolo[1,5-a]pyridin-6-yl)ethyl)acetamide | 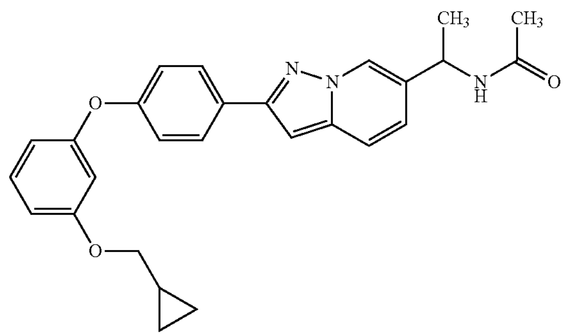 [SMILES: CC(=O)NC(C)c1ccc2cc(-c3ccc(Oc4cccc(OCC5CC5)c4)cc3)nn2c1] | 442.1 |
| 87 | N-(1-(2-(4-(3-(cyclopropylmethoxy)-phenoxy)-3-fluorophenyl)-1,3-benzoxazol-6-yl)ethyl)acetamide | 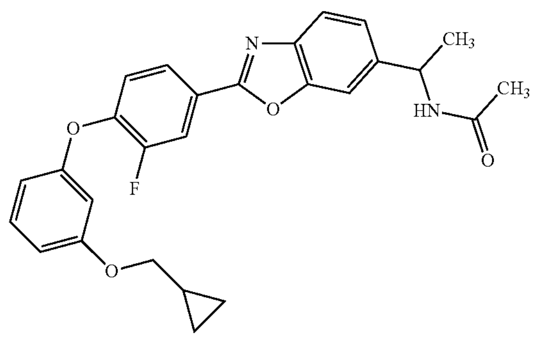 [SMILES: CC(=O)NC(C)c1ccc2nc(-c3ccc(Oc4cccc(OCC5CC5)c4)c(F)c3)oc2c1] | 461.2 |
| 88 | N-(1-(2-(3-(3-(cyclopropylmethoxy)-phenoxy)pyrrolidin-1-yl)quinazolin-6-yl)ethyl)acetamide | 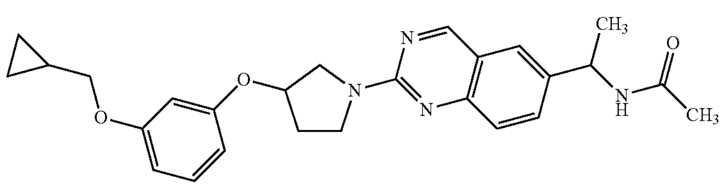 [SMILES: CC(=O)NC(C)c1ccc2nc(N3CCC(Oc4cccc(OCC5CC5)c4)C3)ncc2c1] | 447.1 |
| 89 | N-(1-(2-(3-bromo-4-(3-(cyclopropylmethoxy)-phenoxy)phenyl)-1,3-benzoxazol-6-yl)ethyl)acetamide | 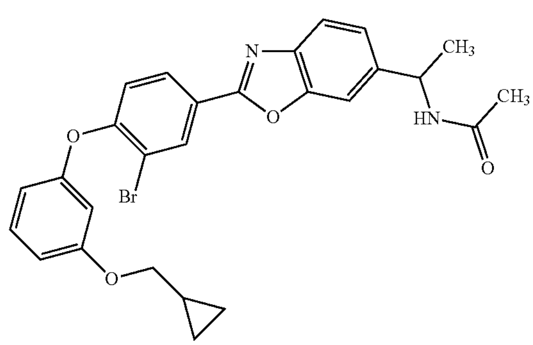 [SMILES: CC(=O)NC(C)c1ccc2nc(-c3ccc(Oc4cccc(OCC5CC5)c4)c(Br)c3)oc2c1] | 521.1 |

TABLE 1-11-continued

| Ex. No. | IUPAC name | Structure | MS |
|---|---|---|---|
| 90 | N-(1-(2-(4-(3-(cyclopropylmethoxy)-phenoxy)phenyl)-7-fluoro-1,3-benzoxazol-6-yl)ethyl)acetamide | 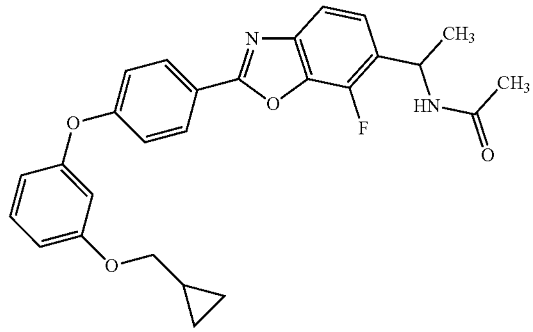 [SMILES: CC(=O)NC(C)c1ccc2nc(-c3ccc(Oc4cccc(OCC5CC5)c4)cc3)oc2c1F] | 461.2 |
| 91 | N-(1-(2-(3-(3-(cyclopropylmethoxy)-phenoxy)azetidin-1-yl)quinazolin-6-yl)ethyl)acetamide | 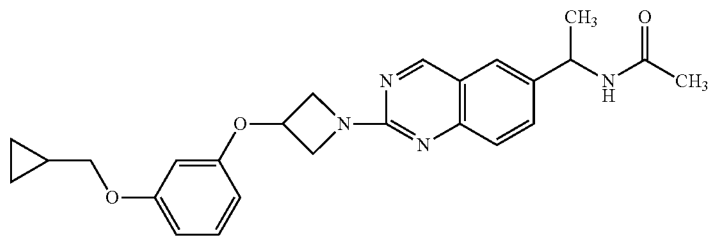 [SMILES: CC(=O)NC(C)c1ccc2nc(N3CC(Oc4cccc(OCC5CC5)c4)C3)ncc2c1] | 433.1 |

TABLE 1-12

| Ex. No. | IUPAC name | Structure | MS |
|---|---|---|---|
| 92 | N-(1-(2-(6-((4-(cyclopropylmethoxy)-pyridin-2-yl)oxy)-pyridin-3-yl)-1,3-benzoxazol-6-yl)ethyl)-acetamide | 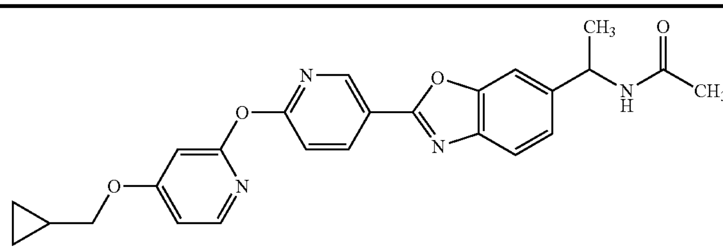 | 445.2 |
| 93 | N-(1-(2-(4-(3-(cyclopropylmethoxy)-phenoxy)phenyl)-7-methyl-1,3-benzoxazol-6-yl)ethyl)acetamide | 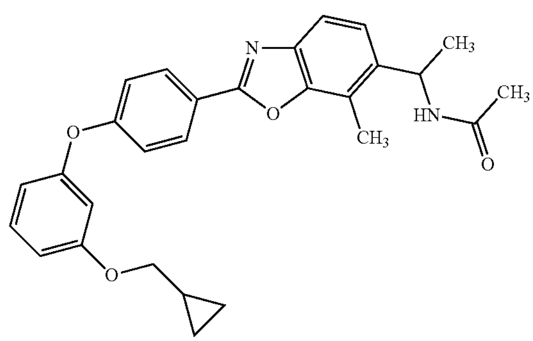 [SMILES: CC(=O)NC(C)c1ccc2nc(-c3ccc(Oc4cccc(OCC5CC5)c4)cc3)oc2c1C] | 457.1 |
| 94 | N-(1-(2-(6-((2-(cyclopropylmethoxy)-pyridin-4-yl)oxy)-pyridin-3-yl)-1,3-benzoxazol-6-yl)ethyl)-acetamide | 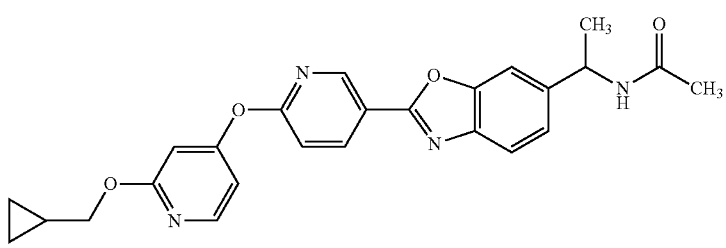 | 445.1 |

TABLE 1-12-continued

| Ex. No. | IUPAC name | Structure | MS |
|---|---|---|---|
| 95 | N-(1-(2-(4-(3-(cyclopropylmethoxy)-phenoxy)phenyl)-4,5,6,7-tetrahydro-1,3-benzoxazol-6-yl)ethyl)-acetamide | 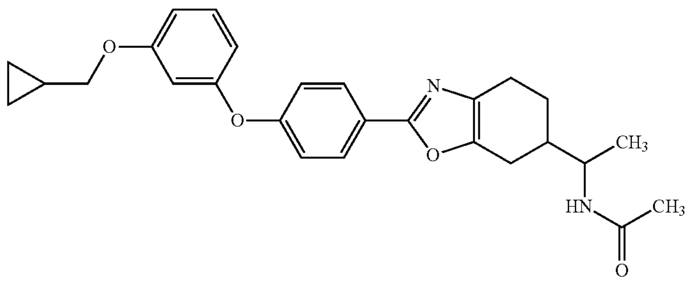 [SMILES: CC(=O)NC(C)C1CCc2nc(-c3ccc(Oc4cccc(OCC5CC5)c4)cc3)oc2C1] | 447.1 |
| 95a | N-(1-(2-(4-(3-(cyclo-propylmethoxy)phenoxy)-phenyl)-4,5,6,7-tetra-hydro-1,3-benzoxazol-6-yl)ethyl)acetamide | 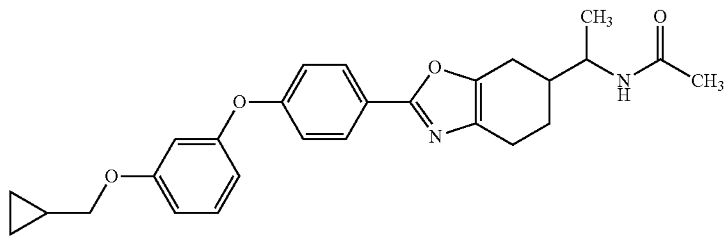 [SMILES: CC(=O)NC(C)C1CCc2nc(-c3ccc(Oc4cccc(OCC5CC5)c4)cc3)oc2C1] | 447.1 |
| 95b | N-(1-(2-(4-(3-(cyclo-propylmethoxy)phenoxy)-phenyl)-4,5,6,7-tetra-hydro-1,3-benzoxazol-6-yl)ethyl)acetamide | 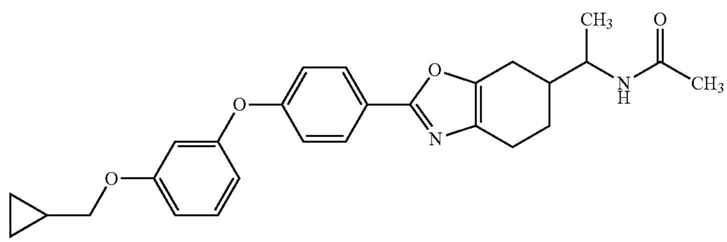 [SMILES: CC(=O)NC(C)C1CCc2nc(-c3ccc(Oc4cccc(OCC5CC5)c4)cc3)oc2C1] | 447.1 |
| 95c | N-(1-(2-(4-(3-(cyclo-propylmethoxy)phenoxy)-phenyl)-4,5,6,7-tetra-hydro-1,3-benzoxazol-6-yl)ethyl)acetamide | 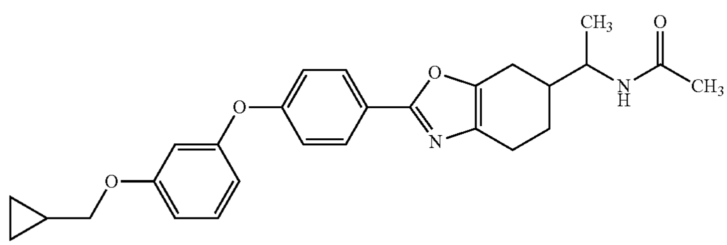 [SMILES: CC(=O)NC(C)C1CCc2nc(-c3ccc(Oc4cccc(OCC5CC5)c4)cc3)oc2C1] | 447.1 |
| 95d | N-(1-(2-(4-(3-(cyclo-propylmethoxy)phenoxy)-phenyl)-4,5,6,7-tetra-hydro-1,3-benzoxazol-6-yl)ethyl)acetamide | 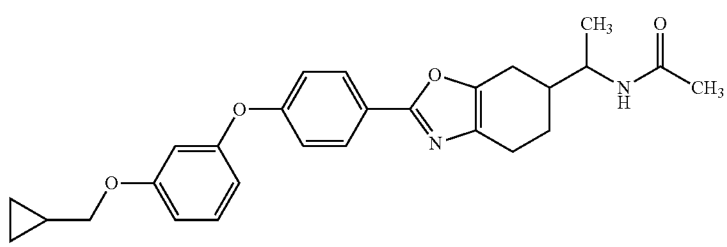 [SMILES: CC(=O)NC(C)C1CCc2nc(-c3ccc(Oc4cccc(OCC5CC5)c4)cc3)oc2C1] | 447.1 |
| 96 | N-(1-(2-(6-(3-(cyclopropylmethoxy)-phenoxy)pyridazin-3-yl)-1,3-benzoxazol-6-yl)ethyl)acetamide | 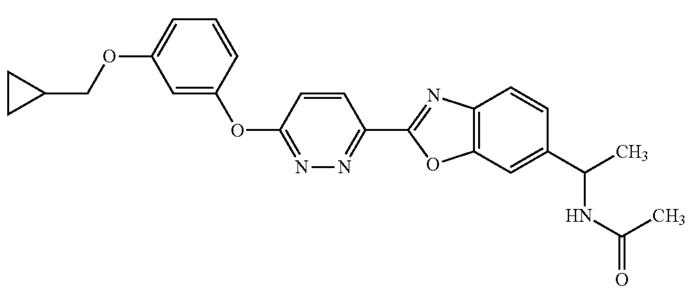 [SMILES: CC(=O)NC(C)c1ccc2nc(-c3ccc(Oc4cccc(OCC5CC5)c4)nn3)oc2c1] | 445.1 |

TABLE 1-13

| Ex. No. | IUPAC name | Structure | MS |
|---|---|---|---|
| 97 | N-(1-(2-(6-(3-(cyclopropylmethoxy)-phenoxy)-4-methylpyridin-3-yl)-1,3-benzoxazol-6-yl)ethyl)-acetamide | 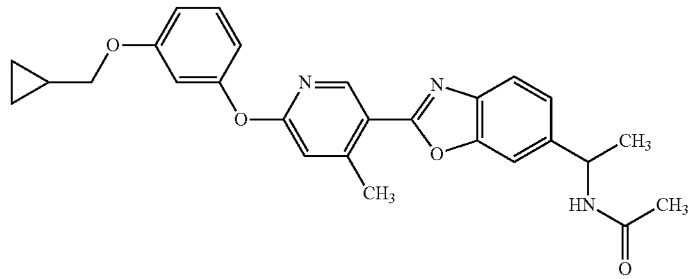 [SMILES: CC(=O)NC(C)c1ccc2nc(-c3cnc(Oc4cccc(OCC5CC5)c4)cc3C)oc2c1] | 458.2 |
| 98 | 1-(1-(2-(6-(3-(cyclopropylmethoxy)phenoxy)-pyridin-3-yl)-1,3-benzoxazol-6-yl)ethyl)-urea | 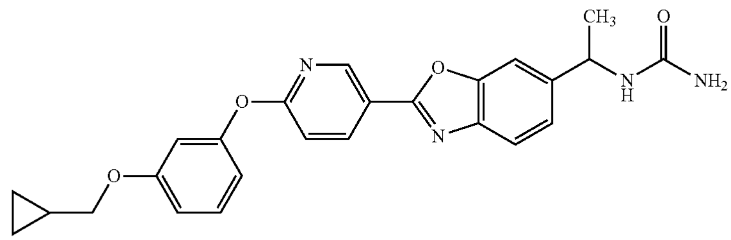 [SMILES: CC(NC(N)=O)c1ccc2nc(-c3ccc(Oc4cccc(OCC5CC5)c4)nc3)oc2c1] | 445.1 |
| 98a | 1-((1R)-1-(2-(6-(3-(cyclopropylmethoxy)-phenoxy)pyridin-3-yl)-1,3-benzoxazol-6-yl)ethyl)urea | 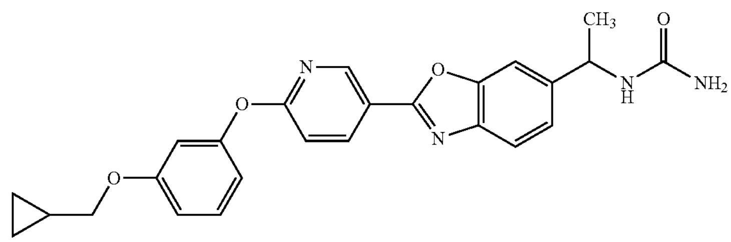 [SMILES: CC(NC(N)=O)c1ccc2nc(-c3ccc(Oc4cccc(OCC5CC5)c4)nc3)oc2c1] | 445.2 |
| 98b | 1-((1S)-1-(2-(6-(3-(cyclopropylmethoxy)-phenoxy)pyridin-3-yl)-1,3-benzoxazol-6-yl)ethyl)urea | 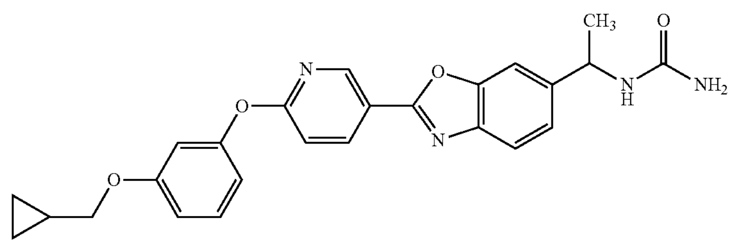 [SMILES: CC(NC(N)=O)c1ccc2nc(-c3ccc(Oc4cccc(OCC5CC5)c4)nc3)oc2c1] | 445.1 |
| 99 | methyl (1-(2-(6-(3-(cyclopropylmethoxy)-phenoxy)pyridin-3-yl)-1,3-benzoxazol-6-yl)ethyl)carbamate | 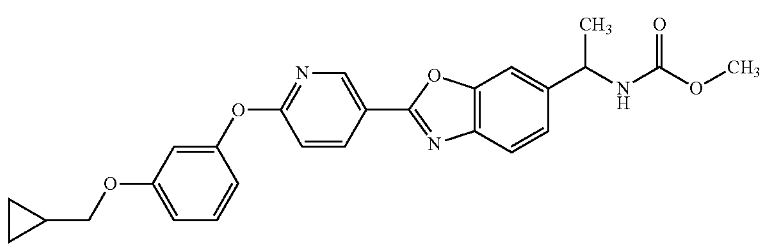 [SMILES: COC(=O)NC(C)c1ccc2nc(-c3ccc(Oc4cccc(OCC5CC5)c4)nc3)oc2c1] | 460.2 |
| 100 | 1-(1-(2-(6-(3-(cyclopropylmethoxy)-phenoxy)pyridin-3-yl)-1,3-benzoxazol-6-yl)ethyl)-3-methylurea | 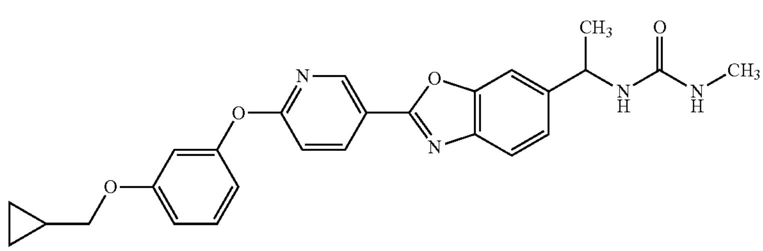 [SMILES: CNC(=O)NC(C)c1ccc2nc(-c3ccc(Oc4cccc(OCC5CC5)c4)nc3)oc2c1] | 459.2 |

TABLE 1-13-continued

| Ex. No. | IUPAC name | Structure | MS |
|---|---|---|---|
| 101 | 3-(1-(2-(6-(3-(cyclopropylmethoxy)-phenoxy)pyridin-3-yl)-1,3-benzoxazol-6-yl)ethyl)-1,1-dimethylurea | 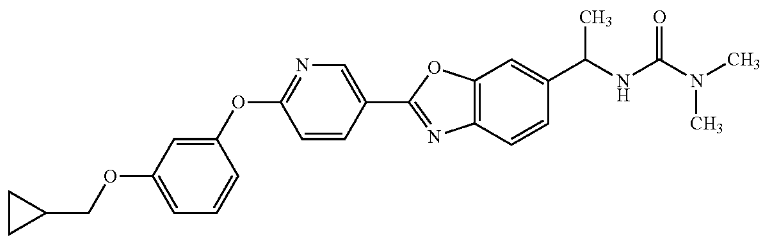 [SMILES: CC(NC(=O)N(C)C)c1ccc2nc(-c3ccc(Oc4cccc(OCC5CC5)c4)nc3)oc2c1] | 473.2 |
| 102 | N-(1-(2-(6-((6-oxo-1-propyl-1,6-dihydropyridin-3-yl)-oxy)pyridin-3-yl)-1,3-benzoxazol-6-yl)ethyl)-acetamide | 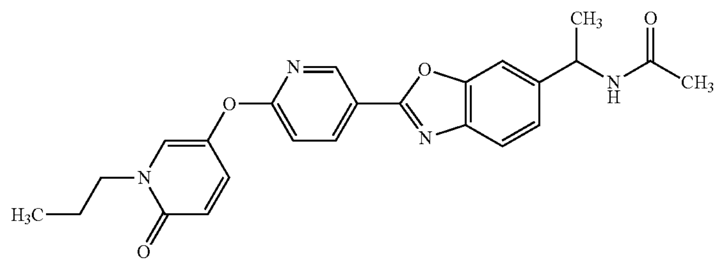 [SMILES: CCCn1cc(Oc2ccc(-c3nc4ccc(C(C)NC(C)=O)cc4o3)cn2)ccc1=O] | 433.0 |
| 103 | N-(1-(5-(5-(3-(cyclopropylmethoxy)-phenoxy)pyrazin-2-yl)-1-benzofuran-2-yl)ethyl)-acetamide | 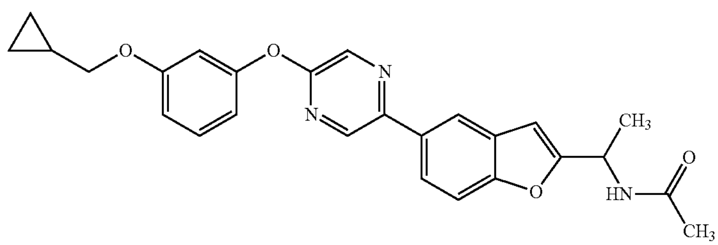 [SMILES: CC(=O)NC(C)c1cc2cc(-c3cnc(Oc4cccc(OCC5CC5)c4)cn3)ccc2o1] | 444.1 |

TABLE 1-14

| Ex. No. | IUPAC name | Structure | MS |
|---|---|---|---|
| 104 | N-(1-(2-(4-(3-(cyclopropylmethoxy)-phenoxy)phenyl)[1,3]-oxazolo[5,4-b]pyridin-5-yl)ethyl)acetamide | 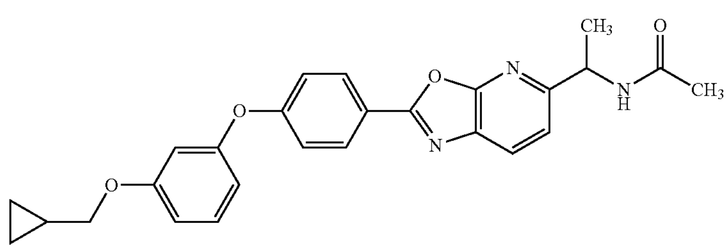 [SMILES: CC(=O)NC(C)c1ccc2nc(-c3ccc(Oc4cccc(OCC5CC5)c4)cc3)oc2n1] | 444.1 |
| 105 | N-(1-(2-(6-((1-butyl-6-oxo-1,6-dihydropyridin-3-yl)oxy)pyridin-3-yl)-1,3-benzoxazol-6-yl)ethyl)acetamide | 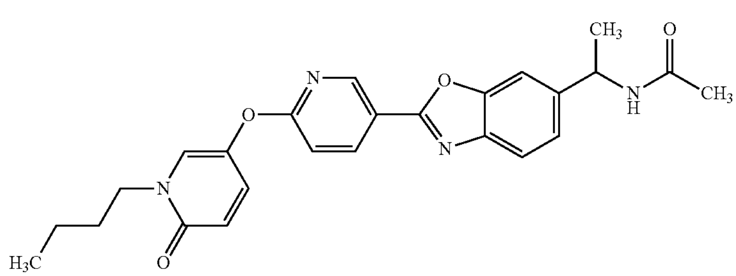 [SMILES: CCCCn1cc(Oc2ccc(-c3nc4ccc(C(C)NC(C)=O)cc4o3)cn2)ccc1=O] | 447.1 |

TABLE 1-14-continued

| Ex. No. | IUPAC name | Structure | MS |
|---|---|---|---|
| 106 | 1-(1-(2-(6-((5-(cyclopropylmethoxy)-pyridin-3-yl)oxy)-pyridin-3-yl)-1,3-benzoxazol-6-yl)ethyl)-urea | 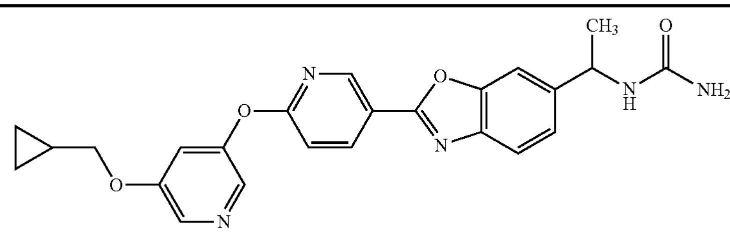 | 446.0 |
| 107 | 1-(1-(2-(6-(3-(2,2-difluoropropoxy)-phenoxy)pyridin-3-yl)-1,3-benzoxazol-6-yl)ethyl)urea | 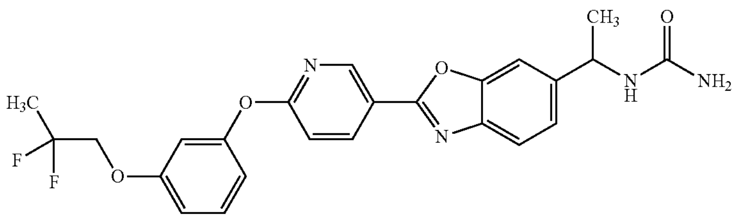 [SMILES: CC(NC(N)=O)c1ccc2nc(-c3ccc(Oc4cccc(OCC(C)(F)F)c4)nc3)oc2c1] | 469.0 |
| 108 | 1-(1-(2-(6-(3-(cyclopropylmethoxy)-phenoxy)pyridin-3-yl)-7-fluoro-1,3-benzoxazol-6-yl)ethyl)urea | 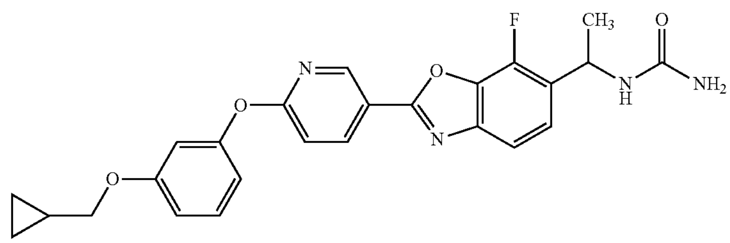 [SMILES: CC(NC(N)=O)c1ccc2nc(-c3ccc(Oc4cccc(OCC5CC5)c4)nc3)oc2c1F] | 463.0 |
| 109 | 1-(1-(2-(5-(3-(cyclopropylmethoxy)-phenoxy)pyrazin-2-yl)-1,3-benzoxazol-6-yl)ethyl)urea | 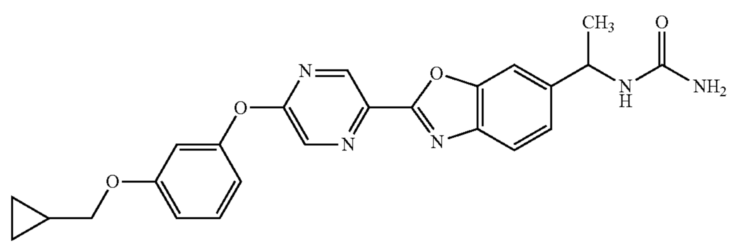 [SMILES: CC(NC(N)=O)c1ccc2nc(-c3cnc(Oc4cccc(OCC5CC5)c4)cn3)oc2c1] | 446.0 |
| 110 | 1-(1-(2-(6-(3-(cyclopropylmethoxy)-phenoxy)pyridazin-3-yl)-1,3-benzoxazol-6-yl)ethyl)urea | 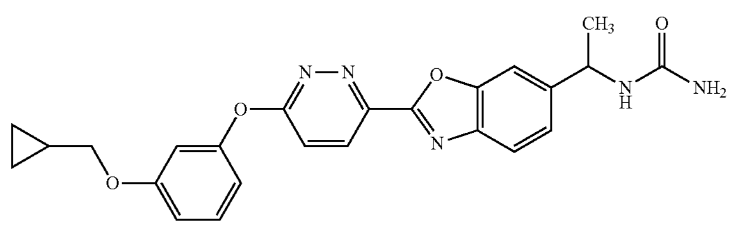 [SMILES: CC(NC(N)=O)c1ccc2nc(-c3ccc(Oc4cccc(OCC5CC5)c4)nn3)oc2c1] | 446.0 |

Experimental Example 1

The ACC2 inhibitory action of the compound of the present invention was evaluated by the following method.

(1) Cloning of Human ACC1 Gene and Preparation of Recombinant Baculovirus

Human ACC1 gene was cloned by PCR using a human liver cDNA library (Clontech) as a template and Primer 1 and Primer 2 shown below. Primer 1 and Primer 2 were prepared by adding SalI, NotI restriction enzyme recognition sequences based on the information of the base sequence of human ACC1 gene (Genbank Accession U19822).

```
Primer 1:
                                            (SEQ ID NO: 1)
5'-AAAAGTCGACCCACCATGGATGAACCTTCTCCCTTGGCCC-3'

Primer 2:
                                            (SEQ ID NO: 2)
5'-AAAAGCGGCCGCCTACGTAGAAGGGGAGTCCATAGTG-3'
```

PCR was performed using Pyrobest DNA polymerase (TAKARA BIO INC.). The obtained PCR product was cloned to pT7 Blue vector (Novagen) and after confirmation of the base sequence, digested with restriction enzymes SalI and XbaI. The obtained DNA fragment was inserted into pFAST-BacHTc (Invitrogen) digested with restriction enzymes SalI and XbaI to give expression plasmid ACC1/pFAST-BacHTc.

Using the expression plasmid ACC1/pFAST-BacHTc and BAC-TO-BAC Baculovirus Expression System (Invitrogen), virus stock BAC-ACC1 of recombinant Baculovirus was prepared.

(2) Preparation of ACC1 Protein

SF-9 cells (Invitrogen) were inoculated to a medium (10 L) for insect cells (Sf-900IISFM medium (Invitrogen) containing 5% fetal bovine serum (Trace), 50 mg/L Gentamicin (Wako Pure Chemical Industries, Ltd.), 0.1% Pluronic F-68 (Invitrogen)) at $1.0 \times 10^6$ cells/mL, and cultured with shaking in Wave Bioreactor (GE Healthcare) at 27° C., 20 rpm, rocking angle 10°, oxygen concentration 30%.

On day 2 of the culture, recombinant Baculovirus BAC-ACC1 was added, and the cells were cultured for 3 days. The culture medium was centrifuged at 4000×g for 10 min to give virus-infected cells. The cells were washed with phosphate buffered saline (Invitrogen) and centrifuged under the same conditions. The obtained cells were cryopreserved at −80° C.

The cryopreserved cells were thawed in ice and suspended in 800 mL of 25 mM HEPES buffer (pH 7.5) containing 10% Glycerol, 0.3 M NaCl, 1 mM EDTA, 25 mM Sodium β-Glycerophosphate and 1 mM Sodium Orthovanadate, and supplemented with Complete Protease Inhibitor (Roche). The obtained suspension was homogenized two times in a polytron homogenizer (Kinematica) at 20,000 rpm for 20 sec. The obtained cell disruption solution was clarified by centrifugation at 186,000×g for 60 min and the supernatant was passed through Ni-NTA Superflow Cartridges (5 mL) (QUIAGEN). Furthermore, it was washed with 25 mM HEPES buffer (pH 7.5) containing 20 mM Imidazole, 0.3 M NaCl, and eluted with 25 mM HEPES buffer (pH 7.5) containing 250 mM Imidazol, 0.3 M NaCl. The eluate was concentrated by Amicon Ultra-15 (Nihon Millipore K.K.) having a fraction molecular weight of 50K. The obtained concentrate was subjected to gel filtration with 50 mM HEPES buffer (pH 7.5) containing 10 mM $MgCl_2$, 2 mM dithiothreitol, 10 mM tripotassium citrate, 0.3 M NaCl by using HiLoad 26/60 Superdex200 prep grade gel filtration column (GE Healthcare) to give ACC1. The obtained ACC1 was cryopreserved at −80° C.

(3) Measurement of ACC1 Inhibitory Activity

ACC1 obtained in the above-mentioned (2) was diluted with an enzyme reaction buffer (50 mM HEPES (pH 7.5), 10 mM $MgCl_2$, 10 mM Tripottasium Citrate, 2 mM Dithiothreitol, 0.001% Fatty acid free BSA) to a concentration of 0.2 μg/ml, and the mixture was added to each well of a 384 well assay plate by 10 μl. A test compound dissolved in dimethyl sulfoxide (DMSO) was diluted with an enzyme reaction buffer and the resulting solution (5 μl) was added to each well. The mixture was incubated at room temperature for 60 min. Then, a substrate solution (50 mM $KHCO_3$, 200 μM ATP, 200 μM Acetyl-CoA, 5 μl) was added to each well, and the mixture was reacted at room temperature for 30 min. The reaction was quenched by adding a reaction quenching liquid (1.3% formic acid, 0.2 μM Malonyl-$^{13}C_3$-CoA) by 60 μL each to the obtained reaction mixtures (test compound addition group).

In addition, a reaction was performed in the same manner as above and without adding the test compound (test compound non-addition group).

Furthermore, a reaction was performed in the same manner as above without adding the test compound and adding ACC1 after addition of a reaction quenching liquid (control group).

The amount of Malonyl-CoA produced was measured by RapidFire-mass spectrometry, and determined by normalizing by the amount of Malonyl-$^{13}C_3$-CoA.

High throughput online solid phase extraction was performed using the RapidFire300™ system (Agilent Technologies). A sample was loaded and desalted in an SPE C4 cartridge (Agilent Technologies) at a flow rate of 1.5 mL/min with 5 mM dibutyl ammonium acetate in ultrapure water, eluted with 5 mM dibutyl ammonium acetate dissolved in acetonitrile/ultrapure water (90/10, v/v), at a flow rate of 1.0 mL/min, and introduced into a mass spectrometry part. The injection needle was washed with ultrapure water (500 milliseconds) and acetonitrile (500 milliseconds) to minimize carryover. The suction time (injection loop 5 μL), load/washing time, elution time, and re-equilibration time were adjusted to 350, 3000, 4500, and 500 milliseconds, respectively, and the total cycle time was adjusted to about 10.0 seconds. The RapidFire300 system was controlled by RapidFire UI software version 3.6 (Agilent Technologies).

Mass spectrometry of the resultant product was performed using API4000™ triple quadrupole mass spectrometer (AB SCIEX) equipped with an electrospray ion sauce (TurboIon Spray™) on a positive selected reaction monitoring (SRM) mode. The conditions of SRM are shown below. The parameter of instrument was optimized as follows: capillary temperature 650° C., ion spray voltage 5.5 kV, collision gas 10, curtain gas 15 psi, ion source gas 1 60 psi, ion source gas 2 60 psi. The mass spectrometer was controlled by Analyst™ software version 1.5.1 (AB SCIEX). The peak area integration was analyzed using RapidFire integrator software version 3.6 (Agilent Technologies).

TABLE 2

| Analyte | Q1 --> Q3 (m/z) | DP (V) | CE (V) | CXP (V) |
|---|---|---|---|---|
| Malonyl-CoA (Product) | 854.2 --> 245.1 | 116 | 43 | 16 |
| Malonyl-$^{13}C_3$—CoA (Internal Standard) | 857.2 --> 248.3 | 116 | 43 | 16 |

ACC1 inhibitory rate (%) was determined according to the following calculation formula.

(1−(produced amount of Malonyl-CoA of test compound addition group−produced amount of Malonyl-CoA of control group)÷(produced amount of Malonyl-CoA of test compound non-addition group−produced amount of Malonyl-CoA of control group))×100

The inhibitory rates (%) against ACC1 at 10 μM of the test compound are shown below.

TABLE 3

| Example No. | ACC1 inhibitory rate (%) at 10 μM |
|---|---|
| 1 | 100 |
| 1b | 96 |
| 8 | 95 |
| 9 | 99 |
| 9b | 99 |
| 12 | 94 |
| 13 | 86 |
| 29 | 82 |
| 31 | 98 |
| 35 | 94 |
| 36 | 100 |
| 36b | 101 |
| 37 | 101 |
| 44 | 100 |

TABLE 3-continued

| Example No. | ACC1 inhibitory rate (%) at 10 μM |
|---|---|
| 47 | 82 |
| 52 | 94 |
| 56 | 94 |
| 67 | 97 |
| 68 | 100 |
| 71 | 95 |
| 73 | 90 |
| 75 | 94 |
| 76 | 99 |
| 80 | 100 |
| 82 | 98 |
| 86 | 95 |
| 90 | 101 |
| 93 | 94 |
| 95 | 97 |
| 95b | 96 |
| 96 | 100 |
| 97 | 92 |
| 98 | 98 |
| 98b | 98 |
| 99 | 98 |
| 100 | 94 |
| 101 | 96 |
| 102 | 94 |
| 103 | 100 |
| 104 | 98 |
| 105 | 96 |
| 106 | 103 |
| 107 | 97 |
| 108 | 100 |
| 109 | 97 |
| 110 | 98 |

As shown in Table 3, the compound of the present invention has a superior ACC1 inhibitory activity.

Experimental Example 2

The growth inhibitory activity of the compound on HCT116 cell was evaluated by the following method.

HCT116 cells were seeded in a 384 well blackplate at 900 cells/30 μL/well, and maintained in an RPMI medium (Wako)) containing an assay medium (2% fetal bovine serum, 50 Unit/mL penicillin, 50 μg/mL streptomycin (Invitrogen). The next day, a test compound dissolved in dimethyl sulfoxide (DMSO) was diluted with the assay medium, and the obtained compound solution was added by 10 μL to each well of a plate containing HCT116 cells and incubated at 37° C., 5% $CO_2$ (test compound addition group).

A similar reaction was performed without adding a test compound (test compound non-addition group).

Furthermore, a similar reaction was performed under the conditions without adding HCT116 cell and a test compound (control group).

After 3 days, 20 μL of a CellTiter-Glo reagent (Promega KK) was added to the well, and the mixture was stirred for 10 min. Thereafter, the luminescence value of each well was measured by the EnVision™ multilabel counter (Perkin Elmer Inc.).

The HCT116 cell proliferation inhibitory rate (%) of the test compound was determined by the following calculation formula.

(1−(luminescence of test compound addition group−
luminescence of control group)÷(luminescence
of test compound nonaddition group−luminescence of control group))×100

The HCT116 cell proliferation inhibitory rates (%) of the test compound (1 μM) are shown below.

TABLE 4

| Example No. | HCT116 cell proliferation inhibitory rate (%) at 10 μM |
|---|---|
| 1 | 12 |
| 1b | 32 |
| 8 | 42 |
| 9 | 45 |
| 9b | 29 |
| 13 | 19 |
| 31 | 42 |
| 35 | 41 |
| 37 | 44 |
| 44 | 14 |
| 52 | 20 |
| 67 | 38 |
| 68 | 39 |
| 71 | 41 |
| 73 | 28 |
| 75 | 40 |
| 76 | 45 |
| 80 | 33 |
| 82 | 40 |
| 86 | 34 |
| 90 | 22 |
| 95 | 11 |
| 95b | 20 |
| 96 | 23 |
| 97 | 22 |
| 98 | 25 |
| 98b | 47 |
| 99 | 26 |
| 100 | 28 |
| 101 | 30 |
| 102 | 30 |
| 103 | 29 |
| 104 | 30 |
| 105 | 46 |
| 106 | 33 |
| 107 | 32 |
| 108 | 36 |
| 109 | 27 |

As shown in Table 4, the compound of the present invention has a superior cell proliferation inhibitory activity on colorectal cancer cells.

Experimental Example 3

The antitumor action of the compound of the present invention on human renal cancer cell line 786-O tumor bearing mouse was evaluated by the following method.

Human renal cancer cell line 786-O (purchased from ATCC (American Type Culture Collection)) was transplanted to 6-week-old BALB/c female nude mouse (Shanghai SINO-British SIPPR/BK Lab Animal Ltd) at $3.0 \times 10^6$ cells by subcutaneous injection. After transplantation, the engrafted tumor was observed, the tumor diameter was measured on day 10 post-transplantation, and the tumor volume was calculated by the following formula.

tumor volume=major axis×minor axis×minor axis×(1/2)

The mice having engrafted tumor with a volume size up to 150 $mm^3$ were selected and used for the experiment (8 per group). The test compound was suspended in 0.5% methylcellulose solution, and orally administered for 28 days at the dose and number of administration shown in the following Table. Finally, for the measurement of the drug effect, the tumor volume was calculated from the tumor diameter of the day before the start of the administration and the final day of the administration, and the tumor growth of the test compound administration group compared to that of the control administration group (T/C) was calculated by the following formula.

T/C (%)=(tumor volume after completion of administration in test compound administration group−tumor volume before start of administration in test compound administration group)/(tumor volume after completion of administration in control administration group−tumor volume before start of administration in control administration group))×100

T/C (%) relative to human renal cancer cell line 786-O tumor bearing mouse at each dose and number of administration of the test compound (specifically, compound shown in Example 98) is shown below.

TABLE 5

| dose (mg/kg) | number of administration (times) per day | T/C (%) |
| --- | --- | --- |
| 30 | 2 | 0.5 |
| 20 | 1 | 19.0 |
| 10 | 2 | 4.5 |
| 3 | 2 | 31.1 |
| 1 | 2 | 37.0 |
| 0.3 | 2 | 50.6 |

As shown in Table 5, the compound of the present invention has a superior antitumor action on renal cancer cells.

Experimental Example 4

The effect of the present compound on liver fibrosis caused by non-alcoholic steatohepatitis was verified by the following method.

For efficacy evaluation of the antifibrotic action, 9-week-old, male, homo low-density lipoprotein receptor deficient mouse was used. The low-density lipoprotein receptor deficient mouse was purchased from Jackson Laboratories (Bar Harbor, Me., USA) and bred in Takeda Pharmaceutical Industry. To induce non-alcoholic steatohepatitis, a choline-deficient amino acid diet (A08111307, Research Diets, New Brunswick, N.J., USA) was fed.

Before administration of the test compound (specifically, compound shown in Example 98), a choline-deficient amino acid diet was fed for one week, and the drug administration was started. The drug was suspended in 0.5% methylcellulose solution, and orally administered by gavage by using a stomach gavage needle once per day for 3 weeks (n=8). A 0.5% methylcellulose solution was administered to the control group (normal diet group n=4, choline-deficient amino acid diet group n=8). The choline-deficient amino acid diet was continuously fed during the drug dosing period.

After administration for 3 weeks, the mouse was sacrificed by euthanasia under isoflurane anesthesia under nonfasting and the liver was removed. A part of the isolated liver was preserved in RNAlater (Ambion, Austin, Tex., USA). Using RNeasy Mini Kit (Qiagen, Valencia, Calif., USA), the total RNA was purified, cDNA was prepared using High Capacity cDNA Reverse Transcription Kit (PN4368814, Applied Biosystems, Foster City, Calif., USA), and collagen I expression was quantified (collagen type I alpha 1, Part Number 4351370, Applied Biosystems) by the quantitative PCR method (TaqMan Gene Expression Master Mix, PN4369016, Applied Biosystems).

The collagen I expression level was normalized by GAPDH, and statistical analysis with the choline-deficient amino acid diet control group was performed by two-tailed Williams' test (#P<0.05 vs. control value). The obtained results are shown in FIG. 1.

As shown in FIG. 1, the compound shown in Example 98 significantly suppressed the expression level of collagen I gene in the liver of a non-alcoholic steatohepatitis model.

| Formulation Example 1 (production of capsule) | |
| --- | --- |
| 1) compound of Example 1 | 30 mg |
| 2) finely-powdered cellulose | 10 mg |
| 3) lactose | 19 mg |
| 4) magnesium stearate | 1 mg |
| | total 60 mg |

1), 2), 3) and 4) are mixed and filled in a gelatin capsule.

| Formulation Example 2 (production of tablets) | |
| --- | --- |
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets | total 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has ACC (acetyl-CoA carboxylase) inhibitory action, and is useful for the prophylaxis or treatment of cancer, NASH and the like.

This application is based on patent application No. 2014-239376 filed in Japan, the contents of which are encompassed in full herein.

The invention claimed is:

1. A compound represented by the formula:

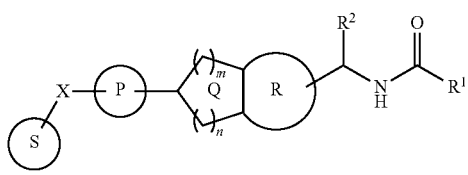

(I)

wherein
ring P is an optionally further substituted, optionally crosslinked 4- to 8-membered ring;
ring Q is an optionally further substituted 5-membered ring;
ring R is an optionally further substituted 6-membered ring;
ring S is an optionally further substituted 4- to 7-membered ring;
X is —O—, —C($R^3$)($R^4$)— or —N($R^5$)—;
$R^1$ is an amino group optionally mono- or di-substituted by an optionally substituted $C_{1-6}$ alkyl group, a $C_{1-6}$ alkyl group optionally substituted by a halogen atom, an optionally substituted $C_{3-6}$ cycloalkyl group or an optionally substituted $C_{1-6}$ alkoxy group;
$R^2$ is a $C_{1-6}$ alkyl group optionally substituted by a halogen atom or an optionally substituted $C_{3-6}$ cycloalkyl group;
$R^3$, $R^4$ and $R^5$ are the same or different and each is a hydrogen atom or a substituent;
m and n are both 1, and m+n is 2,
or a salt thereof.

2. The compound according to claim 1, wherein ring P is
(1) a cyclobutane ring,
(2) a cyclohexane ring,
(3) a benzene ring optionally further substituted by 1-4 substituents selected from a halogen atom, a cyano group and a $C_{1-6}$ alkyl group,
(4) an azetidine ring optionally further substituted by 1-4 substituents selected from a $C_{1-6}$ alkyl group,
(5) a pyrrolidine ring,
(6) a piperidine ring,
(7) a hexahydrocyclopenta[c]pyrrole ring,
(8) a pyrazole ring optionally further substituted by 1-4 substituents selected from a $C_{1-6}$ alkyl group,
(9) a pyridine ring optionally further substituted by 1-4 substituents selected from a $C_{1-6}$ alkyl group,
(10) a pyridazine ring, or
(11) a pyrazine ring,
ring Q is
(1) a dihydrofuran ring,
(2) a furan ring,
(3) a thiophene ring,
(4) a pyrazole ring,
(5) an imidazole ring optionally further substituted by 1-4 substituents selected from a $C_{1-6}$ alkyl group, or
(6) an oxazole ring,
(7) a thiazole ring;
ring R is
(1) a cyclohexene ring,
(2) a benzene ring optionally further substituted by 1-4 substituents selected from a halogen atom and a $C_{1-6}$ alkyl group, or
(3) a pyridine ring;
ring S is
(1) a benzene ring optionally further substituted by 1-4 substituents selected from
(i) a $C_{1-6}$ alkyl group optionally further substituted by 1-4 substituents selected from a $C_{1-6}$ alkoxy group and a halogen atom,
(ii) a $C_{1-6}$ alkoxy group optionally substituted by 1-5 substituents selected from
(a) a halogen atom,
(b) a $C_{3-6}$ cycloalkyl group optionally substituted by 1-4 substituents selected from a halogen atom and a $C_{1-6}$ alkyl group,
(c) a $C_{1-6}$ alkoxy group,
(d) a 4- to 7-membered nonaromatic heterocyclic group optionally substituted by a $C_{1-6}$ alkyl group, and
(e) a $C_{6-14}$ aryl group,
(iii) a $C_{3-6}$ cycloalkyloxy group, and
(iv) a di-$C_{1-6}$ alkylamino group, or
(2) a pyridine ring optionally further substituted by 1-4 substituents selected from
(i) a $C_{1-6}$ alkoxy group optionally substituted by a $C_{3-6}$ cycloalkyl group,
(ii) an oxo group, and
(iii) a $C_{1-6}$ alkyl group;
X is —$CH_2$—, —NH—, —N($CH_3$)— or —O—;
$R^1$ is
(1) a $C_{1-6}$ alkyl group optionally substituted by 1 to 3 halogen atoms,
(2) a $C_{1-6}$ alkoxy group, or
(3) an amino group optionally mono- or di-substituted by a $C_{1-6}$ alkyl group;
$R^2$ is a $C_{1-6}$ alkyl group;
m and n are both 1, and m+n is 2;
or a salt thereof.

3. The compound according to claim 1, wherein the fused ring constituted of ring Q and ring R, that is, a partial structure:

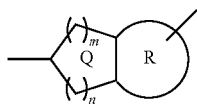

is

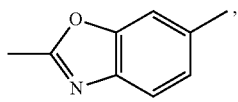, or a salt thereof.

4. N-(1-(2-(6-(3-(cyclopropylmethoxy)phenoxy)pyridin-3-yl)-1,3-benzoxazol-6-yl)ethyl)acetamide, or a salt thereof.

5. 1-(1-(2-(6-(3-(Cyclopropylmethoxy)phenoxy)pyridin-3-yl)-1,3-benzoxazol-6-yl)ethyl)urea, or a salt thereof.

6. N-(1-(2-(6-(((6-oxo-1-propyl-1,6-dihydropyridin-3-yl)oxy)pyridin-3-yl)-1,3-benzoxazol-6-yl)ethyl)acetamide, or a salt thereof.

7. A medicament comprising the compound according to claim 1 or a salt thereof.

8. A method of inhibiting ACC1 in a mammal, comprising administering an effective amount of the compound according to claim 1 or a salt thereof to the mammal.

9. A method for treatment of non-alcoholic steatohepatitis in a mammal, comprising administering an effective amount of the compound according to claim 1 or a salt thereof to the mammal.

* * * * *